United States Patent
Gardai et al.

(10) Patent No.: US 12,071,480 B2
(45) Date of Patent: Aug. 27, 2024

(54) CD47 ANTIBODIES AND USES THEREOF FOR TREATING CANCER

(71) Applicant: Seagen Inc., Bothell, WA (US)

(72) Inventors: Shyra Gardai, Bothell, WA (US); Matthew Levengood, Bothell, WA (US); Vivian Trang, Lynnwood, WA (US); Lori Westendorf, Bothell, WA (US); Christopher Carosino, Duvall, WA (US); Che Leung-Law, Bothell, WA (US); Michael Feldhaus, Boston, MA (US)

(73) Assignee: Seagen Inc., Bothell, WA (US)

( * ) Notice: Subject to any disclaimer, the term of this patent is extended or adjusted under 35 U.S.C. 154(b) by 358 days.

(21) Appl. No.: 17/505,911

(22) Filed: Oct. 20, 2021

(65) Prior Publication Data

US 2022/0135674 A1 May 5, 2022

Related U.S. Application Data

(62) Division of application No. 16/203,809, filed on Nov. 29, 2018, now Pat. No. 11,180,552.

(60) Provisional application No. 62/593,712, filed on Dec. 1, 2017.

(51) Int. Cl.
C07K 16/28 (2006.01)
A61K 39/00 (2006.01)
A61P 35/00 (2006.01)

(52) U.S. Cl.
CPC .......... *C07K 16/2803* (2013.01); *A61P 35/00* (2018.01); *A61K 2039/505* (2013.01); *C07K 2317/24* (2013.01); *C07K 2317/565* (2013.01); *C07K 2317/567* (2013.01); *C07K 2317/732* (2013.01); *C07K 2317/76* (2013.01); *C07K 2317/92* (2013.01); *C07K 2319/50* (2013.01); *C07K 2319/73* (2013.01)

(58) Field of Classification Search
None
See application file for complete search history.

(56) References Cited

U.S. PATENT DOCUMENTS

| | | | |
|---|---|---|---|
| 5,057,604 A | 10/1991 | Brown | |
| 6,111,080 A | 8/2000 | Brown | |
| 7,514,229 B2 | 4/2009 | Jamieson et al. | |
| 7,696,325 B2 | 4/2010 | Fukushima et al. | |
| 8,101,719 B2 | 1/2012 | Kikuchi et al. | |
| 8,562,997 B2 | 10/2013 | Jaiswal et al. | |
| 8,613,922 B2 | 12/2013 | Clemmons et al. | |
| 8,728,476 B2 | 5/2014 | Berg | |
| 8,951,527 B2 | 2/2015 | Senberg et al. | |
| 9,017,675 B2 | 4/2015 | Liu et al. | |
| 9,045,541 B2 | 6/2015 | Eckelman et al. | |
| 9,221,908 B2 | 12/2015 | Frazier et al. | |
| 9,352,037 B2 | 5/2016 | Berg | |
| 9,475,882 B2 | 10/2016 | Clemmons et al. | |
| 9,518,117 B2 | 12/2016 | Frazier et al. | |
| 9,663,575 B2 | 5/2017 | Eckelman et al. | |
| 9,790,275 B2 | 10/2017 | Berg | |
| 10,035,855 B2 | 7/2018 | Swanson et al. | |
| 2004/0197328 A1* | 10/2004 | Young ................ | A61K 51/1045 424/155.1 |
| 2004/0213792 A1 | 10/2004 | Clemmons et al. | |
| 2006/0135749 A1 | 6/2006 | Matozaki et al. | |
| 2007/0111238 A1 | 5/2007 | Jamieson et al. | |
| 2010/0215620 A1 | 8/2010 | Yang et al. | |
| 2011/0206696 A1 | 8/2011 | Frazier et al. | |
| 2013/0142786 A1 | 6/2013 | Liu et al. | |
| 2014/0161799 A1 | 6/2014 | Frazier et al. | |
| 2014/0161825 A1 | 6/2014 | Jaiswal et al. | |
| 2016/0045532 A1 | 2/2016 | Roberts et al. | |
| 2016/0152711 A1 | 6/2016 | Williams et al. | |
| 2016/0257751 A1 | 9/2016 | Swanson et al. | |
| 2017/0002082 A1 | 1/2017 | West et al. | |
| 2017/0035480 A1 | 2/2017 | Dai et al. | |
| 2017/0071918 A1 | 3/2017 | Lui et al. | |
| 2017/0081407 A1 | 3/2017 | Grosveld et al. | |
| 2017/0166645 A1 | 6/2017 | Weissman et al. | |
| 2017/0210803 A1 | 7/2017 | Willingham et al. | |
| 2017/0369572 A1 | 12/2017 | Sato et al. | |
| 2018/0201677 A1 | 7/2018 | Grosveld et al. | |
| 2018/0355065 A1 | 12/2018 | Masternak et al. | |
| 2019/0023784 A1 | 1/2019 | Chalons-Cottavoz et al. | |

FOREIGN PATENT DOCUMENTS

| | | |
|---|---|---|
| EP | 1035132 A1 | 9/2000 |
| EP | 1693385 A1 | 8/2006 |
| EP | 3209769 A1 | 8/2017 |
| EP | 3349787 A2 | 7/2018 |
| EP | 3353209 A1 | 8/2018 |

(Continued)

OTHER PUBLICATIONS

Gura (Science, 1997, 278:1041-1042) (Year: 1997).*
Kaiser (Science, 2006, 313: 1370) (Year: 2006).*
Chames et al (British J. of Pharmacology, 2009, 157, 220-233) (Year: 2009).*
Ahmed et al, "Targeting CD47 as an Apoptotic Trigger of Human Lung Carcinoma Tumors", AICHE Annual Meeting, Conference Proceedings, Nov. 3, 2005, p. 457d.
Arndt et al., "Comparison of In Vivo Selection and Rational Design of Heterodimeric Coiled Coils," Structure (10), Sep. 2002, pp. 1235-1248.

(Continued)

*Primary Examiner* — Peter J Reddig
(74) *Attorney, Agent, or Firm* — McNeill PLLC

(57) ABSTRACT

Humanized antibodies, including masked antibodies that specifically bind to CD47 are provided. Methods for using anti-CD47 antibodies, including masked antibodies, to modulate activity of (e.g., inhibit proliferation of) a CD47-expressing cell, as well as for the treatment of one or more diseases or disorders (e.g., cancer) associated with CD47-expressing cells, are provided.

33 Claims, 56 Drawing Sheets
Specification includes a Sequence Listing.

(56) References Cited

FOREIGN PATENT DOCUMENTS

| | | |
|---|---|---|
| EP | 3411071 A1 | 12/2018 |
| JP | 2012514982 A | 7/2012 |
| JP | 2013534409 A | 9/2013 |
| JP | 2015504899 A | 2/2015 |
| JP | 2017504600 A | 2/2017 |
| WO | 1999040940 A1 | 8/1999 |
| WO | 2004096133 A3 | 12/2005 |
| WO | 2009046541 A1 | 4/2009 |
| WO | 2009091547 A1 | 7/2009 |
| WO | 2009091601 A1 | 7/2009 |
| WO | 2009131453 A1 | 10/2009 |
| WO | 2010017332 A3 | 4/2010 |
| WO | 2010081173 A2 | 7/2010 |
| WO | 2011143624 A2 | 11/2011 |
| WO | 2011143624 A3 | 1/2012 |
| WO | 2012088309 A1 | 6/2012 |
| WO | 2013109752 A1 | 7/2013 |
| WO | 2014093678 A2 | 6/2014 |
| WO | 2014124028 A1 | 8/2014 |
| WO | 2014149477 A1 | 9/2014 |
| WO | 2014160183 A1 | 10/2014 |
| WO | 2014087248 A3 | 11/2014 |
| WO | 2014186761 A2 | 11/2014 |
| WO | 2015048329 A3 | 6/2015 |
| WO | 2015091655 A1 | 6/2015 |
| WO | 2015105995 A2 | 7/2015 |
| WO | 2015086727 A3 | 9/2015 |
| WO | 2015191861 A1 | 12/2015 |
| WO | 2016057980 A1 | 4/2016 |
| WO | 2016065329 A1 | 4/2016 |
| WO | 2016081423 A1 | 5/2016 |
| WO | 2016109415 A1 | 7/2016 |
| WO | 2016179335 A1 | 11/2016 |
| WO | 2017012771 A1 | 1/2017 |
| WO | 2017049251 A2 | 3/2017 |
| WO | 2017053423 A1 | 3/2017 |
| WO | 2017121771 A1 | 7/2017 |
| WO | 2017196793 A1 | 11/2017 |
| WO | 2017197495 A1 | 11/2017 |
| WO | 2017215585 A1 | 12/2017 |
| WO | 2018075857 A1 | 4/2018 |
| WO | 2018089508 A2 | 5/2018 |
| WO | 2018095428 A1 | 5/2018 |
| WO | 2018107125 A1 | 6/2018 |
| WO | 2018130513 A1 | 7/2018 |
| WO | 2018137705 A1 | 8/2018 |
| WO | 2018014067 A9 | 1/2019 |
| WO | 2019027903 A1 | 2/2019 |
| WO | 2019042119 A1 | 3/2019 |
| WO | 2019042285 A1 | 3/2019 |

OTHER PUBLICATIONS

Blazer et al, "CD47 (Integrin-associated Protein) Engagement of Dendritic Cell and Macrophage Counterreceptors Is Required to Prevent the Clearance of Donor Lymphohematopoietic Cells," J. Exp. Med., (194)(4), Aug. 20, 2001, pp. 541-549.
Brown et al., "Integrin-associated protein (CD47) and its ligands," Trends in Cell Biology (11)(3), Mar. 2001, pp. 130-135.
Campbell et al., "An Ovarian Tumor Marker with Homology to Vaccinia Virus Contains an IgV-like Region and Multiple Transmembrane Domains," Cancer Research (52), Oct. 1, 1992, pp. 5416-5420.
Chao et al., "Anti-CD47 Antibody Synergizes with Rituximab to Promote Phagocytosis and Eradicate Non-Hodgkin Lymphoma," Cell (142), Sep. 3, 2010, pp. 699-713.
Chen et al., "Selective antibody activation through protease-activated pro-antibodies that mask binding sites with inhibitory domains", Nature—Scientific Reports (7)(1), Sep. 14, 2017, pp. 1-12, XP55586093, DOI: 10.1038/s41598-017-11886-7.
Gardai et al. "Cell-Surface Calreticulin Initiates Clearance of Viable or Apoptotic Cells through trans-Activation of LRP on the Phagocyte," Cell (123), Oct. 21, 2005, pp. 321-334.

Han et al., "CD47, a ligand for the macrophage fusion receptor, participates in macrophage multinucleation," Journal of Biological Chemistry (275)(48), Dec. 1, 2000, pp. 37984-37992.
International Search Report issued Jul. 15, 2019 for International Application No. PCT/US2018-062961, 32 pages.
Invitation to Pay Additional Fees and, Where Applicable, Protest Fee issued in PCT/US2018/062961, dated Apr. 1, 2019, 18 pages.
Jamieson et al., "Increased Expression of CD47 Is a Constant Marker in Mouse and Human Myeloid Leukemias," Blood 106:3260 (2005).
Kikuchi et al., "Apoptosis inducing bivalent single-chain antibody fragments against CD47 showed antitumor potency for multiple myeloma," Leukemia Research (29), 2005, pp. 445-450.
Kim et al., "Association of CD47 with Natural Killer Cell-Mediated Cytotoxicity of Head-and-Neck Squamous Cell Carcinoma Lines," Tumor Biol (29), Sep. 1, 2007, pp. 28-34, DOI: 10.1159-000132568.
Liu et al., "Signal Regulatory Protein (SIRPa), a Cellular Ligand for CD47, Regulates Neutrophil Transmigration," Journal of Biological Chemistry (277)(12), Mar. 22, 2002, pp. 10028-10036.
Majeti et al., CD47 Is An Independent Prognostic Factor and Therapeutic Antibody Target on Human Acute Myeloid Leukemia Stem Cells, 2008, Bood (112), abstract a766.
Manna et al, "CD47 mediates killing of breast tumor cells via Gi-dependent inhibition of protein kinase A," Cancer Research (64), Feb. 1, 2004, pp. 1026-1036.
Manna et al., "The Mechanism of CD47-Dependent Killing of T Cells: Heterotrimeric Gi-Dependent Inhibition of Protein Kinase A," J. Immunology (170), 2003, pp. 3544-3553.
Mateo et al., "Mechanisms of CD47-induced caspase-independent cell death in normal and leukemic cells: link between phosphatidylserine exposure and cytoskeleton organization," Blood (100)(8), 2002, pp. 2882-2890.
Mateo, V. et al., "CD47 ligation induces caspase-independent cell death in chronic lymphocytic leukemia," Nature Medicine. 1999. v5(11), 1277-1284.
Mawby et al., "Isolation and characterization of CD47 glycoprotein: a multispanning membrane protein which is the same as integrin-associated protein (IAP) and the ovarian tumour marker OA3," Biochem. J.,(304), 1994, pp. 525-530.
Oldenborg et al., "CD47-Signal Regulatory Protein a (SIRPa) Regulates Fcy and Complement Receptor-mediated Phagocytosis," J.Exp. Med. (193)(7), Apr. 2, 2001, pp. 855-861.
Oldenborg et al., "Role of CD47 as a Marker of Self on Red Blood Cells," Science (288), Jun. 16, 2000, pp. 2051-2054.
Oldenborg et al., "Role of CD47 in Erythroid Cells and in Autoimmunity," Leukemia & Lymphoma (45)(7), Jul. 2004, pp. 1319-1327.
Pettersen et al., "CD47 Signals T Cell Death," J Immunol (162), 1999; pp. 7031-7040.
Rath et al., "The C-terminal CD47/IAP-binding domain of thrombospondin-1 prevents camptothecin-and doxorubicin-induced apoptosis in human thyroid carcinoma cells," Biochimica et Biophysica Acta (BBA)-Molecular Cell Research (1763), 2006, pp. 1125-1134.
Rebres et al., "Novel CD47-dependent intercellular adhesion modulates cell migration," Journal of Cellular Physiology (205), 2005, pp. 182-193.
Sagawa et al., "A New Disulfide-Linked Dimer of a Single-Chain Antibody Fragment Against Human CD47 Induces Apoptosis in Lymphoid Malignant Cells In Vitro and In Vivo via the HIF-1α Pathway: A Possible Novel Therapeutic Agent for B-CLL," Blood (108)(11), 2006. p. 2097.
Schmidt, Michael, "Engineering antibodies for improved targeting of solid tumors," Villanova University Thesis, Dec. 2009, pp. 1-154.
Seiffert et al., "Human Signal-Regulatory Protein Is Expressed on Normal, But Not on Subsets of Leukemic Myeloid Cells and Mediates Cellular Adhesion Involving Its Counterreceptor CD47," Blood (94)(11), Dec. 1, 1999; pp. 3633-3643.
Shimizu et al., "Novel Human Monoclonal antibody Against CD47 Induces Cell Death in Lymphoid Malignant Cells In Vitro and In

(56) References Cited

OTHER PUBLICATIONS

Vivo: Potential Novel Therapeutic Agent for B-CLL," Blood (104), 2004, a2511.

Uno, et al., "Antitumor activity of a monoclonal antibody against CD47 in xenograft models of human leukemia," Oncology Reports (17), 2007, pp. 1189-1194.

Van Beek et al., "Signal regulatory proteins in the immune system," J Immunol (175), 2005, pp. 7781-7787.

Van den Berg et al., "Innate immune 'self' recognition: a role for CD47-SIRPalpha interactions in hematopoietic stem cell transplantation," Trends in Immunol (29)(5), 2008, pp. 203-206.

Waclavicek et al., "T cell stimulation via CD47: Agonistic and antagonistic effects of CD47 monoclonal antibody 1/1A4," Journal of Immunology (159), 1997, pp. 5345-5354.

Washington University School of Medicine. "Scientists Discover New Way to Distinguish Self From Other." ScienceDaily. ScienceDaily, Jun. 19, 2000.

Willingham et al., "The CD47-signal regulatory protein alpha (SIRPa) interaction is a therapeutic target for human solid tumors," Proceedings of the National Academy of Sciences of the United States of America (PNAS), (109)(17), Apr. 24, 2012, pp. 6662-6667.

Zhao et al., "Is targeting of CD47-SIRPα enough for treating hematopoietic malignancy?," Blood (119), May 3, 2012, 4333-4334.

\* cited by examiner

```
                        10        20        30        40        50        60
                ....|....|....|....|....|....|....|....|....|....|....|....|....
Mu B6H12 vH     EVQLVESGGDLVKPGGSLKLSCAASGFTFSGYGMSWVRQTPDKRLEWVATITSGGTYTYYPDSVKGRFTI
Hu IGHV3-23/HJ4 EVQLLESGGGLVQPGGSLRLSCAASGFTFSSYAMSWVRQAPGKGLEWVSAISGSGGSTYYADSVKGRFTI
hvH1            EVQLLESGGGLVQPGGSLRLSCAASGFTFSGYGMSWVRQAPGKGLEWVATITSGGTYTYADSVKGRFTI
hvH2            EVQLLESGGGLVQPGGSLRLSCAASGFTFSSYAMSWVRQAPGKGLEWVATITSGGTYTYADSVKGRFTI
hvH3            EVQLLESGGGLVQPGGSLRLSCAASGFTFSSYAMSWVRQAPGKGLEWVATITSGGTYTYADSVKGRFTI
Kabat CDRs                                     *****               **************
IMGT CDRs                                   ++++++++                 ++++++++

70        80        90       100       110
                ....|....|....|....|....|....|....|....|....|....|....
Mu B6H12 vH     SRDNAKNTLYLQIDSLKSEDTAIYFCARSLAGNAMDYWGQGTSVTVSS  (SEQ ID NO: 1)
Hu IGHV3-23/HJ4 SRDNSKNTLYLQMNSLRAEDTAVYFCARSLAGNAMDYWGQGTLVTVSS  (SEQ ID NO: 88)
hvH1            SRDNSKNTLYLQMNSLRAEDTAIYFCARSLAGNAMDY-----YFDYWGQGTLVTVSS  (SEQ ID NO: 3)
hvH2            SRDNSKNTLYLQMNSLRAEDTAVYFCARSLAGNAMDYWGQGTLVTVSS  (SEQ ID NO: 4)
hvH3            SRDNSKNTLYLQINSLRAEDTAVYFCARSLAGNAMDYWGQGTLVTVSS  (SEQ ID NO: 5)
Kabat CDRs             ********
IMGT CDRs          ++++++++++++
```

FIG. 1A

```
                        10        20        30        40        50        60
                ....|....|....|....|....|....|....|....|....|....|....|....|....
Mu B6H12 vH     EVQLVESGGDLVKPGGSLKLSCAASGFTFSGYGMSWVRQTPDKRLEWVATITSGGTYTYYPDSVKGRFTI
Hu IGHV3-48/HJ4 EVQLVESGGGLVQPGGSLRLSCAASGFTFSSYEMNWVRQAPGKGLEWVSYISSSGSTIYYADSVKGRFTI
hvH4            EVQLVESGGGLVQPGGSLRLSCAASGFTFSSYGMNWVRQAPGKGLEWVATITSGGTYTYADSVKGRFTI
Kabat CDRs                                     *****               **************
IMGT CDRs                                   ++++++++                 ++++++++

70        80        90       100       110
                ....|....|....|....|....|....|....|....|....|....|....
Mu B6H12 vH     SRDNAKNTLYLQIDSLKSEDTAIYFCARSLAGNAMDYWGQGTSVTVSS  (SEQ ID NO: 1)
Hu IGHV3-48/HJ4 SRDNAKNSLYLQMNSLRAEDTAVYYCAR-----YFDYWGQGTLVTVSS  (SEQ ID NO: 89)
hvH4            SRDNAKNSLYLQMNSLRAEDTAVYYCARSLAGNAMDYWGQGTLVTVSS  (SEQ ID NO: 6)
Kabat CDRs             ********
IMGT CDRs          ++++++++++++
```

FIG. 1B

```
                   10        20        30        40        50        60
                    |         |         |         |         |         |
Mu B6H12 vH        EVQLVESGGDLVKPGGSLKLSCAASGFTFSGYGMSWVRQTPDKRLEWVATITSGGTYTYPDSVKGRFTI
Hu IGHV3-66/HJ4    EVQLVESGGGLVQPGGSLRLSCAASGFTVSSNYMSWVRQAPGKGLEWVSVIYSGGS-TYYADSVKGRFTI
hvH5               EVQLVESGGGLVQPGGSLRLSCAASGFTFSGYGMSWVRQAPGKGLEWVATITSGGTYTYADSVKGRFTI
Kabat CDRs                                        *****                 ************
IMGT CDRs                              ++++++++                 ++++++++

70        80        90        100       110
                    |         |         |         |         |
Mu B6H12 vH        SRDNAKNTLYLQIDSLKSEDTAIYFCARSLAGNAMDYWGQGTSVTVSS       (SEQ ID NO: 1)
Hu IGHV3-66/HJ4    SRDNSKNTLYLQMNSLRAEDTAVYYCARS-----YFDYWGQGTLVTVSS      (SEQ ID NO: 90)
hvH5               SRDNSKNTLYLQINSLRAEDTAVYYCARSLAGNAMDYWGQGTLVTVSS       (SEQ ID NO: 7)
Kabat CDRs                                   **********
IMGT CDRs                                ++++++++++++
```

FIG. 1C

```
                   10        20        30        40        50        60
                    |         |         |         |         |         |
Mu B6H12 vH        EVQLVESGGDLVKPGGSLKLSCAASGFTFSGYGMSWVRQTPDKRLEWVATITSGGTYTYPDSVKGRFTI
Hu IGHV3-74/HJ4    EVQLVESGGGLVQPGGSLRLSCAASGFTFSSYWMHWVRQAPGKGLVWVSRINSDGSSTSYADSVKGRFTI
hvH6               EVQLVESGGGLVQPGGSLRLSCAASGFTFSSYGMHWVRQAPGKGLVWVATITSGGTYTSYADSVKGRFTI
Kabat CDRs                                        *****                 ************
IMGT CDRs                              ++++++++                 +++++++++

70        80        90        100       110
                    |         |         |         |         |
Mu B6H12 vH        SRDNAKNTLYLQIDSLKSEDTAIYFCARSLAGNAMDYWGQGTSVTVSS       (SEQ ID NO: 1)
Hu IGHV3-74/HJ4    SRDNAKNTLYLQMNSLRAEDTAVYYCAR-----YFDYWGQGTLVTVSS       (SEQ ID NO: 91)
hvH6               SRDNAKNTLYLQMNSLRAEDTAVYYCARSLAGNAMDYWGQGTLVTVSS       (SEQ ID NO: 8)
Kabat CDRs                                   **********
IMGT CDRs                                +++++++++++++
```

FIG. 1D

```
                 10        20        30        40        50        60
         ....|....|....|....|....|....|....|....|....|....|....|....|....
hvH1     EVQLLESGGGLVQPGGSLRLSCAASGFTFSGYGMSWVRQAPGKRLEWVATITSGGTYTYYPDSVKGRFTI
hvH2     EVQLLESGGGLVQPGGSLRLSCAASGFTFSSYAMSWVRQAPGKGLEWVATITSGGTYTYYADSVKGRFTI
hvH3     EVQLLESGGGLVQPGGSLRLSCAASGFTFSSYAMSWVRQAPGKGLEWVATITSGGTYTYYADSVKGRFTI
hvH4     EVQLVESGGGLVQPGGSLRLSCAASGFTFSGYGMNWVRQAPGKGLEWVATITSGGTYIYYADSVKGRFTI
hvH5     EVQLVESGGGLVQPGGSLRLSCAASGFTFSGYGMSWVRQAPGKGLEWVATITSGGTYTYYADSVKGRFTI
hvH6     EVQLVESGGGLVQPGGSLRLSCAASGFTFSSYGMHWVRQAPGKGLVWVATITSGGTYTSYADSVKGRFTI
Kabat CDRs                                    *****                *********
IMGT CDRs                                ++++++++              ++++++++

70        80        90       100       110
         ....|....|....|....|....|....|....|....|....|....|....
hvH1     SRDNSKNTLYLQMNSLRAEDTAIYFCARSLAGNAMDYWGQGTLVTVSS (SEQ ID NO: 3)
hvH2     SRDNSKNTLYLQMNSLRAEDTAVYFCARSLAGNAMDYWGQGTLVTVSS (SEQ ID NO: 4)
hvH3     SRDNSKNTLYLQINSLRAEDTAVYFCARSLAGNAMDYWGQGTLVTVSS (SEQ ID NO: 5)
hvH4     SRDNAKNSLYLQMNSLRAEDTAVYYCARSLAGNAMDYWGQGTLVTVSS (SEQ ID NO: 6)
hvH5     SRDNSKNTLYLQINSLRAEDTAVYYCARSLAGNAMDYWGQGTLVTVSS (SEQ ID NO: 7)
hvH6     SRDNAKNTLYLQMNSLRAEDTAVYYCARSLAGNAMDYWGQGTLVTVSS (SEQ ID NO: 8)
Kabat CDRs             *********
IMGT CDRs           ++++++++++

FIG. 1E 10        20        30        40        50        60
                 ....|....|....|....|....|....|....|....|....|....|....|....|....
hB6H12.3 vH (hvH1)  EVQLLESGGGLVQPGGSLRLSCAASGFTFSGYGMSWVRQAPGKRLEWVATITSGGTYTYYPDSVKGRFTI
Mu B6H12 vH         EVQLVESGGDLVKPGGSLKLSCAASGFTFSGYGMSWVRQTPDKRLEWVATITSGGTYTYYPDSVKGRFTI
Ab47 vH             EVQLVESGGGLVQPGGSLRLSCAASGFTFSGYGMSWVRQAPGKGLEWVATITSGGTYTYYPDSVKGRFTI
Kabat CDRs                                          *****                *********
IMGT CDRs                                      ++++++++              ++++++++

70        80        90       100       110
                 ....|....|....|....|....|....|....|....|....|....|....
hB6H12.3 vH (hvH1)  SRDNSKNTLYLQMNSLRAEDTAIYFCARSLAGNAMDYWGQGTLVTVSS (SEQ ID NO: 3)
Mu B6H12 vH         SRDNAKNTLYLQIDSLKSEDTAIYFCARSLAGNAMDYWGQGTSVTVSS (SEQ ID NO: 1)
Ab47 vH             SRDNAKNSLYLQMNSLRAEDTAVYYCARSLAGNAMDYWGQGTLVTVSS (SEQ ID NO: 2)
Kabat CDRs                    *********
IMGT CDRs                 ++++++++++

FIG. 1F
```

```
                    10        20        30        40        50        60        70
                    ....|....|....|....|....|....|....|....|....|....|....|....|....|....|
Mu B6H12 vK         DIVMTQSPATLSVTPGDRVSLSCRASQTISDYLHWYQQKSHESPRLLIKFASQSISGIPSRFSGSGSGSD
Hu IGKV6-21/KJ2     EIVLTQSPDFQSVTPKEKVTITCRASQSIGSSLHWYQQKPDQSPKLLIKYASQSISGVPSRFSGSGSGTD
hvK1                EIVMTQSPDFQSVTPKEKVTLTCRASQTISDYLHWYQQKPDQSPKLLIKFASQSISGVPSRFSGSGSGTD
hvK2                EIVMTQSPDFQSVTPKEKVTLTCRASQTISDYLHWYQQKPDQSPKLLIKFASQSISGVPSRFSGSGSGTD
hvK3                EIVMTQSPDFQSVTPKEKVTLTCRASQTISDYLHWYQQKPDQSPKLLIKFASQSISGVPSRFSGSGSGTD
Kabat CDRs                                  ***********
IMGT CDRs                                                      ++++++

80        90        100
                    ....|....|....|....|....|....|....|....
Mu B6H12 vK         FTLSINSVEPEDVGVYYCQNGHGFPRTFGGGTKLEIKR    (SEQ ID NO:  9)
Hu IGKV6-21/KJ2     FTLTINSLEAEDAATYYCHQSSSLP-TFGQGTKLEIKR    (SEQ ID NO: 92)
hvK1                FTLTINSLEAEDAAVYYCQNGHGFPRTFGQGTKLEIKR    (SEQ ID NO: 11)
hvK2                FTLTINSLEAEDAATYYCQNGHGFPRTFGQGTKLEIKR    (SEQ ID NO: 12)
hvK3                FTLTINSLEAEDAATYYCQNGHGFPRTFGQGTKLEIKR    (SEQ ID NO: 13)
Kabat CDRs                        **********
IMGT CDRs                          ++++++++
```

FIG. 1G

```
                    10        20        30        40        50        60        70
                    ....|....|....|....|....|....|....|....|....|....|....|....|....|....|
Mu B6H12 vK         DIVMTQSPATLSVTPGDRVSLSCRASQTISDYLHWYQQKSHESPRLLIKFASQSISGIPSRFSGSGSGSD
Hu IGKV1-27/KJ2     DIQMTQSPSSLSASVGDRVTITCRASQGISNYLAWYQQKPGKVPKLLIYAASTLQSGVPSRFSGSGSGTD
hvK4                DIQMTQSPSSLSASVGDRVTLTCRASQTISNYLAWYQQKPGKVPKLLIKFASTLQSGVPSRFSGSGSGTD
Kabat CDRs                                  ***********
IMGT CDRs                                                      ++++++

80        90        100
                    ....|....|....|....|....|....|....|....
Mu B6H12 vK         FTLSINSVEPEDVGVYYCQNGHGFPRTFGGGTKLEIKR    (SEQ ID NO:  9)
Hu IGKV1-27/KJ2     FTLTISSLQPEDVATYYCQKYNSAP-TFGQGTKLEIKR    (SEQ ID NO: 93)
hvK4                FTLTISSLQPEDVATYYCQNGHGFPRTFGQGTKLEIKR    (SEQ ID NO: 14)
Kabat CDRs                        **********
IMGT CDRs                          ++++++++
```

FIG. 1H

```
              10        20        30        40        50        60        70
              ....|....|....|....|....|....|....|....|....|....|....|....|....|....|
hvK1          EIVMTQSPDFQSVTPKEKVTLTCRASQTISDYLHWYQQKPDQSPKLLIKFASQSISGVPSRFSGSGSGTD
hvK2          EIVMTQSPDFQSVTPKEKVTLTCRASQTISDYLHWYQQKPDQSPKLLIKFASQSISGVPSRFSGSGSGTD
hvK3          EIVMTQSPDFQSVTPKEKVTLTCRASQTISDYLHWYQQKPDQSPKLLIKFASQSISGVPSRFSGSGSGSD
hvK4          DIQMTQSPSSLSASVGDRVTLTCRASQTISNYLAWYQQKPGKVPKLLIKFASTLQSGVPSRFSGSGSGSD
Kabat CDRs                                   *******                 +++
IMGT CDRs                                        +++

80        90       100
              ....|....|....|....|....|....|
hvK1          FTLTINSLEAEDAATYYCQNGHGFPRTFGQGTKLEIKR   (SEQ ID NO: 11)
hvK2          FTLTINSLEAEDAATYYCQNGHGFPRTFGQGTKLEIKR   (SEQ ID NO: 12)
hvK3          FTLTINSLEAEDAATYYCQNGHGFPRTFGQGTKLEIKR   (SEQ ID NO: 13)
hvK4          FTLTISSLQPEDVATYYCQNGHGFPRTFGQGTKLEIKR   (SEQ ID NO: 14)
Kabat CDRs                      *********
IMGT CDRs                       ++++++++++

FIG. 1I 10        20        30        40        50        60        70
                   ....|....|....|....|....|....|....|....|....|....|....|....|....|....|
hB6H12.3 vK (hvK3) EIVMTQSPDFQSVTPKEKVTLTCRASQTISDYLHWYQQKPDQSPKLLIKFASQSISGVPSRFSGSGSGSD
Mu B6H12 vK        DIVMTQSPATLSVTPGDRVSLSCRASQTISDYLHWYQQKSHESPRLLIKFASQSISGIPSRFSGSGSGSD
Ab47 vK            EIVLTQSPATLSLSPGERATLSCRASQTISDYLHWYQQKPGQAPRLLIKFASQSISGIPARFSGSGSGTD
Kabat CDRs                                     *******                 +++
IMGT CDRs                                          +++

80        90       100
                   ....|....|....|....|....|....|
hB6H12.3 vK (hvK3) FTLTINSLEAEDAATYYCQNGHGFPRTFGQGTKLEIKR   (SEQ ID NO: 13)
Mu B6H12 vK        FTLSINSVEPEDVGVYYCQNGHGFPRTFGGGTKLEIKR   (SEQ ID NO: 9)
Ab47 vK            FTLTISSLEPEDFAVYYCQNGHGFPRTFGQGTKVEIKR   (SEQ ID NO: 10)
Kabat CDRs                      *********
IMGT CDRs                       ++++++++++

| | | | MMP2 Sequence | |
|---|---|---|---|---|
| M11 CC | Light | -LEIRAAFLRQRNTALRTEVAELEQEVQRLENEVSQYETRYSGGGGGPLG*VRGGGGS | | (SEQ ID NO: 47) |
| | Heavy | -LEIEAAFLERENTALETRVAELRQRVQRARNRVSQYRTRYSGGGGGPLG*VRGGGGS | | (SEQ ID NO: 46) |

| | | | MMP2 Sequence | |
|---|---|---|---|---|
| M15 CC | Light | -LEIEAAFLEQENTALETETEVAELRQEVQRLENIVSQYETRYSGGGGGPLG*VRGGGGS | | (SEQ ID NO: 49) |
| | Heavy | -LEIRAAFLRQRNTALRTRVAELRQRVQRLRNIVSQYETRYSGGGGGPLG*VRGGGGS | | (SEQ ID NO: 48) |

| | | | MMP2 sequence (IPV) | |
|---|---|---|---|---|
| Vel CC | Light | -GASTTVAQLEEKVKTLRAENYELKSEVQRLEEQVAQLGSIPVS*LRSG | | (SEQ ID NO: 51) |
| | Heavy | -GASTSVDELQAEVDQLEDENYALKTKVAQLRKKVEKLGSIPVS*LRSG | | (SEQ ID NO: 50) |

Fig. 34

Tumor, 1 mg/kg

- mIAP301
- Vel-IPV-mIAP301
- Vel-M2-mIAP301

*FIG. 37E*

Tumor, 10 mg/kg

- mIAP301
- Vel-IPV-mIAP301
- Vel-M2-mIAP301

Cleaved Ab (4day in 37C)
20ug/ml of Vel-IPV-hB6H12.3 spiked in patient plasma

*FIG. 45C*

CD47 ANTIBODIES AND USES THEREOF FOR TREATING CANCER

CROSS-REFERENCE TO RELATED APPLICATIONS

This application is a divisional of U.S. application Ser. No. 16/203,809, filed Nov. 29, 2018, which claims the benefit of priority of U.S. Provisional Application No. 62/593,712, filed Dec. 1, 2017, each of which is incorporated by reference herein in its entirety for any purpose.

SEQUENCE LISTING

This application contains a Sequence Listing, which has been submitted electronically in ASCII format and is hereby incorporated by reference in its entirety. Said ASCII copy was created Nov. 29, 2018, is named 2018-11-29_01218-0002-00US_Seq_List_ST25.txt, and is 52,525 bytes in size.

FIELD OF THE INVENTION

The present invention relates to the field of antibody-based cancer therapeutics. In particular, the present invention relates to novel humanized anti-CD47 antibodies and antigen-binding fragments or conjugates thereof, that may optionally be associated with a removable masking agent, and their use in the treatment of CD47-expressing cancers.

BACKGROUND

Cluster of Differentiation 47 (CD47), also known as integrin associated protein (IAP), is a transmembrane receptor belonging to the immunoglobulin superfamily of proteins. CD47 is ubiquitously expressed on cells and serves as a marker for self-recognition, preventing phagocytosis by serving as a "don't eat me" signal. CD47 mediates its effects through interactions with several other proteins, including thrombospondin (TSP) and signal regulatory protein-alpha (SIRPα). The interaction between SIRPα on phagocytic cells and CD47 on target cells helps ensure that target cells do not become engulfed.

Certain cancers co-opt the CD47-based immune evasion mechanism of a cell by increasing expression of CD47 on the cell surface of the cancer cell, thus avoiding clearance by the immune system. However, therapies known in the art that target CD47-expressing cells in a subject target both cancerous and non-cancerous cells, which leads to toxicities in the subject, such as peripheral red blood cell and platelet depletion. Accordingly, there is a need for compositions and methods to selectively target CD47 in cancer cells without targeting non-cancerous cells.

SUMMARY

The present disclosure is based on the discovery of novel humanized anti-CD47 antibodies and antigen-binding fragments thereof. In certain aspects of the invention, humanized anti-CD47 antibodies or antigen-binding fragments thereof are provided that comprise a removable masking agent (e.g., a coiled coil masking agent) that prevents binding of the anti-CD47 antibodies or the antigen-binding fragments thereof to a CD47 protein. In certain embodiments, the masking agent can be removed (e.g., cleaved) by one or more molecules (e.g., proteases) that are present in a cancer cell environment. Removal of the masking agent restores the ability of the anti-CD47 antibodies or the antigen-binding fragments thereof to bind CD47, thus enabling specific targeting of the anti-CD47 antibodies or the antigen-binding fragments thereof to the CD47 protein in the context of cancer cells.

In some embodiments, a humanized antibody or antigen-binding fragment thereof that specifically binds human CD47 is provided, wherein the antibody or antigen-binding fragment comprising a light chain variable region and a heavy chain variable region, wherein the heavy chain variable region comprises HCDR1 selected from SEQ ID NOs: 16, 19, 21, and 23; HCDR2 selected from SEQ ID NOs: 17, 20, 22, and 24; and HCDR3 of SEQ ID NO: 18; wherein the light chain variable region comprises LCDR1 selected from SEQ ID NOs: 31 and 34; LCDR2 selected from SEQ ID NOs: 32 and 35; and LCDR3 selected from SEQ ID NOs: 33 and 36; wherein the heavy chain variable region comprises an amino acid sequence with at least 90%, 91%, 92%, 93%, 94%, 95%, 96%, 97%, 98% or 99% identity to an amino acid sequence selected from SEQ ID NOs: 2, 3, 4, 5, 6, 7 and 8; and wherein the light chain variable region comprises an amino acid sequence with at least 80%, 85%, 90%, 91%, 92%, 93%, 94%, 95%, 96%, 97%, 98% or 99% identity to an amino acid sequence selected from SEQ ID NOs: 10, 11, 12, 13, 14 and 15.

In some embodiments, a humanized antibody or antigen-binding fragment thereof that specifically binds human CD47 is provided, the antibody or antigen-binding fragment comprising a light chain variable region and a heavy chain variable region, wherein the heavy chain variable region comprises HCDR1 selected from SEQ ID NOs: 16, 19, 21, and 23; HCDR2 selected from SEQ ID NOs: 17, 20, 22, and 24; and HCDR3 of SEQ ID NO: 18; wherein the light chain variable region comprises LCDR1 selected from SEQ ID NOs: 31 and 34; LCDR2 selected from SEQ ID NOs: 32 and 35; and LCDR3 selected from SEQ ID NOs: 33 and 36; wherein the heavy chain variable region comprises:
  a) a human IGHV3-23/HJ4 framework set forth in SEQ ID NO: 88, wherein framework positions H44, H49, H82, H89, H91, and H94 are donor residues, according to Kabat numbering; or
  b) a human IGHV3-48/HJ4 framework set forth in SEQ ID NO: 89, wherein framework position H49 is a donor residue, according to Kabat numbering; or
  c) a human IGHV3-66/HJ4 framework set forth in SEQ ID NO: 90, wherein framework position H29, H49, and H82 is a donor residue, according to Kabat numbering; or
  d) a human IGHV3-74/HJ4 framework set forth in SEQ ID NO: 91, wherein framework position H49 is a donor residue, according to Kabat numbering; and
wherein the light chain variable region comprises:
  a) a human IGKV6-21/KJ2 framework set forth in SEQ ID NO: 92, wherein framework positions L4, L21, L69, and L85 are donor residues, according to Kabat numbering; or
  b) a human IGKV1-27/KJ2 framework set forth in SEQ ID NO: 93, wherein framework positions L21, L49, and L69 are donor residues, according to Kabat numbering.

In some embodiments, the heavy chain variable region comprises HCDR1, HCDR2, and HCDR3 selected from: SEQ ID NOs: 16, 17, and 18; SEQ ID NOs: 19, 20, and 18; SEQ ID NOs: 21, 22, and 18; SEQ ID NOs: 16, 20, and 18; and SEQ ID NOs: 23, 24, and 18. In some embodiments, the light chain variable region comprises LCDR1, LCDR2, and LCDR3 selected from SEQ ID NOs: 31, 32, and 33; SEQ ID NOs: 31, 32, and 36; and SEQ ID NOs: 34, 35, and 33. In some embodiments, the antibody or antigen-binding fragment thereof comprises HCDR1, HCDR2, HCDR3, LCDR1, LCDR2, and LCDR3 selected from SEQ ID NOs: 16, 17, 18, 31, 32, and 33; SEQ ID NOs: 16, 17, 18, 34, 35, and 33; SEQ ID NOs: 19, 20, 18, 31, 32, and 33; SEQ ID NOs: 19, 20, 18, 34, 35, and 33; SEQ ID NOs: 21, 22, 18, 31, 32, and 33; SEQ ID NOs: 21, 22, 18, 34, 35, and 33; SEQ ID NOs: 16, 20, 18, 31, 32, and 33; SEQ ID NOs: 16, 20, 18, 34, 35, and 33; SEQ ID NOs: 23, 24, 18, 31, 32, and 33; SEQ ID NOs: 23, 24, 18, 34, 35, and 33; SEQ ID NOs: 16, 17, 18, 31, 32, and 36; SEQ ID NOs: 19, 20, 18, 31, 32, and 36; SEQ ID NOs: 21, 22, 18, 31, 32, and 36; 16, 20, 18, 31, 32, and 36; and SEQ ID NOs: 23, 24, 18, 31, 32, and 36.

In some embodiments, a humanized antibody or antigen-binding fragment thereof that specifically binds human CD47 is provided, the antibody or antigen-binding fragment comprising a light chain variable region and a heavy chain variable region, wherein the heavy chain variable region comprises HCDR1 selected from SEQ ID NOs: 25, 28, and 29; HCDR2 selected from SEQ ID NOs: 26 and 30; and HCDR3 of SEQ ID NO: 27; and wherein the light chain variable region comprises LCDR1 selected from SEQ ID NOs: 37 and 40; LCDR2 of SEQ ID NO: 38; and LCDR3 selected from SEQ ID NOs: 39 and 41; wherein the heavy chain variable region comprises an amino acid sequence with at least 90%, 91%, 92%, 93%, 94%, 95%, 96%, 97%, 98% or 99% identity to an amino acid sequence selected from SEQ ID NOs: 2, 3, 4, 5, 6, 7 and 8; and wherein the light chain variable region comprises an amino acid sequence with at least 80%, 85%, 90%, 91%, 92%, 93%, 94%, 95%, 96%, 97%, 98% or 99% identity to an amino acid sequence selected from SEQ ID NOs: 10, 11, 12, 13, 14 and 15.

In some embodiments, a humanized antibody or antigen-binding fragment thereof that specifically binds human CD47 is provided, the antibody or antigen-binding fragment comprising a light chain variable region and a heavy chain variable region, wherein the heavy chain variable region comprises HCDR1 selected from SEQ ID NOs: 25, 28, and 29; HCDR2 selected from SEQ ID NOs: 26 and 30; and HCDR3 of SEQ ID NO: 27; and wherein the light chain variable region comprises LCDR1 selected from SEQ ID NOs: 37 and 40; LCDR2 of SEQ ID NO: 38; and LCDR3 selected from SEQ ID NOs: 39 and 41; wherein the heavy chain variable region comprises:
  a) a human IGHV3-23/HJ4 framework set forth in SEQ ID NO: 88, wherein framework positions H44, H49, H82, H89, H91, and H94 are donor residues, according to Kabat numbering; or
  b) a human IGHV3-48/HJ4 framework set forth in SEQ ID NO: 89, wherein framework position H49 is a donor residue, according to Kabat numbering; or
  c) a human IGHV3-66/HJ4 framework set forth in SEQ ID NO: 90, wherein framework position H29, H49, and H82 is a donor residue, according to Kabat numbering; or
  d) a human IGHV3-74/HJ4 framework set forth in SEQ ID NO: 91, wherein framework position H49 is a donor residue, according to Kabat numbering; and
wherein the light chain variable region comprises:
  a) a human IGKV6-21/KJ2 framework set forth in SEQ ID NO: 92, wherein framework positions L4, L21, L69, and L85 are donor residues, according to Kabat numbering; or
  b) a human IGKV1-27/KJ2 framework set forth in SEQ ID NO: 93, wherein framework positions L21, L49, and L69 are donor residues, according to Kabat numbering.

In some embodiments, the heavy chain variable region comprises HCDR1, HCDR2, and HCDR3 selected from: SEQ ID NOs: 25, 26, and 27; SEQ ID NOs: 28, 26, and 27; SEQ ID NOs: 29, 30, and 27; and SEQ ID NOs: 29, 26, and 27. In some embodiments, the light chain variable region comprises LCDR1, LCDR2, and LCDR3 selected from SEQ ID NOs: 37, 38, and 39; SEQ ID NOs: 40, 38, and 39; and SEQ ID NOs: 37, 38, and 41. In some embodiments, the antibody or antigen-binding fragment thereof comprises HCDR1, HCDR2, HCDR3, LCDR1, LCDR2, and LCDR3 selected from SEQ ID NOs: 25, 26, 27, 37, 38, and 39; SEQ ID NOs: 25, 26, 27, 40, 38, and 39; SEQ ID NOs: 25, 26, 27, 37, 38, and 41; SEQ ID NOs: 28, 26, 27, 37, 38, and 39; SEQ ID NOs: 28, 26, 27, 40, 38, and 39; SEQ ID NOs: 28, 26, 27, 37, 38, and 41; SEQ ID NOs: 29, 30, 27, 37, 38, and 39; SEQ ID NOs: 29, 30, 27, 40, 38, and 39; SEQ ID NOs: 29, 30, 27, 37, 38, and 41; SEQ ID NOs: 29, 26, 27, 37, 38, and 39; SEQ ID NOs: 29, 26, 27, 40, 38, and 39; and SEQ ID NOs: 29, 26, 27, 37, 38, and 41.

In some embodiments, the heavy chain variable region comprises an amino acid sequence selected from SEQ ID NOs: 2, 3, 4, 5, 6, 7 and 8. In some embodiments, the light chain variable region comprises an amino acid sequence selected from SEQ ID NOs: 10, 11, 12, 13, 14 and 15. In some embodiments, the heavy chain variable region and light chain variable region comprise SEQ ID NOs: 2 and 10; SEQ ID NOs: 3 and 11; SEQ ID NOs: 3 and 12; SEQ ID NOs: 3 and 13; SEQ ID NOs: 3 and 14; SEQ ID NOs: 4 and 11; SEQ ID NOs: 4 and 12; SEQ ID NOs: 4 and 13; SEQ ID NOs: 4 and 14; SEQ ID NOs: 5 and 11; SEQ ID NOs: 5 and 12; SEQ ID NOs: 5 and 13; SEQ ID NOs: 5 and 14; SEQ ID NOs: 6 and 11; SEQ ID NOs: 6 and 12; SEQ ID NOs: 6 and 13; SEQ ID NOs: 6 and 14; SEQ ID NOs: 7 and 11; SEQ ID NOs: 7 and 12; SEQ ID NOs: 7 and 13; SEQ ID NOs: 7 and 14; SEQ ID NOs: 8 and 11; SEQ ID NOs: 8 and 12; SEQ ID NOs: 8 and 13; SEQ ID NOs: 8 and 14; SEQ ID NOs: 3 and 15.

In some embodiments, a humanized antibody or antigen-binding fragment thereof that specifically binds human CD47 is provided, the antibody or antigen-binding fragment comprising a light chain variable region and a heavy chain variable region, wherein the heavy chain variable region comprises HCDR1 of SEQ ID NO: 16, HCDR2 of SEQ ID NO: 17, and HCDR3 of SEQ ID NO: 18; and wherein the light chain variable region comprises LCDR1 of SEQ ID NO: 31, LCDR2 of SEQ ID NO: 32, and LCDR3 of SEQ ID NO: 33; and wherein the heavy chain variable region comprises an amino acid sequence with at least 90%, 91%, 92%, 93%, 94%, 95%, 96%, 97%, 98% or 99% identity to SEQ ID NO: 3 and the light chain variable region comprises an amino acid sequence with at least 80%, 85%, 90%, 91%, 92%, 93%, 94%, 95%, 96%, 97%, 98% or 99% identity to SEQ ID NO: 13; and wherein the antibody has reduced hemagglutination of red blood cells compared to Ab47. In some embodiments, the heavy chain variable region comprises the amino acid sequence of SEQ ID NO: 3 and the light chain variable region comprises the amino acid sequence of SEQ ID NO: 13.

In some embodiments of the humanized antibody or antigen-binding fragment thereof provided herein, the heavy chain variable region comprises:

a) a human IGHV3-23/HJ4 framework set forth in SEQ ID NO: 88, wherein framework positions H44, H49, H82, H89, H91, and H94 are donor residues, according to Kabat numbering; or b) a human IGHV3-48/HJ4 framework set forth in SEQ ID NO: 89, wherein framework position H49 is a donor residue, according to Kabat numbering; or c) a human IGHV3-66/HJ4 framework set forth in SEQ ID NO: 90, wherein framework position H29, H49, and H82 is a donor residue, according to Kabat numbering; or d) a human IGHV3-74/HJ4 framework set forth in SEQ ID NO: 91, wherein framework position H49 is a donor residue, according to Kabat numbering.

In some such embodiments, H29 is F, H44 is R or G, H49 is A, H82 is M or I, H89 is I or V, H91 is F or Y, and H94 is R, according to Kabat numbering.

In some embodiments of the humanized antibody or antigen-binding fragment thereof provided herein, the light chain variable region comprises:

a) a human IGKV6-21/KJ2 framework set forth in SEQ ID NO: 92, wherein framework positions L4, L21, L69, and L85 are donor residues, according to Kabat numbering; or b) a human IGKV1-27/KJ2 framework set forth in SEQ ID NO: 93, wherein framework positions L21, L49, and L69 are donor residues, according to Kabat numbering.

In some such embodiments, L4 is M, L21 is L, L49 is K, L69 is T or S, and L85 is V or T, according to Kabat numbering.

In some embodiments, the antibody or antigen-binding fragment thereof is of an IgG1 isotype. In some embodiments, the antibody or antigen-binding fragment thereof has enhanced antibody dependent cellular cytotoxicity (ADCC) compared to its parental antibody. In some embodiments, the antibody or antigen-binding fragment thereof has enhanced antibody dependent cellular phagocytosis (ADCP) compared to its parental antibody. In some embodiments, the antibody or antigen-binding fragment thereof has enhanced complement-dependent cytotoxicity (CDC) compared to its parental antibody. In some embodiments, the antibody or antigen-binding fragment thereof is a Fab, a Fab', a F(ab')$_2$, a Fv fragment, a diabody, a single-chain antibody, an scFv fragment or an scFv-Fc. In some embodiments, the antibody or antigen-binding fragment thereof induces apoptosis of CD47-expressing cells in vitro and/or in vivo. In some embodiments, the antibody or antigen-binding fragment thereof has reduced core fucosylation compared to its parental antibody. In some embodiments, the antibody or antigen-binding fragment thereof is afucosylated. In some embodiments, the antibody or antigen-binding fragment thereof blocks an interaction between CD47 and SIRPα. In some embodiments, the antibody or antigen-binding fragment thereof has reduced hemagglutination of red blood cells compared to Ab47.

In some embodiments, a nucleic acid sequence is provided that encodes an antibody or antigen-binding fragment provided herein. In some embodiments, an expression vector is provided that comprises the nucleic acid sequence. In some embodiments, a host cell is provided that comprises the nucleic acid or the expression vector. In some embodiments, a host cell is provided that expresses an antibody or antigen-binding fragment provided herein. In some embodiments, a method of producing the antibody or antigen-binding fragment provided herein comprises culturing the host cell. In some embodiments, the method further comprises isolating the antibody or antigen-binding fragment thereof.

In some embodiments, methods of treating a CD47-expressing cancer in a subject are provided, comprising administering to the subject a therapeutically effective amount of an anti-CD47 antibody or antigen-binding fragment thereof provided herein.

In some embodiments, methods of treating a CD47-expressing cancer in a subject are provided, comprising:

a) identifying a subject as having a CD47-expressing cancer; and b) administering to the subject a therapeutically effective amount of an anti-CD47 antibody or antigen-binding fragment thereof provided herein.

In some such embodiments, step a) comprises:
 i) isolating cancer tissue; and
 ii) detecting CD47 in the isolated cancer tissue.

In some embodiments, methods for treating a CD47-expressing cancer in a subject are provided, comprising:

a) identifying a subject as having elevated levels of macrophage infiltration in cancer tissue relative to non-cancer tissue; and b) administering to the subject a therapeutically effective amount of an anti-CD47 antibody or antigen-binding fragment thereof provided herein.

In some such embodiments, step a) comprises:
 i) isolating cancer tissue and surrounding non-cancer tissue from the subject;
 ii) detecting macrophages in the isolated cancer tissue and in non-cancer tissue; and
 iii) comparing the amount of staining in the cancer tissue relative to the non-cancer tissue.

In some embodiments, the macrophage staining is performed with an anti-CD163 antibody.

In some embodiments, methods of treating cancer comprise identifying a subject as having a CD47-expressing cancer and elevated levels of macrophage infiltration in cancer tissue relative to non-cancer tissue.

In some embodiments, a method of inducing apoptosis of a CD47-expressing cell is provided, comprising contacting the cell with an antibody or antigen-binding fragment thereof provided herein. In some embodiments, the cell in in vitro. In some embodiments, the cell is in vivo.

In some embodiments, a masked antibody is provided, comprising an antibody or antigen-binding fragment thereof that specifically binds to the human CD47 protein and at least one masking domain, wherein at least one masking domain comprises an amino acid sequence selected from SEQ ID NOs: 44-55, 75-86, 94, and 95. In some embodiments, a masked antibody is provided that comprises an antibody or antigen-binding fragment thereof provided herein and at least one masking domain. In some embodiments, at least one masking domain comprises an amino acid sequence selected from SEQ ID NOs: 44-55, 75-86, 94, and 95.

In some embodiments, the at least one masking domain reduces binding affinity of the antibody or antigen-binding fragment to human CD47 protein compared to the antibody or antigen-binding fragment thereof without the at least one masking domain. In some embodiments, the binding affinity is reduced at least about 100-fold compared to the antibody or antigen-binding fragment thereof without the at least one masking domain. In some embodiments, the binding affinity is reduced between about 200-fold and about 1500-fold compared to the antibody or antigen-binding fragment thereof without the at least one masking domain.

In some embodiments, the antibody or antigen binding fragment thereof comprises a heavy chain and a light chain, wherein the heavy chain is linked to a first masking domain; or wherein the light chain is linked to a second masking domain; or wherein the heavy chain is linked to a first masking domain and the light chain is linked to a second masking domain. In some embodiments, the first masking domain comprises an amino acid sequence selected from SEQ ID NOs: 44, 46, 48, 50, 52, 54, 75, 77, 79, 81, 83, 85, and 94; and the second masking domain comprises an amino acid sequence selected from SEQ ID NOs: 45, 47, 49, 51, 53, 55, 76, 78, 80, 82, 84, 86, and 95. In some embodiments, the first masking domain and the second masking domain are a pair of masking domains selected from: SEQ ID NOs: 44 and 45; SEQ ID NOs: 46 and 47; SEQ ID NOs: 48 and 49; SEQ ID NOs:50 and 51; SEQ ID NOs:52 and 53; SEQ ID NOs:54 and 55; SEQ ID NOs: 75 and 76; SEQ ID NOs:77 and 78; SEQ ID NOs:79 and 80; SEQ ID NOs:81 and 82; SEQ ID NOs: 83 and 84; SEQ ID NOs: 85 and 86; and SEQ ID NOs: 94 and 95. In some embodiments, the first masking domain is linked to the N-terminus of the heavy chain and the second masking domain is linked to the N-terminus of the light chain.

In some embodiments, each masking domain comprises a protease-cleavable linker and is linked to the heavy chain or light chain via the protease-cleavable linker. In some embodiments, the protease-cleavable linker comprises a matrix metalloprotease (MMP) cleavage site. In some embodiments, the MMP cleavage site is selected from an MMP2 cleavage site, an MMP7 cleavage site, an MMP9 cleavage site and an MMP13 cleavage site. In some embodiments, following cleavage by an MMP, the heavy chain and/or light chain of the antibody or antigen-binding fragment thereof comprises a stub amino acid remnant of the MMP cleavage site. In some embodiments, the stub amino acid remnant comprises the sequence LRSG, SG, or VR at the N terminus of the antibody.

In some embodiments, the antibody or antigen-binding fragment thereof is an antibody or antigen-binding fragment thereof provided herein. In some embodiments, the masked antibody comprises a heavy chain linked to a first masking domain and having the amino acid sequence of SEQ ID NO: 42 and a light chain linked to a second masking domain and having the amino acid sequence of SEQ ID NO: 43.

In some embodiments, a nucleic acid sequence is provided that encodes a masked antibody provided herein. In some embodiments, an expression vector is provided that comprises the nucleic acid. In some embodiments, a host cell is provided that expresses masked antibody provided herein. In some embodiments, a method of producing the masked antibody provided herein comprises culturing the host cell. In some embodiments, the method further comprises isolating the masked antibody.

In some embodiments, methods of treating a CD47-expressing cancer in a subject are provided, comprising administering to the subject a therapeutically effective amount of a masked antibody provided herein.

In some embodiments, methods for treating a CD47-expressing cancer in a subject are provided, comprising:
 a) identifying a subject as having elevated levels of MMP in the cancer relative to surrounding non-cancer tissue; and
 b) administering to the subject a therapeutically effective amount of a masked antibody provided herein, wherein each masking domain of the masked antibody comprises a protease-cleavable linker and wherein the protease-cleavable linker comprises a matrix metalloprotease (MMP) cleavage site. In some embodiments, the MMP cleavage site is selected from an MMP2 cleavage site, an MMP7 cleavage site, an MMP9 cleavage site and an MMP13 cleavage site. In some embodiments, the MMP is selected from MMP2, MMP7, MMP9, and MMP13. In some embodiments, step a) comprises:
 i) isolating cancer tissue and non-cancer tissue from the subject;
 ii) detecting MMPs in the isolated cancer tissue and the non-cancer tissue; and
 iii) comparing the amount of staining in the cancer tissue relative to the non-cancer tissue.

In some embodiments, methods for treating a CD47-expressing cancer in a subject are provided, comprising:
 a) identifying a subject as having a CD47-expressing cancer; and
 b) administering to the subject a therapeutically effective amount of a masked antibody provided herein.

In some embodiments, step a) comprises:
 i) isolating cancer tissue; and
 ii) detecting CD47 in the isolated cancer tissue.

In some embodiments, methods for treating a CD47-expressing cancer in a subject are provided, comprising:
 a) identifying a subject as having elevated levels of macrophage infiltration in cancer tissue relative to non-cancer tissue; and
 b) administering to the subject a therapeutically effective amount of a masked antibody provided herein.

In some embodiments, step a) comprises:
 i) isolating cancer tissue and surrounding non-cancer tissue from the subject;
 ii) detecting macrophages in the isolated cancer tissue and in non-cancer tissue; and
 iii) comparing the amount of staining in the cancer tissue relative to the non-cancer tissue.

In some embodiments, the macrophage staining is performed with an anti-CD163 antibody.

In some embodiments, methods for treating a CD47-expressing cancer in a subject are provided, comprising identifying a subject as having (a) elevated levels of MMP in the cancer relative to surrounding non-cancer tissue, and (b) a CD47-expressing cancer. In some embodiments, methods for treating a CD47-expressing cancer in a subject are provided, comprising identifying a subject as having (a) elevated levels of MMP in the cancer relative to surrounding non-cancer tissue, and (b) elevated levels of macrophage infiltration in cancer tissue relative to non-cancer tissue. In some embodiments, methods for treating a CD47-expressing cancer in a subject are provided, comprising identifying a subject as having (a) a CD47-expressing cancer, and (b) elevated levels of macrophage infiltration in cancer tissue relative to non-cancer tissue. In some embodiments, methods for treating a CD47-expressing cancer in a subject are provided, comprising identifying a subject as having (a) elevated levels of MMP in the cancer relative to surrounding non-cancer tissue, (b) a CD47-expressing cancer, and (c) elevated levels of macrophage infiltration in cancer tissue relative to non-cancer tissue.

In some embodiments, the masked antibody comprises at least one masking domain comprising a protease-cleavable linker, and wherein the protease-cleavable linker is cleaved in the tumor microenvironment. In some embodiments, following cleavage of the protease-cleavable linker in the tumor microenvironment, the masking domain is released from the anti-CD47 antibody or antigen-binding fragment thereof. In some embodiments, the protease-cleavable linker comprises the amino acid sequence IPVSLRSG (SEQ ID NO: 73) or GPLGVR (SEQ ID NO: 57). In some embodiments, the protease-cleavable linker comprises a MMP cleavage site. In some embodiments, the MMP cleavage site is selected from an MMP2 cleavage site, an MMP7 cleavage site, an MMP9 cleavage site and an MMP13 cleavage site. In some embodiments, following release of the anti-CD47 antibody or antigen-binding fragment thereof, the anti-CD47 antibody or antigen-binding fragment thereof has a stub amino acid remnant of the protease-cleavable linker. In some embodiments, the stub amino acid remnant comprises the sequence of LRSG, SG, or VR at the N terminus of the antibody.

In various embodiments, the CD47-expressing cancer is a hematological cancer or a solid cancer. In some embodiments, the CD47-expressing cancer is selected from non-Hodgkin lymphoma, B-lymphoblastic lymphoma; B-cell chronic lymphocytic leukemia/small lymphocytic lymphoma, Richter's syndrome, follicular lymphoma, multiple myeloma, myelofibrosis, polycythemia vera, cutaneous T-cell lymphoma, monoclonal gammopathy of unknown significance (MGUS), myelodysplastic syndrome (MDS), immunoblastic large cell lymphoma, precursor B-lymphoblastic lymphoma, acute myeloid leukemia (AML), and anaplastic large cell lymphoma. In some embodiments, the CD47-expressing cancer is selected from lung cancer, pancreatic cancer, breast cancer, liver cancer, ovarian cancer, testicular cancer, kidney cancer, bladder cancer, spinal cancer, brain cancer, cervical cancer, endometrial cancer, colorectal cancer, anal cancer, endometrial cancer, esophageal cancer, gallbladder cancer, gastrointestinal cancer, gastric cancer, carcinoma, head and neck cancer, skin cancer, melanoma, prostate cancer, pituitary cancer, stomach cancer, uterine cancer, vaginal cancer and thyroid cancer. In some embodiments, the CD47-expressing cancer is selected from lung cancer, sarcoma, colorectal cancer, head and neck cancer, ovarian cancer, pancreatic cancer, gastric cancer, melanoma, and breast cancer.

In some embodiments, the anti-CD47 antibody or antigen-binding fragment thereof, or the masked antibody, is administered in combination with an inhibitor of an immune checkpoint molecule chosen from one or more of programmed cell death protein 1 (PD-1), programmed death-ligand 1 (PD-L1), PD-L2, cytotoxic T lymphocyte-associated protein 4 (CTLA-4), T cell immunoglobulin and mucin domain containing 3 (TIM-3), lymphocyte activation gene 3 (LAG-3), carcinoembryonic antigen related cell adhesion molecule 1 (CEACAM-1), CEACAM-5, V-domain Ig suppressor of T cell activation (VISTA), B and T lymphocyte attenuator (BTLA), T cell immunoreceptor with Ig and ITIM domains (TIGIT), leukocyte-associated immunoglobulin-like receptor 1 (LAIR1), CD160, 2B4 or TGFR. In some embodiments, the anti-CD47 antibody or antigen-binding fragment thereof, or the masked antibody, is administered in combination with an agonistic anti-CD40 antibody. In some embodiments, the agonistic anti-CD40 antibody has low fucosylation levels or is afucosylated. In some embodiments, the anti-CD47 antibody or antigen-binding fragment thereof, or the masked antibody, is administered in combination with an antibody drug conjugate (ADC), wherein the antibody of the ADC specifically binds to a protein that is expressed on the extracellular surface of a cancer cell and the antibody is conjugated to a drug-linker comprising a cytotoxic agent. In some embodiments, the cytotoxic agent is an auristatin. In some embodiments, the antibody of the ADC is conjugated to a drug-linker selected from vcMMAE and mcMMAF.

In some embodiments, the anti-CD47 antibody or antigen-binding fragment thereof or the anti-CD47 antibody or antigen-binding fragment thereof of the masked antibody exhibits reduced hemagglutination in vitro compared to its parental anti-CD47 antibody. In some embodiments, the parental antibody is Ab47. In some embodiments, administration of the anti-CD47 antibody or masked antibody does not induce hemagglutination in the subject. In some embodiments, the anti-CD47 antibody or masked antibody induces apoptosis of CD47-expressing cells in vitro and/or in vivo. In some embodiments, the anti-CD47 antibody or masked antibody induces apoptosis of CD47-expressing cells in vivo. In some embodiments, the CD47-expressing cells are cancer cells.

In one aspect, a humanized antibody or antigen-binding fragment thereof that specifically binds human CD47, the antibody or antigen-binding fragment comprising a light chain variable region and a heavy chain variable region, the heavy chain variable comprising CDRs set forth as SEQ ID NOs: 16 (GYGMS), 17 (TITSGGTYTYYPDSVKG), and 18 (SLAGNAMDY), and a human IGHV3-23/HJ4 framework set forth in SEQ ID NO: 88 [FIG. 1A], wherein framework positions H44, H49, H82, H89, H91, and H94 are donor residues, according to Kabat numbering, is provided.

In another aspect, a humanized antibody or antigen-binding fragment thereof that specifically binds human CD47, the antibody or antigen-binding fragment comprising a light chain variable region and a heavy chain variable region, the heavy chain variable comprising CDRs set forth as SEQ ID NOs: 16 (GYGMS), 17 (TITSGGTYTYYPDSVKG), and 18 (SLAGNAMDY), and a human IGHV3-48/HJ4 framework set forth in SEQ ID NO: 89 [FIG. 1B], wherein framework position H49 is a donor residue, according to Kabat numbering, is provided.

In yet another aspect, a humanized antibody or antigen-binding fragment thereof that specifically binds human CD47, the antibody or antigen-binding fragment comprising a light chain variable region and a heavy chain variable region, the heavy chain variable comprising CDRs set forth as SEQ ID NOs: 16 (GYGMS), 17 (TITSGGTYTYYPDSVKG), and 18 (SLAGNAMDY), and a human IGHV3-66/HJ4 framework set forth in SEQ ID NO: 90 [FIG. 1C], wherein framework position H29, H49, and H82 is a donor residue, according to Kabat numbering, is provided.

In still another aspect, a humanized antibody or antigen-binding fragment thereof that specifically binds human CD47, the antibody or antigen-binding fragment comprising a light chain variable region and a heavy chain variable region, the heavy chain variable comprising CDRs set forth as SEQ ID NOs: 16 (GYGMS), 17 (TITSGGTYTYYPDSVKG), and 18 (SLAGNAMDY), and a human IGHV3-74/HJ4 framework set forth in SEQ ID NO: 91 [FIG. 1D], wherein framework position H49 is a donor residue, according to Kabat numbering, is provided.

In still another aspect, a humanized antibody or antigen-binding fragment thereof that specifically binds human CD47, the antibody or antigen-binding fragment comprising a light chain variable region and a heavy chain variable region, the heavy chain variable comprising CDRs set forth as SEQ ID NOs: 31 (RASQTISDYLH), 32 (FASQSIS), and 33 (QNGHGFPRT); and a human IGKV6-21/KJ2 framework set forth in SEQ ID NO: 92 [FIG. 1G], wherein framework positions L4, L21, L69, and L85 are donor residues, according to Kabat numbering, is provided.

In still another aspect, a humanized antibody or antigen-binding fragment thereof that specifically binds human CD47, the antibody or antigen-binding fragment comprising a light chain variable region and a heavy chain variable region, the heavy chain variable comprising CDRs set forth as SEQ ID NOs: 31 (RASQTISDYLH), 32 (FASQSIS), and 33 (QNGHGFPRT); and a human IGKV1-27/KJ2 framework set forth in SEQ ID NO: 93 [FIG. 1H], wherein framework positions L21, L49, and L69 are donor residues, according to Kabat numbering, is provided.

In an embodiment, the framework position L4 is occupied by M, L21 is occupied by L, L49 is occupied by K, L69 is occupied by T or S, and L85 is occupied by V or T, according to Kabat numbering.

In an embodiment, the antibody or antigen-binding fragment comprises a heavy chain variable region (HCVR) having at least 90% sequence identity to any one of SEQ ID NOs: 2, 3, 4, 5, 6, 7 and 8, and a light chain variable region (LCVR) having at least 90% sequence identity to any one of SEQ ID NOs: 10, 11, 12, 13, 14 and 15.

In an embodiment, the antibody or antigen-binding fragment further comprises a G91A mutation in LCDR3, according to Kabat numbering.

In an embodiment, the antibody or antigen-binding fragment is of an IgG1 isotype.

In an embodiment, the antibody or antigen-binding fragment has enhanced antibody dependent cellular cytotoxicity (ADCC) compared to its parental antibody.

In an embodiment, the antibody or antigen-binding fragment has enhanced antibody dependent cellular phagocytosis (ADCP) compared to its parental antibody.

In an embodiment, the antibody or antigen-binding fragment has reduced core fucosylation compared to its parental antibody.

In an embodiment, the antibody or antigen-binding fragment blocks an interaction between CD47 and SIRPα.

In an embodiment, the antibody or antigen-binding fragment has reduced hemagglutination of red blood cells compared to its parental antibody.

In one aspect, a nucleic acid sequence encoding a humanized antibody or antigen-binding fragment thereof that specifically binds human CD47, is provided.

In an embodiment, the antigen-binding fragment comprises a Fab, a Fab', a F(ab')$_2$, a Fv fragment, a diabody, a single-chain antibody, an scFv fragment or an scFv-Fc.

In one aspect, a method for treating a CD47-expressing cancer in a subject, comprising administering to the subject a therapeutically effective amount of an anti-CD47 antibody or antigen-binding fragment thereof comprising a masking agent (also referred to as a "masking domain"), wherein the masking agent comprises one or more coiled coil peptides that reduce binding affinity of the antibody or antigen-binding fragment to human CD47 compared to the antibody or antigen-binding fragment thereof without the masking agent, is provided.

In an embodiment, a protease-cleavable linker attaches the masking agent to the antibody or antigen-binding fragment thereof.

In an embodiment, the protease-cleavable linker has an amino acid sequence comprising IPVSLRSG (SEQ ID NO: 73) or GPLGVR (SEQ ID NO: 57).

In an embodiment, the protease-cleavable linker comprises a matrix metalloprotease (MMP) cleavage site.

In an embodiment, the MMP cleavage site is selected from an MMP2 cleavage site, an MMP7 cleavage site, an MMP9 cleavage site and an MMP13 cleavage site.

In an embodiment, the masking agent is released from the anti-CD47 antibody or antigen-binding fragment thereof subsequent to cleavage of an MMP cleavage site in a tumor microenvironment by an MMP.

In an embodiment, the cleaved anti-CD47 antibody has a stub amino acid remnant of the MMP cleavage site.

In an embodiment, the stub amino acid remnant comprises the sequence of LRSG, SG, or VR at the N terminus of the antibody.

In an embodiment, one or more the coiled coil peptides comprise one or more sequences selected from SEQ ID NOs: 44, 45, 46, 47, 48, 49, 50, 51, 52, 53, 54, and 55. In an embodiment, one or more the coiled coil peptides comprise one or more sequences selected from SEQ ID NOs: 75, 76, 77, 78, 79, 80, 81, 82, 83, 84, 85, and 86. In an embodiment, one or more the coiled coil peptides comprise one or more sequences selected from SEQ ID NOs: 94 and 95.

In an embodiment, the antibody or antigen-binding fragment binding to CD47 is reduced at least about 100-fold compared to the antibody or antigen-binding fragment thereof without the masking agent.

In an embodiment, the antibody or antigen-binding fragment binding to CD47 is reduced between about 200-fold and about 1500-fold compared to the antibody or antigen-binding fragment thereof without the masking agent.

In an embodiment, the CD47-expressing cancer is a hematological cancer that causes a solid cancer.

In an embodiment, the hematological cancer is selected from non-Hodgkin lymphoma, B-lymphoblastic lymphoma; B-cell chronic lymphocytic leukemia/small lymphocytic lymphoma, Richter's syndrome, follicular lymphoma, multiple myeloma, myelofibrosis, polycythemia vera, cutaneous T-cell lymphoma, monoclonal gammopathy of unknown significance (MGUS), myelodysplastic syndrome (MDS), immunoblastic large cell lymphoma, precursor B-lymphoblastic lymphoma, acute myeloid leukemia (AML), and anaplastic large cell lymphoma.

In an embodiment, the CD47-expressing cancer is a solid tumor.

In an embodiment, the solid tumor is selected from lung cancer, pancreatic cancer, breast cancer, liver cancer, ovarian cancer, testicular cancer, kidney cancer, bladder cancer, spinal cancer, brain cancer, cervical cancer, endometrial cancer, colorectal cancer, anal cancer, endometrial cancer, esophageal cancer, gallbladder cancer, gastrointestinal cancer, gastric cancer, sarcoma, head and neck cancer, melanoma, skin cancer, prostate cancer, pituitary cancer, stomach cancer, uterine cancer, vaginal cancer and thyroid cancer.

In an embodiment, the solid tumor is selected from lung cancer, sarcoma, ovarian cancer, pancreatic cancer, gastric cancer, melanoma, colorectal cancer, head and neck cancer, and breast cancer.

In an embodiment, the subject is a human suffering from a solid cancer.

In an embodiment, the anti-CD47 antibody is administered in combination with an inhibitor of an immune checkpoint molecule chosen from one or more of programmed cell death protein 1 (PD-1), programmed death-ligand 1 (PD-L1), PD-L2, cytotoxic T lymphocyte-associated protein 4 (CTLA-4), T cell immunoglobulin and mucin domain containing 3 (TIM-3), lymphocyte activation gene 3 (LAG-3), carcinoembryonic antigen related cell adhesion molecule 1 (CEACAM-1), CEACAM-5, V-domain Ig suppressor of T cell activation (VISTA), B and T lymphocyte attenuator (BTLA), T cell immunoreceptor with Ig and ITIM domains (TIGIT), leukocyte-associated immunoglobulin-like receptor 1 (LAIR1), CD160, 2B4 or TGFR.

In one aspect, an antibody or antigen-binding fragment thereof that specifically binds to the human CD47 protein comprising a masking agent, wherein the masking agent comprises one or more coiled coil peptides comprising the sequence of SEQ ID NO: 95 (QGASTTVAQLEEKVKTLRAENYELKSEVQRLEEQVAQLGS) and/or SEQ ID NO: 94 (QGASTSVDELQAEVDQLEDENYALKTKVAQLRKKVEKLGS), and wherein the one or more coiled coil peptides reduce binding affinity of the antibody or antigen-binding fragment to human CD47 protein compared to the antibody or antigen-binding fragment thereof without the masking agent, is provided.

In an embodiment, the antibody or antigen-binding fragment comprises a heavy chain variable region (HCVR) having at least 90% sequence identity to any one of SEQ ID NOs: 2, 3, 4, 5, 6, 7 and 8, and a light chain variable region (LCVR) having at least 90% sequence identity to any one of SEQ ID NOs: 10, 11, 12, 13, 14 and 15.

In an embodiment, the masking agent is attached to the antibody or antigen-binding fragment thereof via a protease-cleavable linker.

In an embodiment, the protease-cleavable linker has an amino acid sequence comprising IPVSLRSG (SEQ ID NO: 73) or GPLGVR (SEQ ID NO: 57).

In an embodiment, the protease-cleavable linker comprises a matrix metalloprotease (MMP) cleavage site.

In an embodiment, the MMP cleavage site is selected from an MMP2 cleavage site, an MMP7 cleavage site, an MMP9 cleavage site and an MMP13 cleavage site.

In an embodiment, the masking agent is removed from the anti-CD47 antibody after cleavage of an MMP cleavage site by an MMP.

In an embodiment, the anti-CD47 antibody has a stub amino acid remnant of the MMP cleavage site after cleavage of an MMP cleavage site by an MMP.

In an embodiment, the stub amino acid remnant comprises the sequence of LRSG, SG, or VR at the N terminus of the antibody.

In an embodiment, the binding is reduced at least about 100-fold compared to the antibody or antigen-binding fragment thereof without the masking agent.

In an embodiment, the binding is reduced between about 200-fold and about 1500-fold compared to the antibody or antigen-binding fragment compared without the masking agent.

In an embodiment, the antibody or antigen-binding fragment comprises a heavy chain sequence of SEQ ID NO: 42 and a light chain sequence of SEQ ID NO: 43.

In an embodiment, the antibody or antigen-binding fragment comprises a variant Fc region which confers enhanced effector function selected from ADCC and/or CDC activity.

In an embodiment, the antibody or antigen-binding fragment is afucosylated.

In one aspect, a humanized antibody or antigen-binding fragment thereof that specifically binds human CD47, wherein the antibody is an IgG1 isotype, is provided.

In an embodiment, the antibody comprises enhanced ADCC, enhanced ADCP, and/or enhanced CDC activity.

In one aspect, a method for treating a CD47-expressing cancer in a subject, comprising the steps of:
  a) identifying the subject as having elevated levels of MMP in the cancer relative to surrounding non-cancer tissue; and
  b) administering to the subject a therapeutically effective amount of an anti-CD47 antibody or antigen-binding fragment thereof comprising a masking agent, wherein the masking agent comprises coiled coil peptides that reduce binding affinity of the antibody or antigen-binding fragment to human CD47 compared to the antibody or antigen-binding fragment thereof without the masking agent, if the subject has elevated levels of MMP in the cancer relative to surrounding non-cancer tissue, is provided.

In an embodiment, the MMP is selected from the group consisting of: MMP2, MMP7, MMP9, and MMP13.

In an embodiment, step a) comprises:
  i) isolating cancer tissue and non-cancer tissue from the subject;
  ii) detecting MMPs in the isolated cancer tissue and the non-cancer tissue; and
  iii) comparing the amount of staining in the cancer tissue relative to the non-cancer tissue.

In one aspect, a method for treating a CD47-expressing cancer in a subject, comprising the steps of:
  a) identifying the subject as having elevated levels of CD47 in the cancer relative to surrounding non-cancer tissue; and
  b) administering to the subject a therapeutically effective amount of an anti-CD47 antibody or antigen-binding fragment thereof comprising a masking agent, wherein the masking agent comprises coiled coil peptides that reduce binding affinity of the antibody or antigen-binding fragment to human CD47 compared to the antibody or antigen-binding fragment thereof without the masking agent, if the subject has elevated levels of CD47 in the cancer relative to surrounding non-cancer tissue, is provided.

In an embodiment, step a) comprises:
  i) isolating cancer tissue and surrounding non-cancer tissue from the subject;
  ii) detecting CD47 in the isolated cancer tissue and surrounding non-cancer tissue; and
  iii) comparing the amount of CD47 staining in the cancer tissue relative to CD47 staining the non-cancer tissue.

In one aspect, a method for treating a CD47-expressing cancer in a subject, comprising the steps of:
  a) identifying the subject as having elevated levels of macrophage infiltration in cancer tissue relative to non-cancer tissue; and
  b) administering to the subject a therapeutically effective amount of an anti-CD47 antibody or antigen-binding fragment thereof comprising a masking agent, wherein the masking agent comprises one or more coiled coil peptides that reduce binding affinity of the antibody or antigen-binding fragment to human CD47 compared to the antibody or antigen-binding fragment thereof without the masking agent, if the subject has elevated levels of macrophage infiltration in the cancer relative to the non-cancer tissue, is provided.

In an embodiment, step a) comprises:
  i) isolating cancer tissue and surrounding non-cancer tissue from the subject;
  ii) detecting macrophages in the isolated cancer tissue and in non-cancer tissue; and
  iii) comparing the amount of staining in the cancer tissue relative to the non-cancer tissue.

In an embodiment, the macrophage staining is performed with an anti-CD163 antibody.

In one aspect, a humanized antibody or antigen-binding fragment thereof that specifically binds human CD47, comprising a heavy chain variable region (HCVR) having at least 90% sequence identity to any one of SEQ ID NOs: 2, 3, 4, 5, 6, 7 and 8, and a light chain variable region (LCVR) having at least 90% sequence identity to any one of SEQ ID NOs: 10, 11, 12, 13, 14 and 15, wherein the antibody further comprises the sequence LRSG, SG, or VR at the N terminus of the HCVR and/or the LCVR, is provided.

In one aspect, a method of treating cancer by administering a combination of the masked CD47 antibody of the invention with an agonistic CD40 antibody.

In an embodiment, the agonistic CD40 antibody has low fucosylation levels, e.g., SEA-CD40 antibody.

In one aspect, a method of treating cancer by administering a combination of the masked CD47 antibody of claim 37 with an antibody drug conjugate (ADC), wherein the antibody of the ADC specifically binds to a protein that is expressed on the extracellular surface of a cancer cell and the antibody is conjugated to a drug-linker comprising a cytotoxic agent, is provided.

In an embodiment, the cytotoxic agent is an auristatin.

In an embodiment, the antibody of the ADC is conjugated to a drug linker selected from vcMMAE and mcMMAF.

The summary of the disclosure described above is non-limiting, and other features and advantages of the disclosed antibodies and methods of making and using them will be apparent from the following drawings, the detailed description, the examples and the claims.

BRIEF DESCRIPTION OF THE DRAWINGS

FIG. 1A-FIG. 1J depict antibody sequence alignments. FIG. 1A shows a sequence alignment of hB6H12 heavy chain variants with human VH donor sequence, HV3-23/HJ4. FIG. 1B shows a sequence alignment of hB6H12 heavy chain variants with human VH donor sequence, HV3-48/HJ4. FIG. 1C show a sequence alignment of hB6H12 heavy chain variants with human VH donor sequence, HV3-66/HJ4. FIG. 1D shows a sequence alignment of hB6H12 heavy chain variants with human VH donor sequence, HV3-74/HJ4. FIG. 1E shows a sequence alignment of hB6H12 heavy chain variants. FIG. 1F shows a sequence alignment of hB6H12.3 heavy chain (hvH1) compared to mB6H12 and Ab47. FIG. 1G shows a sequence alignment of hB6H12 light chain variants with human VH Donor Sequence, KV1-3/KJ2. FIG. 1H shows a sequence alignment of hB6H12 light chain variants with human VH donor sequence, KV1-27/KJ2. FIG. 1I shows a sequence alignment of hB6H12 light chain variants. FIG. 1J shows a sequence alignment of hB6H12.3 light chain (hvK3) compared to mB6H12 and Ab47.

FIG. 2A shows CD47 saturating cellular FACS with exemplary anti-CD47 antibodies. FIG. 2B shows CD47 saturating ELISA with exemplary anti-CD47 antibodies. FIG. 2C shows CD47 binding kinetics with exemplary anti-CD47 antibodies.

FIG. 3A and FIG. 3B shows antibody-mediated phagocytosis of CD47+ human red blood cells (RBCs) with exemplary anti-CD47 antibodies.

FIG. 4A shows an image capture of the formation of dispersed non-sedimenting RBCs. FIG. 4B shows percent hemagglutination of RBCs with anti-CD47 antibodies Ab47 and hB6H12.3.

FIG. 12 depicts saturation binding of anti-CD47 antibodies to human red blood cells. Vel-IPV-masked hB6H12 antibodies were tested along with re-activated comparators (stub IPV-hB6H12.3 or MMP2-cleaved Vel-IPV-hB6H12.3). Cleaved Vel-IPV- and stub-IPV antibodies possessed a remnant LRSG sequence at the antibody N-termini. The cleaved antibody was generated through cleavage with MMP2 whereas stub-IPV antibody was generated recombinantly.

FIG. 34 depicts the M11, M15, and Vel coiled coil sequences. Also shown are the MMP2 cleavage sequences.

FIG. 37A-FIG. 37F depict concentrations of mIAP301 and masked Vel-IPV-mIAP301 and Vel-M2-mIAP301 in plasma (FIG. 37A and FIG. 37B), spleen (FIG. 37C and FIG. 37D), and tumor (FIG. 37E and FIG. 37F).

FIG. 39A-FIG. 39C Tolerability of masked Ab47 (FIG. 39A) or masked hB6H12.3 (FIG. 39B) was determined by measuring the circulating plasma cytokine monocyte chemoattractant protein-1 (MCP-1). Pharmacokinetic analysis using a Generic TAb ELISA was performed on masked and non-masked hB6H12.3 (FIG. 39C).

FIG. 45A-FIG. 45C depict measurement of binding of Vel-IPV-hB6H12.3-FITC and hB6H12.3-FITC to whole blood sample representative of 16 out of 17 patient samples (FIG. 45A) or of one outlier sample (FIG. 45B); and $EC_{50}$ values obtained using an ELISA following incubation of plasma with recombinant CD47 and hB6H12.3 ("Donor 1-hB6H12.3 spiked") or Vel-IPV-hB6H12.3 (Sarcoma Pt1-10) (FIG. 45C).

FIG. 46A shows production of IP-10 and FIG. 46B shows production of IL-1RA.

DETAILED DESCRIPTION

Figure 2A:
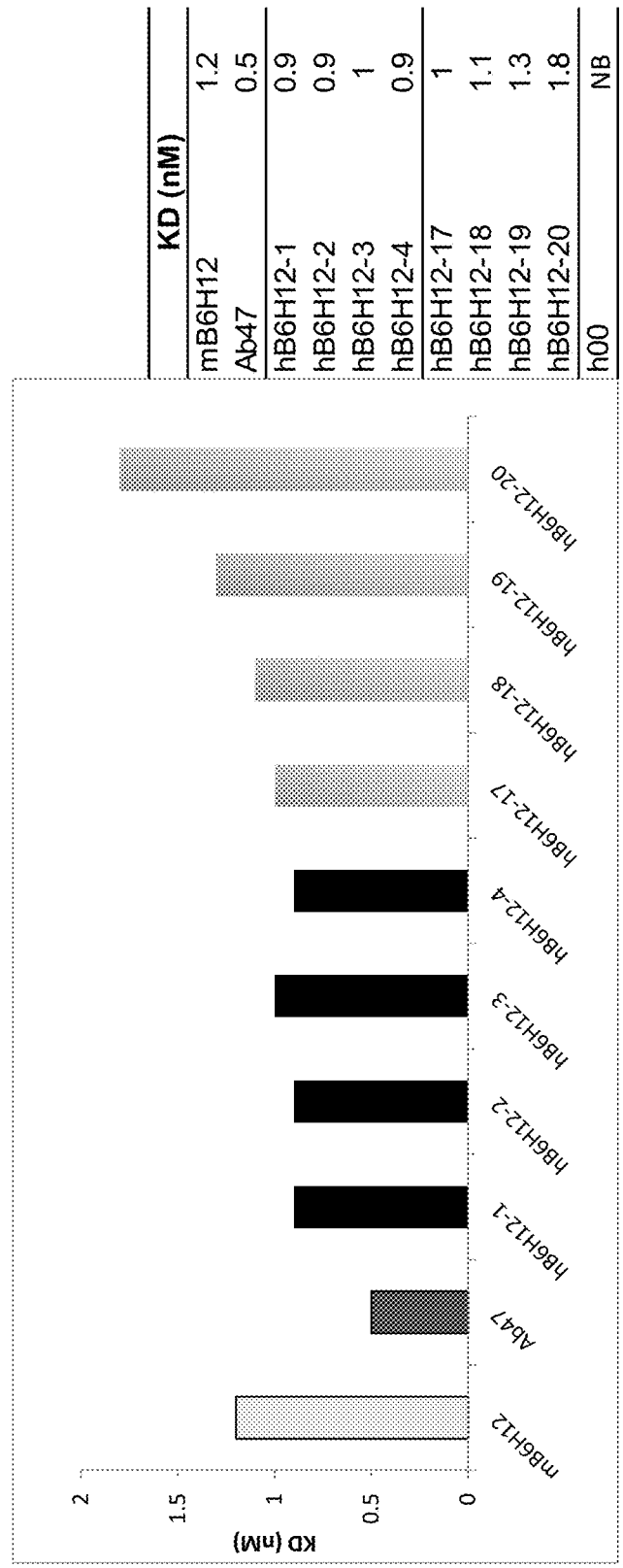
FIG. 2A-2C depict antibody binding affinity and kinetics.

Anti-CD47 IgG3 antibodies known in the art at the time of filing exhibit toxicities such as peripheral red blood cell depletion and platelet depletion, which decrease their usefulness as effective therapeutics against CD47-associated disorders such as, e.g., CD47 expressing cancers. Applicants have surprisingly discovered novel anti-CD47 IgG1 antibodies and antigen-binding fragments thereof that can be activated by unmasking in the context of a tumor microenvironment, to effectively target the antibodies and antigen-binding fragments thereof of the present invention specifically to CD47-expressing solid tumors. The humanized anti-CD47 antibodies and antigen-binding fragments thereof (either masked or unmasked) described herein are useful for treating CD47-related disorders, e.g., such as CD47-expressing cancers.

In certain exemplary embodiments, antibodies and antigen-binding fragments thereof are provided that comprise a removable mask (e.g., a coiled coil mask) that blocks binding of the antibody or antigen-binding fragment thereof to its antigenic target. In certain embodiments, a removable mask is attached to the N-terminus of one or more of the heavy and/or light chains of the antibody or antigen-binding fragment thereof via a matrix metalloproteinase (MMP)-cleavable linker sequence.

In the tumor microenvironment, altered proteolysis leads to unregulated tumor growth, tissue remodeling, inflammation, tissue invasion, and metastasis (Kessenbrock (2011) Cell 141:52). MMPs represent the most prominent family of proteinases associated with tumorigenesis, and MMPs mediate many of the changes in the microenvironment during tumor progression. Id. Upon exposure of the antibody or antigen-binding fragment thereof of the present invention to an MMP, the MMP linker sequence is cleaved, thus allowing removal of the coiled coil mask and enabling the antibody or antigen-binding fragment thereof to bind its target antigen in a tumor microenvironment-specific manner.

The novel anti-CD47 IgG1 antibodies and antigen-binding fragments thereof of the present invention (both masked and un-masked) advantageously demonstrate increased pharmacokinetics and decreased off target effects compared with anti-CD47 IgG3 antibodies known in the art at the time of filing. The novel humanized anti-CD47 antibodies described herein advantageously exhibit one or more of: 1) enhanced antigen binding relative to a reference antibody (e.g., a murine parental antibody); 2) enhanced Antibody Dependent Cellular Cytotoxicity (ADCC) relative to a reference antibody (e.g., a murine parental antibody); 3) enhanced phagocytosis (e.g., enhanced Antibody Dependent Cellular Phagocytosis (ADCP)) relative to a reference antibody (e.g., a murine parental antibody); 4) reduced red blood cell hemagglutination (HA), relative to a reference antibody (e.g., a murine parental antibody); 5) binding to the same three-dimensional (i.e., non-linear) CD47 epitope.

So that the invention may be more readily understood, certain technical and scientific terms are specifically defined below. Unless specifically defined elsewhere in this document, all other technical and scientific terms used herein

I. Definitions

As used herein, including the appended claims, the singular forms of words such as "a," "an," and "the," include their corresponding plural references unless the context clearly dictates otherwise.

An "antibody-drug conjugate" refers to an antibody conjugated to a cytotoxic agent or cytostatic agent. Typically, antibody-drug conjugates bind to a target antigen (e.g., CD47) on a cell surface, followed by internalization of the antibody-drug conjugate into the cell and subsequent release of the drug into the cell.

A "polypeptide" or "polypeptide chain" is a polymer of amino acid residues joined by peptide bonds, whether produced naturally or synthetically. Polypeptides of less than about 10 amino acid residues are commonly referred to as "peptides."

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures. Substituents such as carbohydrate groups are generally not specified, but may be present nonetheless.

The terms "amino-terminal" and "carboxy-terminal" denote positions within polypeptides. Where the context allows, these terms are used with reference to a particular sequence or portion of a polypeptide to denote proximity or relative position. For example, a certain sequence positioned carboxy-terminal to a reference sequence within a polypeptide is located proximal to the carboxy terminus of the reference sequence, but is not necessarily at the carboxy terminus of the complete polypeptide.

For purposes of classifying amino acids substitutions as conservative or nonconservative, the following amino acid substitutions are considered conservative substitutions: serine substituted by threonine, alanine, or asparagine; threonine substituted by proline or serine; asparagine substituted by aspartic acid, histidine, or serine; aspartic acid substituted by glutamic acid or asparagine; glutamic acid substituted by glutamine, lysine, or aspartic acid; glutamine substituted by arginine, lysine, or glutamic acid; histidine substituted by tyrosine or asparagine; arginine substituted by lysine or glutamine; methionine substituted by isoleucine, leucine or valine; isoleucine substituted by leucine, valine, or methionine; leucine substituted by valine, isoleucine, or methionine; phenylalanine substituted by tyrosine or tryptophan; tyrosine substituted by tryptophan, histidine, or phenylalanine; proline substituted by threonine; alanine substituted by serine; lysine substituted by glutamic acid, glutamine, or arginine; valine substituted by methionine, isoleucine, or leucine; and tryptophan substituted by phenylalanine or tyrosine. Conservative substitutions can also mean substitutions between amino acids in the same class. Classes are as follows: Group I (hydrophobic side chains): met, ala, val, leu, ile; Group II (neutral hydrophilic side chains): cys, ser, thr; Group III (acidic side chains): asp, glu; Group IV (basic side chains): asn, gin, his, lys, arg; Group V (residues influencing chain orientation): gly, pro; and Group VI (aromatic side chains): trp, tyr, phe.

Two amino acid sequences have "100% amino acid sequence identity" if the amino acid residues of the two amino acid sequences are the same when aligned for maximal correspondence. Sequence comparisons can be performed using standard software programs such as those included in the LASERGENE bioinformatics computing suite, which is produced by DNASTAR (Madison, Wisconsin). Other methods for comparing two nucleotide or amino acid sequences by determining optimal alignment are well-known to those of skill in the art. (See, e.g., Peruski and Peruski, The Internet and the New Biology: Tools for Genomic and Molecular Research (ASM Press, Inc. 1997); Wu et al. (eds.), "Information Superhighway and Computer Databases of Nucleic Acids and Proteins," in Methods in Gene Biotechnology 123-151 (CRC Press, Inc. 1997); Bishop (ed.), Guide to Human Genome Computing (2nd ed., Academic Press, Inc. 1998).) Two amino acid sequences are considered to have "substantial sequence identity" if the two sequences have at least about 80%, at least about 85%, at about least 90%, or at least about 95% sequence identity relative to each other.

Percentage sequence identities are determined with antibody sequences maximally aligned by the Kabat numbering convention. After alignment, if a subject antibody region (e.g., the entire variable domain of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

Compositions or methods "comprising" one or more recited elements may include other elements not specifically recited. For example, a composition that comprises antibody may contain the antibody alone or in combination with other ingredients.

Designation of a range of values includes all integers within or defining the range.

In antibodies or other proteins described herein, reference to amino acid residues corresponding to those specified by SEQ ID NO includes post-translational modifications of such residues.

The term "antibody" denotes immunoglobulin proteins produced by the body in response to the presence of an antigen and that bind to the antigen, as well as antigen-binding fragments and engineered variants thereof. Hence, the term "antibody" includes, for example, intact monoclonal antibodies (e.g., antibodies produced using hybridoma technology) and antigen-binding antibody fragments, such as a F(ab')$_2$, a Fv fragment, a diabody, a single-chain antibody, an scFv fragment, or an scFv-Fc. Genetically, engineered intact antibodies and fragments such as chimeric antibodies, humanized antibodies, single-chain Fv fragments, single-chain antibodies, diabodies, minibodies, linear antibodies, multivalent or multi-specific (e.g., bispecific) hybrid antibodies, and the like, are also included. Thus, the term "antibody" is used expansively to include any protein that comprises an antigen-binding site of an antibody and is capable of specifically binding to its antigen.

The term antibody or antigen-binding fragment thereof includes a "naked" antibody or antigen-binding fragment thereof that is not bound (i.e., covalently or non-covalently bound) to a masking compound of the invention. The term antibody also embraces a "masked" antibody or antigen-binding fragment thereof that is covalently or non-covalently bound to one or more masking compounds such as, e.g., coiled coil peptides, as described further herein. The term antibody or antigen-binding fragment thereof includes a "conjugated" antibody or antigen-binding fragment thereof or an "antibody-drug conjugate (ADC)" in which an antibody or antigen-binding fragment thereof is covalently or non-covalently bound to a pharmaceutical agent, e.g., to a cytostatic or cytotoxic drug. In certain embodiments, an antibody or antigen-binding fragment thereof is a naked antibody or antigen-binding fragment that optionally is conjugated to a pharmaceutical agent, e.g., to a cytostatic or cytotoxic drug. In other embodiments, an antibody or antigen-binding fragment thereof is a masked antibody or antigen-binding fragment that optionally is conjugated to a pharmaceutical agent, e.g., to a cytostatic or cytotoxic drug.

The term "genetically engineered antibodies" refers to an antibody in which the amino acid sequence has been varied from that of the native or parental antibody. The possible variations are many, and range from the changing of just one or a few amino acids to the complete redesign of, for example, the variable or constant region. Changes in the constant region are, in general, made to improve or alter characteristics such as, e.g., complement binding and other effector functions. Typically, changes in the variable region are made to improve antigen-binding characteristics, improve variable region stability, and/or reduce the risk of immunogenicity.

The term "chimeric antibody" refers to an antibody in which a portion of the heavy and/or light chain is identical with or homologous to corresponding sequences in an antibody derived from a particular species (e.g., human) or belonging to a particular antibody class or subclass, while the remainder of the chain(s) is identical with or homologous to corresponding sequences in an antibody derived from another species (e.g., mouse) or belonging to another antibody class or subclass, as well as fragments of such antibodies, so long as they exhibit the desired biological activity.

An "antigen-binding site of an antibody" is that portion of an antibody that is sufficient to bind to its antigen. The minimum such region is typically a variable domain or a genetically engineered variant thereof. Single domain binding sites can be generated from camelid antibodies (see Muyldermans and Lauwereys, Mol. Recog. 12: 131-140, 1999; Nguyen et al., EMBO J. 19:921-930, 2000) or from VH domains of other species to produce single-domain antibodies ("dAbs," see Ward et al., Nature 341:544-546, 1989; U.S. Pat. No. 6,248,516 to Winter et al). Commonly, an antigen-binding site of an antibody comprises both a heavy chain variable (VH) domain and a light chain variable (VL) domain that bind to a common epitope. Within the context of the present invention, an antibody may include one or more components in addition to an antigen-binding site, such as, for example, a second antigen-binding site of an antibody (which may bind to the same or a different epitope or to the same or a different antigen), a peptide linker, an immunoglobulin constant region, an immunoglobulin hinge, an amphipathic helix (see Pack and Pluckthun, Biochem. 31: 1579-1584, 1992), a non-peptide linker, an oligonucleotide (see Chaudri et al, FEBS Letters 450:23-26, 1999), a cytostatic or cytotoxic drug, and the like, and may be a monomeric or multimeric protein. Examples of molecules comprising an antigen-binding site of an antibody are known in the art and include, for example, Fv, single-chain Fv (scFv), Fab, Fab', F(ab')2, F(ab)c, diabodies, minibodies, nanobodies, Fab-scFv fusions, bispecific (scFv)4-IgG, and bispecific (scFv)2-Fab. (See, e.g., Hu et al, Cancer Res. 56:3055-3061, 1996; Atwell et al., Molecular Immunology 33: 1301-1312, 1996; Carter and Merchant, Curr. Op. Biotechnol. 8:449-454, 1997; Zuo et al., Protein Engineering 13:361-367, 2000; and Lu et al., J. Immunol. Methods 267:213-226, 2002.)

The term "immunoglobulin" refers to a protein consisting of one or more polypeptides substantially encoded by immunoglobulin gene(s). One form of immunoglobulin constitutes the basic structural unit of native (i.e., natural or parental) antibodies in vertebrates. This form is a tetramer and consists of two identical pairs of immunoglobulin chains, each pair having one light chain and one heavy chain. In each pair, the light and heavy chain variable regions (VL and VH) are together primarily responsible for binding to an antigen, and the constant regions are primarily responsible for the antibody effector functions. Five classes of immunoglobulin protein (IgG, IgA, IgM, IgD, and IgE) have been identified in higher vertebrates. IgG comprises the major class, and it normally exists as the second most abundant protein found in plasma. In humans, IgG consists of four subclasses, designated IgG1, IgG2, IgG3, and IgG4. Each immunoglobulin heavy chain possesses a constant region that consists of constant region protein domains (CH1, hinge, CH2, and CH3; IgG3 also contains a CH4 domain) that are essentially invariant for a given subclass in a species.

DNA sequences encoding human and non-human immunoglobulin chains are known in the art. (See, e.g., Ellison et al, DNA 1: 11-18, 1981; Ellison et al, Nucleic Acids Res. 10:4071-4079, 1982; Kenten et al., Proc. Natl. Acad. Set USA 79:6661-6665, 1982; Seno et al., Nucl. Acids Res. 11:719-726, 1983; Riechmann et al., Nature 332:323-327, 1988; Amster et al., Nucl. Acids Res. 8:2055-2065, 1980; Rusconi and Kohler, Nature 314:330-334, 1985; Boss et al., Nucl. Acids Res. 12:3791-3806, 1984; Bothwell et al., Nature 298:380-382, 1982; van der Loo et al., Immunogenetics 42:333-341, 1995; Karlin et al., J. Mol. Evol. 22: 195-208, 1985; Kindsvogel et al., DNA 1:335-343, 1982; Breiner et al., Gene 18: 165-174, 1982; Kondo et al., Eur. J. Immunol. 23:245-249, 1993; and GenBank Accession No. J00228.) For a review of immunoglobulin structure and function see Putnam, The Plasma Proteins, Vol V, Academic Press, Inc., 49-140, 1987; and Padlan, Mol. Immunol. 31: 169-217, 1994. The term "immunoglobulin" is used herein for its common meaning, denoting an intact antibody, its component chains, or fragments of chains, depending on the context.

Full-length immunoglobulin "light chains" (about 25 kDa or 214 amino acids) are encoded by a variable region gene at the amino-terminus (encoding about 110 amino acids) and a by a kappa or lambda constant region gene at the carboxyl-terminus. Full-length immunoglobulin "heavy chains" (about 50 kDa or 446 amino acids) are encoded by a variable region gene (encoding about 116 amino acids) and a gamma, mu, alpha, delta, or epsilon constant region gene (encoding about 330 amino acids), the latter defining the antibody's isotype as IgG, IgM, IgA, IgD, or IgE, respectively. Within light and heavy chains, the variable and constant regions are joined by a "J" region of about 12 or more amino acids, with the heavy chain also including a "D" region of about 10 more amino acids. (See generally Fundamental Immunology (Paul, ed., Raven Press, N.Y., 2nd ed. 1989), Ch. 7).

An immunoglobulin light or heavy chain variable region (also referred to herein as a "light chain variable domain" ("VL domain") or "heavy chain variable domain" ("VH domain"), respectively) consists of a "framework" region interrupted by three "complementarity determining regions" or "CDRs." The framework regions serve to align the CDRs for specific binding to an epitope of an antigen. Thus, the term "CDR" refers to the amino acid residues of an antibody that are primarily responsible for antigen binding. From amino-terminus to carboxyl-terminus, both VL and VH domains comprise the following framework (FR) and CDR regions: FR1, CDR1, FR2, CDR2, FR3, CDR3, FR4.

The assignment of amino acids to each variable region domain is in accordance with the definitions of Kabat, Sequences of Proteins of Immunological Interest (National Institutes of Health, Bethesda, MD, 1987 and 1991). Kabat also provides a widely used numbering convention (Kabat numbering) in which corresponding residues between different heavy chain variable regions or between different light chain variable regions are assigned the same number. CDRs 1, 2 and 3 of a VL domain are also referred to herein, respectively, as CDR-L1, CDR-L2 and CDR-L3. CDRs 1, 2 and 3 of a VH domain are also referred to herein, respectively, as CDR-H1, CDR-H2 and CDR-H3. If so noted, the assignment of CDRs can be in accordance with IMGT® (Lefranc et al., Developmental & Comparative Immunology 27:55-77; 2003) in lieu of Kabat.

Numbering of the heavy chain constant region is via the EU index as set forth in Kabat (Kabat, Sequences of Proteins of Immunological Interest, National Institutes of Health, Bethesda, MD, 1987 and 1991).

Unless the context dictates otherwise, the term "monoclonal antibody" is not limited to antibodies produced through hybridoma technology. The term "monoclonal antibody" can include an antibody that is derived from a single clone, including any eukaryotic, prokaryotic or phage clone. In particular embodiments, the antibodies described herein are monoclonal antibodies.

The term "humanized VH domain" or "humanized VL domain" refers to an immunoglobulin VH or VL domain comprising some or all CDRs entirely or substantially from a non-human donor immunoglobulin (e.g., a mouse or rat) and variable domain framework sequences entirely or substantially from human immunoglobulin sequences. The non-human immunoglobulin providing the CDRs is called the "donor" and the human immunoglobulin providing the framework is called the "acceptor." In some instances, humanized antibodies will retain some non-human residues within the human variable domain framework regions to enhance proper binding characteristics (e.g., mutations in the frameworks may be required to preserve binding affinity when an antibody is humanized).

A "humanized antibody" is an antibody comprising one or both of a humanized VH domain and a humanized VL domain. Immunoglobulin constant region(s) need not be present, but if they are, they are entirely or substantially from human immunoglobulin constant regions.

A humanized antibody is a genetically engineered antibody in which the CDRs from a non-human "donor" antibody are grafted into human "acceptor" antibody sequences (see, e.g., Queen, U.S. Pat. Nos. 5,530,101 and 5,585,089; Winter, U.S. Pat. No. 5,225,539; Carter, U.S. Pat. No. 6,407,213; Adair, U.S. Pat. No. 5,859,205; and Foote, U.S. Pat. No. 6,881,557). The acceptor antibody sequences can be, for example, a mature human antibody sequence, a composite of such sequences, a consensus sequence of human antibody sequences, or a germline region sequence. Human acceptor sequences can be selected for a high degree of sequence identity in the variable region frameworks with donor sequences to match canonical forms between acceptor and donor CDRs among other criteria. Thus, a humanized antibody is an antibody having CDRs entirely or substantially from a donor antibody and variable region framework sequences and constant regions, if present, entirely or substantially from human antibody sequences. Similarly, a humanized heavy chain typically has all three CDRs entirely or substantially from a donor antibody heavy chain, and a heavy chain variable region framework sequence and heavy chain constant region, if present, substantially from human heavy chain variable region framework and constant region sequences. Similarly, a humanized light chain typically has all three CDRs entirely or substantially from a donor antibody light chain, and a light chain variable region framework sequence and light chain constant region, if present, substantially from human light chain variable region framework and constant region sequences. A CDR in a humanized antibody is substantially from a corresponding CDR in a non-human antibody when at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% of corresponding residues (as defined by Kabat numbering), or wherein about 100% of corresponding residues (as defined by Kabat numbering), are identical between the respective CDRs. The variable region framework sequences of an antibody chain or the constant region of an antibody chain are substantially from a human variable region framework sequence or human constant region respectively when at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% of corresponding residues (as defined by Kabat numbering for the variable region and EU numbering for the constant region), or about 100% of corresponding residues (as defined by Kabat numbering for the variable region and EU numbering for the constant region) are identical.

Although humanized antibodies often incorporate all six CDRs (preferably as defined by Kabat or IMGT®) from a mouse antibody, they can also be made with fewer than all six CDRs (e.g., at least 3, 4, or 5) CDRs from a mouse antibody (e.g., Pascalis et al., J. Immunol. 169:3076, 2002; Vajdos et al., Journal of Molecular Biology, 320: 415-428, 2002; Iwahashi et al., Mol. Immunol. 36:1079-1091, 1999; Tamura et al, Journal of Immunology, 164: 1432-1441, 2000).

A CDR in a humanized antibody is "substantially from" a corresponding CDR in a non-human antibody when at least 60%, at least 85%, at least 90%, at least 95% or 100% of corresponding residues (as defined by Kabat (or IMGT)) are identical between the respective CDRs. In particular variations of a humanized VH or VL domain in which CDRs are substantially from a non-human immunoglobulin, the CDRs of the humanized VH or VL domain have no more than six (e.g., no more than five, no more than four, no more than three, no more than two, or nor more than one) amino acid substitutions (preferably conservative substitutions) across all three CDRs relative to the corresponding non-human VH or VL CDRs. The variable region framework sequences of an antibody VH or VL domain or, if present, a sequence of an immunoglobulin constant region, are "substantially from" a human VH or VL framework sequence or human constant region, respectively, when at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% of corresponding residues (as defined by Kabat numbering for the variable region and EU numbering for the constant region), or about 100% of corresponding residues (as defined by Kabat numbering for the variable region and EU numbering for the constant region) are identical. Hence, all parts of a humanized antibody, except the CDRs, are typically entirely or substantially from corresponding parts of natural human immunoglobulin sequences.

Antibodies are typically provided in isolated form. This means that an antibody is typically at least about 50% w/w pure of interfering proteins and other contaminants arising from its production or purification but does not exclude the possibility that the antibody is combined with an excess of pharmaceutical acceptable carrier(s) or other vehicle intended to facilitate its use. Sometimes antibodies are at least about 60%, about 70%, about 80%, about 90%, about 95% or about 99% w/w pure of interfering proteins and contaminants from production or purification. Antibodies, including isolated antibodies, can be conjugated to cytotoxic agents and provided as antibody drug conjugates and/or masked, e.g., with associated coiled coils.

Specific binding of an antibody to its target antigen typically refers an affinity of at least about $10^6$, about $10^7$, about $10^8$, about $10^9$, or about $10^{10}$ M$^{-1}$. Specific binding is detectably higher in magnitude and distinguishable from non-specific binding occurring to at least one non-specific target. Specific binding can be the result of formation of bonds between particular functional groups or particular spatial fit (e.g., lock and key type), whereas nonspecific binding is typically the result of van der Waals forces.

The term "epitope" refers to a site of an antigen to which an antibody binds. An epitope can be formed from contiguous amino acids or noncontiguous amino acids juxtaposed by tertiary folding of one or more proteins. Epitopes formed from contiguous amino acids are typically retained upon exposure to denaturing agents, e.g., solvents, whereas epitopes formed by tertiary folding are typically lost upon treatment with denaturing agents, e.g., solvents. An epitope typically includes at least about 3, and more usually, at least about 5, at least about 6, at least about 7, or about 8-10 amino acids in a unique spatial conformation. Methods of determining spatial conformation of epitopes include, for example, x-ray crystallography and two-dimensional nuclear magnetic resonance. See, e.g., Epitope Mapping Protocols, in Methods in Molecular Biology, Vol. 66, Glenn E. Morris, Ed. (1996).

Antibodies that recognize the same or overlapping epitopes can be identified in a simple immunoassay showing the ability of one antibody to compete with the binding of another antibody to a target antigen. The epitope of an antibody can also be defined by X-ray crystallography of the antibody bound to its antigen to identify contact residues.

Alternatively, two antibodies have the same epitope if all amino acid mutations in the antigen that reduce or eliminate binding of one antibody reduce or eliminate binding of the other (provided that such mutations do not produce a global alteration in antigen structure). Two antibodies have overlapping epitopes if some amino acid mutations that reduce or eliminate binding of one antibody reduce or eliminate binding of the other antibody.

Competition between antibodies can be determined by an assay in which a test antibody inhibits specific binding of a reference antibody to a common antigen (see, e.g., Junghans et al., Cancer Res. 50: 1495, 1990). A test antibody competes with a reference antibody if an excess of a test antibody inhibits binding of the reference antibody.

Antibodies identified by competition assay (competing antibodies) include antibodies that bind to the same epitope as the reference antibody and antibodies that bind to an adjacent epitope sufficiently proximal to the epitope bound by the reference antibody for steric hindrance to occur. Antibodies identified by a competition assay also include those that indirectly compete with a reference antibody by causing a conformational change in the target protein thereby preventing binding of the reference antibody to a different epitope than that bound by the test antibody.

An antibody effector function refers to a function contributed by an Fc region of an Ig. Such functions can be, for example, antibody-dependent cellular cytotoxicity (ADCC), antibody-dependent cellular phagocytosis (ADCP), or complement-dependent cytotoxicity (CDC). Such function can be effected by, for example, binding of an Fc region to an Fc receptor on an immune cell with phagocytic or lytic activity or by binding of an Fc region to components of the complement system. Typically, the effect(s) mediated by the Fc-binding cells or complement components result in inhibition and/or depletion of the CD47-targeted cell. Fc regions of antibodies can recruit Fc receptor (FcR)-expressing cells and juxtapose them with antibody-coated target cells. Cells expressing surface FcR for IgGs including FcγRIII (CD16), FcγRII (CD32) and FcγRIII (CD64) can act as effector cells for the destruction of IgG-coated cells. Such effector cells include monocytes, macrophages, natural killer (NK) cells, neutrophils and eosinophils. Engagement of FcγR by IgG activates ADCC or ADCP. ADCC is mediated by CD16+ effector cells through the secretion of membrane pore-forming proteins and proteases, while phagocytosis is mediated by CD32+ and CD64+ effector cells (see Fundamental Immunology, 4$^{th}$ ed., Paul ed., Lippincott-Raven, N.Y., 1997, Chapters 3, 17 and 30; Uchida et al., J. Exp. Med. 199:1659-69, 2004; Akewanlop et al., Cancer Res. 61:4061-65, 2001; Watanabe et al., Breast Cancer Res. Treat. 53: 199-207, 1999).

In addition to ADCC and ADCP, Fc regions of cell-bound antibodies can also activate the complement classical pathway to elicit CDC. C1q of the complement system binds to the Fc regions of antibodies when they are complexed with antigens. Binding of C1q to cell-bound antibodies can initiate a cascade of events involving the proteolytic activation of C4 and C2 to generate the C3 convertase. Cleavage of C3 to C3b by C3 convertase enables the activation of terminal complement components including C5b, C6, C7, C8 and C9. Collectively, these proteins form membrane-attack complex pores on the antibody-coated cells. These pores disrupt the cell membrane integrity, killing the target cell (see Immunobiology, 6$^{th}$ ed., Janeway et al, Garland Science, N.Y., 2005, Chapter 2).

The term "antibody-dependent cellular cytotoxicity" or "ADCC" refers to a mechanism for inducing cell death that depends on the interaction of antibody-coated target cells with immune cells possessing lytic activity (also referred to as effector cells). Such effector cells include natural killer cells, monocytes/macrophages and neutrophils. The effector cells attach to an Fc region of Ig bound to target cells via their antigen-combining sites. Death of the antibody-coated target cell occurs as a result of effector cell activity. In certain exemplary embodiments, an anti-CD47 IgG1 antibody of the invention mediates equal or increased ADCC relative to a parental antibody and/or relative to an anti-CD47 IgG3 antibody.

The term "antibody-dependent cellular phagocytosis" or "ADCP" refers to the process by which antibody-coated cells are internalized, either in whole or in part, by phagocytic immune cells (e.g., by macrophages, neutrophils and/or dendritic cells) that bind to an Fc region of Ig. In certain exemplary embodiments, an anti-CD47 IgG1 antibody of the invention mediates equal or increased ADCP relative to a parental antibody and/or relative to an anti-CD47 IgG3 antibody.

The term "complement-dependent cytotoxicity" or "CDC" refers to a mechanism for inducing cell death in which an Fc region of a target-bound antibody activates a series of enzymatic reactions culminating in the formation of holes in the target cell membrane.

Typically, antigen-antibody complexes such as those on antibody-coated target cells bind and activate complement component C1q, which in turn activates the complement cascade leading to target cell death. Activation of complement may also result in deposition of complement components on the target cell surface that facilitate ADCC by binding complement receptors (e.g., CR3) on leukocytes.

A "cytotoxic effect" refers to the depletion, elimination and/or killing of a target cell. A "cytotoxic agent" refers to a compound that has a cytotoxic effect on a cell, thereby mediating depletion, elimination and/or killing of a target cell. In certain embodiments, a cytotoxic agent is conjugated to an antibody or administered in combination with an antibody. Suitable cytotoxic agents are described further herein.

A "cytostatic effect" refers to the inhibition of cell proliferation. A "cytostatic agent" refers to a compound that has a cytostatic effect on a cell, thereby mediating inhibition of growth and/or expansion of a specific cell type and/or subset of cells. Suitable cytostatic agents are described further herein.

The terms "expression unit" and "expression cassette" are used interchangeably herein and denote a nucleic acid segment encoding a polypeptide of interest and capable of providing expression of the nucleic acid segment in a host cell. An expression unit typically comprises a transcription promoter, an open reading frame encoding the polypeptide of interest, and a transcription terminator, operably linked. In addition to a transcriptional promoter and terminator, an expression unit may further include other nucleic acid segments such as, e.g., an enhancer or a polyadenylation signal.

The term "expression vector" refers to a nucleic acid molecule, linear or circular, comprising one or more expression units. In addition to one or more expression units, an expression vector may also include additional nucleic acid segments such as, for example, one or more origins of replication or one or more selectable markers.

Expression vectors are generally derived from plasmid or viral DNA, or may contain elements of both.

The term "patient" or "subject" includes human and other mammalian subjects such as non-human primates, rabbits, rats, mice, and the like and transgenic species thereof, that receive either prophylactic or therapeutic treatment. In certain exemplary embodiments, a subject is a human patient suffering from or at risk of developing cancer, e.g., a solid tumor, that optionally secretes one or more proteases capable of cleaving a masking domain (e.g., a coiled coil masking domain) of an anti-CD47 antibody described herein.

The term "effective amount," in the context of treatment of a CD47-expressing disorder by administration of an anti-CD47 antibody as described herein, refers to an amount of such antibody that is sufficient to inhibit the occurrence or ameliorate one or more symptoms of a CD47-related disorder (e.g., a CD47-expressing cancer). An effective amount of an antibody is administered in an "effective regimen." The term "effective regimen" refers to a combination of amount of the antibody being administered and dosage frequency adequate to accomplish prophylactic or therapeutic treatment of the disorder (e.g., prophylactic or therapeutic treatment of a CD47-expressing cancer).

The term "pharmaceutically acceptable" means approved or approvable by a regulatory agency of the Federal or a state government or listed in the U.S. Pharmacopeia or other generally recognized pharmacopeia for use in animals, and more particularly in humans. The term "pharmaceutically compatible ingredient" refers to a pharmaceutically acceptable diluent, adjuvant, excipient, or vehicle with which an anti-CD47 antibody is formulated.

The phrase "pharmaceutically acceptable salt," refers to pharmaceutically acceptable organic or inorganic salts. Exemplary salts include sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p toluenesulfonate, and pamoate (i.e., 1,1'-methylene bis-(2 hydroxy-3-naphthoate) salts. A pharmaceutically acceptable salt may further comprise an additional molecule such as, e.g., an acetate ion, a succinate ion or other counterion. A counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

Unless otherwise apparent from the context, when a value is expressed as "about" X or "approximately" X, the stated value of X will be understood to be accurate to ±10%.

Solvates in the context of the invention are those forms of the compounds of the invention that form a complex in the solid or liquid state through coordination with solvent molecules. Hydrates are one specific form of solvates, in which the coordination takes place with water. In certain exemplary embodiments, solvates in the context of the present invention are hydrates.

The term "hemagglutination" refers to the process by which red blood cells are clumped together. Hemagglutination is a known, undesirable side-effect of anti-CD47 antibodies in the art. The humanized anti-CD47 antibodies of the invention optionally mediate reduced hemagglutination relative to a murine parental anti-CD47 antibody and/or relative to one or more anti-CD47 antibodies known in the art.

II. Anti-CD47 Antibodies and Antigen-Binding Fragments

The present invention provides isolated, recombinant and/or synthetic anti-CD47 human, primate, rodent, mammalian, chimeric, humanized and/or CDR-grafted antibodies and antigen-binding fragments thereof, as well as compositions and nucleic acid molecules comprising at least one polynucleotide encoding at least a portion of one anti-CD47 antibody molecule. The present invention further includes, but is not limited to, methods of making and using such nucleic acids and antibodies including diagnostic and therapeutic compositions, methods and devices. In certain exemplary embodiments, humanized anti-CD47 IgG1 antibodies are provided. In other exemplary embodiments, masked humanized anti-CD47 IgG1 antibodies are provided. In still other exemplary embodiments, humanized anti-CD47 IgG1 antibodies comprising a stub are provided.

In particular embodiments of the invention, humanized anti-CD47 antibodies are provided having one or more of the following activities: 1) enhanced antigen binding relative to a reference antibody (e.g., a murine parental antibody); 2) enhanced Antibody Dependent Cellular Cytotoxicity (ADCC) relative to a reference antibody (e.g., a murine parental antibody); 3) enhanced phagocytosis (e.g., Antibody Dependent Cellular Phagocytosis (ADCP)) relative to a reference antibody (e.g., a murine parental antibody); 4) reduced red blood cell hemagglutination (HA), relative to a reference antibody (e.g., a murine parental antibody); 5) binding to a three-dimensional (i.e., non-linear) CD47 epitope.

Exemplary anti-CD47 antibodies and antigen-binding fragments thereof of the invention include the following CD47 antibody heavy chain/light chain pairs: hB6H12.1-hvH1/hvK1; hB6H12.2-hvH1/hvK2; hB6H12.3-hvH1/hvK3; hB6H12.4-hvH1/hvK4; hB6H12.5-hvH2/hvK1; hB6H12.6-hvH2/hvK2; hB6H12.7-hvH2/hvK3; hB6H12.8-hvH2/hvK4; hB6H12.9-hvH3/hvK1; hB6H12.10-hvH3/hvK2; hB6H12.11-hvH3/hvK3; hB6H12.12-hvH3/hvK4; hB6H12.13-hvH4/hvK1; hB6H12.14-hvH4/hvK2; hB6H12.15-hvH4/hvK3; hB6H12.16-hvH4/hvK4; hB6H12.17-hvH5/hvK1; hB6H12.18-hvH5/hvK2; hB6H12.19 hvH5/hvK3; hB6H12.20-hvH5/hvK4; hB6H12.21-hvH6/hvK1; hB6H12.22-hvH6/hvK2; hB6H12.23-hvH6/hvK3; hB6H12.24-hvH6/hvK4; hB6H12.3 (deamidation mutant) hvH1/hvK3 G91A; Ab47-HV3-7/HJ4/KV3D-11/KJ1; and mB6H12-vH1/vL. Exemplary anti-CD47 antibody heavy chain variable region sequences, light chain variable regions, heavy chain CDRs and light chain CDRs can be found at Table 1-Table 6. The amino acid sequences for the heavy chain and light chain of an exemplary humanized anti-CD47 antibody can be found at Table 7.

TABLE 1

Heavy chain variable sequences derived from the murine B6H12 antibody. Kabat CDRs are underlined, and IMGT CDRs are bolded.

| Variant | Sequence |
|---|---|
| mB6h12 vH | EVQLVESGGDLVKPGGSLKLSCAASGFTFSGYGMSWV RQTPDKRLEWVATITSGGTYTYYPDSVKGRFTISRDN AKNTLYLQIDSLKSEDTAIYFCARSLAGNAMDYWGQG TSVTVSS (SEQ ID NO: 1) |
| Ab47vH (HV3-7/HJ4) | EVQLVESGGGLVQPGGSLRLSCAASGFTFSGYGMSWV RQAPGKGLEWVATITSGGTYTYYPDSVKGRFTISRDN AKNSLYLQMNSLRAEDTAVYYCARSLAGNAMDYWGQG TLVTVSS (SEQ ID NO: 2) |
| hvH1 | EVQLLESGGGLVQPGGSLRLSCAASGFTFSGYGMSWV RQAPGKRLEWVATITSGGTYTYYPDSVKGRFTISRDN SKNTLYLQMNSLRAEDTAIYFCARSLAGNAMDYWGQG TLVTVSS (SEQ ID NO: 3) |
| hvH2 | EVQLLESGGGLVQPGGSLRLSCAASGFTFSSYAMSWV RQAPGKGLEWVATITSGGTYTYYADSVKGRFTISRDN SKNTLYLQMNSLRAEDTAVYFCARSLAGNAMDYWGQG TLVTVSS (SEQ ID NO: 4) |
| hvH3 | EVQLLESGGGLVQPGGSLRLSCAASGFTFSSYAMSWV RQAPGKGLEWVATITSGGTYTYYADSVKGRFTISRDN SKNTLYLQINSLRAEDTAVYFCARSLAGNAMDYWGQG TLVTVSS (SEQ ID NO: 5) |

TABLE 1-continued

Heavy chain variable sequences derived from the murine B6H12 antibody. Kabat CDRs are underlined, and IMGT CDRs are bolded.

| Variant | Sequence |
|---|---|
| hvH4 | EVQLVESGGGLVQPGGSLRLSCAASGFTFSSYGMNWV RQAPGKGLEWVATITSGGTYIYYADSVKGRFTISRDN AKNSLYLQMNSLRAEDTAVYYCARSLAGNAMDYWGQG TLVTVSS (SEQ ID NO: 6) |
| hvH5 | EVQLVESGGGLVQPGGSLRLSCAASGFTFSGYGMSWV RQAPGKGLEWVATITSGGTYTYYADSVKGRFTISRDN SKNTLYLQINSLRAEDTAVYYCARSLAGNAMDYWGQG TLVTVSS (SEQ ID NO: 7) |
| hvH6 | EVQLVESGGGLVQPGGSLRLSCAASGFTFSSYGMHWV RQAPGKGLVWVATITSGGTYTSYADSVKGRFTISRDN AKNTLYLQMNSLRAEDTAVYYCARSLAGNAMDYWGQG TLVTVSS (SEQ ID NO: 8) |

TABLE 2

Light chain variable sequences derived from the murine B6H12 antibody. Kabat CDRs are underlined, and IMGT CDRs are bolded.

| Variant | Sequence |
|---|---|
| mB6h12 vL | DIVMTQSPATLSVTPGDRVSLSCRASQTISDYLHWYQQKSH ESPRLLIKFASQSISGIPSRFSGSGSGSDFTLSINSVEPED VGVYYCQNGHGFPRTFGGGTKLEIKR (SEQ ID NO: 9) |
| Ab47vL (KV3D-11/KJ1) | EIVLTQSPATLSLSPGERATLSCRASQTISDYLHWYQQKPG QAPRLLIKFASQSISGIPARFSGSGSGTDFTLTISSLEPED FAVYYCQNGHGFPRTFGQGTKVEIKR (SEQ ID NO: 10) |
| hvK1 | EIVMTQSPDFQSVTPKEKVTLTCRASQTISDYLHWYQQKPD QSPKLLIKFASQSISGVPSRFSGSGSGTDFTLTINSLEAED AAVYYCQNGHGFPRTFGQGTKLEIK(R) (SEQ ID NO: 11) |
| hvK2 | EIVMTQSPDFQSVTPKEKVTLTCRASQTISDYLHWYQQKPD QSPKLLIKFASQSISGVPSRFSGSGSGTDFTLTINSLEAED AATYYCQNGHGFPRTFGQGTKLEIK(R) (SEQ ID NO: 12) |
| hvK3 | EIVMTQSPDFQSVTPKEKVTLTCRASQTISDYLHWYQQKPD QSPKLLIKFASQSISGVPSRFSGSGSGSDFTLTINSLEAED AATYYCQNGHGFPRTFGQGTKLEIK(R) (SEQ ID NO: 13) |
| hvK4 | DIQMTQSPSSLSASVGDRVTLTCRASQTISNYLAWYQQKPG KVPKLLIKFASTLQSGVPSRFSGSGSGSDFTLTISSLQPED VATYYCQNGHGFPRTFGQGTKLEIK(R) (SEQ ID NO: 14) |
| hvK3 (G91A) | EIVMTQSPDFQSVTPKEKVTLTCRASQTISDYLHWYQQKPD QSPKLLIKFASQSISGVPSRFSGSGSGSDFTLTINSLEAED AATYYCQN<u>A</u>HGFPRTFGQGTKLEIKR (SEQ ID NO: 15) |

TABLE 3

Heavy chain CDR sequences of variant antibodies (Kabat).

| CDR | Sequence |
|---|---|
| hvH1 & hvH5 HCDR1 (Kabat) | GYGMS (SEQ ID NO: 16) |
| hvH1 HCDR2 (Kabat) | TITSGGTYTYYPDSVKG (SEQ ID NO: 17) |

TABLE 3-continued

Heavy chain CDR sequences of variant antibodies (Kabat).

| CDR | Sequence |
| --- | --- |
| hvH1-hvH6 HCDR3 (Kabat) | SLAGNAMDY (SEQ ID NO: 18) |
| hvH2 & hvH3 HCDR1 (Kabat) | SYAMS (SEQ ID NO: 19) |
| hvH2, hvH3, & hvH5 HCDR2 (Kabat) | TITSGGTYTYYADSVKG (SEQ ID NO: 20) |
| hvH4 HCDR1 (Kabat) | SYGMN (SEQ ID NO: 21) |
| hvH4 HCDR2 (Kabat) | TITSGGTYIYYADSVKG (SEQ ID NO: 22) |
| hvH6 HCDR1 (Kabat) | SYGMH (SEQ ID NO: 23) |
| hvH6 HCDR2 (Kabat) | TITSGGTYTSYADSVKG (SEQ ID NO: 24) |

TABLE 4

Heavy chain CDR sequences of variant antibodies (IMGT).

| CDR | Sequence |
| --- | --- |
| hvH1 & hvH5 HCDR1 (IMGT) | GFTFSGYG (SEQ ID NO: 25) |
| hvH1-hvH3, hvH5-hvH6 HCDR2 (IMGT) | ITSGGTYT (SEQ ID NO: 26) |
| hvH1-hvH6 HCDR3 (IMGT) | ARSLAGNAMDY (SEQ ID NO: 27) |
| hvH2 & hvH3 HCDR1 (IMGT) | GFTFSSYA (SEQ ID NO: 28) |
| hvH4 & hvH6 HCDR1 (IMGT) | GFTFSSYG (SEQ ID NO: 29) |
| hvH4 HCDR2 (IMGT) | ITSGGTYI (SEQ ID NO: 30) |

TABLE 5

Light chain CDR sequences of variant antibodies (Kabat).

| CDR | Sequence |
| --- | --- |
| hvK1-hvK3 LCDR1 (Kabat) | RASQTISDYLH (SEQ ID NO: 31) |
| hvK1-hvK3 LCDR2 (Kabat) | FASQSIS (SEQ ID NO: 32) |
| hvK1-hvK4 LCDR3 (Kabat) | QNGHGFPRT (SEQ ID NO: 33) |
| hvK4 LCDR1 (Kabat) | RASQTISNYLA (SEQ ID NO: 34) |
| hvK4 LCDR2 (Kabat) | FASTLQS (SEQ ID NO: 35) |
| hvK3 (G91A) LCDR3 (Kabat) | QNAHGFPRT (SEQ ID NO: 36) |

TABLE 6

Light chain CDR sequences of variant antibodies (IMGT).

| CDR | Sequence |
| --- | --- |
| hvK1-hvK3 LCDR1 (IMGT) | QTISDY (SEQ ID NO: 37) |
| hvK1-hvK4 LCDR2 (IMGT) | FAS (SEQ ID NO: 38) |
| hvK1-hvK4 LCDR3 (IMGT) | QNGHGFPRT (SEQ ID NO: 39) |
| hvK4 LCDR1 (IMGT) | QTISNY (SEQ ID NO: 40) |
| hvK3 (G91A) LCDR3 (IMGT) | QNAHGFPRT (SEQ ID NO: 41) |

TABLE 7

Complete heavy and light chain sequences of a masked anti-CD47 antibody according to a preferred embodiment of the invention. Heavy chain and light chain sequences are in plain text (SEQ ID NOs: 42 and 43, respectively), masking sequences are in bold text, and protease cleavage sequences are underlined.

| Antibody Chain | Sequence |
| --- | --- |
| Heavy Chain | QGASTSVDELQAEVDQLEDENYALKTKVAQLRKK VEKLGSIPVSLRSGEVQLLESGGGLVQPGGSLRL SCAASGFTFSGYGMSWVRQAPGKRLEWVATITSG GTYTYYPDSVKGRFTISRDNSKNTLYLQMNSLRA EDTAIYFCARSLAGNAMDYWGQGTLVTVSSASTK GPSVFPLAPSSKSTSGGTAALGCLVKDYFPEPVT VSWNSGALTSGVHTFPAVLQSSGLYSLSSVVTVP SSSLGTQTYICNVNHKPSNTKVDKKVEPKSCDKT HTCPPCPAPELLGGPSVFLFPPKPKDTLMISRTP EVTCVVVDVSHEDPEVKFNWYVDGVEVHNAKTKP REEQYNSTYRVVSVLTVLHQDWLNGKEYKCKVSN KALPAPIEKTISKAKGQPREPQVYTLPPSRDELT KNQVSLTCLVKGFYPSDIAVEWESNGQPENNYKT TPPVLDSDGSFFLYSKLTVDKSRWQQGNVFSCSV MHEALHNHYTQK (SEQ ID NO: 42) |
| Heavy Chain masking sequence | QGASTSVDELQAEVDQLEDENYALKTKVAQLRKK VEKLGS (SEQ ID NO: 94) |
| Light Chain | QGASTTVAQLEEKVKTLRAENYELKSEVQRLEEQ VAQLGSIPVSLRSGEIVMTQSPDFQSVTPKEKVT LTCRASQTISDYLHWYQQKPDQSPKLLIKFASQS ISGVPSRFSGSGSGSDFTLTINSLEAEDAATYYC QNGHGFPRTFGQGTKLEIKRTVAAPSVFIFPPSD EQLKSGTASVVCLLNNFYPREAKVQWKVDNALQS GNSQESVTEQDSKDSTYSLSSTLTLSKADYEKHK VYACEVTHQGLSSPVTKSFNRGEC (SEQ ID NO: 43) |
| Light Chain masking sequence | QGASTTVAQLEEKVKTLRAENYELKSEVQRLEEQ VAQLGS (SEQ ID NO: 95) | hB6H12.1

In certain exemplary embodiments, an anti-CD47 antibody or antigen-binding fragment thereof comprises CDRs from a HCVR set forth as SEQ ID NO: 3 and/or CDRs from a LCVR set forth as SEQ ID NO: 11. In other embodiments, an anti-CD47 antibody or antigen-binding fragment thereof comprises heavy chain CDRs of SEQ ID NOs: 16, 17 and 18 and/or light chain CDRs of SEQ ID NOs: 31, 32 and 33. In some embodiments, an anti-CD47 antibody or antigen-binding fragment thereof comprises heavy chain CDRs of SEQ ID NOs: 25, 26 and 27 and/or light chain CDRs of SEQ ID NOs: 37, 38 and 39. In other embodiments, an anti-CD47 antibody or antigen-binding fragment thereof comprises the HCVR/LCVR pair SEQ ID NO: 3/SEQ ID NO: 11. In other embodiments, an anti-CD47 antibody or antigen-binding fragment thereof comprises a HCVR that has at least about 80% homology or identity (e.g., 80%, 85%, 90%, 91%, 92%, 93%, 94%, 95%, 96%, 97%, 98% or 99%) to SEQ ID NO: 3 and/or comprises a LCVR that has at least about 80% homology or identity (e.g., 80%, 85%, 90%, 91%, 92%, 93%, 94%, 95%, 96%, 97%, 98% or 99%) to SEQ ID NO: 11.

hB6H12.2

In certain exemplary embodiments, an anti-CD47 antibody or antigen-binding fragment thereof comprises CDRs from a HCVR set forth as SEQ ID NO: 3 and/or CDRs from a LCVR set forth as SEQ ID NO: 12. In other embodiments, an anti-CD47 antibody or antigen-binding fragment thereof comprises heavy chain CDRs of SEQ ID NOs: 16, 17 and 18 and/or light chain CDRs of SEQ ID NOs: 31, 32 and 33. In some embodiments, an anti-CD47 antibody or antigen-binding fragment thereof comprises heavy chain CDRs of SEQ ID NOs: 25, 26 and 27 and/or light chain CDRs of SEQ ID NOs: 37, 38 and 39. In other embodiments, an anti-CD47 antibody or antigen-binding fragment thereof comprises the HCVR/LCVR pair SEQ ID NO: 3/SEQ ID NO: 12. In other embodiments, an anti-CD47 antibody or antigen-binding fragment thereof comprises a HCVR that has at least about 80% homology or identity (e.g., 80%, 85%, 90%, 91%, 92%, 93%, 94%, 95%, 96%, 97%, 98% or 99%) to SEQ ID NO: 3 and/or comprises a LCVR that has at least about 80% homology or identity (e.g., 80%, 85%, 90%, 91%, 92%, 93%, 94%, 95%, 96%, 97%, 98% or 99%) to SEQ ID NO: 12.

hB6H12.3

In certain exemplary embodiments, an anti-CD47 antibody or antigen-binding fragment thereof comprises CDRs from a HCVR set forth as SEQ ID NO: 3 and/or CDRs from a LCVR set forth as SEQ ID NO: 13. In other embodiments, an anti-CD47 antibody or antigen-binding fragment thereof comprises heavy chain CDRs of SEQ ID NOs: 16, 17 and 18 and/or light chain CDRs of SEQ ID NOs: 31, 32 and 33. In some embodiments, an anti-CD47 antibody or antigen-binding fragment thereof comprises heavy chain CDRs of SEQ ID NOs: 25, 26 and 27 and/or light chain CDRs of SEQ ID NOs: 37, 38 and 39. In other embodiments, an anti-CD47 antibody or antigen-binding fragment thereof comprises the HCVR/LCVR pair SEQ ID NO: 3/SEQ ID NO: 13. In other embodiments, an anti-CD47 antibody or antigen-binding fragment thereof comprises a HCVR that has at least about 80% homology or identity (e.g., 80%, 85%, 90%, 91%, 92%, 93%, 94%, 95%, 96%, 97%, 98% or 99%) to SEQ ID NO: 3 and/or comprises a LCVR that has at least about 80% homology or identity (e.g., 80%, 85%, 90%, 91%, 92%, 93%, 94%, 95%, 96%, 97%, 98% or 99%) to SEQ ID NO: 13.

hB6H12.4

In certain exemplary embodiments, an anti-CD47 antibody or antigen-binding fragment thereof comprises CDRs from a HCVR set forth as SEQ ID NO: 3 and/or CDRs from a LCVR set forth as SEQ ID NO: 14. In other embodiments, an anti-CD47 antibody or antigen-binding fragment thereof comprises heavy chain CDRs of SEQ ID NOs: 16, 17 and 18 and/or light chain CDRs of SEQ ID NOs: 34, 35, and 33. In some embodiments, an anti-CD47 antibody or antigen-binding fragment thereof comprises heavy chain CDRs of SEQ ID NOs: 25, 26 and 27 and/or light chain CDRs of SEQ ID NOs: 40, 38 and 39. In other embodiments, an anti-CD47 antibody or antigen-binding fragment thereof comprises the HCVR/LCVR pair SEQ ID NO: 3/SEQ ID NO: 14. In other embodiments, an anti-CD47 antibody or antigen-binding fragment thereof comprises a HCVR that has at least about 80% homology or identity (e.g., 80%, 85%, 90%, 91%, 92%, 93%, 94%, 95%, 96%, 97%, 98% or 99%) to SEQ ID NO: 3 and/or comprises a LCVR that has at least about 80% homology or identity (e.g., 80%, 85%, 90%, 91%, 92%, 93%, 94%, 95%, 96%, 97%, 98% or 99%) to SEQ ID NO: 14.

hB6H12.5

In certain exemplary embodiments, an anti-CD47 antibody or antigen-binding fragment thereof comprises CDRs from a HCVR set forth as SEQ ID NO: 4 and/or CDRs from a LCVR set forth as SEQ ID NO: 11. In other embodiments, an anti-CD47 antibody or antigen-binding fragment thereof comprises heavy chain CDRs of SEQ ID NOs: 19, 20, and 18 and/or light chain CDRs of SEQ ID NOs: 31, 32 and 33. In some embodiments, an anti-CD47 antibody or antigen-binding fragment thereof comprises heavy chain CDRs of SEQ ID NOs: 28, 26 and 27 and/or light chain CDRs of SEQ ID NOs: 37, 38 and 39. In other embodiments, an anti-CD47 antibody or antigen-binding fragment thereof comprises the HCVR/LCVR pair SEQ ID NO: 4/SEQ ID NO: 11. In other embodiments, an anti-CD47 antibody or antigen-binding fragment thereof comprises a HCVR that has at least about 80% homology or identity (e.g., 80%, 85%, 90%, 91%, 92%, 93%, 94%, 95%, 96%, 97%, 98% or 99%) to SEQ ID NO: 4 and/or comprises a LCVR that has at least about 80% homology or identity (e.g., 80%, 85%, 90%, 91%, 92%, 93%, 94%, 95%, 96%, 97%, 98% or 99%) to SEQ ID NO: 11.

hB6H12.6

In certain exemplary embodiments, an anti-CD47 antibody or antigen-binding fragment thereof comprises CDRs from a HCVR set forth as SEQ ID NO: 4 and/or CDRs from a LCVR set forth as SEQ ID NO: 12. In other embodiments, an anti-CD47 antibody or antigen-binding fragment thereof comprises heavy chain CDRs of SEQ ID NOs: 19, 20, and 18 and/or light chain CDRs of SEQ ID NOs: 31, 32 and 33. In some embodiments, an anti-CD47 antibody or antigen-binding fragment thereof comprises heavy chain CDRs of SEQ ID NOs: 28, 26 and 27 and/or light chain CDRs of SEQ ID NOs: 37, 38 and 39. In other embodiments, an anti-CD47 antibody or antigen-binding fragment thereof comprises the HCVR/LCVR pair SEQ ID NO: 4/SEQ ID NO: 12. In other embodiments, an anti-CD47 antibody or antigen-binding fragment thereof comprises a HCVR that has at least about 80% homology or identity (e.g., 80%, 85%, 90%, 91%, 92%, 93%, 94%, 95%, 96%, 97%, 98% or 99%) to SEQ ID NO: 4 and/or comprises a LCVR that has at least about 80% homology or identity (e.g., 80%, 85%, 90%, 91%, 92%, 93%, 94%, 95%, 96%, 97%, 98% or 99%) to SEQ ID NO: 12.

hB6H12.7

In certain exemplary embodiments, an anti-CD47 antibody or antigen-binding fragment thereof comprises CDRs from a HCVR set forth as SEQ ID NO: 4 and/or CDRs from a LCVR set forth as SEQ ID NO: 13. In other embodiments, an anti-CD47 antibody or antigen-binding fragment thereof comprises heavy chain CDRs of SEQ ID NOs: 19, 20, and 18 and/or light chain CDRs of SEQ ID NOs: 31, 32 and 33. In some embodiments, an anti-CD47 antibody or antigen-binding fragment thereof comprises heavy chain CDRs of SEQ ID NOs: 28, 26 and 27 and/or light chain CDRs of SEQ ID NOs: 37, 38 and 39. In other embodiments, an anti-CD47 antibody or antigen-binding fragment thereof comprises the HCVR/LCVR pair SEQ ID NO: 4/SEQ ID NO: 13. In other embodiments, an anti-CD47 antibody or antigen-binding fragment thereof comprises a HCVR that has at least about 80% homology or identity (e.g., 80%, 85%, 90%, 91%, 92%, 93%, 94%, 95%, 96%, 97%, 98% or 99%) to SEQ ID NO: 4 and/or comprises a LCVR that has at least about 80% homology or identity (e.g., 80%, 85%, 90%, 91%, 92%, 93%, 94%, 95%, 96%, 97%, 98% or 99%) to SEQ ID NO: 13.

hB6H12.8

In certain exemplary embodiments, an anti-CD47 antibody or antigen-binding fragment thereof comprises CDRs from a HCVR set forth as SEQ ID NO: 4 and/or CDRs from a LCVR set forth as SEQ ID NO: 14. In other embodiments, an anti-CD47 antibody or antigen-binding fragment thereof comprises heavy chain CDRs of SEQ ID NOs: 19, 20, and 18 and/or light chain CDRs of SEQ ID NOs: 34, 35, and 33. In some embodiments, an anti-CD47 antibody or antigen-binding fragment thereof comprises heavy chain CDRs of SEQ ID NOs: 28, 26 and 27 and/or light chain CDRs of SEQ ID NOs: 40, 38 and 39. In other embodiments, an anti-CD47 antibody or antigen-binding fragment thereof comprises the HCVR/LCVR pair SEQ ID NO: 4/SEQ ID NO: 14. In other embodiments, an anti-CD47 antibody or antigen-binding fragment thereof comprises a HCVR that has at least about 80% homology or identity (e.g., 80%, 85%, 90%, 91%, 92%, 93%, 94%, 95%, 96%, 97%, 98% or 99%) to SEQ ID NO: 4 and/or comprises a LCVR that has at least about 80% homology or identity (e.g., 80%, 85%, 90%, 91%, 92%, 93%, 94%, 95%, 96%, 97%, 98% or 99%) to SEQ ID NO: 14.

hB6H12.9

In certain exemplary embodiments, an anti-CD47 antibody or antigen-binding fragment thereof comprises CDRs from a HCVR set forth as SEQ ID NO: 5 and/or CDRs from a LCVR set forth as SEQ ID NO: 11. In other embodiments, an anti-CD47 antibody or antigen-binding fragment thereof comprises heavy chain CDRs of SEQ ID NOs: 19, 20, and 18 and/or light chain CDRs of SEQ ID NOs: 31, 32 and 33. In some embodiments, an anti-CD47 antibody or antigen-binding fragment thereof comprises heavy chain CDRs of SEQ ID NOs: 28, 26 and 27 and/or light chain CDRs of SEQ ID NOs: 37, 38 and 39. In other embodiments, an anti-CD47 antibody or antigen-binding fragment thereof comprises the HCVR/LCVR pair SEQ ID NO: 5/SEQ ID NO: 11. In other embodiments, an anti-CD47 antibody or antigen-binding fragment thereof comprises a HCVR that has at least about 80% homology or identity (e.g., 80%, 85%, 90%, 91%, 92%, 93%, 94%, 95%, 96%, 97%, 98% or 99%) to SEQ ID NO: 5 and/or comprises a LCVR that has at least about 80% homology or identity (e.g., 80%, 85%, 90%, 91%, 92%, 93%, 94%, 95%, 96%, 97%, 98% or 99%) to SEQ ID NO: 11.

hB6H12.10

In certain exemplary embodiments, an anti-CD47 antibody or antigen-binding fragment thereof comprises CDRs from a HCVR set forth as SEQ ID NO: 5 and/or CDRs from a LCVR set forth as SEQ ID NO: 12. In other embodiments, an anti-CD47 antibody or antigen-binding fragment thereof comprises heavy chain CDRs of SEQ ID NOs: 19, 20, and 18 and/or light chain CDRs of SEQ ID NOs: 31, 32 and 33. In some embodiments, an anti-CD47 antibody or antigen-binding fragment thereof comprises heavy chain CDRs of SEQ ID NOs: 28, 26 and 27 and/or light chain CDRs of SEQ ID NOs: 37, 38 and 39. In other embodiments, an anti-CD47 antibody or antigen-binding fragment thereof comprises the HCVR/LCVR pair SEQ ID NO: 5/SEQ ID NO: 12. In other embodiments, an anti-CD47 antibody or antigen-binding fragment thereof comprises a HCVR that has at least about 80% homology or identity (e.g., 80%, 85%, 90%, 91%, 92%, 93%, 94%, 95%, 96%, 97%, 98% or 99%) to SEQ ID NO: 5 and/or comprises a LCVR that has at least about 80% homology or identity (e.g., 80%, 85%, 90%, 91%, 92%, 93%, 94%, 95%, 96%, 97%, 98% or 99%) to SEQ ID NO: 12.

hB6H12.11

In certain exemplary embodiments, an anti-CD47 antibody or antigen-binding fragment thereof comprises CDRs from a HCVR set forth as SEQ ID NO: 5 and/or CDRs from a LCVR set forth as SEQ ID NO: 13. In other embodiments, an anti-CD47 antibody or antigen-binding fragment thereof comprises heavy chain CDRs of SEQ ID NOs: 19, 20, and 18 and/or light chain CDRs of SEQ ID NOs: 31, 32 and 33. In some embodiments, an anti-CD47 antibody or antigen-binding fragment thereof comprises heavy chain CDRs of SEQ ID NOs: 28, 26 and 27 and/or light chain CDRs of SEQ ID NOs: 37, 38 and 39. In other embodiments, an anti-CD47 antibody or antigen-binding fragment thereof comprises the HCVR/LCVR pair SEQ ID NO: 5/SEQ ID NO: 13. In other embodiments, an anti-CD47 antibody or antigen-binding fragment thereof comprises a HCVR that has at least about 80% homology or identity (e.g., 80%, 85%, 90%, 91%, 92%, 93%, 94%, 95%, 96%, 97%, 98% or 99%) to SEQ ID NO: 5 and/or comprises a LCVR that has at least about 80% homology or identity (e.g., 80%, 85%, 90%, 91%, 92%, 93%, 94%, 95%, 96%, 97%, 98% or 99%) to SEQ ID NO: 13.

hB6H12.12

In certain exemplary embodiments, an anti-CD47 antibody or antigen-binding fragment thereof comprises CDRs from a HCVR set forth as SEQ ID NO: 5 and/or CDRs from a LCVR set forth as SEQ ID NO: 14. In other embodiments, an anti-CD47 antibody or antigen-binding fragment thereof comprises heavy chain CDRs of SEQ ID NOs: 19, 20, and 18 and/or light chain CDRs of SEQ ID NOs: 34, 35, and 33. In some embodiments, an anti-CD47 antibody or antigen-binding fragment thereof comprises heavy chain CDRs of SEQ ID NOs: 28, 26 and 27 and/or light chain CDRs of SEQ ID NOs: 40, 38 and 39. In other embodiments, an anti-CD47 antibody or antigen-binding fragment thereof comprises the HCVR/LCVR pair SEQ ID NO: 5/SEQ ID NO: 14. In other embodiments, an anti-CD47 antibody or antigen-binding fragment thereof comprises a HCVR that has at least about 80% homology or identity (e.g., 80%, 85%, 90%, 91%, 92%, 93%, 94%, 95%, 96%, 97%, 98% or 99%) to SEQ ID NO: 5 and/or comprises a LCVR that has at least about 80% homology or identity (e.g., 80%, 85%, 90%, 91%, 92%, 93%, 94%, 95%, 96%, 97%, 98% or 99%) to SEQ ID NO: 14.

hB6H12.13

In certain exemplary embodiments, an anti-CD47 antibody or antigen-binding fragment thereof comprises CDRs from a HCVR set forth as SEQ ID NO: 6 and/or CDRs from a LCVR set forth as SEQ ID NO: 11. In other embodiments, an anti-CD47 antibody or antigen-binding fragment thereof comprises heavy chain CDRs of SEQ ID NOs: 21, 22, and 18 and/or light chain CDRs of SEQ ID NOs: 31, 32 and 33. In some embodiments, an anti-CD47 antibody or antigen-binding fragment thereof comprises heavy chain CDRs of SEQ ID NOs: 29, 30 and 27 and/or light chain CDRs of SEQ ID NOs: 37, 38 and 39. In other embodiments, an anti-CD47 antibody or antigen-binding fragment thereof comprises the HCVR/LCVR pair SEQ ID NO: 6/SEQ ID NO: 11. In other embodiments, an anti-CD47 antibody or antigen-binding fragment thereof comprises a HCVR that has at least about 80% homology or identity (e.g., 80%, 85%, 90%, 91%, 92%, 93%, 94%, 95%, 96%, 97%, 98% or 99%) to SEQ ID NO: 6 and/or comprises a LCVR that has at least about 80% homology or identity (e.g., 80%, 85%, 90%, 91%, 92%, 93%, 94%, 95%, 96%, 97%, 98% or 99%) to SEQ ID NO: 11.

hB6H12.14

In certain exemplary embodiments, an anti-CD47 antibody or antigen-binding fragment thereof comprises CDRs from a HCVR set forth as SEQ ID NO: 6 and/or CDRs from a LCVR set forth as SEQ ID NO: 12. In other embodiments, an anti-CD47 antibody or antigen-binding fragment thereof comprises heavy chain CDRs of SEQ ID NOs: 21, 22, and 18 and/or light chain CDRs of SEQ ID NOs: 31, 32 and 33. In some embodiments, an anti-CD47 antibody or antigen-binding fragment thereof comprises heavy chain CDRs of SEQ ID NOs: 29, 30 and 27 and/or light chain CDRs of SEQ ID NOs: 37, 38 and 39. In other embodiments, an anti-CD47 antibody or antigen-binding fragment thereof comprises the HCVR/LCVR pair SEQ ID NO: 6/SEQ ID NO: 12. In other embodiments, an anti-CD47 antibody or antigen-binding fragment thereof comprises a HCVR that has at least about 80% homology or identity (e.g., 80%, 85%, 90%, 91%, 92%, 93%, 94%, 95%, 96%, 97%, 98% or 99%) to SEQ ID NO: 6 and/or comprises a LCVR that has at least about 80% homology or identity (e.g., 80%, 85%, 90%, 91%, 92%, 93%, 94%, 95%, 96%, 97%, 98% or 99%) to SEQ ID NO: 12.

hB6H12.15

In certain exemplary embodiments, an anti-CD47 antibody or antigen-binding fragment thereof comprises CDRs from a HCVR set forth as SEQ ID NO: 6 and/or CDRs from a LCVR set forth as SEQ ID NO: 13. In other embodiments, an anti-CD47 antibody or antigen-binding fragment thereof comprises heavy chain CDRs of SEQ ID NOs: 21, 22, and 18 and/or light chain CDRs of SEQ ID NOs: 31, 32 and 33. In some embodiments, an anti-CD47 antibody or antigen-binding fragment thereof comprises heavy chain CDRs of SEQ ID NOs: 29, 30 and 27 and/or light chain CDRs of SEQ ID NOs: 37, 38 and 39. In other embodiments, an anti-CD47 antibody or antigen-binding fragment thereof comprises the HCVR/LCVR pair SEQ ID NO: 6/SEQ ID NO: 13. In other embodiments, an anti-CD47 antibody or antigen-binding fragment thereof comprises a HCVR that has at least about 80% homology or identity (e.g., 80%, 85%, 90%, 91%, 92%, 93%, 94%, 95%, 96%, 97%, 98% or 99%) to SEQ ID NO: 6 and/or comprises a LCVR that has at least about 80% homology or identity (e.g., 80%, 85%, 90%, 91%, 92%, 93%, 94%, 95%, 96%, 97%, 98% or 99%) to SEQ ID NO: 13.

hB6H12.16

In certain exemplary embodiments, an anti-CD47 antibody or antigen-binding fragment thereof comprises CDRs from a HCVR set forth as SEQ ID NO: 6 and/or CDRs from a LCVR set forth as SEQ ID NO: 14. In other embodiments, an anti-CD47 antibody or antigen-binding fragment thereof comprises heavy chain CDRs of SEQ ID NOs: 21, 22, and 18 and/or light chain CDRs of SEQ ID NOs: 34, 35, and 33. In some embodiments, an anti-CD47 antibody or antigen-binding fragment thereof comprises heavy chain CDRs of SEQ ID NOs: 29, 30 and 27 and/or light chain CDRs of SEQ ID NOs: 40, 38 and 39. In other embodiments, an anti-CD47 antibody or antigen-binding fragment thereof comprises the HCVR/LCVR pair SEQ ID NO: 6/SEQ ID NO: 14. In other embodiments, an anti-CD47 antibody or antigen-binding fragment thereof comprises a HCVR that has at least about 80% homology or identity (e.g., 80%, 85%, 90%, 91%, 92%, 93%, 94%, 95%, 96%, 97%, 98% or 99%) to SEQ ID NO: 6 and/or comprises a LCVR that has at least about 80% homology or identity (e.g., 80%, 85%, 90%, 91%, 92%, 93%, 94%, 95%, 96%, 97%, 98% or 99%) to SEQ ID NO: 14.

hB6H12.17

In certain exemplary embodiments, an anti-CD47 antibody or antigen-binding fragment thereof comprises CDRs from a HCVR set forth as SEQ ID NO: 7 and/or CDRs from a LCVR set forth as SEQ ID NO: 11. In other embodiments, an anti-CD47 antibody or antigen-binding fragment thereof comprises heavy chain CDRs of SEQ ID NOs: 16, 20, and 18 and/or light chain CDRs of SEQ ID NOs: 31, 32 and 33. In some embodiments, an anti-CD47 antibody or antigen-binding fragment thereof comprises heavy chain CDRs of SEQ ID NOs: 25, 26 and 27 and/or light chain CDRs of SEQ ID NOs: 37, 38 and 39. In other embodiments, an anti-CD47 antibody or antigen-binding fragment thereof comprises the HCVR/LCVR pair SEQ ID NO: 7/SEQ ID NO: 11. In other embodiments, an anti-CD47 antibody or antigen-binding fragment thereof comprises a HCVR that has at least about 80% homology or identity (e.g., 80%, 85%, 90%, 91%, 92%, 93%, 94%, 95%, 96%, 97%, 98% or 99%) to SEQ ID NO: 7 and/or comprises a LCVR that has at least about 80% homology or identity (e.g., 80%, 85%, 90%, 91%, 92%, 93%, 94%, 95%, 96%, 97%, 98% or 99%) to SEQ ID NO: 11.

hB6H12.18

In certain exemplary embodiments, an anti-CD47 antibody or antigen-binding fragment thereof comprises CDRs from a HCVR set forth as SEQ ID NO: 7 and/or CDRs from a LCVR set forth as SEQ ID NO: 12. In other embodiments, an anti-CD47 antibody or antigen-binding fragment thereof comprises heavy chain CDRs of SEQ ID NOs: 16, 20, and 18 and/or light chain CDRs of SEQ ID NOs: 31, 32 and 33. In some embodiments, an anti-CD47 antibody or antigen-binding fragment thereof comprises heavy chain CDRs of SEQ ID NOs: 25, 26 and 27 and/or light chain CDRs of SEQ ID NOs: 37, 38 and 39. In other embodiments, an anti-CD47 antibody or antigen-binding fragment thereof comprises the HCVR/LCVR pair SEQ ID NO: 7/SEQ ID NO: 12. In other embodiments, an anti-CD47 antibody or antigen-binding fragment thereof comprises a HCVR that has at least about 80% homology or identity (e.g., 80%, 85%, 90%, 91%, 92%, 93%, 94%, 95%, 96%, 97%, 98% or 99%) to SEQ ID NO: 7 and/or comprises a LCVR that has at least about 80% homology or identity (e.g., 80%, 85%, 90%, 91%, 92%, 93%, 94%, 95%, 96%, 97%, 98% or 99%) to SEQ ID NO: 12.

hB6H12.19

In certain exemplary embodiments, an anti-CD47 antibody or antigen-binding fragment thereof comprises CDRs from a HCVR set forth as SEQ ID NO: 7 and/or CDRs from a LCVR set forth as SEQ ID NO: 13. In other embodiments, an anti-CD47 antibody or antigen-binding fragment thereof comprises heavy chain CDRs of SEQ ID NOs: 16, 20, and 18 and/or light chain CDRs of SEQ ID NOs: 31, 32 and 33. In some embodiments, an anti-CD47 antibody or antigen-binding fragment thereof comprises heavy chain CDRs of SEQ ID NOs: 25, 26 and 27 and/or light chain CDRs of SEQ ID NOs: 37, 38 and 39. In other embodiments, an anti-CD47 antibody or antigen-binding fragment thereof comprises the HCVR/LCVR pair SEQ ID NO: 7/SEQ ID NO: 13. In other embodiments, an anti-CD47 antibody or antigen-binding fragment thereof comprises a HCVR that has at least about 80% homology or identity (e.g., 80%, 85%, 90%, 91%, 92%, 93%, 94%, 95%, 96%, 97%, 98% or 99%) to SEQ ID NO: 7 and/or comprises a LCVR that has at least about 80% homology or identity (e.g., 80%, 85%, 90%, 91%, 92%, 93%, 94%, 95%, 96%, 97%, 98% or 99%) to SEQ ID NO: 13.

hB6H12.20

In certain exemplary embodiments, an anti-CD47 antibody or antigen-binding fragment thereof comprises CDRs from a HCVR set forth as SEQ ID NO: 7 and/or CDRs from a LCVR set forth as SEQ ID NO: 14. In other embodiments, an anti-CD47 antibody or antigen-binding fragment thereof comprises heavy chain CDRs of SEQ ID NOs: 16, 20, and 18 and/or light chain CDRs of SEQ ID NOs: 34, 35, and 33. In some embodiments, an anti-CD47 antibody or antigen-binding fragment thereof comprises heavy chain CDRs of SEQ ID NOs: 25, 26 and 27 and/or light chain CDRs of SEQ ID NOs: 40, 38 and 39. In other embodiments, an anti-CD47 antibody or antigen-binding fragment thereof comprises the HCVR/LCVR pair SEQ ID NO: 7/SEQ ID NO: 14. In other embodiments, an anti-CD47 antibody or antigen-binding fragment thereof comprises a HCVR that has at least about 80% homology or identity (e.g., 80%, 85%, 90%, 91%, 92%, 93%, 94%, 95%, 96%, 97%, 98% or 99%) to SEQ ID NO: 7 and/or comprises a LCVR that has at least about 80% homology or identity (e.g., 80%, 85%, 90%, 91%, 92%, 93%, 94%, 95%, 96%, 97%, 98% or 99%) to SEQ ID NO: 14.

hB6H12.21

In certain exemplary embodiments, an anti-CD47 antibody or antigen-binding fragment thereof comprises CDRs from a HCVR set forth as SEQ ID NO: 8 and/or CDRs from a LCVR set forth as SEQ ID NO: 11. In other embodiments, an anti-CD47 antibody or antigen-binding fragment thereof comprises heavy chain CDRs of SEQ ID NOs: 23, 24, and 18 and/or light chain CDRs of SEQ ID NOs: 31, 32 and 33. In some embodiments, an anti-CD47 antibody or antigen-binding fragment thereof comprises heavy chain CDRs of SEQ ID NOs: 29, 26 and 27 and/or light chain CDRs of SEQ ID NOs: 37, 38 and 39. In other embodiments, an anti-CD47 antibody or antigen-binding fragment thereof comprises the HCVR/LCVR pair SEQ ID NO: 8/SEQ ID NO: 11. In other embodiments, an anti-CD47 antibody or antigen-binding fragment thereof comprises a HCVR that has at least about 80% homology or identity (e.g., 80%, 85%, 90%, 91%, 92%, 93%, 94%, 95%, 96%, 97%, 98% or 99%) to SEQ ID NO: 8 and/or comprises a LCVR that has at least about 80% homology or identity (e.g., 80%, 85%, 90%, 91%, 92%, 93%, 94%, 95%, 96%, 97%, 98% or 99%) to SEQ ID NO: 11.

hB6H12.22

In certain exemplary embodiments, an anti-CD47 antibody or antigen-binding fragment thereof comprises CDRs from a HCVR set forth as SEQ ID NO: 8 and/or CDRs from a LCVR set forth as SEQ ID NO: 12. In other embodiments, an anti-CD47 antibody or antigen-binding fragment thereof comprises heavy chain CDRs of SEQ ID NOs: 23, 24, and 18 and/or light chain CDRs of SEQ ID NOs: 31, 32 and 33. In some embodiments, an anti-CD47 antibody or antigen-binding fragment thereof comprises heavy chain CDRs of SEQ ID NOs: 29, 26 and 27 and/or light chain CDRs of SEQ ID NOs: 37, 38 and 39. In other embodiments, an anti-CD47 antibody or antigen-binding fragment thereof comprises the HCVR/LCVR pair SEQ ID NO: 8/SEQ ID NO: 12. In other embodiments, an anti-CD47 antibody or antigen-binding fragment thereof comprises a HCVR that has at least about 80% homology or identity (e.g., 80%, 85%, 90%, 91%, 92%, 93%, 94%, 95%, 96%, 97%, 98% or 99%) to SEQ ID NO: 8 and/or comprises a LCVR that has at least about 80% homology or identity (e.g., 80%, 85%, 90%, 91%, 92%, 93%, 94%, 95%, 96%, 97%, 98% or 99%) to SEQ ID NO: 12.

hB6H12.23

In certain exemplary embodiments, an anti-CD47 antibody or antigen-binding fragment thereof comprises CDRs from a HCVR set forth as SEQ ID NO: 8 and/or CDRs from a LCVR set forth as SEQ ID NO: 13. In other embodiments, an anti-CD47 antibody or antigen-binding fragment thereof comprises heavy chain CDRs of SEQ ID NOs: 23, 24, and 18 and/or light chain CDRs of SEQ ID NOs: 31, 32 and 33. In some embodiments, an anti-CD47 antibody or antigen-binding fragment thereof comprises heavy chain CDRs of SEQ ID NOs: 29, 26 and 27 and/or light chain CDRs of SEQ ID NOs: 37, 38 and 39. In other embodiments, an anti-CD47 antibody or antigen-binding fragment thereof comprises the HCVR/LCVR pair SEQ ID NO: 8/SEQ ID NO: 13. In other embodiments, an anti-CD47 antibody or antigen-binding fragment thereof comprises a HCVR that has at least about 80% homology or identity (e.g., 80%, 85%, 90%, 91%, 92%, 93%, 94%, 95%, 96%, 97%, 98% or 99%) to SEQ ID NO: 8 and/or comprises a LCVR that has at least about 80% homology or identity (e.g., 80%, 85%, 90%, 91%, 92%, 93%, 94%, 95%, 96%, 97%, 98% or 99%) to SEQ ID NO: 13.

hB6H12.24

In certain exemplary embodiments, an anti-CD47 antibody or antigen-binding fragment thereof comprises CDRs from a HCVR set forth as SEQ ID NO: 8 and/or CDRs from a LCVR set forth as SEQ ID NO: 14. In other embodiments, an anti-CD47 antibody or antigen-binding fragment thereof comprises heavy chain CDRs of SEQ ID NOs: 23, 24, and 18 and/or light chain CDRs of SEQ ID NOs: 34, 35, and 33. In some embodiments, an anti-CD47 antibody or antigen-binding fragment thereof comprises heavy chain CDRs of SEQ ID NOs: 29, 26 and 27 and/or light chain CDRs of SEQ ID NOs: 40, 38 and 39. In other embodiments, an anti-CD47 antibody or antigen-binding fragment thereof comprises the HCVR/LCVR pair SEQ ID NO: 8/SEQ ID NO: 14. In other embodiments, an anti-CD47 antibody or antigen-binding fragment thereof comprises a HCVR that has at least about 80% homology or identity (e.g., 80%, 85%, 90%, 91%, 92%, 93%, 94%, 95%, 96%, 97%, 98% or 99%) to SEQ ID NO: 8 and/or comprises a LCVR that has at least about 80% homology or identity (e.g., 80%, 85%, 90%, 91%, 92%, 93%, 94%, 95%, 96%, 97%, 98% or 99%) to SEQ ID NO: 14.

hB6H12.3 G91A

In certain exemplary embodiments, an anti-CD47 antibody or antigen-binding fragment thereof comprises CDRs from a HCVR set forth as SEQ ID NO: 3 and/or CDRs from a LCVR set forth as SEQ ID NO: 15. In other embodiments, an anti-CD47 antibody or antigen-binding fragment thereof comprises heavy chain CDRs of SEQ ID NOs: 16, 17 and 18 and/or light chain CDRs of SEQ ID NOs: 34, 35 and 36. In some embodiments, an anti-CD47 antibody or antigen-binding fragment thereof comprises heavy chain CDRs of SEQ ID NOs: 25, 26 and 27 and/or light chain CDRs of SEQ ID NOs: 40, 38 and 41. In other embodiments, an anti-CD47 antibody or antigen-binding fragment thereof comprises the HCVR/LCVR pair SEQ ID NO: 3/SEQ ID NO: 15. In other embodiments, an anti-CD47 antibody or antigen-binding fragment thereof comprises a HCVR that has at least about 80% homology or identity (e.g., 80%, 85%, 90%, 91%, 92%, 93%, 94%, 95%, 96%, 97%, 98% or 99%) to SEQ ID NO: 3 and/or comprises a LCVR that has at least about 80% homology or identity (e.g., 80%, 85%, 90%, 91%, 92%, 93%, 94%, 95%, 96%, 97%, 98% or 99%) to SEQ ID NO: 15.

Ab47

In certain exemplary embodiments, an anti-CD47 antibody or antigen-binding fragment thereof comprises CDRs from a HCVR set forth as SEQ ID NO: 2 and/or CDRs from a LCVR set forth as SEQ ID NO: 10. In other embodiments, an anti-CD47 antibody or antigen-binding fragment thereof comprises heavy chain CDRs of SEQ ID NOs: 16, 17 and 18 and/or light chain CDRs of SEQ ID NOs: 31, 32 and 33. In some embodiments, an anti-CD47 antibody or antigen-binding fragment thereof comprises heavy chain CDRs of SEQ ID NOs: 25, 26 and 27 and/or light chain CDRs of SEQ ID NOs: 37, 38 and 39. In other embodiments, an anti-CD47 antibody or antigen-binding fragment thereof comprises the HCVR/LCVR pair SEQ ID NO: 2/SEQ ID NO: 10. In other embodiments, an anti-CD47 antibody or antigen-binding fragment thereof comprises a HCVR that has at least about 80% homology or identity (e.g., 80%, 85%, 90%, 91%, 92%, 93%, 94%, 95%, 96%, 97%, 98% or 99%) to SEQ ID NO: 2 and/or comprises a LCVR that has at least about 80% homology or identity (e.g., 80%, 85%, 90%, 91%, 92%, 93%, 94%, 95%, 96%, 97%, 98% or 99%) to SEQ ID NO: 10.

mB6H12

In certain exemplary embodiments, an anti-CD47 antibody or antigen-binding fragment thereof comprises CDRs from a HCVR set forth as SEQ ID NO: 1 and/or CDRs from a LCVR set forth as SEQ ID NO: 9. In other embodiments, an anti-CD47 antibody or antigen-binding fragment thereof comprises heavy chain CDRs of SEQ ID NOs: 16, 17 and 18 and/or light chain CDRs of SEQ ID NOs: 31, 32 and 33. In some embodiments, an anti-CD47 antibody or antigen-binding fragment thereof comprises heavy chain CDRs of SEQ ID NOs: 25, 26 and 27 and/or light chain CDRs of SEQ ID NOs: 37, 38 and 39. In other embodiments, an anti-CD47 antibody or antigen-binding fragment thereof comprises the HCVR/LCVR pair SEQ ID NO: 1/SEQ ID NO: 9. In other embodiments, an anti-CD47 antibody or antigen-binding fragment thereof comprises a HCVR that has at least about 80% homology or identity (e.g., 80%, 85%, 90%, 91%, 92%, 93%, 94%, 95%, 96%, 97%, 98% or 99%) to SEQ ID NO: 1 and/or comprises a LCVR that has at least about 80% homology or identity (e.g., 80%, 85%, 90%, 91%, 92%, 93%, 94%, 95%, 96%, 97%, 98% or 99%) to SEQ ID NO: 9.

Anti-CD47 antibodies and antigen-binding fragments thereof described herein can be expressed in a modified form. For instance, a region of additional amino acids, particularly charged amino acids, can be added to the N-terminus of an anti-CD47 antibody or an antigen-binding fragment thereof to improve stability and persistence in the host cell, during purification, or during subsequent handling and storage. Also, peptide moieties can be added to an anti-CD47 antibody or an antigen-binding fragment thereof of the present invention to facilitate purification. Such regions can be removed prior to final preparation of an antibody molecule or at least one fragment thereof. Such methods are described in many standard laboratory manuals, such as Sambrook, supra; Ausubel, et al., ed., Current Protocols In Molecular Biology, John Wiley & Sons, Inc., NY, N.Y. (1987-2001).

The anti-CD47 antibodies or antigen-binding fragments thereof described herein typically bind CD47 with an equilibrium binding constant of ≤1 µM, e.g., ≤100 nM, preferably ≤10 nM, and more preferably ≤1 nM, as measured using standard binding assays, for example, the Biacore-based binding assay.

Antibody molecules of the present invention may be characterized relative to a reference anti-CD47 antibody, for example, B6H12, 2D3, MABL, CC2C6, or BRIC126. Antibody B6H12 is described, for example, in U.S. Pat. Nos. 5,057,604 and 9,017,675, is commercially available from Abcam, PLC, Santa Cruz Biotechnology, Inc., and eBioscience, Inc.

Glycosylation Variants

Anti-CD47 antibodies and antigen-binding fragments thereof may be glycosylated at conserved positions in their constant regions (Jefferis and Lund, (1997) Chem. Immunol. 65:111-128; Wright and Morrison, (1997) TibTECH 15:26-32). The oligosaccharide side chains of the immunoglobulins affect the protein's function (Boyd et al., (1996) Mol. Immunol. 32:1311-1318; Wittwe and Howard, (1990) Biochem. 29:4175-4180), and the intramolecular interaction between portions of the glycoprotein which can affect the conformation and presented three-dimensional surface of the glycoprotein (Jefferis and Lund, supra; Wyss and Wagner, (1996) Current Op. Biotech. 7:409-416). Oligosaccharides may also serve to target a given glycoprotein to certain molecules based upon specific recognition structures. For example, it has been reported that in agalactosylated IgG, the oligosaccharide moiety 'flips' out of the inter-CH2 space and terminal N-acetylglucosamine residues become available to bind mannose binding protein (Malhotra et al., (1995) Nature Med. 1:237-243). Removal by glycopeptidase of the oligosaccharides from CAMPATH-1H (a recombinant humanized murine monoclonal IgG1 antibody which recognizes the CDw52 antigen of human lymphocytes) produced in Chinese Hamster Ovary (CHO) cells resulted in a complete reduction in complement mediated lysis (CMCL) (Boyd et al., (1996) Mol. Immunol. 32:1311-1318), while selective removal of sialic acid residues using neuraminidase resulted in no loss of DMCL. Glycosylation of antibodies has also been reported to affect antibody-dependent cellular cytotoxicity (ADCC). In particular, CHO cells with tetracycline-regulated expression of α(1,4)-N-acetylglucosaminyltransferase III (GnTIII), a glycosyltransferase catalyzing formation of bisecting GlcNAc, was reported to have improved ADCC activity (Umana et al. (1999) Mature Biotech. 17:176-180).

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Glycosylation variants of antibodies are variants in which the glycosylation pattern of an antibody is altered. By altering is meant deleting one or more carbohydrate moieties found in the antibody, adding one or more carbohydrate moieties to the antibody, changing the composition of glycosylation (glycosylation pattern), the extent of glycosylation, etc.

Addition of glycosylation sites to an anti-CD47 antibody or an antigen-binding fragment thereof can be accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites). Similarly, removal of glycosylation sites can be accomplished by amino acid alteration within the native glycosylation sites of the antibody.

The amino acid sequence is usually altered by altering the underlying nucleic acid sequence. These methods include isolation from a natural source (in the case of naturally-occurring amino acid sequence variants) or preparation by oligonucleotide-mediated (or site-directed) mutagenesis, PCR mutagenesis, and cassette mutagenesis of an earlier prepared variant or a non-variant version of the antibody.

The glycosylation (including glycosylation pattern) of antibodies may also be altered without altering the amino acid sequence or the underlying nucleotide sequence. Glycosylation largely depends on the host cell used to express the antibody. Since the cell type used for expression of recombinant glycoproteins, e.g., antibodies, as potential therapeutics is rarely the native cell, significant variations in the glycosylation pattern of the antibodies can be expected. See, e.g., Hse et al., (1997) J. Biol. Chem. 272:9062-9070. In addition to the choice of host cells, factors which affect glycosylation during recombinant production of antibodies include growth mode, media formulation, culture density, oxygenation, pH, purification schemes and the like. Various methods have been proposed to alter the glycosylation pattern achieved in a particular host organism including introducing or overexpressing certain enzymes involved in oligosaccharide production (U.S. Pat. Nos. 5,047,335; 5,510,261; 5,278,299). Glycosylation, or certain types of glycosylation, can be enzymatically removed from the glycoprotein, for example using endoglycosidase H (Endo H). In addition, the recombinant host cell can be genetically engineered, e.g., make defective in processing certain types of polysaccharides. These and similar techniques are well known in the art.

The glycosylation structure of antibodies can be readily analyzed by conventional techniques of carbohydrate analysis, including lectin chromatography, NMR, Mass spectrometry, HPLC, GPC, monosaccharide compositional analysis, sequential enzymatic digestion, and HPAEC-PAD, which uses high pH anion exchange chromatography to separate oligosaccharides based on charge. Methods for releasing oligosaccharides for analytical purposes are also known, and include, without limitation, enzymatic treatment (commonly performed using peptide-N-glycosidase F/endo-β-galactosidase), elimination using harsh alkaline environment to release mainly O-linked structures, and chemical methods using anhydrous hydrazine to release both N- and O-linked oligosaccharides.

A preferred form of modification of glycosylation of antibodies is reduced core fucosylation. "Core fucosylation" refers to addition of fucose ("fucosylation") to N-acetylglucosamine ("GlcNAc") at the reducing terminal of an N-linked glycan.

A "complex N-glycoside-linked sugar chain" is typically bound to asparagine 297 (according to the number of Kabat). As used herein, the complex N-glycoside-linked sugar chain has a biantennary composite sugar chain, mainly having the following structure:

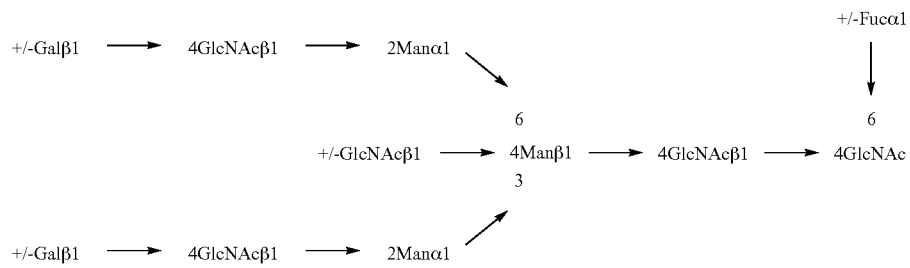

where +/− indicates the sugar molecule can be present or absent, and the numbers indicate the position of linkages between the sugar molecules. In the above structure, the sugar chain terminal which binds to asparagine is called a reducing terminal (at right), and the opposite side is called a non-reducing terminal. Fucose is usually bound to N-acetylglucosamine ("GlcNAc") of the reducing terminal, typically by an α1,6 bond (the 6-position of GlcNAc is linked to the 1-position of fucose). "Gal" refers to galactose, and "Man" refers to mannose.

A "complex N-glycoside-linked sugar chain" includes 1) a complex type, in which the non-reducing terminal side of the core structure has one or more branches of galactose-N-acetylglucosamine (also referred to as "gal-GlcNAc") and the non-reducing terminal side of Gal-GlcNAc optionally has a sialic acid, bisecting N-acetylglucosamine or the like; or 2) a hybrid type, in which the non-reducing terminal side of the core structure has both branches of a high mannose N-glycoside-linked sugar chain and complex N-glycoside-linked sugar chain.

In some embodiments, the "complex N-glycoside-linked sugar chain" includes a complex type in which the non-reducing terminal side of the core structure has zero, one or more branches of galactose-N-acetylglucosamine (also referred to as "gal-GlcNAc") and the non-reducing terminal side of Gal-GlcNAc optionally further has a structure such as a sialic acid, bisecting N-acetylglucosamine or the like.

According to the present methods, typically only a minor amount of fucose is incorporated into the complex N-glycoside-linked sugar chain(s) of humanized or chimeric antibodies. For example, in various embodiments, less than about 60%, less than about 50%, less than about 40%, less than about 30%, less than about 20%, less than about 15%, less than about 10%, less than about 5%, or less than about 3% of the molecules of an antibody have core fucosylation by fucose. In some embodiments, about 2% of the molecules of the antibody has core fucosylation by fucose.

In certain embodiments, only a minor amount of a fucose analog (or a metabolite or product of the fucose analog) is incorporated into the complex N-glycoside-linked sugar chain(s). For example, in various embodiments, less than about 60%, less than about 50%, less than about 40%, less than about 30%, less than about 20%, less than about 15%, less than about 10%, less than about 5%, or less than about 3% of humanized or chimeric antibodies have core fucosylation by a fucose analog or a metabolite or product of the fucose analog. In some embodiments, about 2% of humanized or chimeric antibodies have core fucosylation by a fucose analog or a metabolite or product of the fucose analog.

Methods of making non-fucosylated antibodies by incubating antibody-producing cells with a fucose analogue are described, e.g., in WO2009/135181. Briefly, cells that have been engineered to express humanized or chimeric antibodies antibody are incubated in the presence of a fucose analogue or an intracellular metabolite or product of the fucose analog. An intracellular metabolite can be, for example, a GDP-modified analog or a fully or partially de-esterified analog. A product can be, for example, a fully or partially de-esterified analog. In some embodiments, a fucose analogue can inhibit an enzyme(s) in the fucose salvage pathway. For example, a fucose analog (or an intracellular metabolite or product of the fucose analog) can inhibit the activity of fucokinase, or GDP-fucose-pyrophosphorylase. In some embodiments, a fucose analog (or an intracellular metabolite or product of the fucose analog) inhibits fucosyltransferase (preferably a 1,6-fucosyltransferase, e.g., the FUT8 protein). In some embodiments, a fucose analog (or an intracellular metabolite or product of the fucose analog) can inhibit the activity of an enzyme in the de novo synthetic pathway for fucose. For example, a fucose analog (or an intracellular metabolite or product of the fucose analog) can inhibit the activity of GDP-mannose 4,6-dehydratase or/or GDP-fucose synthetase. In some embodiments, the fucose analog (or an intracellular metabolite or product of the fucose analog) can inhibit a fucose transporter (e.g., GDP-fucose transporter).

In one embodiment, the fucose analogue is 2-flurofucose. Methods of using fucose analogues in growth medium and other fucose analogues are disclosed, e.g., in WO/2009/135181, which is herein incorporated by reference.

Other methods for engineering cell lines to reduce core fucosylation included gene knock-outs, gene knock-ins and RNA interference (RNAi). In gene knock-outs, the gene encoding FUT8 (alpha 1,6-fucosyltransferase enzyme) is inactivated. FUT8 catalyzes the transfer of a fucosyl residue from GDP-fucose to position 6 of Asn-linked (N-linked) GlcNac of an N-glycan. FUT8 is reported to be the only enzyme responsible for adding fucose to the N-linked biantennary carbohydrate at Asn297. Gene knock-ins add genes encoding enzymes such as GNTIII or a Golgi alpha mannosidase II. An increase in the levels of such enzymes in cells diverts monoclonal antibodies from the fucosylation pathway (leading to decreased core fucosylation), and having increased amount of bisecting N-acetylglucosamines. RNAi typically also targets FUT8 gene expression, leading to decreased mRNA transcript levels or knocking out gene expression entirely. Any of these methods can be used to generate a cell line that would be able to produce a non-fucosylated antibody, e.g., a humanized or chimeric antibody.

Many methods are available to determine the amount of fucosylation on an antibody. Methods include, e.g., LC-MS via PLRP-S chromatography and electrospray ionization quadrupole TOF MS.

Coiled Coil Masking Agents

In certain embodiments of the invention, an anti-CD47 antibody or antigen-binding fragment thereof is associated with a coiled coil masking agent (also referred to as a "coiled coil masking domain" or a "masking domain") that prevents binding of the anti-CD47 antibody or antigen-binding fragment thereof to CD47. In various embodiments, an anti-CD47 antibody or antigen-binding fragment thereof associated with a masking domain is referred to as a "masked antibody."

A coiled coil is a structural motif in proteins and peptides in which two or more alpha-helices wind around each other to form a supercoil. There can be two, three or four helices in a coiled coil bundle and the helices can either run in the same (parallel) or in the opposite (antiparallel) directions.

Coiled coils typically comprise sequence elements of three and four residues whose hydrophobicity pattern and residue composition are compatible with the structure of amphipathic alpha-helices. The alternating three and four residue sequence elements constitute heptad repeats in which the amino-acids are designated 'a,' 'b,' 'c,' 'd,' 'e,' 'f' and 'g.' Residues in positions 'a' and 'd' are generally hydrophobic and form a zig-zag pattern of knobs and holes that interlock with a similar pattern on another strand to form a tight-fitting hydrophobic core. Of the remaining residues, 'b,' 'c' and 'f' tend to be charged. Therefore, the formation of a heptad repeat depends on the physical properties of hydrophobicity and charge that are required at a particular position, not on a specific amino acid. In certain exemplary embodiments, coiled coils of the present invention are formed from two coiled coil-forming peptides.

Examples of consensus formulae for heptad repeats in coiled coil-forming peptides are provided by WO2011034605, incorporated herein by reference in its entirety for all purposes.

Exemplary consensus formulae according to certain embodiments are set forth below:

Formula 1: (X1, X2, X3, X4, X5, X6, X7)n, wherein:
X1 is a hydrophobic amino acid or asparagine;
X2, X3 and X6 are any amino acid;
X4 is a hydrophobic amino acid;
X5 and X7 are each a charged amino acid residue; and
n is a positive integer.
Formula 2: (X1', X2', X3', X4', X5, X6, X7)n, wherein:
X1' is a hydrophobic amino acid or asparagine;
X2', X'3 and X'6 are each any amino acid residue;
X4' is hydrophobic amino acid;
X5' and X7' are each a charged amino acid residue;
wherein n in formula 1 and 2 is greater or equal to 2; and
n is a positive integer.

In certain embodiments in which peptides of Formula 1 and Formula 2 form a coiled coil, X5 of Formula 1 is opposite in charge to X'7 of Formula 2, and X7 or Formula 1 is opposite in charge to X'S of Formula 2. Heptad repeats within a coiled coil forming peptide can be the same or different from each other while conforming to Formula 1 and/or 2.

Coiled coils can be homodimeric or heterodimeric. Examples of peptides that can form coiled coil according to certain exemplary embodiments are shown in Table 8. The peptide sequences can be used as is, or their components can be used in other combinations. For example, the Vel coiled coil-forming peptide can be used with other linker sequences. Sequences shown for light chains can also be used with heavy chains and vice versa.

In certain exemplary embodiments, a bivalent antibody comprising two light and heavy chain pairs is provided, wherein the N-termini of one or more of the light chains and/or the heavy chains are linked via linkers comprising a protease cleavage site to coiled coil-forming peptides that associate to form a coiled coil, reducing binding affinity of the light and heavy chain pair to a target. Optionally, the peptides associate without forming a disulfide bridge.

Optionally, the two light and heavy chain pairs are the same. Optionally, the two light and heavy chain pairs are different. Optionally, the light chains include a light chain variable region and light chain constant region and the heavy chains include a heavy chain variable region and heavy chain constant region. Optionally, the heavy chain region includes CH1, hinge, CH2 and CH3 regions. Optionally, the two light chain are linked to a first heterologous peptide and the two heavy chains to a second heterologous peptide.

Optionally, the protease cleavage site is an MMP1 or MMP2 cleavage site.

Optionally, the target is CD47.

Optionally, antigen binding is reduced at least 100-fold by the presence of a masking agent (e.g., a coiled coil masking agent). Optionally, antigen binding is reduced 200-1500-fold by the presence of a masking agent (e.g., a coiled coil masking agent). Optionally, cytotoxicity of the conjugate is reduced at least 100-fold by the presence of a masking agent (e.g., a coiled coil masking agent). Optionally, cytotoxicity of the conjugate is reduced at least 200-1500-fold by the presence of a masking agent (e.g., a coiled coil masking agent).

Optionally, the coiled coil forming peptides are linked to the N-termini of the heavy and light chains in the same orientation. Optionally, the coiled coil-forming peptides are linked to the N-termini of the heavy and light chains in opposing orientations. Optionally, multiple copies of the coiled coil forming peptide are linked in tandem to the N-termini of the heavy and light chains.

Exemplary coiled coil-forming peptides linkers and protease sites according to certain embodiments of the invention are shown in FIG. 34.

According to certain exemplary embodiments, a peptide comprising or consisting of SEQ ID NO: 51 (Vel LC in Table 8) is used to provide a linker including a protease cleavage site and a coiled coil-forming peptide linked to the N-terminus of the light chain, and a peptide of sequence SEQ ID NO: 50 (Vel HC in Table 8) to provide a linker including a protease cleavage site and the coiled coil forming peptide linked to the N-terminus of the heavy chain, or vice versa. Peptides comprising these sequences can be linked to any of the antibodies disclosed herein.

In certain exemplary embodiments, amino acid substitutions in a variant peptide that forms a coiled coil are conservative substitutions. In other exemplary embodiments, a repeating heptad pattern is retained in a variant peptide whereby a coiled coil forming peptide can be subdivided into contiguous heptad segments conforming to a formula categorizing amino acids occupying positions in the formula by amino acid type, such as in Formula 1 and/or in Formula 2. In certain embodiments, there are no more than 1 or 2 substitutions per heptad of amino acids, and any such substitutions are conservative. In other embodiments, a variant can have at least about 80%, 81%, 82%, 83%, 84%, 85%, 86%, 87%, 88%, 89%, 90%, 91%, 92%, 93%, 94%, 95%, 96%, 97%, 98% or 99% sequence identity to a coiled coil-forming peptide described herein, and be capable of forming a coiled coil.

Exemplary peptides that form coiled coils are set forth at Table 8A and Table 8B.

TABLE 8A

Masking domain sequences according to certain exemplary embodiments. Cleavage sequences are underlined.

| Masking Peptide | Sequence |
|---|---|
| A2B1 HC | GASTSVDELQAEVDQLQDENYALKTKVAQLRKKVEKL SEGGGGGPLGVRGGGGS (SEQ ID NO: 44) |
| A2B1 LC | GASTTVAQLRERVKTLRAQNYELESEVQRLREQVAQL ASGGGGGPLGVRGGGGS (SEQ ID NO: 45) |
| M11 HC | LEIEAAFLERENTALETRVAELRQRVQRARNRVSQYR TRYGGGGGPLGVRGGGGS (SEQ ID NO: 46) |
| M11 LC | LEIRAAFLRQRNTALRTEVAELEQEVQRLENEVSQYE TRYGGGGGPLGVRGGGGS (SEQ ID NO: 47) |
| M15 HC | LEIRAAFLRRRNTALRTRVAELRQRVQRLRNIVSQYE TRYGGGGGGPLGVRGGGGS (SEQ ID NO: 48) |
| M15 LC | LEIEAAFLEQENTALETEVAELEQEVQRLENIVSQYE TRYGGGGGGPLGVRGGGGS (SEQ ID NO: 49) |
| Vel HC | GASTSVDELQAEVDQLEDENYALKTKVAQLRKKVEKL GSIPVSLRSG (SEQ ID NO: 50) |
| Vel LC | GASTTVAQLEEKVKTLRAENYELKSEVQRLEEQVAQL GSIPVSLRSG (SEQ ID NO: 51) |
| Fos-Jun HC | GALTDTLQAETDQLEDKKSALQTEIANLLKEKEKLEF ILAAHGGGGGPLGVRGGGGS (SEQ ID NO: 52) |
| Fos-Jun LC | GARIARLEEKVKTLKAQNSELASTANMLREQVAQLKQ KVMNYGGGGGPLGVRGGGGS (SEQ ID NO: 53) |
| A4B4 HC | GKIAALKQKIAALKYKNAALKKKIAALKQGGGGGPLG VRGGGS (SEQ ID NO: 54) |
| A4B4 LC | GEIAALEQEIAALEKENAALEWEIAALEQGGGGGPLG VRGGGS (SEQ ID NO: 55) |

TABLE 8B

Masking domain sequences according to certain exemplary embodiments. Cleavage sequences are underlined. EAC residues are included.

| Masking Peptide | Sequence |
|---|---|
| CA2B1 HC | EACGASTSVDELQAEVDQLQDENYALKTKVAQLRKKV EKLSEGGGGGPLGVRGGGGS (SEQ ID NO: 75) |
| CA2B1 LC | EACGASTTVAQLRERVKTLRAQNYELESEVQRLREQV AQLASGGGGGPLGVRGGGGS (SEQ ID NO: 76) |
| CM11 HC | EACLEIEAAFLERENTALETRVAELRQRVQRARNRVS QYRTRYGGGGGPLGVRGGGGS (SEQ ID NO: 77) |
| CM11 LC | EACLEIRAAFLRQRNTALRTEVAELEQEVQRLENEVS QYETRYGGGGGPLGVRGGGGS (SEQ ID NO: 78) |
| CM15 HC | EACLEIRAAFLRRRNTALRTRVAELRQRVQRLRNIVS QYETRYGGGGGGPLGVRGGGGS (SEQ ID NO: 79) |
| CM15 LC | EACLEIEAAFLEQENTALETEVAELEQEVQRLENIVS QYETRYGGGGGGPLGVRGGGGS (SEQ ID NO: 80) |
| CVel HC | EACGASTSVDELQAEVDQLEDENYALKTKVAQLRKKV EKLGSIPVSLRSG (SEQ ID NO: 81) |
| CVel LC | EACGASTTVAQLEEKVKTLRAENYELKSEVQRLEEQV |

TABLE 8B-continued

Masking domain sequences according to certain exemplary embodiments. Cleavage sequences are underlined. EAC residues are included.

| Masking Peptide | Sequence |
|---|---|
| | AQLGSIPVSLRSG (SEQ ID NO: 82) |
| CFos-Jun HC | EACGALTDTLQAETDQLEDKKSALQTEIANLLKEKEK LEFILAAHGGGGGPLGVRGGGGS (SEQ ID NO: 83) |
| CFos-Jun LC | EACGARIARLEEKVKTLKAQNSELASTANMLREQVAQ LKQKVMNYGGGGGPLGVRGGGGS (SEQ ID NO: 84) |
| CA4B4 HC | EACGKIAALKQKIAALKYKNAALKKKIAALKQGGGGG PLGVRGGGGS (SEQ ID NO: 85) |
| CA4B4 LC | EACGEIAALEQEIAALEKENAALEWEIAALEQGGGGG PLGVRGGGGS (SEQ ID NO: 86) |

Linkers and Cleavage Sites

In certain embodiments of the invention, a linker is used to bind a coiled coil masking agent to an anti-CD47 antibody or antigen-binding fragment thereof. The linkers can be any segments of amino acids conventionally used as linker for joining peptide domains. Suitable linkers can vary in length, such as from 1-20, 2-15, 3-12, 4-10, 5, 6, 7, 8, 9 or 10. Some such linkers include a segment of polyglycine. Some such linkers include one or more serine residues, often at positions flanking the glycine residues. Other linkers include one or more alanine residues. Glycine and glycine-serine polymers are relatively unstructured, and therefore may be able to serve as a neutral tether between components. Glycine accesses significantly more phi-psi space than even alanine, and is much less restricted than residues with longer side chains (see Scheraga, Rev. Computational Chem. 11173-142 (1992)). Some exemplary linkers are in the form S(G)nS, wherein n is from 5-20. Other exemplary linkers are (G)n, glycine-serine polymers (including, for example, (GS)n, (GSGGS)n [(GSGGS) is SEQ ID NO: 59) and (GGGS)n, [(GGGS) is SEQ ID NO: 60) where n is an integer of at least one), glycine-alanine polymers, alanine-serine polymers, and other flexible linkers known in the art. Some examples of linkers are Ser-(Gly)10-Ser (SEQ ID NO: 61), Gly-Gly-Ala-Ala (SEQ ID NO: 62), Gly-Gly-Gly-Gly-Ser (SEQ ID NO: 63), Leu-Ala-Ala-Ala-Ala (SEQ ID NO: 64), Gly-Gly-Ser-Gly (SEQ ID NO: 65), Gly-Gly-Ser-Gly-Gly (SEQ ID NO: 66), Gly-Ser-Gly-Ser-Gly (SEQ ID NO: 67), Gly-Ser-Gly-Gly-Gly (SEQ ID NO: 68), Gly-Gly-Gly-Ser-Gly (SEQ ID NO: 69), Gly-Ser-Ser-Ser-Gly (SEQ ID NO: 70), and the like.

The protease site is preferably recognized and cleaved by a protease expressed extracellularly so it contacts a masked antibody, releasing the masked antibody and allowing it to contact its target, such as a receptor extracellular domain or soluble ligand. Several matrix metalloproteinase sites (MMP1-28) are suitable. MMPs play a role in tissue remodeling and are implicated in neoplastic processes such as morphogenesis, angiogenesis and metastasis. Some exemplary protease sites are PLG-XXX (SEQ ID NO: 71), a well-known endogenous sequence for MMPs, PLG-VR (SEQ ID NO: 72) (WO2014193973) and IPVSLRSG (SEQ ID NO: 73) (Turk et al., Nat. Biotechnol., 2001, 19, 661-667), LSGRSDNY (SEQ ID NO: 74) (Cytomyx) and GPLGVR (SEQ ID NO: 57) (Chang et al., Clin. Cancer Res. 2012 Jan. 1; 18(1):238-47). Additional examples of MMPs are provided in US 2013/0309230, WO 2009/025846, WO 2010/081173, WO 2014/107599, WO 2015/048329, US 20160160263, and Ratnikov et al., Proc. Natl. Acad. Sci. USA, 111: E4148-E4155 (2014).

TABLE 9

Protease cleavage sequences. The MMP-cleavage site is indicated by * while the uPA/matriptase/legumain cleavage sites are indicated by **.

| Cleavage Site Name | Sequence |
|---|---|
| M2 | GPLG*VR** (SEQ ID NO: 57) |
| IPV | IPVS*LR**SG (SEQ ID NO: 58) |

Linking Coiled Coil Masking Agents to Anti-CD47 Antibodies

Coiled coils forming peptides are linked to the N-termini of antibody variable regions via a linker including a protease site. A typical antibody includes a heavy and light chain variable region, in which case a coiled coil forming peptide is linked to the N-termini of each. A bivalent antibody has two binding sites, which may or may not be the same. In a normal monospecific antibody, the binding sites are the same and the antibody has two identical light and heavy chain pairs. In this case, each heavy chain is linked to the same coiled coil forming peptide and each light chain to the same coiled coil forming peptide (which may or may not be the same as the peptide linked to the heavy chain). In a bispecific antibody, the binding sites are different and formed from two different heavy and light chain pairs. In such a case, the heavy and light chain variable region of one binding site are respectively linked to coiled coil forming peptides as are the heavy and light chain variable regions of the other binding site. Typically both heavy chain variable regions are linked to the same type of coiled coil forming peptide as are both light chain variable regions.

A coiled coil-forming peptide can be linked to an antibody variable region via a linker including a protease site. Typically, the same linker with the same protease cleavage site is used for linking each heavy or light chain variable region of an antibody to a coiled coil peptide. The protease cleavage site should be one amenable to cleavage by a protease present extracellularly in the intended target tissue or pathology, such as a cancer, such that cleavage of the linker releases the antibody from the coiled coil masking its activity allowing the antibody to bind to its intended target, such as a cell-surface antigen or soluble ligand.

As well as the variable regions, a masked antibody typically includes all or part of a constant region, which can include any or all of a light chain constant region, CH1, hinge, CH2 and CH3 regions. As with other antibodies one or more C-terminal residues can be proteolytically processed or derivatized.

Coiled coils can be formed from the same peptide forming a homodimer or two different peptides forming a heterodimer. For formation of a homodimer, light and heavy antibody chains are linked to the same coiled coil forming peptide. For formation of a heterodimer, light and heavy antibody chains are linked to different coiled coils peptides. For some pairs of coiled coil forming peptides, it is preferred that one of the pair be linked to the heavy chain and the other to the light chain of an antibody although the reverse orientation is also possible.

Each antibody chain can be linked to a single coiled coil forming peptide or multiple such peptides in tandem (e.g., two, three, four or five copies of a peptide). If the latter, the peptides in tandem linkage are usually the same. Also if tandem linkage is employed, light and heavy chains are usually linked to the same number of peptides.

Linkage of antibody chains to coiled coil forming peptides can reduce the binding affinity of an antibody by at least about 10-fold, about 50-fold, about 100-fold, about 200-fold, about 500-fold, about 1000-fold or about 1500-fold relative to the same antibody without such linkage or after cleavage of such linkage. In some such antibodies, binding affinity is reduced between about 50-1500-fold, between about 100-1500-fold, between about 200-1500-fold, between about 500-1500-fold, between about 50-1000-fold, between about 100-1000-fold, between about 200-1000-fold, between about 500-1000-fold, between about 50-500-fold, or between about 100-500-fold. Effector functions of the antibody, such as ADCC, phagocytosis, and CDC or cytotoxicity as a result of linkage to a drug in an antibody drug conjugate can be reduced by the same factors or ranges. Upon proteolytic cleavage that serves to unmask an antibody or otherwise remove the mask from the antibody, the restored antibody typically has an affinity or effect function that is within a factor of 2, 1.5 or preferably unchanged within experimental error compared with an otherwise identical control antibody, which has never been masked.

Antibody-Drug Conjugates

In certain embodiments, the anti-CD47 antibodies of the invention can be combined with antibody drug conjugates (ADCs). Particular ADCs may comprise cytotoxic agents (e.g., chemotherapeutic agents), prodrug converting enzymes, radioactive isotopes or compounds, or toxins (these moieties being collectively referred to as a therapeutic agent). For example, an ADC can be conjugated to a cytotoxic agent such as a chemotherapeutic agent, or a toxin (e.g., a cytostatic or cytocidal agent such as, for example, abrin, ricin A, pseudomonas exotoxin, or diphtheria toxin). Examples of useful classes of cytotoxic agents include, for example, DNA minor groove binders, DNA alkylating agents, and tubulin inhibitors. Exemplary cytotoxic agents include, for example, auristatins, camptothecins, calicheamicins, duocarmycins, etoposides, maytansinoids (e.g., DM1, DM2, DM3, DM4), taxanes, benzodiazepines (e.g., pyrrolo[1,4]benzodiazepines, indolinobenzodiazepines, and oxazolidinobenzodiazepines including pyrrolo[1,4]benzodiazepine dimers, indolinobenzodiazepine dimers, and oxazolidinobenzodiazepine dimers) and vinca alkaloids.

An ADC can be conjugated to a pro-drug converting enzyme. The pro-drug converting enzyme can be recombinantly fused to the antibody or chemically conjugated thereto using known methods. Exemplary pro-drug converting enzymes are carboxypeptidase G2, beta-glucuronidase, penicillin-V-amidase, penicillin-G-amidase, β-lactamase, β-glucosidase, nitroreductase and carboxypeptidase A.

Techniques for conjugating therapeutic agents to proteins, and in particular to antibodies, are well-known. (See, e.g., Alley et al., Current Opinion in Chemical Biology 2010 14: 1-9; Senter, Cancer J., 2008, 14(3): 154-169.) The therapeutic agent can be conjugated in a manner that reduces its activity unless it is cleaved off the antibody (e.g., by hydrolysis, by proteolytic degradation, or by a cleaving agent). In some aspects, the therapeutic agent is attached to the antibody with a cleavable linker that is sensitive to cleavage in the intracellular environment of the CD47-expressing cancer cell but is not substantially sensitive to the extracellular environment, such that the conjugate is cleaved from the antibody when it is internalized by the CD47-expressing cancer cell (e.g., in the endosomal or, for example by virtue of pH sensitivity or protease sensitivity, in the lysosomal environment or in the caveolear environment). In some embodiments, the therapeutic agent can also be attached to the antibody with a non-cleavable linker.

In certain exemplary embodiments, an ADC can include a linker region between a cytotoxic or cytostatic agent and the antibody. As noted supra, typically, the linker can be cleavable under intracellular conditions, such that cleavage of the linker releases the therapeutic agent from the antibody in the intracellular environment (e.g., within a lysosome or endosome or caveolea). The linker can be, e.g., a peptidyl linker that is cleaved by an intracellular peptidase or protease enzyme, including a lysosomal or endosomal protease. Cleaving agents can include cathepsins B and D and plasmin (see, e.g., Dubowchik and Walker, Pharm. Therapeutics 83:67-123, 1999). Most typical are peptidyl linkers that are cleavable by enzymes that are present in CD47-expressing cells. For example, a peptidyl linker that is cleavable by the thiol-dependent protease cathepsin-B, which is highly expressed in cancerous tissue, can be used (e.g., a linker comprising a Phe-Leu or a Val-Cit peptide).

A cleavable linker can be pH-sensitive, i.e., sensitive to hydrolysis at certain pH values. Typically, the pH-sensitive linker is hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used. (See, e.g., U.S. Pat. Nos. 5,122,368; 5,824,805; 5,622,929; Dubowchik and Walker, Pharm. Therapeutics 83:67-123, 1999; Neville et al, Biol. Chem. 264: 14653-14661, 1989.) Such linkers are relatively stable under neutral pH conditions, such as those in the blood, but are unstable at below pH 5.5 or 5.0, the approximate pH of the lysosome.

Other linkers are cleavable under reducing conditions (e.g., a disulfide linker). Disulfide linkers include those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio)toluene), SPDB and SMPT. (See, e.g., Thorpe et al., Cancer Res. 47:5924-5931, 1987; Wawrzynczak et al., In Immunoconjugates: Antibody Conjugates in Radioimagery and Therapy of Cancer (C. W. Vogel ed., Oxford U. Press, 1987. See also U.S. Pat. No. 4,880,935.)

The linker can also be a malonate linker (Johnson et al, Anticancer Res. 15: 1387-93, 1995), a maleimidobenzoyl linker (Lau et al., Bioorg-Med-Chem. 3: 1299-1304, 1995), or a 3'-N-amide analog (Lau et al., Bioorg-Med-Chem. 3: 1305-12, 1995).

The linker also can be a non-cleavable linker, such as an maleimido-alkylene or maleimide-aryl linker that is directly attached to the therapeutic agent and released by proteolytic degradation of the antibody.

Typically, the linker is not substantially sensitive to the extracellular environment, meaning that no more than about 20%, typically no more than about 15%, more typically no more than about 10%, and even more typically no more than about 5%, no more than about 3%, or no more than about 1% of the linkers in a sample of the ADC is cleaved when the ADC is present in an extracellular environment (e.g., in plasma). Whether a linker is not substantially sensitive to the extracellular environment can be determined, for example, by incubating independently with plasma both (a) the ADC (the "ADC sample") and (b) an equal molar amount of unconjugated antibody or therapeutic agent (the "control sample") for a predetermined time period (e.g., 2, 4, 8, 16, or 24 hours) and then comparing the amount of unconjugated antibody or therapeutic agent present in the ADC sample with that present in control sample, as measured, for example, by high performance liquid chromatography.

The linker can also promote cellular internalization. The linker can promote cellular internalization when conjugated to the therapeutic agent (i.e., in the milieu of the linker-therapeutic agent moiety of the ADC or ADC derivate as described herein). Alternatively, the linker can promote cellular internalization when conjugated to both the therapeutic agent and the antibody (i.e., in the milieu of the ADC as described herein).

The antibody can be conjugated to the linker via a heteroatom of the antibody. These heteroatoms can be present on the antibody in its natural state or can be introduced into the antibody. In some aspects, the antibody will be conjugated to the linker via a nitrogen atom of a lysine residue. In other aspects, the antibody will be conjugated to the linker via a sulfur atom of a cysteine residue. Methods of conjugating linker and drug-linkers to antibodies are known in the art.

Exemplary antibody-drug conjugates include auristatin based antibody-drug conjugates meaning that the drug component is an auristatin drug. Auristatins bind tubulin, have been shown to interfere with microtubule dynamics and nuclear and cellular division, and have anticancer activity. Typically the auristatin based antibody-drug conjugate comprises a linker between the auristatin drug and the anti-CD47 antibody. The linker can be, for example, a cleavable linker (e.g., a peptidyl linker) or a non-cleavable linker (e.g., linker released by degradation of the antibody). Auristatins include MMAF, and MMAE. The synthesis and structure of exemplary auristatins are described in U.S. Pat. Nos. 7,659,241, 7,498,298, 2009-0111756, 2009-0018086, and 7,968, 687 each of which is incorporated herein by reference in its entirety and for all purposes.

Other exemplary antibody-drug conjugates include maytansinoid antibody-drug conjugates meaning that the drug component is a maytansinoid drug, and benzodiazepine antibody drug conjugates meaning that the drug component is a benzodiazepine (e.g., pyrrolo[1,4]benzodiazepine dimers, indolinobenzodiazepine dimers, and oxazolidino-benzodiazepine dimers).

In certain embodiments, the anti-CD47 antibody of the invention may be combined with an ADC with binding specificity to a different target. Exemplary ADCs that may be combined with the anti-CD47 antibody include brentuximab vedotin (anti-CD30 ADC), enfortumab vedotin (anti-nectin-4 ADC), ladiratuzumab vedotin (anti-LIV-1 ADC), denintuzumab mafodotin (anti-CD19 ADC), glembatumumab vedotin (anti-GPNMB ADC), anti-TIM-1 ADC, polatuzumab vedotin (anti-CD79b ADC), anti-MUC16 ADC, depatuxizumab mafodotin, telisotuzumab vedotin, anti-PSMA ADC, anti-C4.4a ADC, anti-BCMA ADC, anti-AXL ADC, tisotuumab vedotin (anti-tissue factor ADC).

Antibody Molecule Expression

Nucleic acids of the present invention can be expressed in a host cell that contains endogenous DNA encoding an antibody or masked antibody of the present invention. Such methods are well known in the art, e.g., as described in U.S. Pat. Nos. 5,580,734, 5,641,670, 5,733,746, and 5,733,761. Also see, e.g., Sambrook, et al., supra, and Ausubel, et al., supra. Those of ordinary skill in the art are knowledgeable in the numerous expression systems available for expression of a nucleic acid encoding a protein of the present invention. Illustrative of cell cultures useful for the production of the antibodies, masked antibodies, specified portions or variants thereof, are mammalian cells. Mammalian cell systems often will be in the form of monolayers of cells although mammalian cell suspensions or bioreactors can also be used. A number of suitable host cell lines capable of expressing intact glycosylated proteins have been developed in the art, and include the COS-1 (e.g., ATCC CRL 1650), COS-7 (e.g., ATCC CRL-1651), HEK293, BHK21 (e.g., ATCC CRL-10), CHO (e.g., ATCC CRL 1610) and BSC-1 (e.g., ATCC CRL-26) cell lines, hep G2 cells, P3X63Ag8.653, SP2/0-Ag14, HeLa cells and the like, which are readily available from, for example, American Type Culture Collection, Manassas, VA Yeast and bacterial host cells may also be used and are well known to those of skill in the art. Other cells useful for production of nucleic acids or proteins of the present invention are known and/or available, for instance, from the American Type Culture Collection Catalogue of Cell Lines and hybridomas or other known or commercial sources.

Expression vectors can include one or more of the following expression control sequences, such as, but not limited to an origin of replication; a promoter (e.g., late or early SV40 promoters, the CMV promoter (U.S. Pat. Nos. 5,168, 062; 5,385,839), an HSV tk promoter, a pgk (phosphoglycerate kinase) promoter, an EF-1 alpha promoter (U.S. Pat. No. 5,266,491), at least one human immunoglobulin promoter; an enhancer, and/or processing information sites, such as ribosome binding sites, RNA splice sites, polyadenylation sites (e.g., an SV40 large T Ag poly A addition site), and transcriptional terminator sequences). See, e.g., Ausubel et al., supra; Sambrook, et al., supra.

Expression vectors optionally include at least one selectable marker. Such markers include, e.g., but are not limited to, methotrexate (MTX), dihydrofolate reductase (DHFR, U.S. Pat. Nos. 4,399,216; 4,634,665; 4,656,134; 4,956,288; 5,149,636; 5,179,017), ampicillin, neomycin (G418), mycophenolic acid, or glutamine synthetase (GS, U.S. Pat. Nos. 5,122,464; 5,770,359; and 5,827,739), resistance for eukaryotic cell culture, and tetracycline or ampicillin resistance genes for culturing in E. coli and other bacteria or prokaryotes. Appropriate culture media and conditions for the above-described host cells are known in the art. Suitable vectors will be readily apparent to the skilled artisan. Introduction of a vector construct into a host cell can be effected by calcium phosphate transfection, DEAE-dextran mediated transfection, cationic lipid-mediated transfection, electroporation, transduction, infection or other known methods. Such methods are described in the art, such as Sambrook, supra; Ausubel, supra.

The nucleic acid insert should be operatively linked to an appropriate promoter. The expression constructs will further contain sites for transcription initiation, termination and, in the transcribed region, a ribosome binding site for translation. The coding portion of the mature transcripts expressed by the constructs will preferably include a translation initiating at the beginning and a termination codon (e.g., UAA, UGA or UAG) appropriately positioned at the end of the mRNA to be translated, with UAA and UAG preferred for mammalian or eukaryotic cell expression.

The nucleic acid insert is optionally in frame with a coiled coil sequence and/or an MMP cleavage sequence, e.g., at the N-terminus of one or more heavy chain and/or light chain sequences. Alternatively, a coiled coil sequence and/or an MMP cleavage sequence can be post-translationally added to an antibody or antigen-binding fragment thereof, e.g., via a disulfide bond or the like.

When eukaryotic host cells are employed, polyadenylation or transcription terminator sequences are typically incorporated into the vector. An example of a terminator sequence is the polyadenylation sequence from the bovine growth hormone gene. Sequences for accurate splicing of the transcript can also be included. An example of a splicing sequence is the VP1 intron from SV40 (Sprague, et al. (1983) J. Virol. 45:773-781). Additionally, gene sequences to control replication in the host cell can be incorporated into the vector, as known in the art.

Antibody Isolation and Purification

Anti-CD47 antibodies or masked antibodies described herein can be recovered and purified from recombinant cell cultures by well-known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography (HPLC) can also be employed for purification. See, e.g., Colligan, Current Protocols in Immunology, or Current Protocols in Protein Science, John Wiley & Sons, New York, N.Y., (1997-2001).

Antibodies and masked antibodies described herein can include purified products, products of chemical synthetic procedures, and products produced by recombinant techniques from a eukaryotic host, including, for example, yeast, higher plant, insect and mammalian cells. Depending upon the host employed in a recombinant production procedure, the antibody or masked antibody of the present invention can be glycosylated or can be non-glycosylated, with glycosylated preferred. Such methods are described in many standard laboratory manuals, such as Sambrook, supra; Ausubel, supra, Colligan, Protein Science, supra.

Nucleic Acid Molecules

Nucleic acid molecules of the present invention can be in the form of RNA, such as mRNA, hnRNA, tRNA or any other form, or in the form of DNA, including, but not limited to, cDNA and genomic DNA obtained by cloning or produced synthetically, or any combinations thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand.

Isolated nucleic acid molecules of the present invention can include nucleic acid molecules comprising an open reading frame (ORF), optionally with one or more introns, e.g., but not limited to, at least one specified portion of at least one CDR, as CDR1, CDR2 and/or CDR3 of at least one heavy chain or light chain; nucleic acid molecules comprising the coding sequence for an anti-CD47 antibody or masked antibody, or an anti-CD47 antibody or masked antibody variable region; and nucleic acid molecules which comprise a nucleotide sequence substantially different from those described above but which, due to the degeneracy of the genetic code, still encode at least one anti-CD47 antibody or masked antibody as described herein and/or as known in the art. Given that the genetic code is well-known in the art, it is routine for one skilled in the art to generate such degenerate nucleic acid variants that code for specific anti-CD47 antibodies or masked antibodies of the present invention.

As indicated herein, nucleic acid molecules of the present invention which comprise a nucleic acid encoding an anti-CD47 antibody molecule can include, but are not limited to, those encoding the amino acid sequence of an antibody fragment, by itself; the coding sequence for the entire antibody or a portion thereof; the coding sequence for an antibody, fragment or portion, as well as additional sequences, such as one or both of a masking agent (e.g., a coiled coil masking agent) and/or an MMP cleavage sequence, or such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, non-translated sequences that play a role in transcription, mRNA processing, including splicing and polyadenylation signals (for example—ribosome binding and stability of mRNA); an additional coding sequence that codes for additional amino acids, such as those that provide additional functionalities. In some embodiments, the sequence encoding an antibody can be fused to a marker sequence, such as a sequence encoding a peptide that facilitates purification of the fused antibody comprising an antibody fragment or portion.

Construction of Nucleic Acids

The isolated nucleic acids of the present invention can be made using (a) recombinant methods, (b) synthetic techniques, (c) purification techniques, or combinations thereof, as well-known in the art. The nucleic acids can conveniently comprise sequences in addition to a polynucleotide of the present invention. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the present invention. For example, a hexa-histidine marker sequence provides a convenient means to purify the proteins of the present invention. The nucleic acid of the present invention—excluding the coding sequence—is optionally a vector, adapter, or linker for cloning and/or expression of a polynucleotide of the present invention. Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra.)

The isolated nucleic acid compositions of this invention, such as RNA, cDNA, genomic DNA, or any combination thereof, can be obtained from biological sources using any number of cloning methodologies known to those of skill in the art. In some embodiments, oligonucleotide probes that selectively hybridize, under stringent conditions, to the polynucleotides of the present invention are used to identify the desired sequence in a cDNA or genomic DNA library. The isolation of RNA, and construction of cDNA and genomic libraries, is well known to those of ordinary skill in the art. (See, e.g., Ausubel, supra; or Sambrook, supra.)

III. Therapeutic Applications

The invention provides methods of treating disorders associated with cells that express CD47, e.g., cancers. The cells may or may not express elevated levels of CD47 relative to cells that are not associated with a disorder of interest. As a result, the invention provides a method of treating a subject, for example, a subject with a cancer, using the anti-CD47 antibodies or masked antibodies described herein. The method comprises administering an effective amount of an anti-CD47 antibody or masked antibody or a composition comprising an anti-CD47 antibody or masked antibody to a subject in need thereof.

As used herein, the terms "subject" and "patient" refer to organisms to be treated by the methods of the present invention. Such organisms preferably include, but are not limited to, mammals (e.g., murines, simians, equines, bovines, porcines, canines, felines, and the like), and more preferably includes humans. As used herein, the terms, "treat," "treatment" and "treating" includes any effect, e.g., lessening, reducing, modulating, ameliorating or eliminating, that results in the improvement of the condition, disease, disorder, and the like, or ameliorating a symptom thereof, such as for example, reduced number of cancer cells, reduced tumor size, reduced rate of cancer cell infiltration into peripheral organs, or reduced rate of tumor metastasis or tumor growth.

Positive therapeutic effects in cancer can be measured in a number of ways (See, W. A. Weber, J. Null. Med. 50:1S-10S (2009); Eisenhauer et al., supra). In some preferred embodiments, response to an anti-CD47 antibody or masked antibody is assessed using RECIST 1.1 criteria. In some embodiments, the treatment achieved by a therapeutically effective amount is any of a partial response (PR), a complete response (CR), progression free survival (PFS), disease free survival (DFS), objective response (OR) or overall survival (OS). The dosage regimen of a therapy described herein that is effective to treat a primary or a secondary hepatic cancer patient may vary according to factors such as the disease state, age, and weight of the patient, and the ability of the therapy to elicit an anti-cancer response in the subject. While an embodiment of the treatment method, medicaments and uses of the present invention may not be effective in achieving a positive therapeutic effect in every subject, it should do so in a statistically significant number of subjects as determined by any statistical test known in the art such as the Student's t-test, the chi2-test, the U-test according to Mann and Whitney, the Kruskal-Wallis test (H-test), Jonckheere-Terpstra-test and the Wilcoxon-test.

"RECIST 1.1 Response Criteria" as used herein means the definitions set forth in Eisenhauer et al., E. A. et al., Eur. J Cancer 45:228-247 (2009) for target lesions or non-target lesions, as appropriate, based on the context in which response is being measured.

"Tumor" as it applies to a subject diagnosed with, or suspected of having, a primary or a secondary hepatic cancer, refers to a malignant or potentially malignant neoplasm or tissue mass of any size. A solid tumor is an abnormal growth or mass of tissue that usually does not contain cysts or liquid areas. Different types of solid tumors are named for the type of cells that form them. Examples of solid tumors are sarcomas, carcinomas, and lymphomas. Leukemias (cancers of the blood) generally do not form solid tumors (National Cancer Institute, Dictionary of Cancer Terms). Nonlimiting exemplary sarcomas include soft tissue sarcoma and osteosarcoma.

"Tumor burden" also referred to as "tumor load," refers to the total amount of tumor material distributed throughout the body. Tumor burden refers to the total number of cancer cells or the total size of tumor(s) throughout the body, including lymph nodes and bone narrow. Tumor burden can be determined by a variety of methods known in the art, such as, e.g., by measuring the dimensions of tumor(s) upon removal from the subject, e.g., using calipers, or while in the body using imaging techniques, e.g., ultrasound, bone scan, computed tomography (CT) or magnetic resonance imaging (MM) scans.

The term "tumor size" refers to the total size of the tumor which can be measured as the length and width of a tumor. Tumor size may be determined by a variety of methods known in the art, such as, e.g. by measuring the dimensions of tumor(s) upon removal from the subject, e.g., using calipers, or while in the body using imaging techniques, e.g., bone scan, ultrasound, CT or MRI scans.

As used herein, the term "effective amount" refers to the amount of a compound (e.g., an anti-CD47 antibody or masked antibody) sufficient to effect beneficial or desired results. An effective amount can be administered in one or more administrations, applications or dosages and is not intended to be limited to a particular formulation or administration route. Generally, a therapeutically effective amount of active component is in the range of 0.1 mg/kg to 100 mg/kg, e.g., 1 mg/kg to 100 mg/kg, 1 mg/kg to 10 mg/kg. The dosage administered can vary depending upon known factors, such as the pharmacodynamic characteristics of the particular agent, and its mode and route of administration; the age, health, and weight of the recipient; the type and extent of disease or indication to be treated, the nature and extent of symptoms, kind of concurrent treatment, frequency of treatment, and the effect desired. The initial dosage can be increased beyond the upper level in order to rapidly achieve the desired blood-level or tissue-level. Alternatively, the initial dosage can be smaller than the optimum, and the daily dosage may be progressively increased during the course of treatment. Human dosage can be optimized, e.g., in a conventional Phase I dose escalation study designed to run from 0.5 mg/kg to 20 mg/kg. Dosing frequency can vary, depending on factors such as route of administration, dosage amount, serum half-life of the antibody, and the disease being treated. Exemplary dosing frequencies are once per day, once per week and once every two weeks. Formulation of monoclonal antibody-based drugs is within ordinary skill in the art. In some embodiments, a monoclonal antibody is lyophilized, and then reconstituted in buffered saline, at the time of administration.

In certain exemplary embodiments, the present invention provides a method for treating cancer in a cell, tissue, organ, animal or patient. In particular embodiments, the present invention provides a method for treating a solid cancer in a human. Exemplary cancers are those that possess CD47 expression in a cell having the cancer (i.e., "CD47-expressing cancers"). Examples of cancers include, but are not limited to, solid tumors, soft tissue tumors, hematopoietic tumors that give rise to solid tumors, and metastatic lesions. Examples of hematopoietic tumors that have the potential to give rise to solid tumors include, but are not limited to, diffuse large B-cell lymphomas (DLBCL), follicular lymphoma, myelodysplastic syndrome (MDS), a lymphoma, Hodgkin's disease, a malignant lymphoma, non-Hodgkin's lymphoma, Burkitt's lymphoma, multiple myeloma, Richter's Syndrome (Richter's Transformation) and the like. Examples of solid tumors include, but are not limited to, malignancies, e.g., sarcomas (including soft tissue sarcoma and osteosarcoma), adenocarcinomas, and carcinomas, of the various organ systems, such as those affecting head and neck (including pharynx), thyroid, lung (small cell or non-small cell lung carcinoma (NSCLC)), breast, lymphoid, gastrointestinal tract (e.g., oral, esophageal, stomach, liver, pancreas, small intestine, colon and rectum, anal canal), genitals and genitourinary tract (e.g., renal, urothelial, bladder, ovarian, uterine, cervical, endometrial, prostate, testicular), central nervous system (e.g., neural or glial cells, e.g., neuroblastoma or glioma), skin (e.g., melanoma) and the like. In certain embodiments, the solid tumor is an NMDA receptor positive teratoma. In other embodiments, the cancer is selected from breast cancer, colon cancer, pancreatic cancer (e.g., a pancreatic neuroendocrine tumors (PNET) or a pancreatic ductal adenocarcinoma (PDAC)), stomach cancer, uterine cancer, and ovarian cancer.

In certain embodiments, the cancer is selected from, but not limited to, leukemia's such as acute lymphoblastic leukemia (ALL), chronic lymphocytic leukemia (CLL), acute myelogenous leukemia (AML), chronic myelogenous leukemia (CIVIL), hairy cell leukemia (HCL), T-cell prolymphocytic leukemia (T-PLL), large granular lymphocytic leukemia, adult T-cell leukemia, and acute monocytic leukemia (AMoL).

In one embodiment, the cancer is a solid tumor that is associated with ascites. Ascites is a symptom of many types of cancer and can also be caused by a number of conditions, such as advanced liver disease. The types of cancer that are likely to cause ascites include, but are not limited to, cancer of the breast, lung, large bowel (colon), stomach, pancreas, ovary, uterus (endometrium), peritoneum and the like. In some embodiments, the solid tumor associated with ascites is selected from breast cancer, colon cancer, pancreatic cancer, stomach, uterine cancer, and ovarian cancer. In some embodiments, the cancer is associated with pleural effusions, e.g., lung cancer.

Additional hematological cancers that give rise to solid tumors include, but are not limited to, non-Hodgkin lymphoma (e.g., diffuse large B cell lymphoma, mantle cell lymphoma, B lymphoblastic lymphoma, peripheral T cell lymphoma and Burkitt's lymphoma), B-lymphoblastic lymphoma; B-cell chronic lymphocytic leukemia/small lymphocytic lymphoma; lymphoplasmacytic lymphoma; splenic marginal zone B-cell lymphoma (±villous lymphocytes); plasma cell myeloma/plasmacytoma; extranodal marginal zone B-cell lymphoma of the MALT type; nodal marginal zone B-cell lymphoma (±monocytoid B cells); follicular lymphoma; diffuse large B-cell lymphomas; Burkitt's lymphoma; precursor T-lymphoblastic lymphoma; T adult T-cell lymphoma (HTLV 1-positive); extranodal NK/T-cell lymphoma, nasal type; enteropathy-type T-cell lymphoma; hepatosplenic γ-δ T-cell lymphoma; subcutaneous panniculitis-like T-cell lymphoma; mycosis fungoides/sezary syndrome; anaplastic large cell lymphoma, T/null cell, primary cutaneous type; anaplastic large cell lymphoma, T-/null-cell, primary systemic type; peripheral T-cell lymphoma, not otherwise characterized; angioimmunoblastic T-cell lymphoma, multiple myeloma, polycythemia vera or myelofibrosis, cutaneous T-cell lymphoma, small lymphocytic lymphoma (SLL), marginal zone lymphoma, CNS lymphoma, immunoblastic large cell lymphoma, precursor B-lymphoblastic lymphoma and the like.

In particular embodiments, the cancer is sarcoma, colorectal cancer, head and neck cancer, lung cancer, ovarian cancer, pancreatic cancer, gastric cancer, melanoma, and/or breast cancer.

Anti-CD47 antibodies and masked antibodies as described herein can also be used to treat disorders associated with cancer, e.g., cancer-induced encephalopathy.

The methods and compositions of the invention can be used in combination with other therapeutic agents and/or modalities. The term administered "in combination," as used herein, is understood to mean that two (or more) different treatments are delivered to the subject during the course of the subject's affliction with the disorder, such that the effects of the treatments on the patient overlap at a point in time. In certain embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive (i.e., a synergistic response). The delivery can be such that an effect of the first treatment delivered is still detectable when the second is delivered.

In one embodiment, the methods of the invention include administering to the subject an anti-CD47 antibody or masked antibody as described herein, e.g., a composition or preparation, in combination with one or more additional therapies, e.g., surgery, radiation therapy, or administration of another therapeutic preparation. In one embodiment, the additional therapy may include chemotherapy, e.g., a cytotoxic agent. In one embodiment the additional therapy may include a targeted therapy, e.g. a tyrosine kinase inhibitor, a proteasome inhibitor, or a protease inhibitor. In one embodiment, the additional therapy may include an anti-inflammatory, anti-angiogenic, anti-fibrotic, or anti-proliferative compound, e.g., a steroid, a biologic immunomodulatory, such as an inhibitor of an immune checkpoint molecule, a monoclonal antibody, an antibody fragment, an aptamer, an siRNA, an antisense molecule, a fusion protein, a cytokine, a cytokine receptor, a bronchodilator, a statin, an anti-inflammatory agent (e.g. methotrexate), or an NSAID. In another embodiment, the additional therapy could include combining therapeutics of different classes. The anti-CD47 antibody or masked antibody preparation and the additional therapy can be administered simultaneously or sequentially.

An "immune checkpoint molecule," as used herein, refers to a molecule in the immune system that either turns up a signal (a stimulatory molecule) or turns down a signal (an inhibitory molecule). Many cancers evade the immune system by inhibiting T cell signaling.

Exemplary immune checkpoint molecules include, but are not limited to, programmed cell death protein 1 (PD-1), programmed death-ligand 1 (PD-L1), PD-L2, cytotoxic T lymphocyte-associated protein 4 (CTLA-4), T cell immunoglobulin and mucin domain containing 3 (TIM-3), lymphocyte activation gene 3 (LAG-3), carcinoembryonic antigen related cell adhesion molecule 1 (CEACAM-1), CEACAM-5, V-domain Ig suppressor of T cell activation (VISTA), B and T lymphocyte attenuator (BTLA), T cell immunoreceptor with Ig and ITIM domains (TIGIT), leukocyte-associated immunoglobulin-like receptor 1 (LAIR1), CD160, TGFR, adenosine 2A receptor (A2AR), B7-H3 (also known as CD276), B7-H4 (also called VTCN1), indoleamine 2,3-dioxygenase (IDO), 2B4, killer cell immunoglobulin-like receptor (KIR), and the like.

An "immune checkpoint inhibitor," as used herein, refers to a molecule (e.g., a small molecule, a monoclonal antibody, an antibody fragment, etc.) that inhibit and/or block one or more inhibitory checkpoint molecules.

Exemplary immune checkpoint inhibitors include, but are not limited to, the following monoclonal antibodies: PD-1 inhibitors such as pembrolizumab (Keytruda, Merck) and nivolumab (Opdivo, Bristol-Myers Squibb); PD-L1 inhibitors such as atezolizumab (Tecentriq, Genentech), avelumab (Bavencio, Pfizer), durvalumab (Imfinzi, AstraZeneca); and CTLA-1 inhibitors such as ipilimumab (Yervoy, Bristol-Myers Squibb).

Exemplary cytotoxic agents include anti-microtubule agents, topoisomerase inhibitors, antimetabolites, protein synthesis and degradation inhibitors, mitotic inhibitors, alkylating agents, platinating agents, inhibitors of nucleic acid synthesis, histone deacetylase inhibitors (HDAC inhibitors, e.g., vorinostat (SAHA, MK0683), entinostat (MS-275), panobinostat (LBH589), trichostatin A (TSA), mocetinostat (MGCD0103), belinostat (PXD101), romidepsin (FK228, depsipeptide)), DNA methyltransferase inhibitors, nitrogen mustards, nitrosoureas, ethylenimines, alkyl sulfonates, triazenes, folate analogs, nucleoside analogs, ribonucleotide reductase inhibitors, vinca alkaloids, taxanes, epothilones, intercalating agents, agents capable of interfering with a signal transduction pathway, agents that promote apoptosis and radiation, or antibody molecule conjugates that bind surface proteins to deliver a toxic agent. In one embodiment, the cytotoxic agent that can be administered with a preparation described herein is a platinum-based agent (such as cisplatin), cyclophosphamide, dacarbazine, methotrexate, fluorouracil, gemcitabine, capecitabine, hydroxyurea, topotecan, irinotecan, azacytidine, vorinostat, ixabepilone, bortezomib, taxanes (e.g., paclitaxel or docetaxel), cytochalasin B, gramicidin D, ethidium bromide, emetine, mitomycin, etoposide, tenoposide, vincristine, vinblastine, vinorelbine, colchicin, anthracyclines (e.g., doxorubicin or epirubicin) daunorubicin, dihydroxy anthracin dione, mitoxantrone, mithramycin, actinomycin D, adriamycin, 1-dehydrotestosterone, glucocorticoids, procaine, tetracaine, lidocaine, propranolol, puromycin, ricin, or maytansinoids.

The methods and compositions of the invention can be used in the treatment of subjects with CD47 positive cancer. In one embodiment, the CD47 positive cancer expresses one or more Matrix Metalloproteinases (MMPs). Exemplary MMPs include, but are not limited to, MMP1 through MMP28. Particularly exemplary MMPs include MMP2 and MMP9. In one embodiment, the CD47 positive cancer is a tumor in which infiltrating macrophages are present.

The methods and compositions of the invention can be used in the treatment of subjects with a CD47 positive cancer that expresses one or more MMPs and contains infiltrating macrophages.

Methods of determining the presence of CD47 positive cancers, MMP expression, and the presence of tumor infiltrating macrophages are known in the art.

Assessment of CD47 positive cancers in a subject can be determined by conventional methods that include immunohistochemistry (IHC), Western blot, flow cytometry, or RNA sequencing methods. IHC, Western blot, and flow cytometry may be analyzed with any anti-CD47 antibody know in the art, as well as the anti-CD47 antibodies disclosed herein.

Assessment of macrophage infiltration in tissues can be conducted by monitoring for surface markers of macrophages, including F4/80 for mouse macrophages or CD163, CD68, or CD11b by conventional methods that include immunohistochemistry (IHC), Western blot, flow cytometry, or RNA sequencing methods.

Assessment of proteases in tissues can be monitored using a variety of techniques, including both those that monitor protease activity as well as those that can detect proteolytic activity. Conventional methods that can detect the presence of proteases in a tissue, which could include both inactive and active forms of the protease, include IHC, RNA sequencing, Western blot, or ELISA-based methods. Additional techniques can be used to detect protease activity in tissues, which includes zymography, in situ zymography by fluorescence microscopy, or the use of fluorescent proteolytic substrates. In addition, the use of fluorescent proteolytic substrates can be combined with immuno-capture of specific proteases. Additionally, antibodies directed against the active site of a protease can be used by a variety of techniques including IHC, fluorescence microscopy, Western blotting, ELISA, or flow cytometry (See, Sela-Passwell et al. Nature Medicine. 18:143-147. 2012; LeBeau et al. Cancer Research. 75:1225-1235. 2015; Sun et al. Biochemistry. 42:892-900. 2003; Shiryaev et al. 2:e80. 2013.)

Throughout the description, where compositions and kits are described as having, including, or comprising specific components, or where processes and methods are described as having, including, or comprising specific steps, it is contemplated that, additionally, there are compositions and kits of the present invention that consist essentially of, or consist of, the recited components, and that there are processes and methods according to the present invention that consist essentially of, or consist of, the recited processing and method steps.

IV. Pharmaceutical Compositions and Formulations

For therapeutic use, an anti-CD47 antibody or masked antibody is preferably combined with a pharmaceutically acceptable carrier. As used herein, "pharmaceutically acceptable carrier" means buffers, carriers, and excipients suitable for use in contact with the tissues of human beings and animals without excessive toxicity, irritation, allergic response, or other problem or complication, commensurate with a reasonable benefit/risk ratio. The carrier(s) should be "acceptable" in the sense of being compatible with the other ingredients of the formulations and not deleterious to the recipient. Pharmaceutically acceptable carriers include buffers, solvents, dispersion media, coatings, isotonic and absorption delaying agents, and the like, that are compatible with pharmaceutical administration. The use of such media and agents for pharmaceutically active substances is known in the art.

Accordingly, anti-CD47 antibody or masked antibody compositions of the present invention can comprise at least one of any suitable excipients, such as, but not limited to, diluent, binder, stabilizer, buffers, salts, lipophilic solvents, preservative, adjuvant or the like. Pharmaceutically acceptable excipients are preferred. Non-limiting examples of, and methods of preparing such sterile solutions are well known in the art, such as, but not limited to, those described in Gennaro, Ed., Remington's Pharmaceutical Sciences, 18th Edition, Mack Publishing Co. (Easton, Pa.) 1990. Pharmaceutically acceptable carriers can be routinely selected that are suitable for the mode of administration, solubility and/or stability of the antibody molecule, fragment or variant composition as well known in the art or as described herein.

Pharmaceutical excipients and additives useful in the present composition include but are not limited to proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody molecule components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like.

Carbohydrate excipients suitable for use in the invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like. Preferred carbohydrate excipients for use in the present invention are mannitol, trehalose, and raffinose.

Antibody molecule compositions can also include a buffer or a pH adjusting agent; typically, the buffer is a salt prepared from an organic acid or base. Representative buffers include organic acid salts such as salts of citric acid, acetic acid, ascorbic acid, gluconic acid, carbonic acid, tartaric acid, succinic acid, or phthalic acid; Tris, tromethamine hydrochloride, or phosphate buffers.

Additionally, antibody molecule compositions of the invention can include polymeric excipients/additives such as polyvinylpyrrolidones, ficolls (a polymeric sugar), dextrates (e.g., cyclodextrins, such as 2-hydroxypropyl-β-cyclodextrin), polyethylene glycols, flavoring agents, antimicrobial agents, sweeteners, antioxidants, antistatic agents, surfactants (e.g., polysorbates such as "TWEEN 20" and "TWEEN 80"), lipids (e.g., phospholipids, fatty acids), steroids (e.g., cholesterol), and chelating agents (e.g., EDTA).

These and additional known pharmaceutical excipients and/or additives suitable for use in the antibody molecule compositions according to the invention are known in the art, e.g., as listed in "Remington: The Science & Practice of Pharmacy," 19th ed., Williams & Williams, (1995), and in the "Physician's Desk Reference," 52nd ed., Medical Economics, Montvale, N.J. (1998). Preferred carrier or excipient materials are carbohydrates (e.g., saccharides and alditols) and buffers (e.g., citrate) or polymeric agents.

The present invention provides for stable compositions, comprising at least one anti-CD47 antibody molecule in a pharmaceutically acceptable formulation. Preserved formulations contain at least one known preservative or optionally selected from at least one phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, or mixtures thereof in an aqueous diluent. Any suitable concentration or mixture can be used as known in the art, such as 0.001-5%, or any range or value therein, such as, but not limited to 0.001, 0.003, 0.005, 0.009, 0.01, 0.02, 0.03, 0.05, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, or any range or value therein. Non-limiting examples include, no preservative, 0.1-2% m-cresol (e.g., 0.2, 0.3, 0.4, 0.5, 0.9, or 1.0%), 0.1-3% benzyl alcohol (e.g., 0.5, 0.9, 1.1, 1.5, 1.9, 2.0, or 2.5%), 0.001-0.5% thimerosal (e.g., 0.005 or 0.01%), 0.001-2.0% phenol (e.g., 0.05, 0.25, 0.28, 0.5, 0.9, or 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, or 1.0%), and the like.

Pharmaceutical compositions containing an anti-CD47 antibody or masked antibody as disclosed herein can be presented in a dosage unit form and can be prepared by any suitable method. A pharmaceutical composition should be formulated to be compatible with its intended route of administration. Examples of routes of administration are intravenous (IV), intradermal, inhalation, transdermal, topical, transmucosal, and rectal administration. A preferred route of administration for monoclonal antibodies is IV infusion. Useful formulations can be prepared by methods known in the pharmaceutical art. For example, see Remington's Pharmaceutical Sciences (1990) supra. Formulation components suitable for parenteral administration include a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as EDTA; buffers such as acetates, citrates or phosphates; and agents for the adjustment of tonicity such as sodium chloride or dextrose.

For intravenous administration, suitable carriers include physiological saline, bacteriostatic water, Cremophor EL™ (BASF, Parsippany, N.J.) or phosphate buffered saline (PBS). The carrier should be stable under the conditions of manufacture and storage, and should be preserved against microorganisms. The carrier can be a solvent or dispersion medium containing, for example, water, ethanol, polyol (for example, glycerol, propylene glycol, and liquid polyethylene glycol), and suitable mixtures thereof.

Pharmaceutical formulations are preferably sterile. Sterilization can be accomplished by any suitable method, e.g., filtration through sterile filtration membranes. Where the composition is lyophilized, filter sterilization can be conducted prior to or following lyophilization and reconstitution.

The compositions of this invention may be in a variety of forms. These include, for example, liquid, semi-solid and solid dosage forms, such as liquid solutions (e.g., injectable and infusible solutions), dispersions or suspensions, and liposomes. The preferred form depends on the intended mode of administration and therapeutic application. Typical preferred compositions are in the form of injectable or infusible solutions. The preferred mode of administration is parenteral (e.g., intravenous, subcutaneous, intraocular, intraperitoneal, intramuscular). In a preferred embodiment, the preparation is administered by intravenous infusion or injection. In another preferred embodiment, the preparation is administered by intramuscular or subcutaneous injection.

The phrases "parenteral administration" and "administered parenterally" as used herein means modes of administration other than enteral and topical administration, usually by injection, and includes, without limitation, intravenous, intramuscular, subcutaneous, intraarterial, intrathecal, intracapsular, intraorbital, intravitreous, intracardiac, intradermal, intraperitoneal, transtracheal, inhaled, subcutaneous, subcuticular, intraarticular, subcapsular, subarachnoid, intraspinal, epidural and intrasternal injection and infusion.

The present invention provides a kit, comprising packaging material and at least one vial comprising a solution of at least one an anti-CD47 antibody or masked antibody with the prescribed buffers and/or preservatives, optionally in an aqueous diluent. The aqueous diluent optionally further comprises a pharmaceutically acceptable preservative. Preservatives include those selected from phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal, or mixtures thereof. The concentration of preservative used in the formulation is a concentration sufficient to yield an anti-microbial effect. Such concentrations are dependent on the preservative selected and are readily determined by the skilled artisan.

Other excipients, e.g. isotonicity agents, buffers, antioxidants, preservative enhancers, can be optionally and preferably added to the diluent. An isotonicity agent, such as glycerin, is commonly used at known concentrations. A physiologically tolerated buffer is preferably added to provide improved pH control. The formulations can cover a wide range of pHs, such as from about pH 4.0 to about pH 10.0, from about pH 5.0 to about pH 9.0, or about pH 6.0 to about pH 8.0.

Other additives, such as a pharmaceutically acceptable solubilizers like TWEEN 20 (polyoxyethylene (20) sorbitan monolaurate), TWEEN 40 (polyoxyethylene (20) sorbitan monopalmitate), TWEEN 80 (polyoxyethylene (20) sorbitan monooleate), Pluronic F68 (polyoxyethylene polyoxypropylene block copolymers), and PEG (polyethylene glycol) or non-ionic surfactants such as polysorbate 20 or 80 or poloxamer 184 or 188, Pluronic® polyls, other block co-polymers, and chelators such as EDTA and EGTA can optionally be added to the formulations or compositions to reduce aggregation. These additives are particularly useful if a pump or plastic container is used to administer the formulation. The presence of pharmaceutically acceptable surfactant mitigates the propensity for the protein to aggregate.

Various delivery systems can be used to administer anti-CD47 antibodies or masked antibodies to a subject. In certain exemplary embodiments, administration of an anti-CD47 antibody or masked antibody is by intravenous infusion. In some embodiments, administration is by a two hour intravenous infusion.

Any of the formulations described above can be stored in a liquid or frozen form and can be optionally subjected to a preservation process. In some embodiments, the formulations described above are lyophilized, i.e., they are subjected to lyophilization. In some embodiments, the formulations described above are subjected to a preservation process, for example, lyophilization, and are subsequently reconstituted with a suitable liquid, for example, water. By lyophilized, it is meant that the composition has been freeze-dried under a vacuum. Lyophilization typically is accomplished by freezing a particular formulation such that the solutes are separated from the solvent(s). The solvent is then removed by sublimation (i.e., primary drying) and next by desorption (i.e., secondary drying).

The formulations of the present invention can be used with the methods described herein or with other methods for treating disease. The anti-CD47 antibody or masked antibody formulations may be further diluted before administration to a subject. In some embodiments, the formulations will be diluted with saline and held in IV bags or syringes before administration to a subject. Accordingly, in some embodiments, the methods for treating a CD47-expressing cancer in a subject will comprise administering to a subject in need thereof a weekly dose of a pharmaceutical composition comprising an anti-CD47 antibody or masked antibody.

It will be readily apparent to those skilled in the art that other suitable modifications and adaptations of the methods described herein may be made using suitable equivalents without departing from the scope of the embodiments disclosed herein. Having now described certain embodiments in detail, the same will be more clearly understood by reference to the following examples, which are included for purposes of illustration only and are not intended to be limiting. All patents, patent applications and references described herein are incorporated by reference in their entireties for all purposes.

EXAMPLES

Example 1: Antibody Generation

Humanized variants of the murine B6H12 anti-CD47 antibody were generated. For DNA & Vector Generation antibody variable domains sequences were synthesized using non-template PCR. In short, the virtual gene sequence is converted into oligonucleotide sequences using ATUM's proprietary software suite. Oligonucleotides are synthesized, pooled and amplified using PCR. Full length amplicon from the PCR reaction is cloned into the vector using the SapI site, transformed into E. coli and unique colonies are isolated. Colonies are grown up overnight in liquid media and plasmid DNA isolated, purified (Machery-Nagel Midi Prep Kit) and sequence verified using Sanger sequencing. Light chain variable domains are cloned into the Kappa-Hs vector and heavy chain domains are cloned into the IgG1.01-Fc-Hs vectors. For antibody expression a 1:1 ratio of antibody heavy chain and light chain vectors are diluted into LifeTech Optimem media with PolyPlus FectoPro transfection reagent. The DNA/transfection reagent is then added to an Atum-specific HEK293 cells in LifeTech ExpiExpression media and cultured for 5 days. Culture is harvested by centrifugation and 0.2 um filtration. For antibody Purification GE mAb select sure is used for purification of the IgG. Prior to elution, the resin is washed with 10 CV 1M NaCl in PBS, and 10 CV of PBS. The IgG is eluted using 20 mM NaCitrate pH3.2 Buffer. The sample is buffer exchanged using the Pierce Zeba columns into PBS. The sample is then Filter sterilized before a sample is taken for the characterization. Characterization includes A280 concentration and reduced and non-reduced electrophoresis using the Agilent P200 Tape Station 2200 with p200 Tapescreens.

Specific mutations of the parental B6H12 antibody are described in Tables 10-13 as set forth below.

TABLE 10

Humanizing Mutations in hB6H12 Heavy Chain Variants

| vH Variant | IGHV Exon Acceptor Sequence | Murine Donor Framework Residues | Human Acceptor CDR Residues |
|---|---|---|---|
| hvH1 | IGHV3-23/HJ4 | H44, H49, H89, H91, H94 | none |
| hvH2 | IGHV3-23/HJ4 | H49, H91, H94 | H31, H33, H60 |
| hvH3 | IGHV3-23/HJ4 | H49, H82, H91, H94 | H31, H33, H60 |
| hvH4 | IGHV3-48/HJ4 | H49 | H31, H60 |
| hvH5 | IGHV3-66/HJ4 | H29, H49, H82 | H60 |
| hvH6 | IGHV3-74/HJ4 | H49 | H31, H58, H60 |

TABLE 11

Humanizing Mutations in hB6H12 Kappa Light Chain Variants

| vK Variant | IGKV Exon Acceptor Sequence | Murine Donor Framework Residues | Human Acceptor CDR Residues |
|---|---|---|---|
| hvK1 | IGKV6-21/KJ2 | L4, L21, L85 | none |
| hvK2 | IGKV6-21/KJ2 | L4, L21 | none |
| hvK3 | IGKV6-21/KJ2 | L4, L21, L69 | none |
| hvK4 | IGKV1-27/KJ2 | L21, L49, L69 | L31, L34, L53, L54, L55 |

TABLE 12

Specific Murine Framework Mutations in hB6H12 Heavy Chain Variants

| Variant | 29 | 44 | 49 | 82 | 89 | 91 | 94 | % Human |
|---|---|---|---|---|---|---|---|---|
| hvH1 | F | R* | A* | M | I* | F* | R* | 87.8 |
| hvH2 | F | G | A* | M | V | F* | R* | 92.9 |
| hvH3 | F | G | A* | I* | V | F* | R* | 91.8 |
| hvH4 | F | G | A* | M | V | Y | R | 92.9 |
| hvH5 | F* | G | A* | I* | V | Y | R | 89.8 |
| hvH6 | F | G | A* | M | V | Y | R | 92.9 |

*Murine residues.

TABLE 13

Specific Murine Framework Mutations in hB6H12 Kappa Light Chain Variants

| Variant | 4 | 21 | 49 | 69 | 85 | % Human |
|---|---|---|---|---|---|---|
| hvK1 | M* | L* | K | T | V* | 85.3 |
| hvK2 | M* | L* | K | T | T | 86.3 |
| hvK3 | M* | L* | K | S* | T | 85.3 |
| hvK4 | M | L* | K* | S* | T | 89.5 |

*Murine residues.

Example 2: Humanized Anti-CD47 Antibodies

Antibody Production

Antibodies were expressed via transient transfection of Expi HEK or Expi CHO cells or stable transfection of CHO-DG44 and purified using Mab Select SuRe columns (GE Healthcare). Additional preparative size-exclusion chromatography purification using Superdex columns (GE Healthcare) was performed for masked antibodies that were less than 90% monomeric.

Saturation Binding by Flow Cytometry and ELISA

Humanized anti-CD47 B6H12 antibodies with varying heavy and light chain sequences were assessed for their binding affinities to human CD47 either by saturating ELISA or cellular FACS analysis and EC50s or Kds calculated. Only antibodies comprised of the heavy chain 1 sequence (hvH1) (bin A; antibodies 1-4) or heavy chain 5 sequence (hvH5) (bin B, antibodies 17-20) were able to bind to CD47. Antibodies from these bins bound with similar Kd (FIG. 2A) and $EC_{50}$ (FIG. 2B) affinities as the murine antibody mB6H12 and the alternatively humanized antibody Ab47.

For cellular FACS analysis, L450cy cancer lymphoma cells were treated with increasing concentrations of humanized B6H12 antibodies, which were found to retain binding to CD47 and Kd values determined. Alternate humanization frameworks retained similar binding Kds as the murine parent and the alternately humanized antibody Ab47 (FIG. 2A).

Figure 2B:
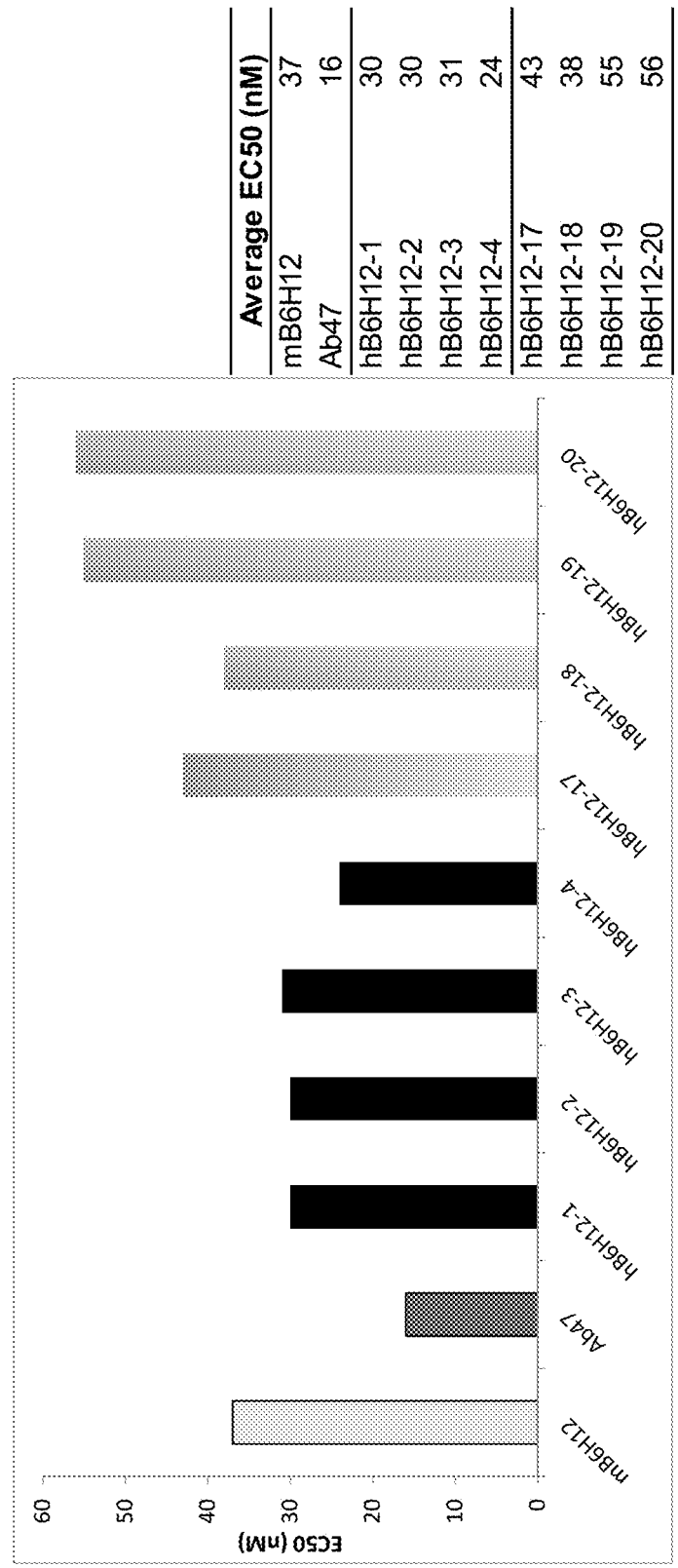

In addition to cellular binding assessment of affinity of the humanized B6H12 antibodies for CD47 was determined by Elisa. Plates coated with human CD47 were treated with increasing concentrations of humanized B6H12 antibodies, which were found to retain binding to CD47 and $EC_{50}$ values determined. Alternate humanization frame works retained similar binding Kds as the murine parent and the alternately humanized antibody Ab47 (FIG. 2B).

Figure 2C:
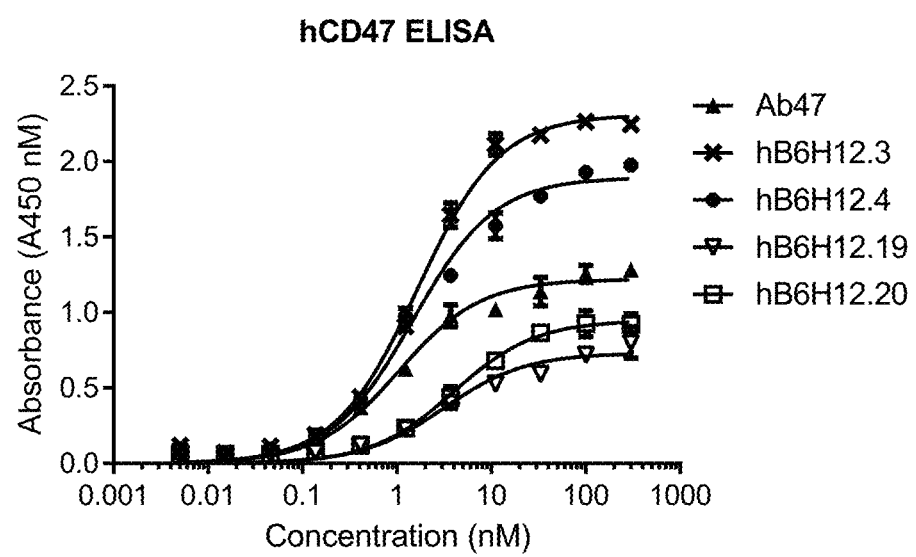

In addition to assessing binding EC50s in the ELISA assay, binding kinetics were also assessed. Unexpectedly, antibodies in Bin A, (hB6H12.3 and hB6H12.4) displayed significantly higher maximal binding (BMax) than the parent antibody, mB6H12, antibodies in Bin B (hB6h12.19 and hB6H12.20), or an alternate humanized antibody, Ab47 (FIG. 2C).

Saturation Binding by Flow Cytometry $2\times10^5$ of indicated cells (SW780 or human red blood cells) were combined with a serial dilution of indicated antibody in staining buffer (PBS, 5% FBS, 0.2% $NaN_3$). Samples were incubated for 1 hour on ice and washed twice with ice-cold staining buffer. Cells were resuspended with anti-human IgG-AF647 (JacksonImmunoResearch, 1:200 dilution in staining buffer) for 1 hour on ice. Cells were washed twice with ice cold staining buffer and resuspended in staining buffer. Labeled cells were examined by flow cytometry on an Invitrogen Attune NxT flow cytometer gated to exclude nonviable cells and analyzed using FlowJo 10 software. The $K_d$ was calculated using GraphPad Prism 6 using non-linear regression.

Saturation Binding by ELISA

Soluble recombinant human CD47-Fc (R&D Systems) was diluted to an appropriate concentration in 50 mM carbonate buffer, pH 9.6. To each well of a 96-well Maxisorb ELISA plate was added 100 μL of soluble antigen. The plate was sealed and stored at 4° C. overnight. The plate was then washed 3-5 times with PBS-T was buffer (PBS, pH 7.4+ 0.05% Tween-20). The wells were blocked using 300 μL/well of PBS-T buffer containing BSA for 1 hour at room temperature, then washed 3-5 times with PBS-T. Dilutions of antibodies were prepared in blocking buffer and added to each well in a volume of 100 μL. The antibodies were incubated for 1 hour at room temperature, and then washed 3-5 times with PBS-T. HRP-conjugated secondary antibodies (either anti-human Fc or anti-human kappa light chain) were then added and incubated for 1 hour at room temperature. The plate was washed 3-5 times with PBS-T. The ELISA was developed by adding 100 μL of TMB solution and incubating for 3-15 min at room temperature. To stop the reaction, 100 μL of 1 N sulfuric acid was added to each well. The absorbance at 450 nm was determined using a Spectramax 190 plate reader (Molecular Biosciences) and the data plotted using GraphPad Prism 6.

B6H12-Mediated Phagocytosis

Functional characterization of humanized B6H12 antibodies was performed including human phagocytosis of human red blood cells and hemagglutination. Human red blood cells labeled with fluorescent red PKH dye were opsonized for 30 minutes with increasing concentrations of humanized B6H12 antibodies from bins A and B. RBCs were washed and fed at a 10:1 ratio to monocyte macrophages for 2 hours. Samples were washed 3 times with ACK hypotonic lysis buffer which allows for lysis and removal of non-ingested red blood cells. Samples were subjected to flow cytometry and phagocytosis assessed. Antibodies from Bin A and B exhibited a similar ability to mediate human red blood cell phagocytosis. Surprisingly, the antibody hB6H12.3 from bin A, mediated phagocytosis better than the murine parent antibody and on par with the alternate humanized antibody Ab47.

Figure 3A:
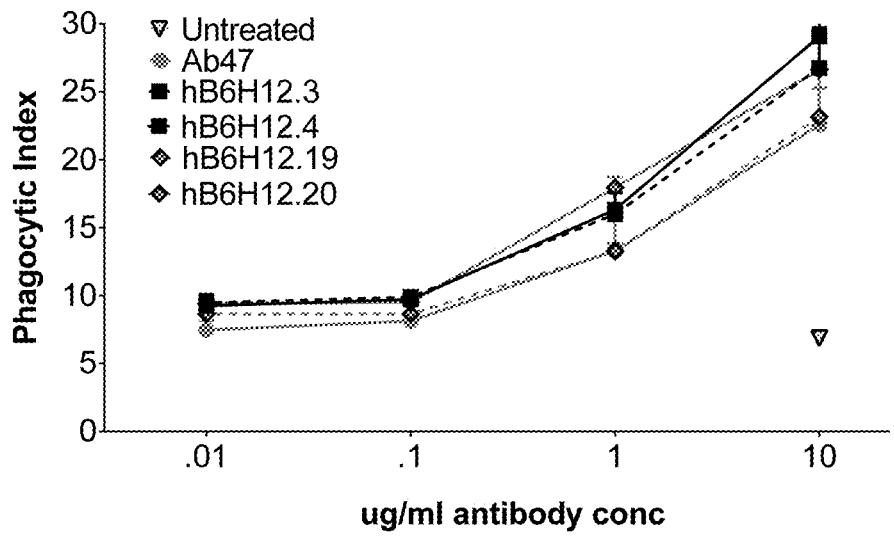
FIG. 3A-FIG. 3B depict antibody-mediated phagocytosis.
Figure 3B:
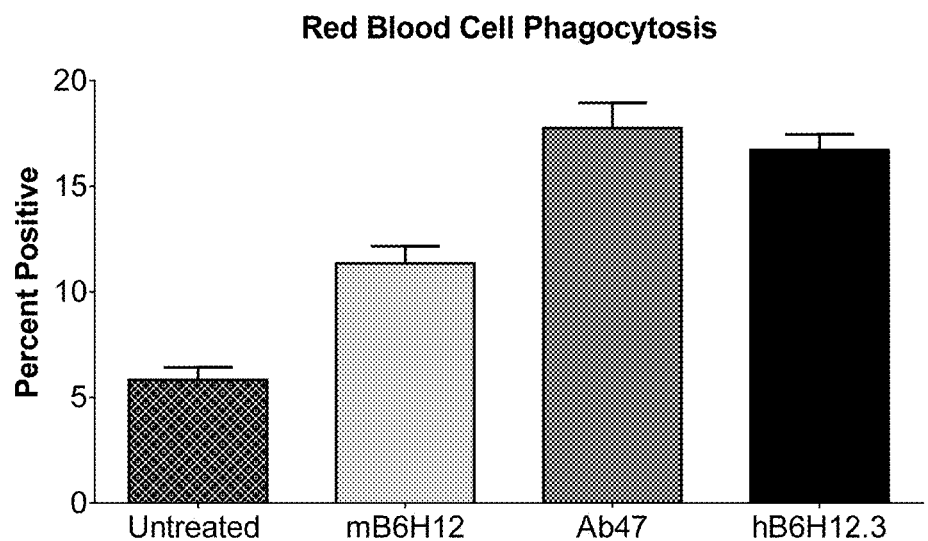

Humanized B6H12 antibodies from antibody bins A and B mediate phagocytosis of CD47 positive human red blood cells similarly. hB6H12.3 stimulated superior phagocytic-promoting activity at 1 µg/ml compared to the murine mB6H12 and similar phagocytic-promoting activity compared to Ab47 (FIG. 3A and FIG. 3B).

B6H12-Mediated Hemagglutination

Figure 4A:
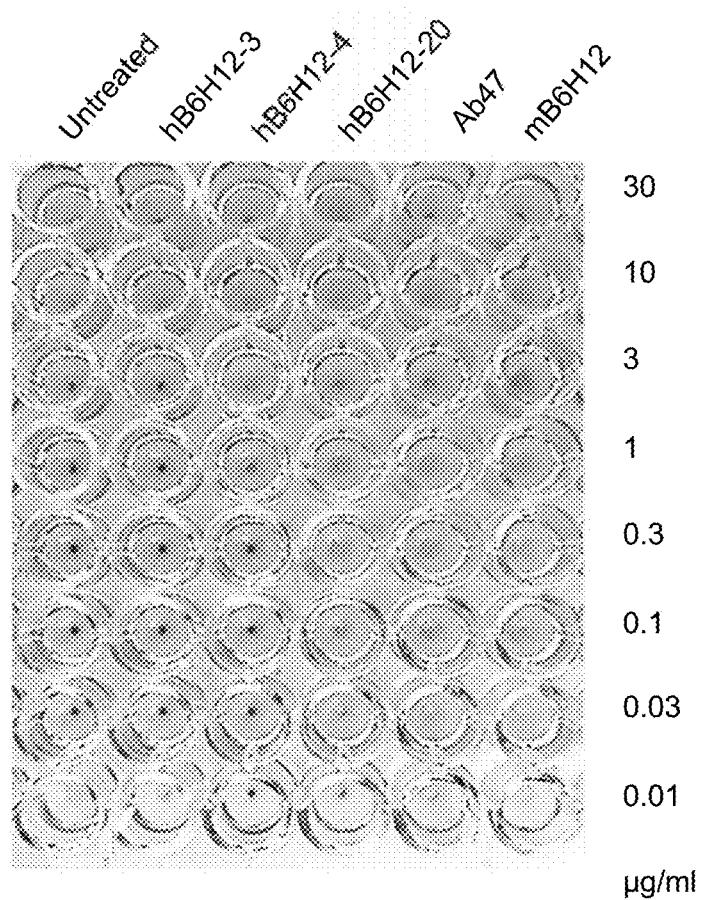
FIG. 4A-FIG. 4B depict antibody-mediated hemagglutination.

A hallmark characteristic of B6H12 is the ability to promote the hemagglutination of human red blood cells. Hemagglutination is an example of a homotypic interaction that allows two CD47 expressing cells to aggregate or clump when treated with a CD47 antibody. The agglutinated lattice maintains the RBC's in a suspended distribution that can be quantified visually by image analysis or by the level of aggregation as monitored by flow cytometry. Human red blood cells suspended in PBS and plated in round bottom 96 well plate were exposed to increasing concentrations of anti-CD47 antibodies. After 30 minutes at 37° C., hemagglutination was monitored optically by a change in RBC density and by flow cytometry as an increase in cellular aggregation. Antibodies within Bin A, in particular hB6H12.3 showed a reduction in hemagglutination compared to the parent antibody mB6H12 and the alternately humanized antibody Ab47 (FIG. 4A).

Figure 4B:
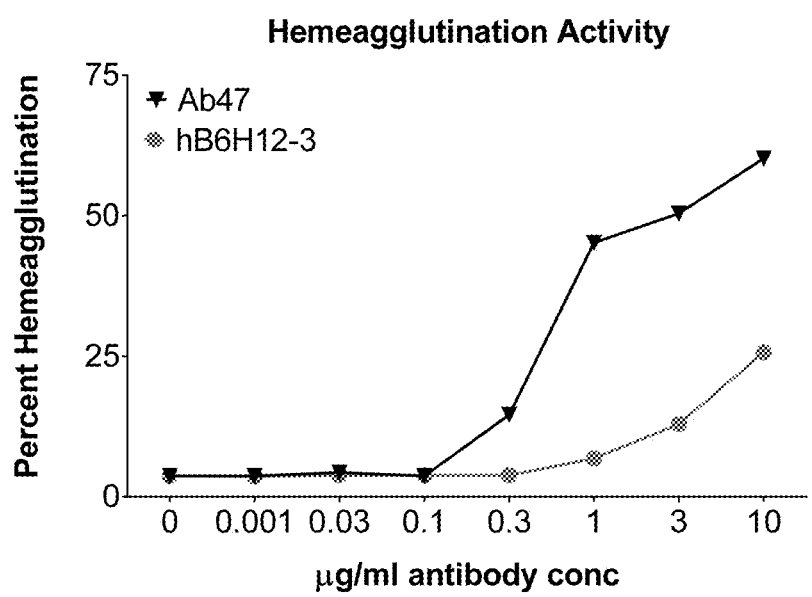

To assess hemagglutination, standard image capture was performed and the formation of dispersed non-sedimenting RBCs assessed. In addition, plates were scanned using the GE In Cell analyzer and the diameter of the apparent spot within the well was assessed. In an effort to assess the hemagglutination in an assay that is amenable for clinical monitoring, flow cytometry was used and hemagglutination was assessed as the overall increase in apparent RBC SSC/FSC, which is a method for monitoring aggregation. This method was used to assess hemagglutination induced by the humanized anti-CD47 antibodies hB6H12.3 and Ab47 (FIG. 4A and FIG. 4B).

B6H12-Mediated Activation of Fcγ Receptors

Figure 5A:
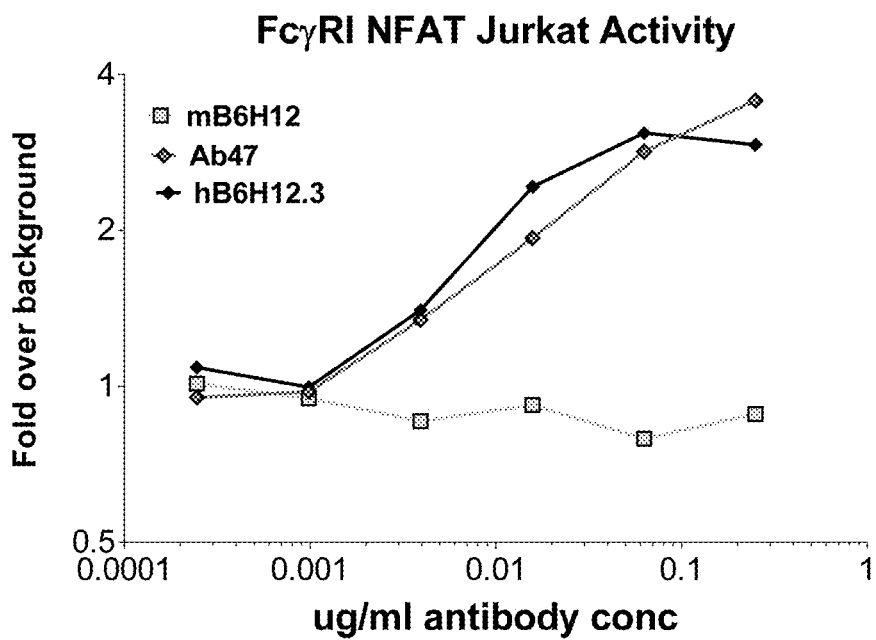
FIG. 5A-FIG. 5B depict antibody-mediated activation of Fcγ receptors. NFAT luciferase reporter activity was measured from Jurkat cells transfected with FcγRI (FIG. 5A) or high affinity FcγRIIIa-H (FIG. 5B) and exposed to WIL2S cells coated with increasing concentrations either mouse B6H12, Ab47 or hB6H12.3.
Figure 5B:
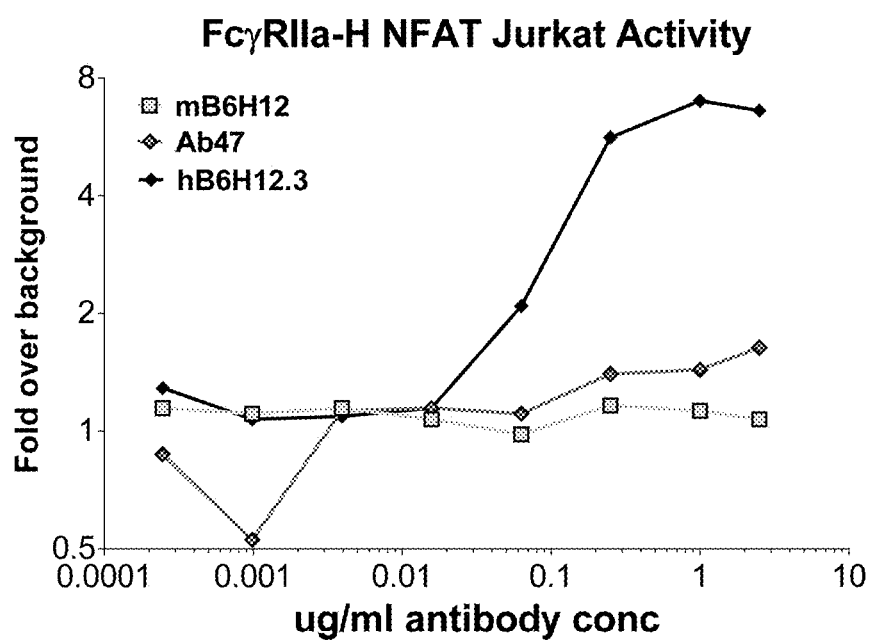

In vivo, monocytes, macrophages, neutrophils and dendritic cells can mediate ADCP via FcγRIIa, FcγRI and FcγRIIIa. While all three receptors can participate in ADCP, FcγRIIa is believed to be the predominant Fcγ receptor involved in this process. Jurkat cells stably transfected with human FcγRI or the high affinity FcγRIIa-H connected to a NFAT-luciferase reporter construct were exposed to WIL2S cells coated with increasing concentrations either mouse B6H12, Ab47, or hB6H12.3. FcγR activation was monitored by luciferase production. Results are shown in FIGS. 5A and 5B. Both Ab47 and hB6H12.3 coated cells dose dependently activated the FcγRI receptor, however only hB6H12.3 was able to drive activation of FcγRIIa-H, the receptor that is most closely linked to directly mediating ADCP activity. Antibody Mediated Activation of Fcγ Receptors Involved in Antibody Mediated Cellular phagocytosis was assessed using engineered Jurkat cells stably expressing the FcγRI or FcγRIIa-H (the high-affinity H131 variant) and an NFAT response element driving expression of firefly luciferase as effector cells. Antibody biological activity is quantified through the luciferase produced as a result of NFAT pathway activation; luciferase activity in the effector cell is quantified with luminescence readout (FIG. 5A and FIG. 5B).

NK Cell-Mediated ADCC Activity

Figure 6A:
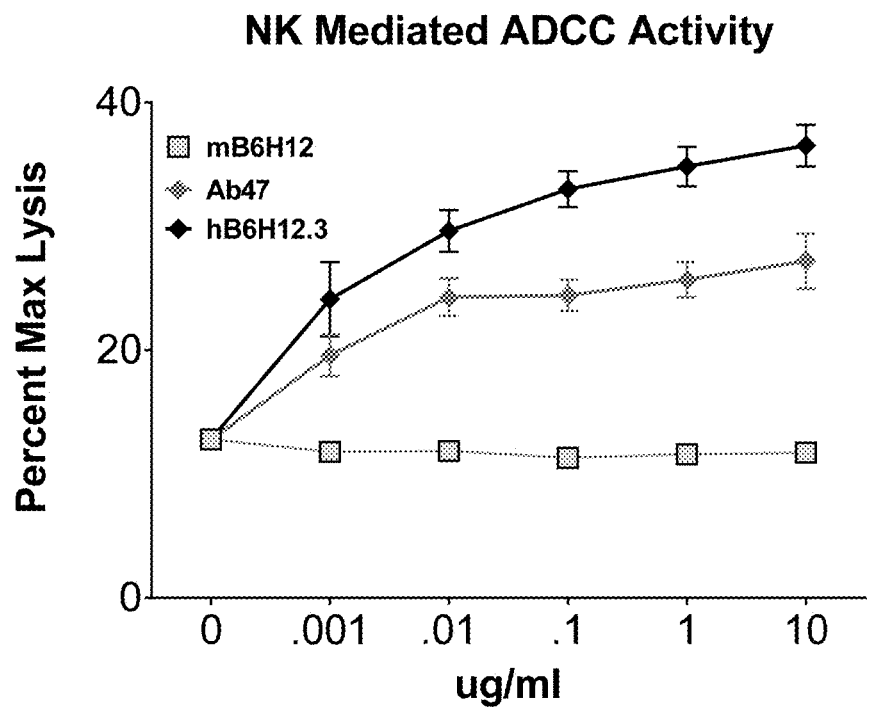
FIG. 6A-FIG. 6B depict NK cell-mediated ADCC and activation of FcγRIIIa. Chromium-loaded WIL2S cells coated with mB6H12, Ab47, or hB6H12.3 were exposed to Jurkat cells stably expressing the high affinity V/V variant of FcγRIIIa and receptor activation assessed as NFAT-driven luciferase activity. ADCC (FIG. 6A) and FcγRIIIa activation (FIG. 6B) were compared between mB6H12, Ab47 and hB6H12.3.
Figure 6B:
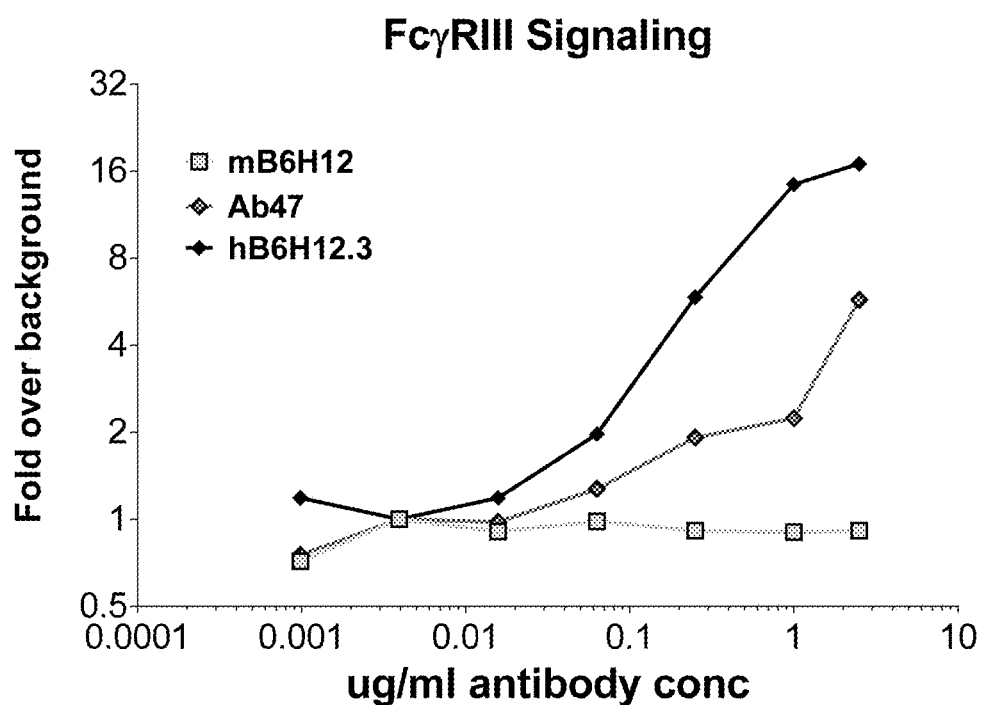

NK cell mediated antibody dependent cellular cytotoxicity (ADCC) and activation of FcγRIIIa by mB6H12, Ab47, and hB6H12.3 was examined. Chromium loaded Wils-2 cells coated with increasing concentrations of antibody were exposed to primary human natural killer (NK) cells for 4 hours and specific lysis assessed by release of radioactive chromium into the tissue culture media. Alternatively, Wils-2 cells coated with increasing concentration of mB6H12, Ab47, or hB6H12.3 were exposed to Jurkat cells stably expressing the high affinity V/V variant of FcγRIIIa and receptor activation assessed as NFAT driven luciferase activity. hB6H12.3 exhibited superior ADCC and FcγRIIIa activation compared to both Ab47 or the murine B6H12 parent antibody. Results are shown in FIGS. 6A and 6B. The IgG1 backbone of hB6H12.3 mediates ADCC activity and drives FcγRIII signaling, a functionality that is absent with current IgG4 clinical antibodies.

To perform the ADCC assay, purified human NK cells negatively selected from Astarte Biologics were thawed and re-suspended in RPMI/1% FBS at a concentration of $7.2\times10^5$ CD16+ cells/Ml (such that 704, contained approximately $5\times10^4$ effector cells). $5\times10^6$ of target cells (WIL2S cells) were collected, centrifuged, and resuspended in 1004, of FBS. 1004, (approximately 100 µCi) of Cr-51 was added to the cells and mixed gently. The cells were placed in a 37° C. $CO_2$-humidified incubator to label for 1 hour. The cells were tapped occasionally to keep suspended. The cells were washed three times with RPMI/1% FBS, being careful to discard radioactive supernatant in appropriate waste receptacle. The cells were then resuspended in 10 mL RPMI/1% FBS and counted. $7.2\times10^5$ cells were removed and suspended in a total volume of 10 mL assay medium such that 704, was equivalent to approximately $5\times10^3$ target cells.

For antibody dilution and plate assembly, the antibodies were diluted in assay medium (prep @ 3×). The antibodies were added to the plate just prior to addition of Cr-labeled target cells. To control wells, 704, and 1404, assay medium was added in place of the antibody. These wells represent total and spontaneous release controls, respectively. The target cells were mixed and 704, was added to each test and control well of the 96-well plate. The targets with antibodies were incubated in a 37° C. incubator for 30 minutes. 70 µL ($5\times10^4$) of effector cells were added to each test well. To the total release wells, 704, of 3% triton X-100 was added and pipetted up-and-down three times to mix. The plates were returned to 37° C., $CO_2$-humidified incubator for 4 hours.

Taken together, the data demonstrates that the novel humanized anti-CD47 antibodies of the invention possess superior and unexpected properties over the murine parental antibody. The humanized anti-CD47 antibodies display superior phagocytic/ADCP capability, as demonstrated by RBC phagocytosis (FIG. 3B) and FcγRII signaling (FIG. 5B). The humanized anti-CD47 antibodies display superior cell lysis/ADCC, as demonstrated by NK cell-mediated cell lysis (FIG. 6A) and FcγRIII signaling (FIG. 6B). The humanized anti-CD47 antibodies display superior FcγRT signaling (FIG. 5A). Finally, the humanized anti-CD47 antibodies also display a superior toxicity profile, as demonstrated by reduced hemagglutination, as demonstrated in hemagglutination assays (FIG. 4A & FIG. 4B). The humanized anti-CD47 antibody, hB6H12.3, is found to be particularly efficacious.

Suppressor Function of Anti-CD47 Antibodies

Figure 7A:
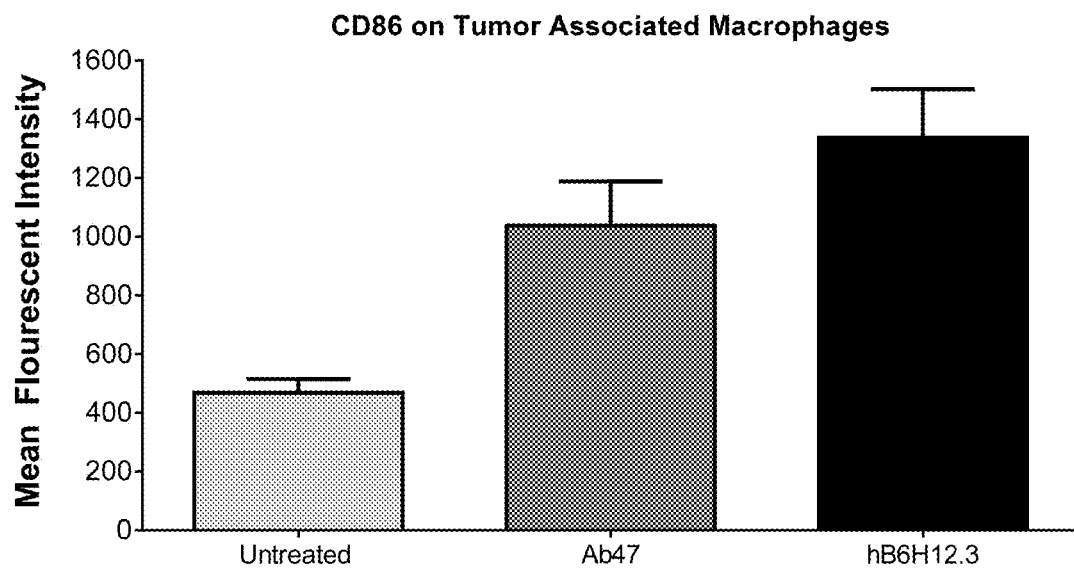
FIG. 7A-FIG. 7D depict suppressor function of anti-CD47 antibodies. Differentiated monocytes with a tumor associated macrophage (TAM) phenotype showed increased levels of macrophage activation markers CD86 (FIG. 7A) and MHCII (FIG. 7B) when exposed to anti-CD47 antibodies. TCR-mediated T cell activation was assessed by detecting up-regulation of MHCII (FIG. 7C) and IFNγ secretion (FIG. 7D) in T cells.
Figure 7B:
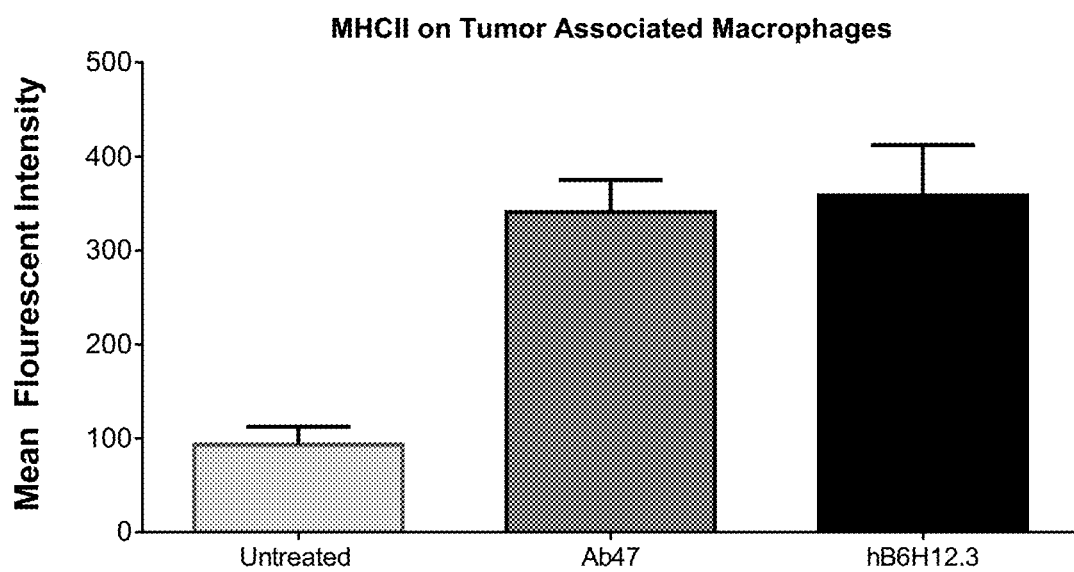
Figure 7C:
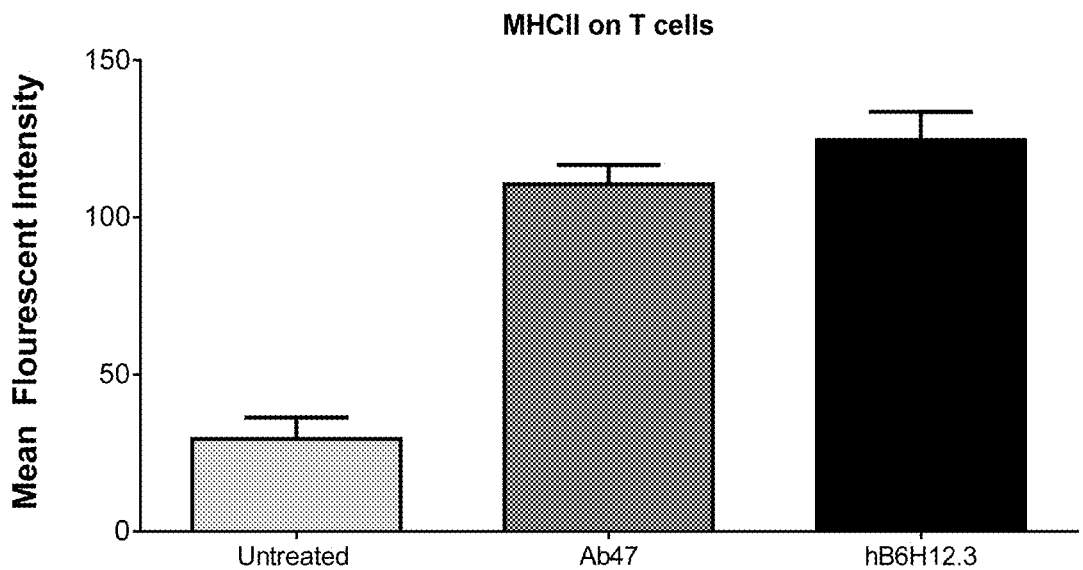
Figure 7D:
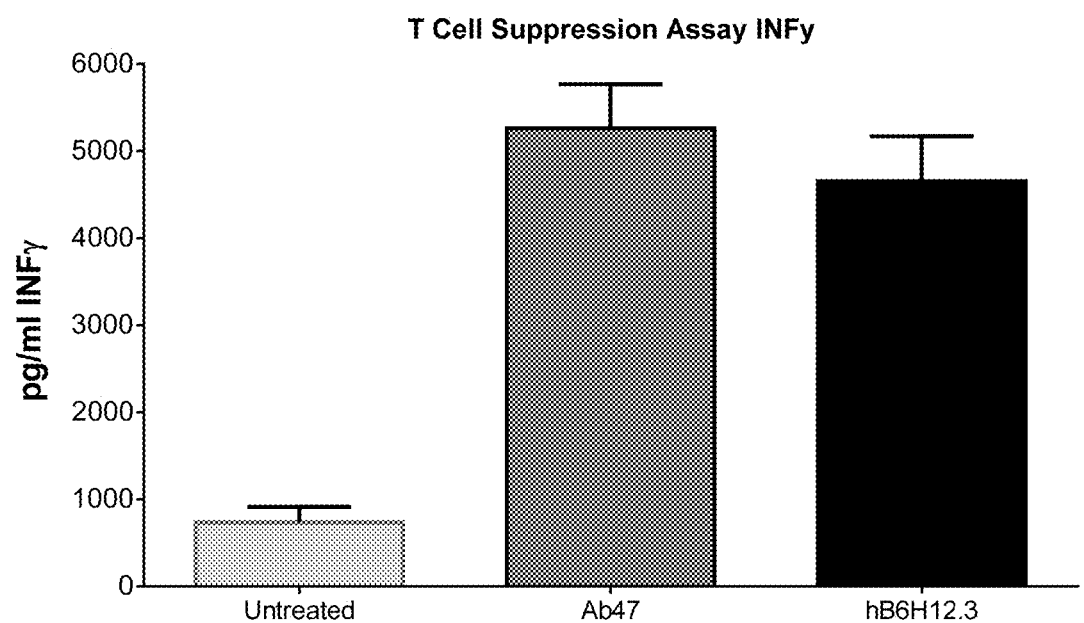

In addition to blocking phagocytic activity, the interaction of CD47 with SIRPα also reduces inflammatory cytokine production through activation of SHP1 and inactivation of downstream signals such as Vav. Human monocytes were treated LPS to drive cytokine production in the presence of absence of the parent and various humanized anti-CD47 antibodies. Treatment with all CD47 target antibodies was able to significantly enhance LPS driven cytokines. One consequence of better cytokine production and innate cellular activation is an ability to drive secondary T cell responses. Tumor associated macrophages are known to exhibit a suppressive phenotype that is unable to support and can actively suppress secondary T cell activation. Human mononuclear cells were differentiated and polarized with IL10 and MSCF to drive them towards an immune suppressive TAM-like phenotype. These differentiated monocytes are able to suppress CD3/CD28 driven proliferation of autologous T cells. Addition of anti-CD47 treatment in this paradigm was able to activate the TAMs and move them towards a more M0/M1 phenotype (CD86/MHCII increase). See, e.g., FIGS. 7A 7B, and 7C. This change in TAM-like phenotype correlated with an ability to support CD3/CD28 mediated T cell proliferation and activation. See, e.g., FIG. 7D.

Suppressor assays utilizing human monocytes differentiated into tumor like macrophages with IL-10 were co-cultured with autologous T cells and the ability to support T cell receptor mediated activation was assessed. CD47 was added to the cultures and was found to cause upregulation of activation markers of the macrophages as measured by upregulation of CD86 and MHCII. In addition, support of TCR mediated T cell activation was assessed by upregulation of MHCII on the T cells and secretion of IFNγ (FIG. 7A-FIG. 7D).

Figure 8A:
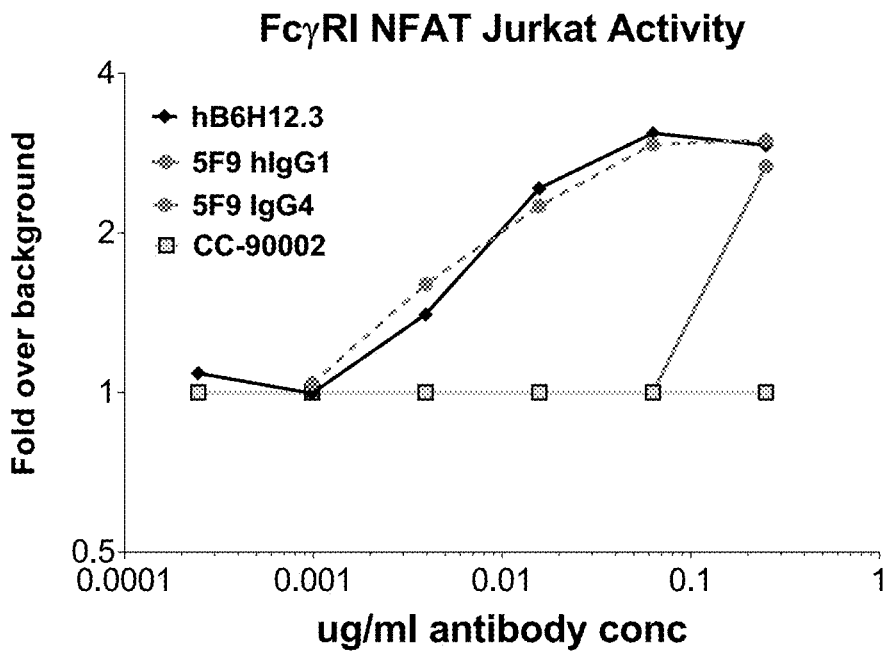
FIG. 8A-FIG. 8D depict a comparison between hB6H12.3 and the anti-CD47 antibody 5F9. FcγRI activation was detected in NFAT luciferase reporter Jurkat cells (FIG. 8A). FcγRII activation was assessed in NFAT luciferase reporter Jurkat cells (FIG. 8B). NK-mediated ADCC activity was determined (FIG. 8C). T cell IFNγ secretion was assessed (FIG. 8D).
Figure 8B:
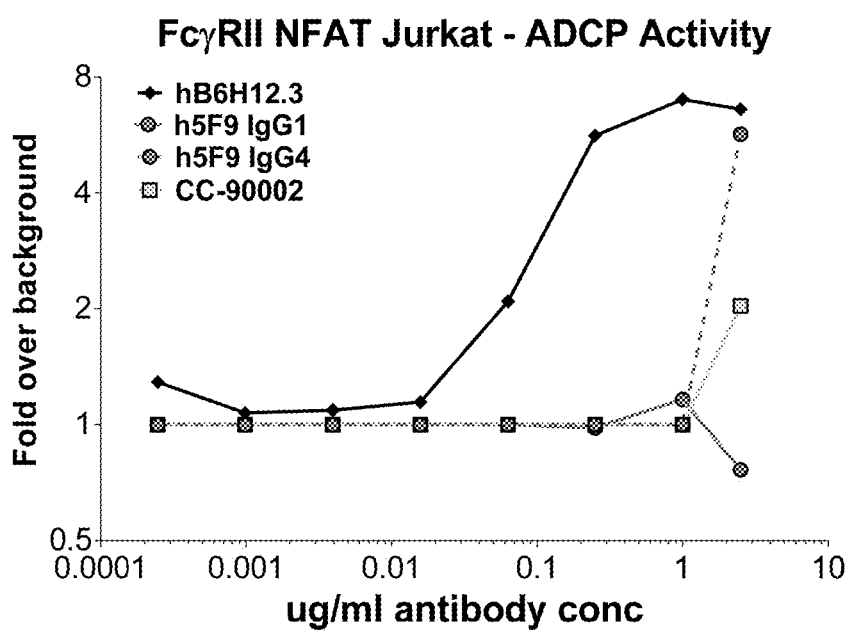

Comparison to Other Anti-CD47 Antibodies hB6H12.3 was compared against other known CD47 antibodies, 5F9 and CC-9002 (See, WO2011/143624). In the comparison, FcγRI and FcγRII activity was measured in the same NFAT-luciferase Jurkat cell assay as described supra. hB6H12.3 displayed a superior ability to activate FcγRI and FcγRII relative to the 5F9 and CC-90002 IgG4 antibodies (FIG. 8A and FIG. 8B).

Figure 8C:
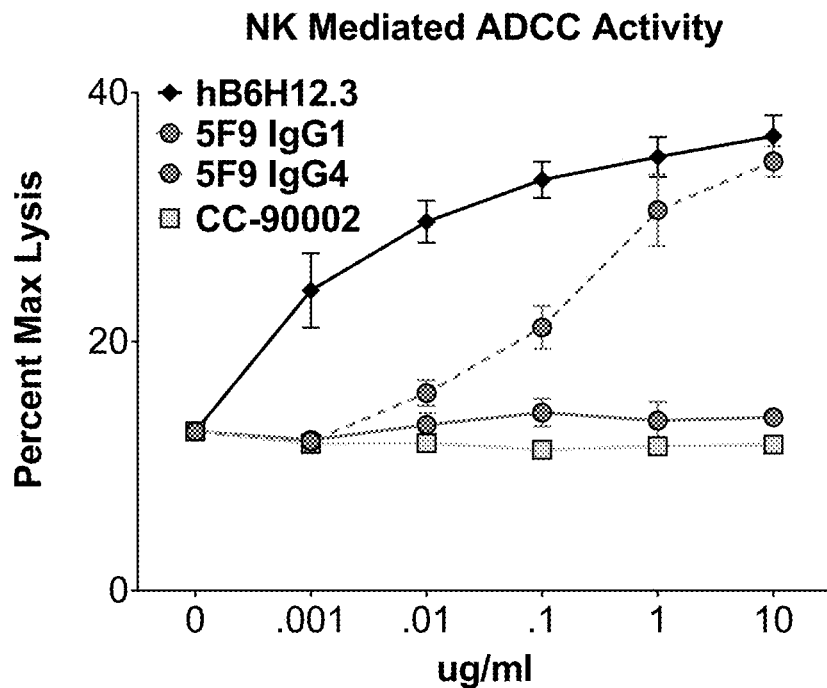
Figure 8D:
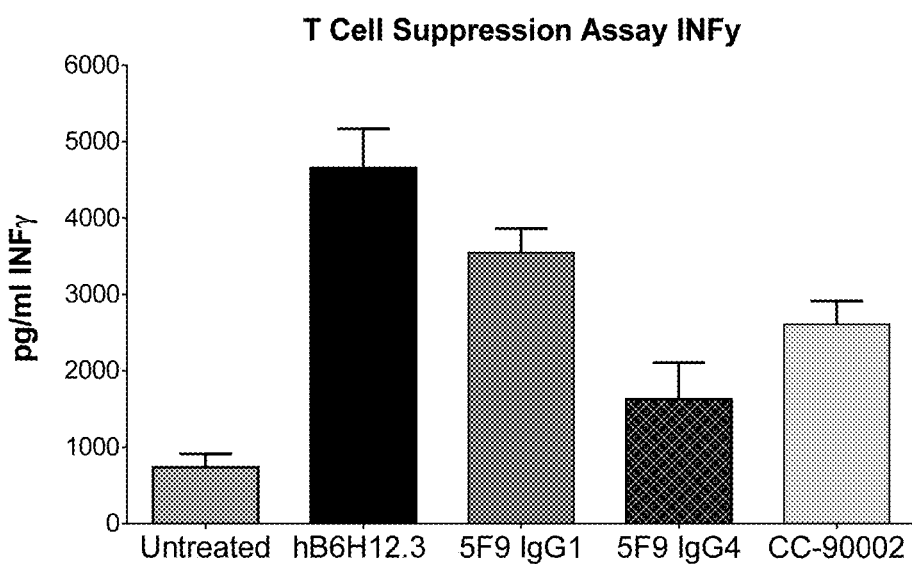

In addition, NK-mediated ADCC and IFNγ secretion was measured as described supra. Once again, hB6H12.3 displayed a superior ability to mediate ADCC and stimulate IFNγ secretion relative to the 5F9 and CC-90002 (FIG. 8C and FIG. 8D).

Example 3: Humanized Anti-CD47 Antibodies with a Mask

Cleavage of Masked Antibodies Using Recombinant Human MMPs for Binding and Functional Studies Recombinant MMPs were all activated via incubation with 1.25 mM 4-aminophenyl mercuric acetate (APMA) at for 1-2 hours 37° C. Typically, 1-2 μg of activated rhMMP2 was added to 0.25-0.5 mg of masked antibody and incubated for 4-16 hours at 37° C. The extent of antibody cleavage was assessed using by reduced antibody reverse-phase LC-MS using a Waters Acquity/Xevo UPLC equipped with a PLRP-MS 3 μm column (Agilent). Data was analyzed using UNIFI software (Waters). Reactivation with MMPs results in site-specific cleavage of the mask at the intended cleavage site. Upon complete reactivation of masked antibodies, the cleaved products were purified using Mab Select SuRe Protein A resin prior to use in binding assays.

Figure 9A:
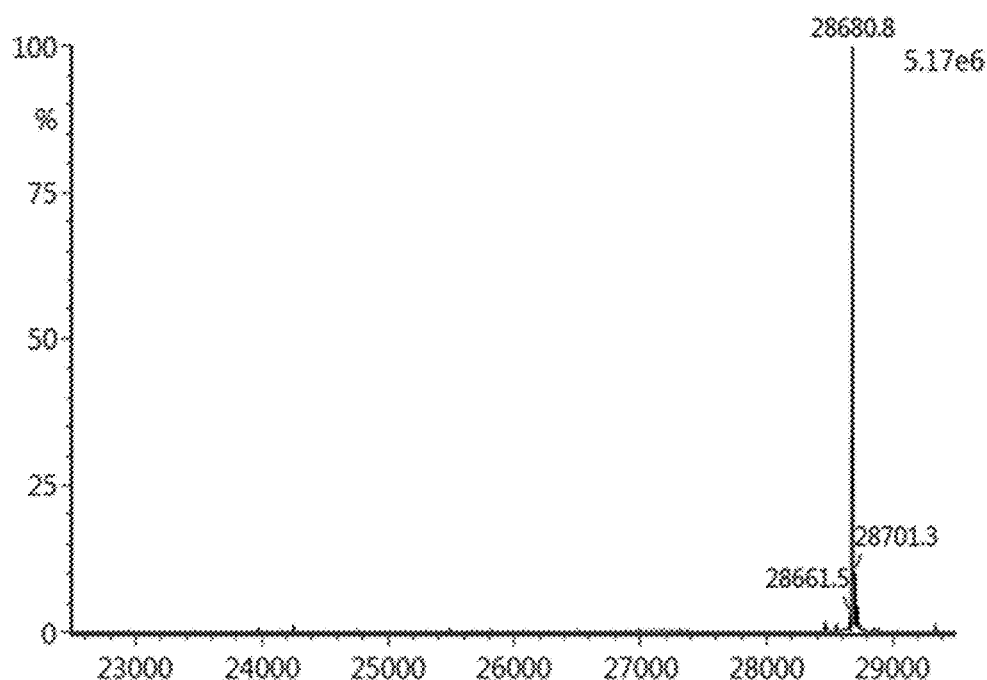
FIG. 9A-FIG. 9B depict mass spectrometry data for MMP2 re-activated masked antibody. Deconvoluted light chain mass for Vel-IPV-hB6H12.3 before (FIG. 9A) and after (FIG. 9B) cleavage with recombinant human MMP2. The expected m/z for intact light chain is 28681 (observed: 28680.8). The expected m/z for MMP2-cleaved antibody (LRSG-hB6H12.3) is 23969 (observed: 23968.4).
Figure 9B:
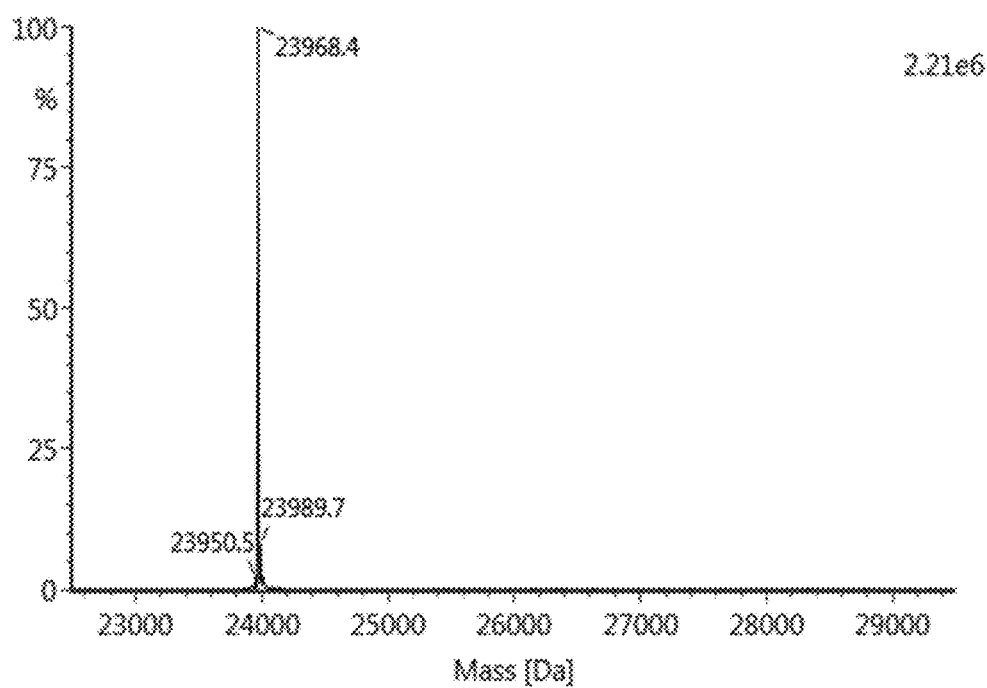

Mass spectrometry data was generated for a MMP2 re-activated masked antibody. Deconvoluted light chain mass for Vel-IPV-hB6H12.3 before (FIG. 9A) and after (FIG. 9B) cleavage with recombinant human MMP2. The expected m/z for intact light chain is 28681 (observed: 28680.8). The expected m/z for MMP2-cleaved antibody (LRSG-hB6H12.3) is 23969 (observed: 23968.4).

Anti-CD47 antibodies bearing a "stub" sequence at the N-terminus that would remain post-proteolysis were also generated through transient expression in either Expi-HEK or Expi-CHO cells. For example, for a masked antibody employing the IPVS-LRSG MMP cleavage sequence, the LRSG sequence remains after MMP activation.

Assessment of Protease Specificity of MMP-Based Cleavage Sequences

MMPs were activated via incubation with 1.25 mM 4-aminophenyl mercuric acetate (APMA) at 37° C. for 1 hour and up to 24 hours. Legumain was activated via 2 hour incubation at 37° C. in 50 mM sodium acetate, 100 mM NaCl, pH 4.0.

To assess the cleavage profile of the cleavage sequences, antibodies (10 μg) were incubated overnight at 37° C. with 400 pmol/min normalized proteases as indicated by manufacturer reported values. The extent of antibody cleavage was assessed using by reduced antibody reverse-phase LC-MS using a Waters Acquity/Xevo UPLC equipped with a PLRP-MS 3 μm column (Agilent). Data was analyzed using UNIFI software (Waters).

The protease cleavage profile of two protease cleavage sites (IPV and M2) were tested against a panel of tumor-associated proteases such as human and murine/rat MMPs, the ADAMs family, uPA, matriptase, and legumain. Additionally, the cleavage of the sequences by extracellular proteases tPA and Factor Xa were also tested. The protease cleavage profiles at these three protease cleavage sites are shown in Table 14.

The peptides (N-terminally fused to the hBU12 antibody backbone) were incubated at 37° C. overnight with 400 pmol/min normalized protease and assessed for cleavage. The M2 site was cleaved by the majority of the MMPs as well as uPA and matriptase. The IPV site was cleaved by almost all MMPs except MMP13 and was untouched by other protease classes.

TABLE 14

Protease cleavage profiles at two different protease cleavage sites.

| Enzyme | Cleavage Sequence: M2 GPLG*VR** (SEQ ID NO: 57) | IPV IPVS*LR**SG (SEQ ID NO: 58) |
|---|---|---|
| Human MMP2 | Complete | Complete |
| Human MMP7 | Complete | Complete |
| Human MMP9 | Complete | Complete |
| Human MMP13 | Complete | Minimal |
| Murine MMP2 | Complete | Partial |
| Murine MMP7 | Partial | Complete |
| Rat MMP9 | Partial | Complete |
| uPA | Partial | None |
| Matriptase | Complete | Minimal |
| Legumain | None | Minimal |
| tPA | — | None |
| Factor Xa | Minimal | None |
| ADAMs (hu, mu) | None | None |

The MMP-cleavage site is indicated by* while the uPA/matriptase/legumain cleavage sites are indicated by**. Cleavage at either site is sufficient to restore antibody binding Saturation Binding of Masked Anti-CD47 Antibodies Saturation binding of anti-CD47 antibodies to SW780 human bladder cancer cells was performed. Vel-IPV-masked hB6H12 antibodies were tested along with MMP2 pre-activated comparators. The cleaved Vel-IPV-antibodies possessed a remnant -LRSG sequence at the antibody N-termini (FIG. 10 and Table 15).

TABLE 15

Figure 10:
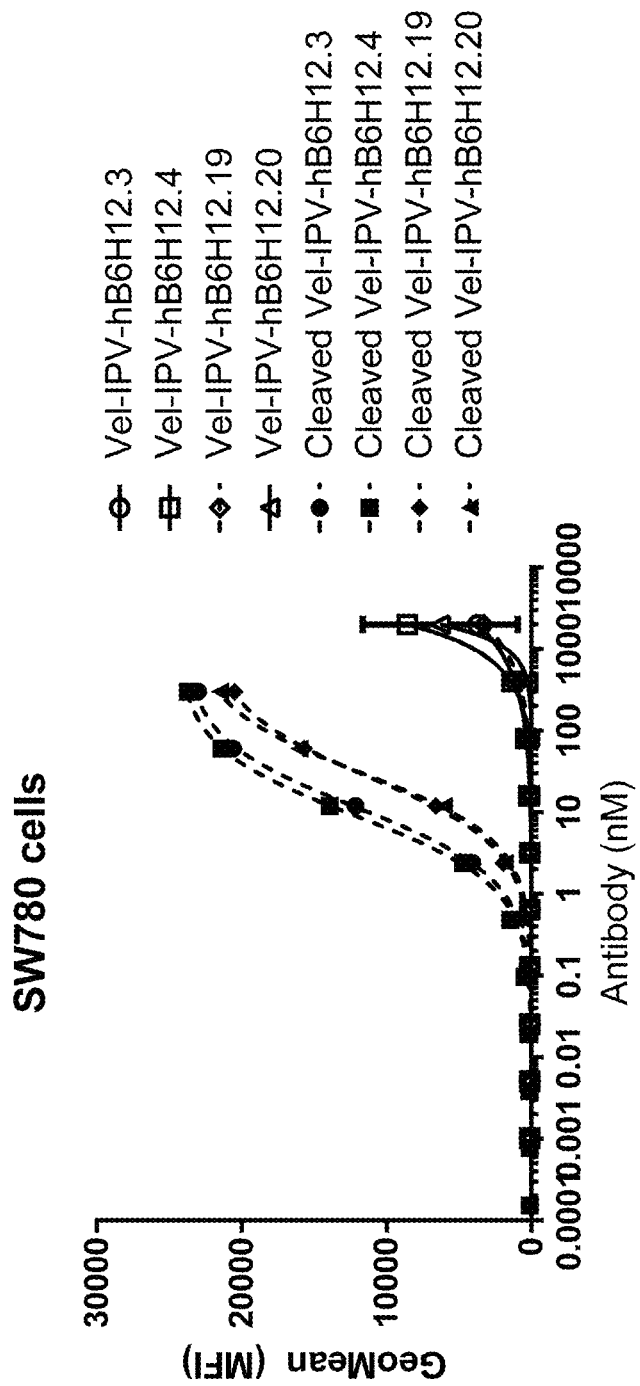
FIG. 10 depicts saturation binding of anti-CD47 antibodies to SW780 human bladder cancer cells. Vel-IPV-masked hB6H12 antibodies were tested along with MMP2 pre-activated comparators. Cleaved Vel-IPV-antibodies possessed a remnant LRSG sequence at the antibody N-termini.

Determination of binding affinity (Kd) to
SW780 cells obtained by saturation binding (FIG. 10).

| Antibody | Kd (nM) |
| --- | --- |
| Cleaved Vel-IPV-hB6H12.3 | 11.4 |
| Cleaved Vel-IPV-hB6H12.4 | 9.2 |
| Cleaved Vel-IPV-hB6H12.19 | 26.6 |
| Cleaved Vel-IPV-hB6H12.20 | 30.2 |
| Vel-IPV-hB6H12.3 | >2000 |
| Vel-IPV-hB6H12.4 | >2000 |
| Vel-IPV-hB6H12.19 | >2000 |
| Vel-IPV-hB6H12.20 | >2000 |

Figure 11:
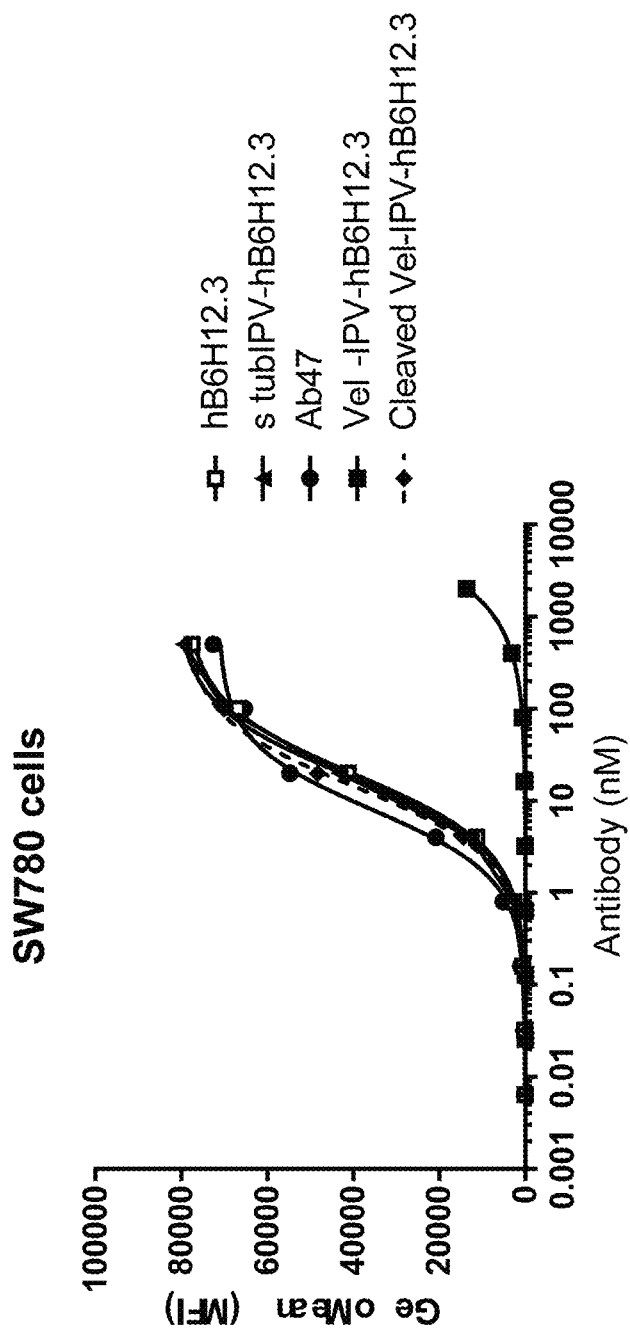
FIG. 11 depicts saturation binding of anti-CD47 antibodies to SW780 human bladder cancer cells. Vel-IPV-masked hB6H12 antibodies were tested along with MMP2 pre-activated comparators. Cleaved Vel-IPV and stub-IPV antibodies possessed a remnant LRSG sequence at the antibody N-termini. The cleaved antibody was generated through cleavage with MMP2, whereas the stub-IPV antibody was generated recombinantly.

Vel-IPV-masked hB6H12 antibodies were tested along with MMP2 pre-activated comparators. Cleaved Vel-IPV- and stub-IPV antibodies possessed a remnant -LRSG sequence at the antibody N-termini. The cleaved antibody was generated through cleavage with MMP2 whereas stub-IPV antibody was generated recombinantly (FIG. 11 and Table 16). As used herein, a "stub," a "stub antibody" or a "stub antigen-binding fragment" refers to an antibody or antigen-binding fragment after cleavage by an MMP or an antibody or antigen-binding fragment that was generated recombinantly, i.e., produced without the coiled coil domain and, therefore, no cleavage was performed. MMP cleavage lead to a short amino acid sequence remnant. For the IPV cleavage site, the remnant, or stub, sequence should be LRSG or SG. For the M2 cleavage site, the remnant, or stub, sequence should be VR.

TABLE 16

Determination of binding affinity (Kd) to SW780 cells
obtained by saturation binding (FIG. 11).

| Antibody | Kd (nM) |
| --- | --- |
| hB6H12.3 | 19.2 |
| Ab47 | 8.0 |
| Vel-IPV-hB6H12.3 | >2000 |
| stubIPV-hB6H12.3 | 18.1 |
| Cleaved Vel-IPV-hB6H12.3 | 14.2 |

Saturation binding of anti-CD47 antibodies to human red blood cells was performed. Vel-IPV-masked hB6H12 antibodies were tested along with re-activated comparators (stub IPV-hB6H12.3 or MMP2-cleaved Vel-IPV-hB6H12.3). Cleaved Vel-IPV- and stub-IPV antibodies possessed a remnant -LRSG sequence at the antibody N-termini. The cleaved antibody was generated through cleavage with MMP2 whereas the stub-IPV antibody was generated recombinantly (FIG. 12 and Table 17).

TABLE 17

Determination of binding affinity (Kd) to human red
blood cells obtained by saturation binding (FIG. 12).

| Antibody | Kd (nM) |
| --- | --- |
| hB6H12.3 | 58.2 |
| Ab47 | 26.5 |
| Vel-IPV-hB6H12.3 | >2000 |
| stubIPV-hB6H12.3 | 46.8 |
| Cleaved Vel-IPV-hB6H12.3 | 41.7 |

Saturation binding of anti-CD47 antibodies to rhCD47 by ELISA was performed. Vel-IPV-hB6H12.3 displayed significantly impaired binding. Binding could be restored upon cleavage by rhMMP2 (FIG. 13 and Table 18).

TABLE 18

Figure 13:
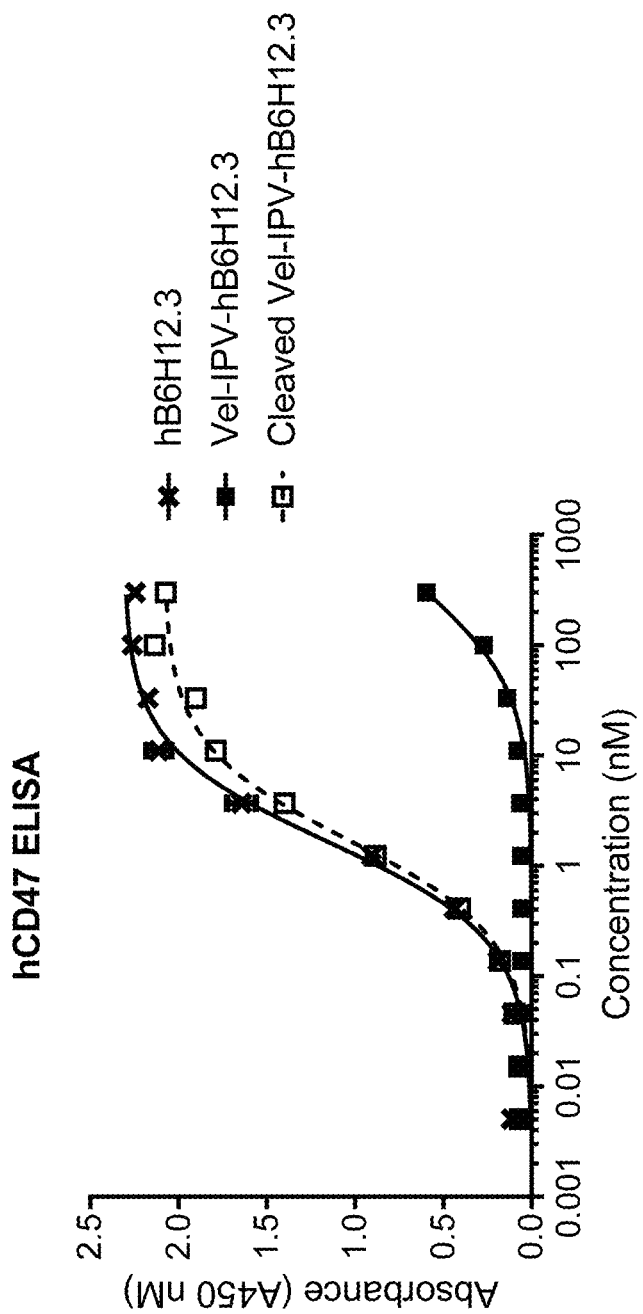
FIG. 13 depicts saturation binding of anti-CD47 antibodies to rhCD47 by as detected ELISA. Vel-IPV-hB6H12.3 displayed significantly impaired binding. Binding could be restored upon cleavage by rhMMP2.

Determination of binding affinity (Kd) to
rhCD47 by ELISA (FIG. 13).

| Antibody | Kd (nM) |
| --- | --- |
| hB6H12.3 | 1.7 |
| Vel-IPV-hB6H12.3 | 1.7 |
| Cleaved Vel-IPV-hB6H12.3 | >250 |

Saturation binding of anti-CD47 antibodies to rhCD47 by ELISA was performed with hB6H12.3 G91A, which has a G91A point mutation in LCDR3. Both hB6H12.3 and hB6H12.3 G91A displayed a higher $B_{max}$ than Ab47 (FIG. 14 and Table 19).

TABLE 19

Figure 14:
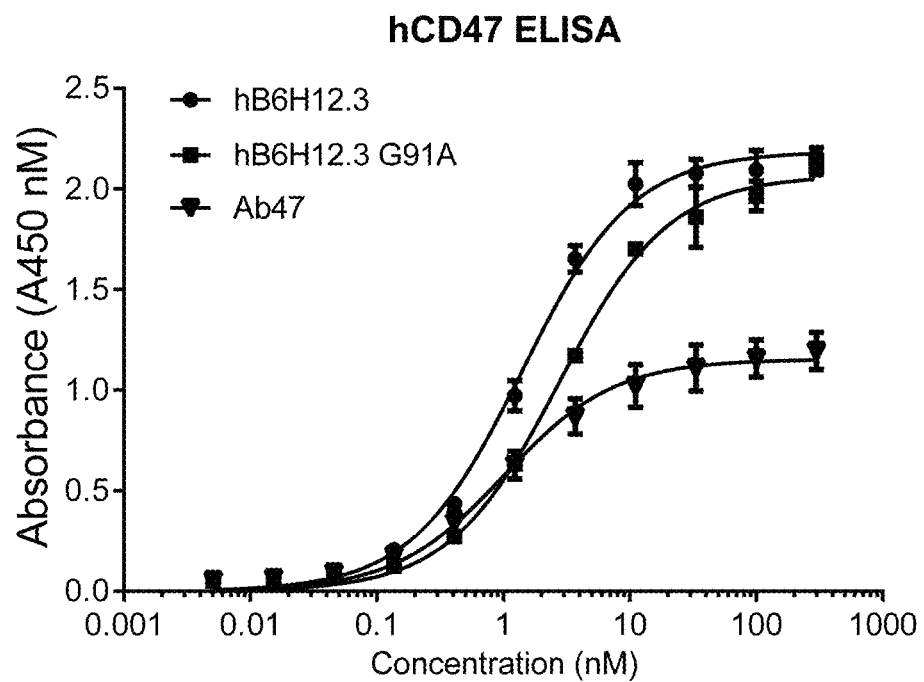
FIG. 14 depicts saturation binding of anti-CD47 antibodies to rhCD47 as detected by ELISA. Both hB6H12.3 and hB6H12.3 G91A display a higher $B_{max}$ than Ab47.

Determination of binding affinity (Kd) to
rhCD47 by ELISA (FIG. 14).

| Antibody | Kd (nM) |
| --- | --- |
| Ab47 | 1.0 |
| hB6H12.3 | 1.4 |
| hB6H12.3 G91A | 2.7 |

Saturation binding of anti-CD47 antibodies to SW780 human bladder cancer cells was performed. Binding of Ab47 and hB6H12.3 was compared to variants bearing a G91A mutation in LCDR3 (FIG. 15 and Table 20).

TABLE 20

Figure 15:
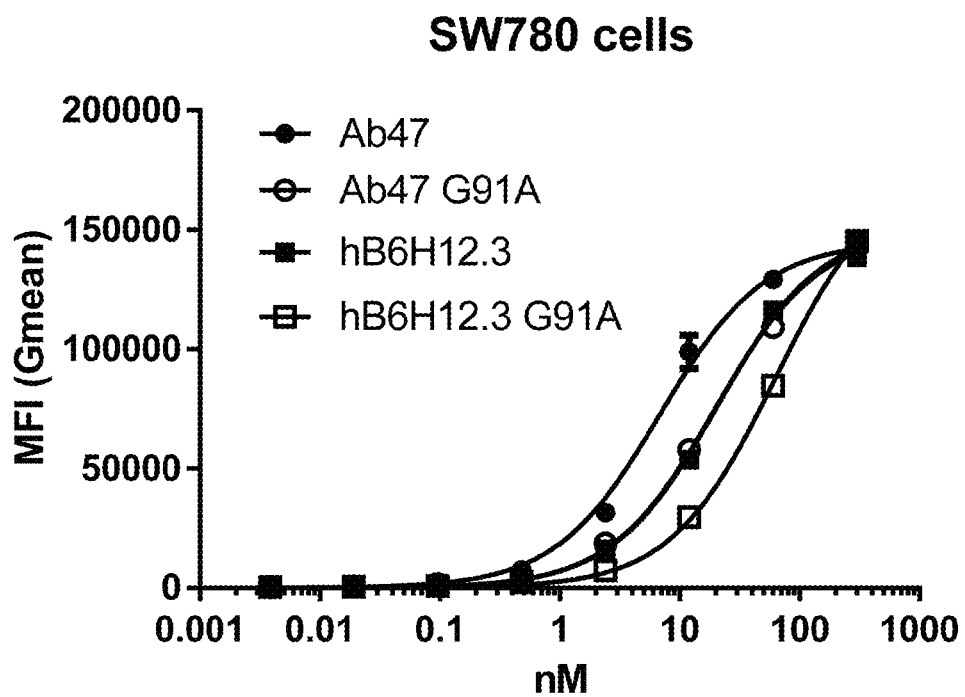
FIG. 15 depicts saturation binding of anti-CD47 antibodies to SW780 human bladder cancer cells. Binding of Ab47 and hB6H12.3 was compared to variants bearing a G91A mutation in CDR-L3.

Determination of binding affinity (Kd) to SW780 human bladder
cancer cells obtained by saturation binding (FIG. 15).

| Antibody | Kd (nM) |
| --- | --- |
| Ab47 | 6.8 |
| Ab47 G91A | 19.8 |
| hB6H12.3 | 20.5 |
| hB6H12.3 G91A | 62.3 |

Saturation binding of anti-CD47 antibodies to human red blood cells was performed. Binding of Ab47 and hB6H12.3 was compared to variants bearing a G91A mutation in LCDR3 (FIG. 16 and Table 21).

TABLE 21

Figure 16:
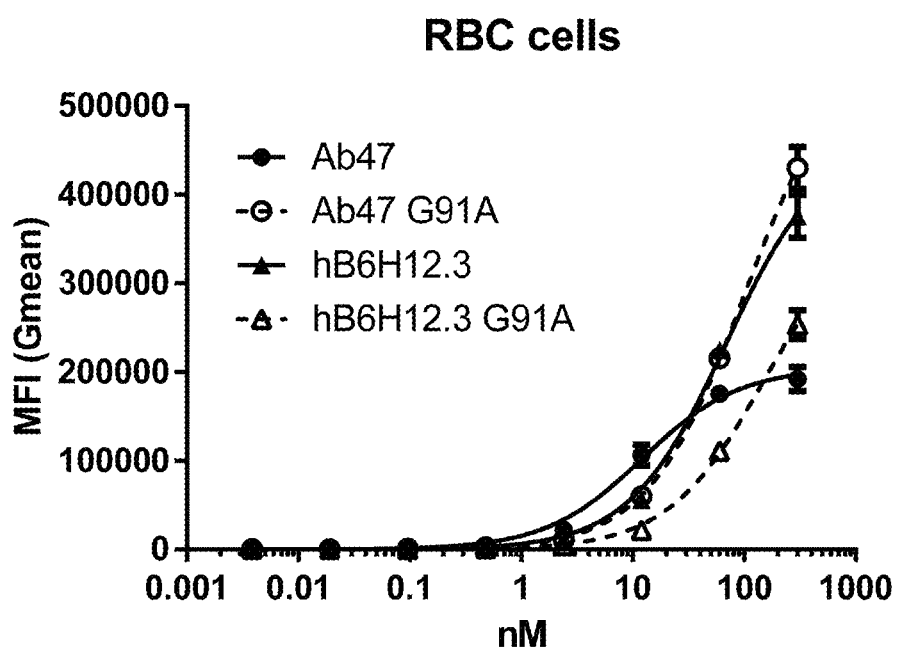
FIG. 16 depicts saturation binding of anti-CD47 antibodies to human red blood cells. Binding of Ab47 and hB6H12.3 was compared to variants bearing a G91A mutation in CDR-L3.

Determination of binding affinity (Kd) to red blood cells
obtained by saturation binding (FIG. 16).

| Antibody | Kd (nM) |
| --- | --- |
| Ab47 | 12.1 |
| Ab47 G91A | 100.3 |
| hB6H12.3 | 68.9 |
| hB6H12.3 G91A | >150 |

Example 4: In Vivo Experiments

Assessment of macrophage infiltration in tissues can be conducted by monitoring for surface markers of macrophages, including F4/80 for mouse macrophages or CD163, CD68, or CD11b by conventional methods that include immunohistochemistry (IHC), Western blot, flow cytometry, or RNA sequencing methods.

Assessment of proteases in tissues can be monitored using a variety of techniques, including both those that monitor protease activity as well as those that can detect proteolytic activity. Conventional methods that can detect the presence of proteases in a tissue, which could include both inactive and active forms of the protease, include IHC, RNA sequencing, Western blot, or ELISA-based methods. Additional techniques can be used to detect protease activity in tissues, which includes zymography, in situ zymography by fluorescence microscopy, or the use of fluorescent proteolytic substrates. In addition, the use of fluorescent proteolytic substrates can be combined with immuno-capture of specific proteases. Additionally, antibodies directed against the active site of a protease can be used by a variety of techniques including IHC, fluorescence microscopy, Western blotting, ELISA, or flow cytometry (See, Sela-Passwell et al. Nature Medicine. 18:143-147. 2012; LeBeau et al. Cancer Research. 75:1225-1235. 2015; Sun et al. Biochemistry. 42:892-900. 2003; Shiryaev et al. 2:e80. 2013.)

Figure 17A:
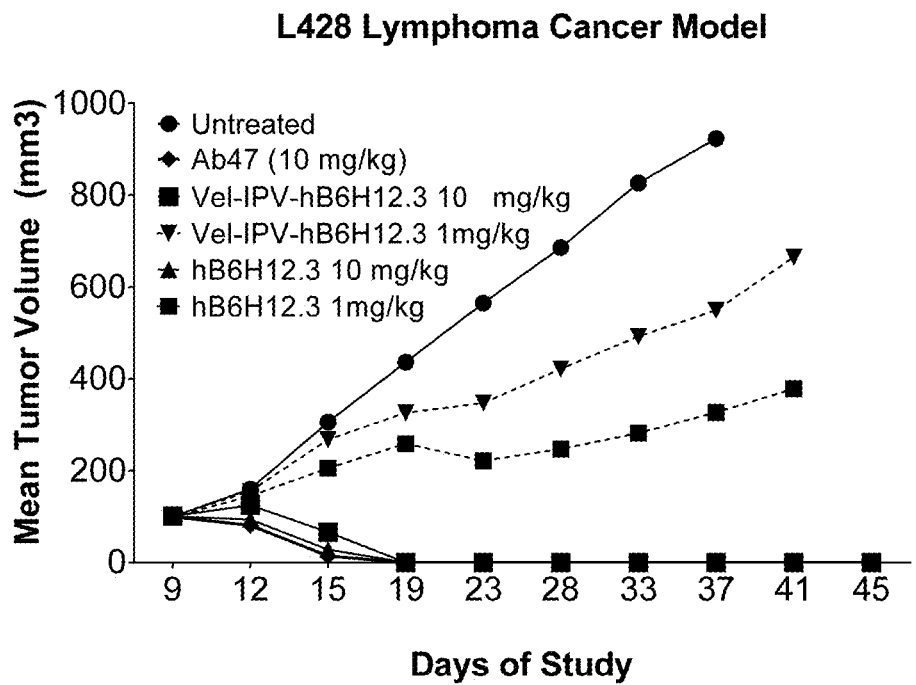
FIG. 17A-FIG. 17B depict the activity of anti-CD47 antibodies in an L428 xenograft tumor model in NSG mice. Antibodies were administered intraperitoneally (i.p.) every four days for four doses (q4d×4) at either 1 or 10 mg/kg (FIG. 17A). Analysis of tumor tissue using the anti-F4/80 macrophage marker showed the presence of murine macrophages in the L428 xenograft tumor model (FIG. 17B).
Figure 17B:
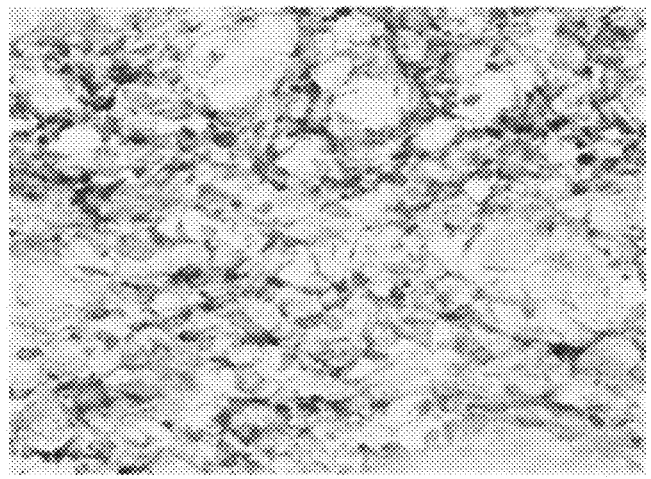

The activity of anti-CD47 antibodies in a L428 lymphoma xenograft tumor model in NSG mice was determined. This xenograft model has high macrophage infiltration, as evidenced by robust staining of mouse F4/80 by IHC. See, e.g., FIG. 17B. Antibodies were administered i.p. q4dx4 at either 1 or 10 mg/kg. The masked antibody Vel-IPV-hB6H12.3 as well as unmasked antibodies Ab47 and hB6H12.3 all effectively reduced tumor volume over the study duration at a dose of 10 mg/kg. At a dose of 1 mg/kg, both Vel-IPV-hB6H12.3 and unmasked hB6H12.3 provide tumor growth delay. The masked antibody, Vel-IPV-hB6H12.3, was slightly less active than the unmasked hB6H12.3 at this dose. (FIG. 17A).

Figure 18A:
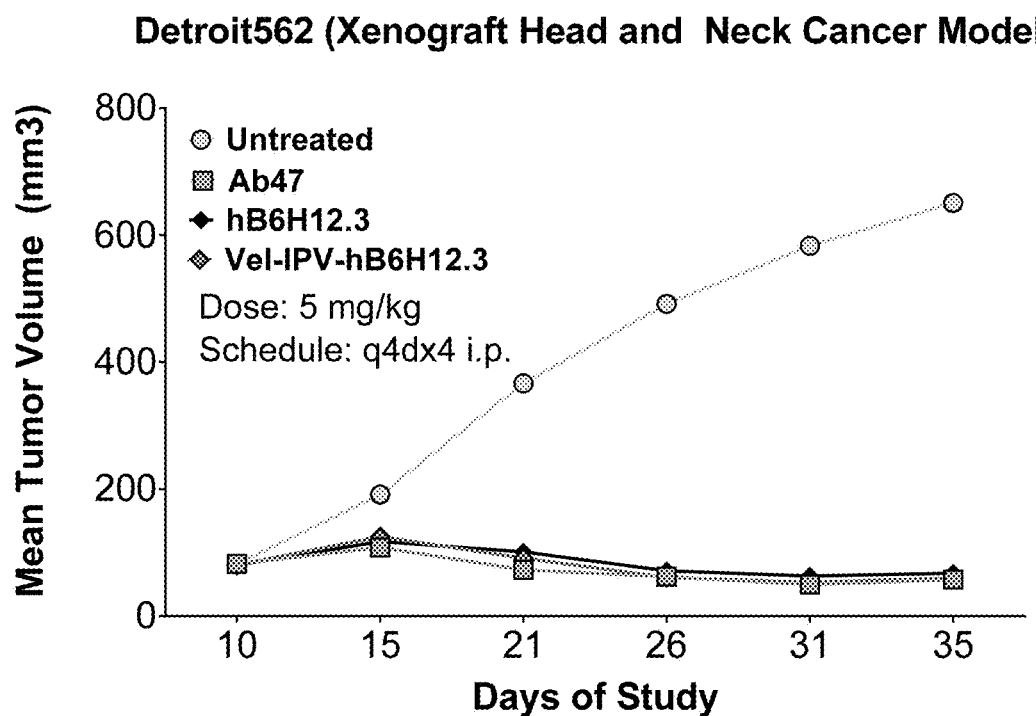
FIG. 18A-FIG. 18D depict the activity of anti-CD47 antibodies in an L428 xenograft tumor model in NSG mice. Antibodies were administered i.p. q4d×4 at either 1 or 10 mg/kg (FIG. 18A). Analysis of tumor tissue using the anti-F4/80 macrophage marker revealed the presence of murine macrophages in the Detroit 562 xenograft tumor model (FIG. 18B). The activity of anti-CD47 antibodies in an SUDHL8 xenograft tumor model in NSG mice was also analyzed (FIG. 18C). Antibodies were administered i.p. q4d×4 at either 1 or 10 mg/kg. Analysis of tumor tissue using the anti-F4/80 macrophage marker showed the presence of murine macrophages in the SUDHL8 xenograft tumor model (FIG. 18D).
Figure 18B:
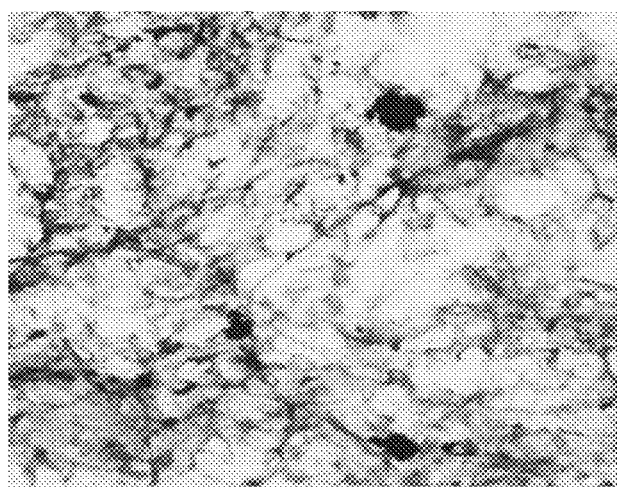
Figure 18C:
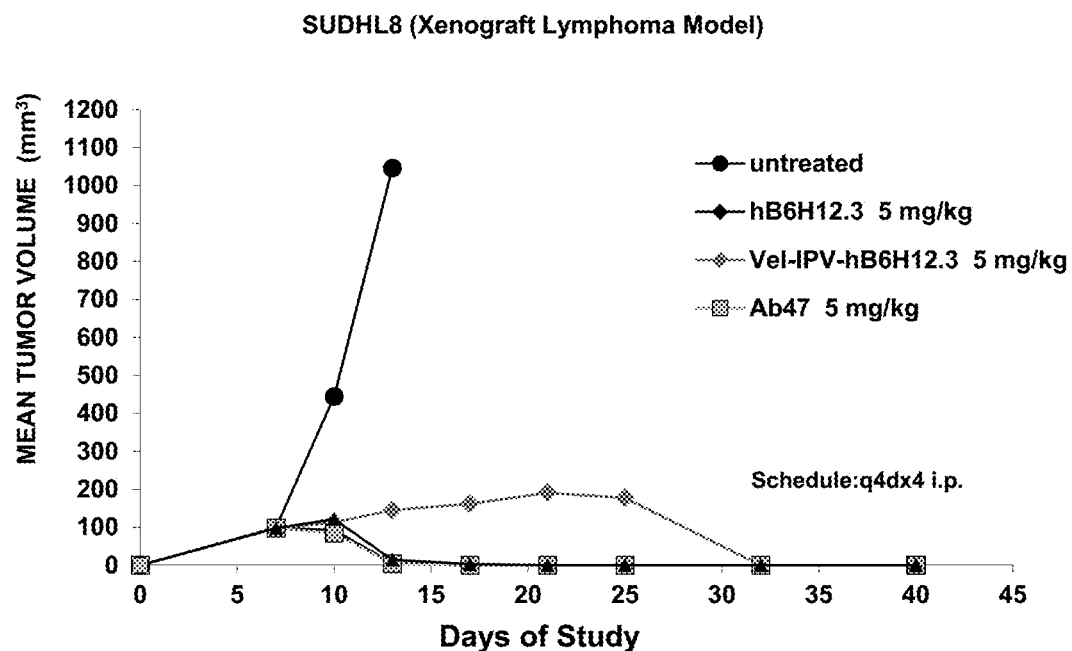
Figure 18D:
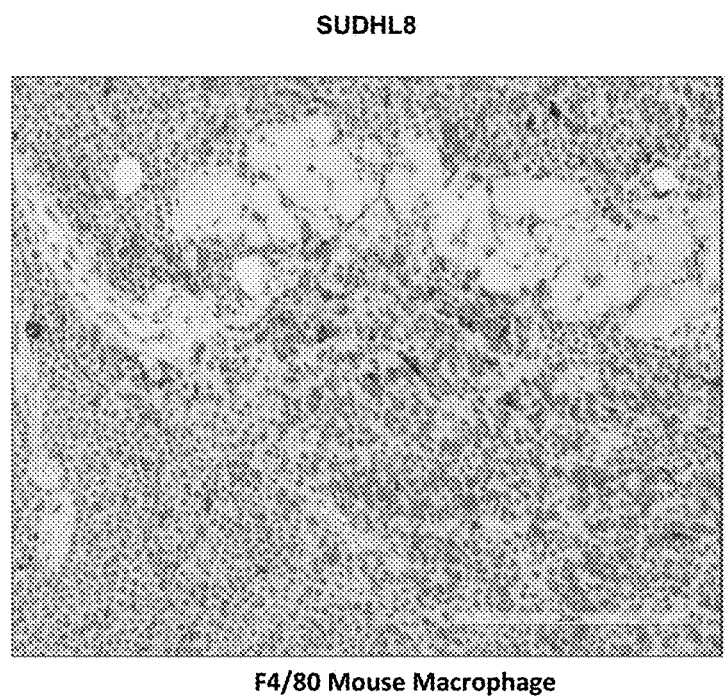

The activity of anti-CD47 antibodies in a Detroit 562 xenograft head and neck tumor model in NSG mice was determined. This xenograft model has high macrophage infiltration, as evidenced by robust staining of mouse F4/80 by IHC. See, FIG. 18B. q4dx4 at 5 mg/kg. The antibodies Ab47, hB6H12.3, and Vel-IPV-hB6H12.3 effectively reduced tumor volume over the study duration (FIG. 18A).

Figure 19A:
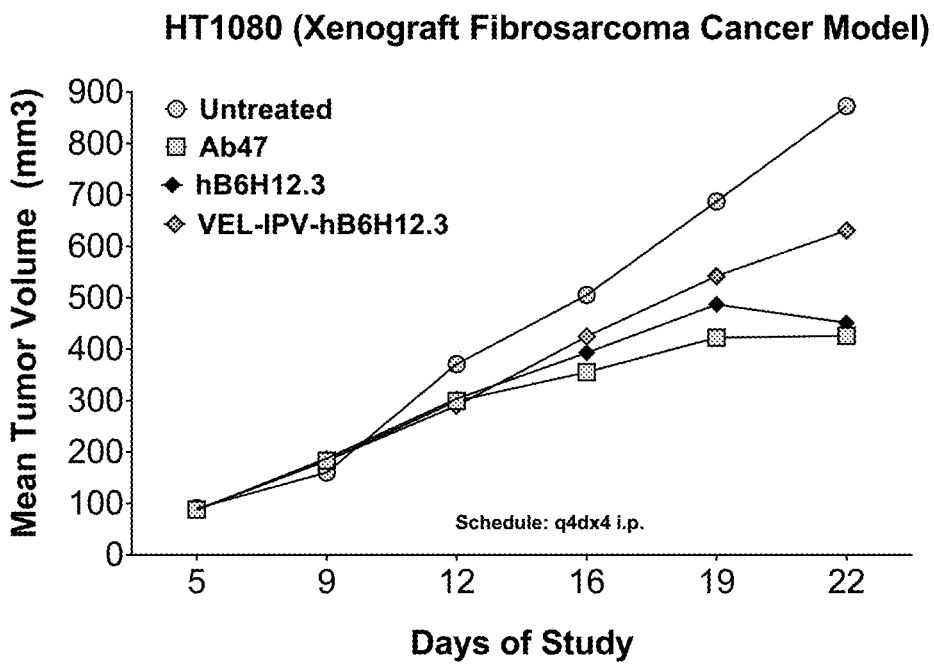
FIG. 19A-FIG. 19D depict the activity of anti-CD47 antibodies in tumor models having low intrinsic macrophage content. An HT1080 Fibrosarcoma cancer model (FIG. 19A & FIG. 19B) and an HepG2 Hepatocellular cancer model (FIG. 19C & FIG. 19D) are depicted. Antibodies were administered i.p. q4d×4 at 10 mg/kg. Analysis of tumor tissue using the anti-F4/80 macrophage marker showed the presence of murine macrophages in the HT1080 Fibrosarcoma cancer model (FIG. 19B) and the HepG2 Hepatocellular cancer model (FIG. 19D).
Figure 19B:
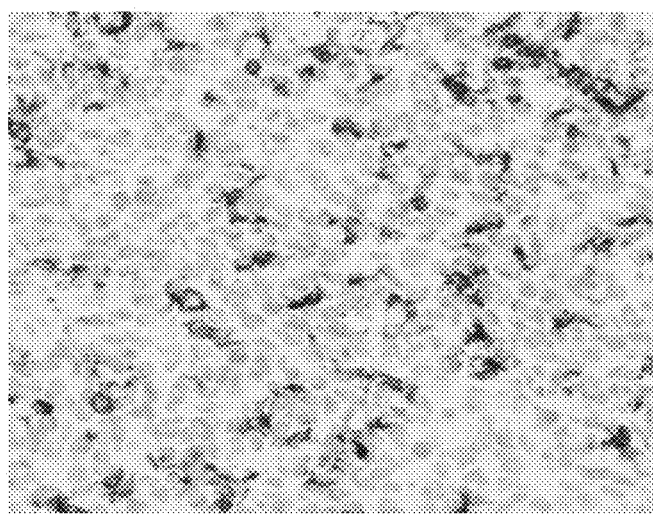
Figure 19C:
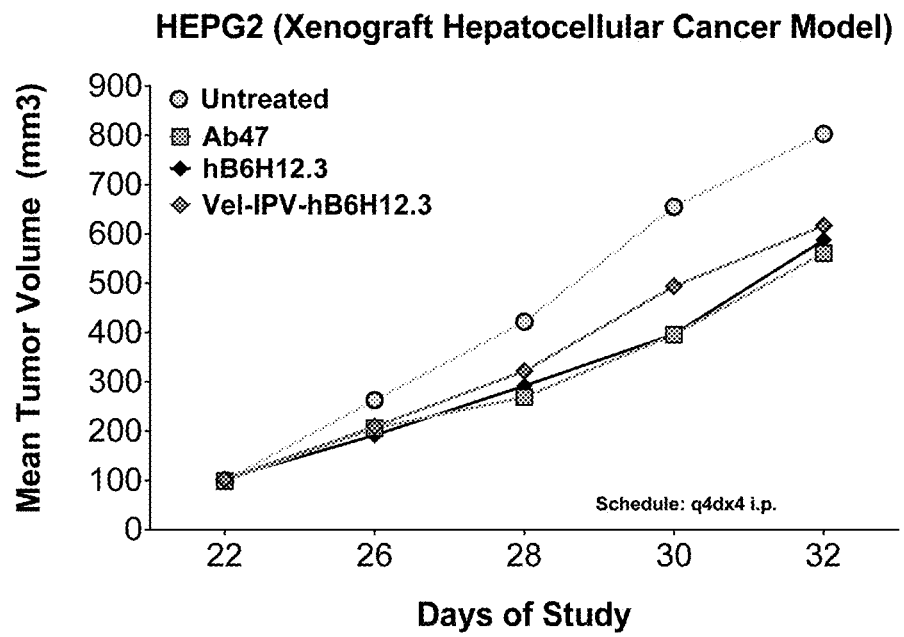
Figure 19D:
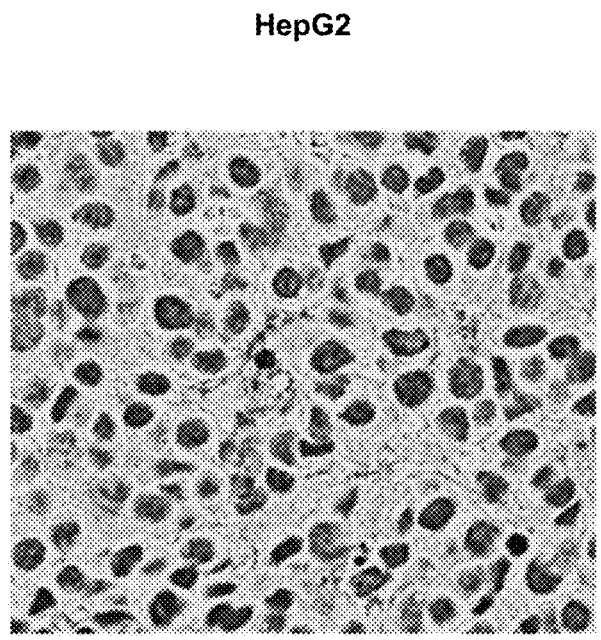

The activity of anti-CD47 antibodies in a HT1080 xenograft fibrosarcoma tumor model (FIGS. 19A and 19B) and a HEPG2 xenograft hepatocellular tumor model (FIGS. 19C and 19D) in NSG mice was determined. These xenograft models have low macrophage infiltration, as evidenced by limited staining of mouse F4/80 by IHC.q4dx4 at 10 mg/kg. The antibodies Ab47, hB6H12.3, and Vel-IPV-hB6H12.3 effectively reduced and/or slowed tumor volume over the study duration.

Figure 35A:
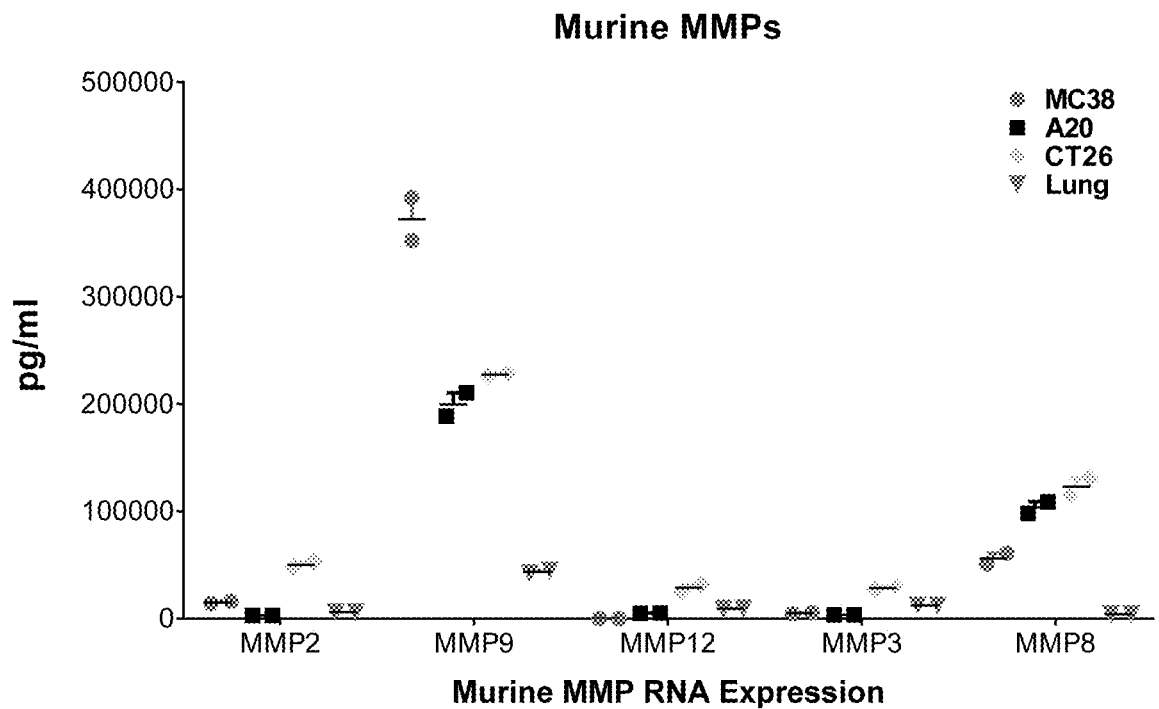
FIG. 35A-FIG. 35B Tumor MMP levels in select murine and human cancers relative with those present within cell culture systems.
Figure 35B:
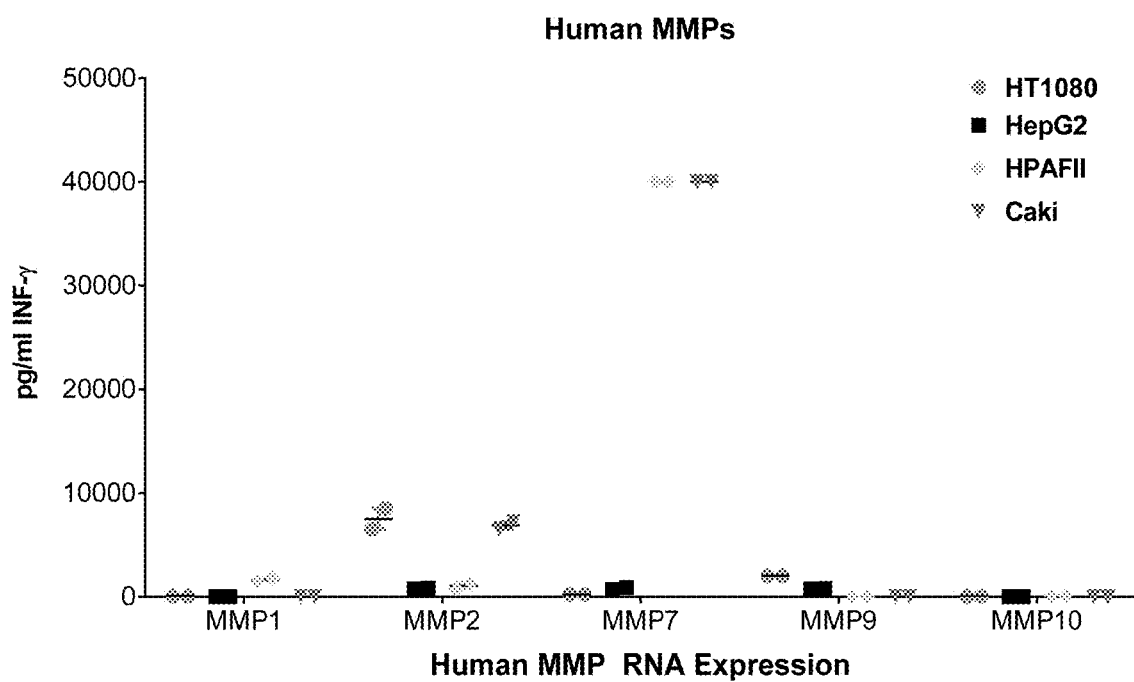

In addition to assessing anti-tumor activity and its correlation with macrophage infiltration, levels of MMPs within these tumors as well as assessment of antibody unmasking has been assessed. Tumors from xenograft and syngeneic tumor models were harvested and subjected to protein and RNA seq assessment to monitor the levels of MMPs within these tumors as well as gain an understanding of the correlation between RNA and protein levels within the TME. Protein analysis using the Luminex multiplex platform revealed that the tumors used to investigate anti-tumor activity of Vel-IPV-hB6H12.3 all contained robust levels of both MMP2 and 9 (Table 22). Additionally, when we compared the tumor MMP levels with those present within cell culture systems, we found a marked increase in the MMP levels at the tumor site that well exceeded the levels seen just in in vitro tissue culture conditions (FIGS. 35A and 35B).

TABLE 22

MMP2 and MMP9 levels in select tumors (pg/ml).

| | | Tumors | | |
| --- | --- | --- | --- | --- |
| | MMPs | HT1080 | HEPG2 | L428 |
| Xenograft Models | MMP2 | 7506 | 787 | 204 |
| | MMP9 | 2020 | 771 | 47 |
| Syngeneic Models | MMP2 | 8453 | 27765 | 47899 |
| | MMP9 | 28137 | 20845 | 22661 |

Figure 20:
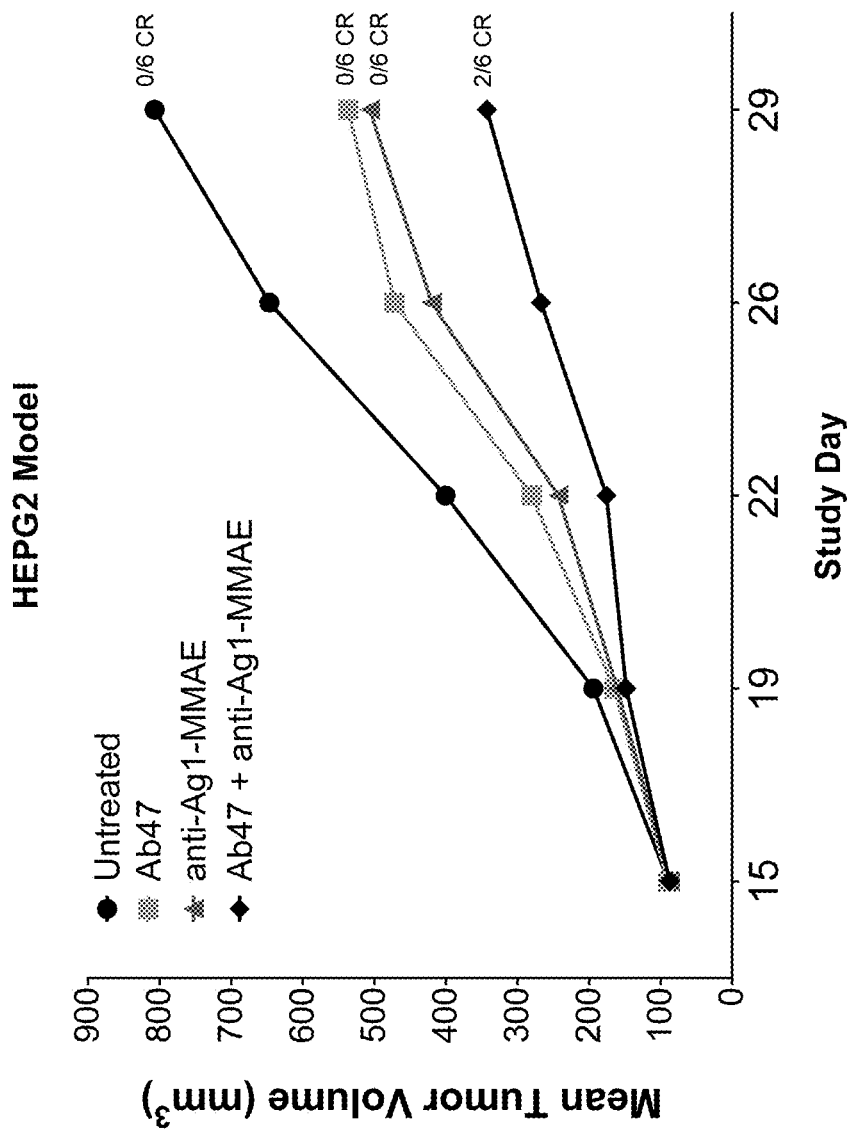
FIG. 20 depicts the activity of anti-CD47 antibodies in tumor models having low intrinsic macrophage content, which can be amplified when combined with a monomethyl auristatin E (MMAE) antibody-drug conjugate (ADC) (which is known to drive macrophage infiltration). Anti-CD47 antibody was administered i.p. q4d×4 at 5 mg/kg while with the MMAE ADC was given once at 1 mg/kg.
Figure 36A:
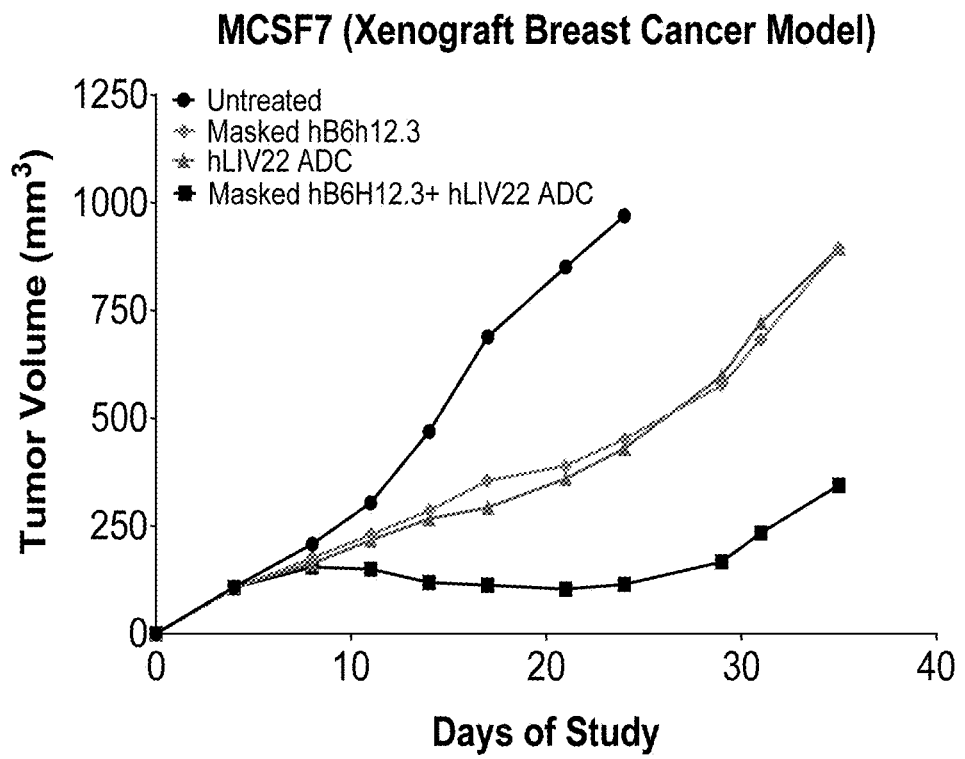
FIG. 36A-FIG. 36B depicts select MMAE containing auristatins (LIV1A and CD30) in combination with an anti-CD47 antibody in the breast cancer xenograft model MCSF7 for Liv1A ADC and the L428 lymphoma model for CD30 ADC.
Figure 36B:
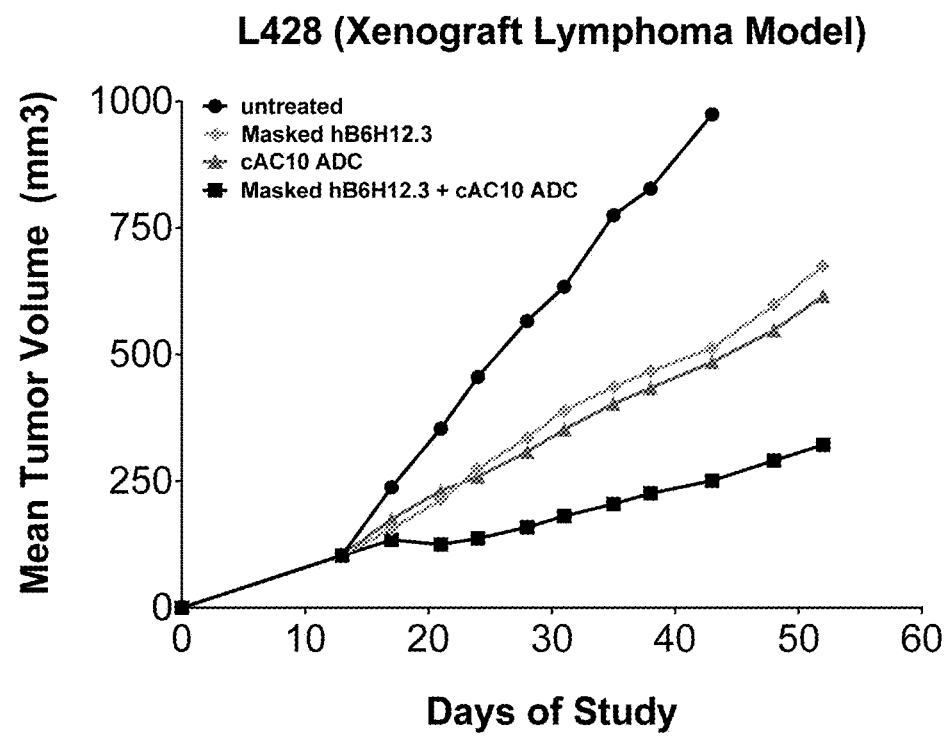

The activity of anti-CD47 antibodies in a tumor model with low intrinsic macrophage content can be amplified when combined with MMAE auristatin ADC which is known to drive macrophage infiltration. This was demonstrated in the HepG2 xenograft tumor model in NSG mice. Anti-CD47 antibodies were administered i.p. q4dx4 at 5 mg/kg while with the MMAE ADC was dosed once at 1 mg/kg. The combination of antibodies was more effective at reducing tumor volume than either antibody alone (FIG. 20). Additional experiments with other MMAE containing auristatins (LIV1A and CD30) have demonstrated similar combinability with anti-CD47 antibody in the breast cancer xenograft model MCSF7 for Liv1A ADC and the L428 lymphoma model for CD30 ADC (FIGS. 36A and 36B).

Figure 21A:
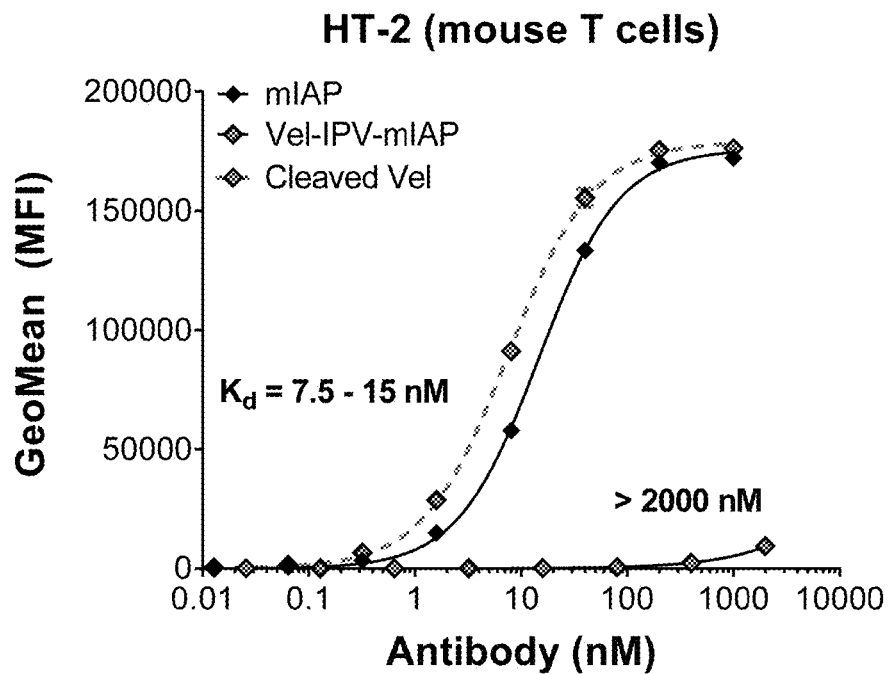
FIG. 21A-FIG. 21B depict that a mouse reactive anti-CD47 antibody, mIAP301, can be masked using the same VEL and IPV sequences used on the human hB6H12.3 antibody (FIG. 21A). Masking with these constructs blocked antibody binding to murine CD47-positive tumors (FIG. 21B), and prevented funct
Figure 21B:
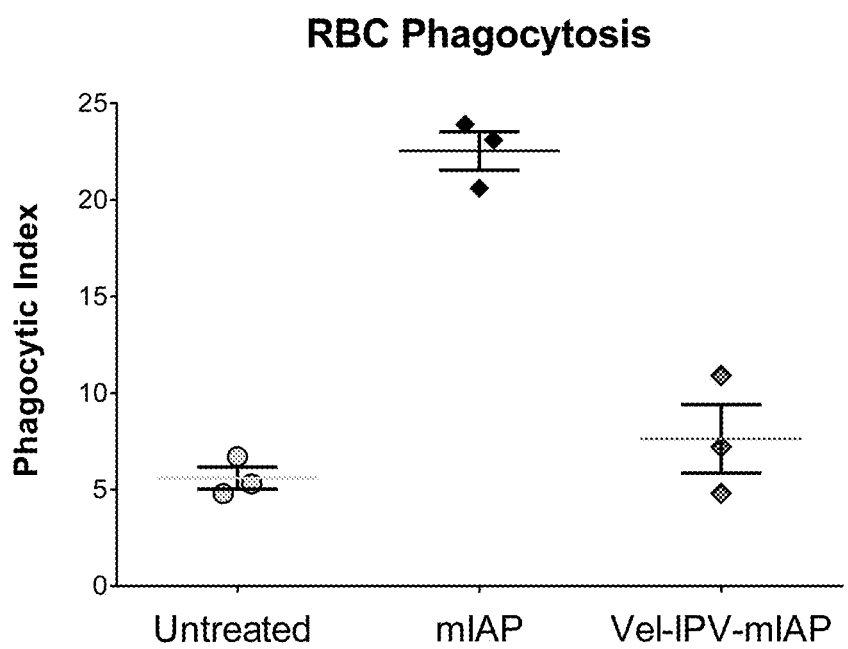

Mouse reactive anti-CD47 antibody mIAP301 (Oldenborg et al., J. Exp. Med. 193:855-861, 2001) could be masked using the same VEL and IPV sequence used on the human hB6H12.3 antibody. Masking with these constructs blocked antibody binding to murine CD47 positive tumors (FIG. 21A) and prevented functionality as measured by RBC phagocytosis (FIG. 21B).

Figure 22A:
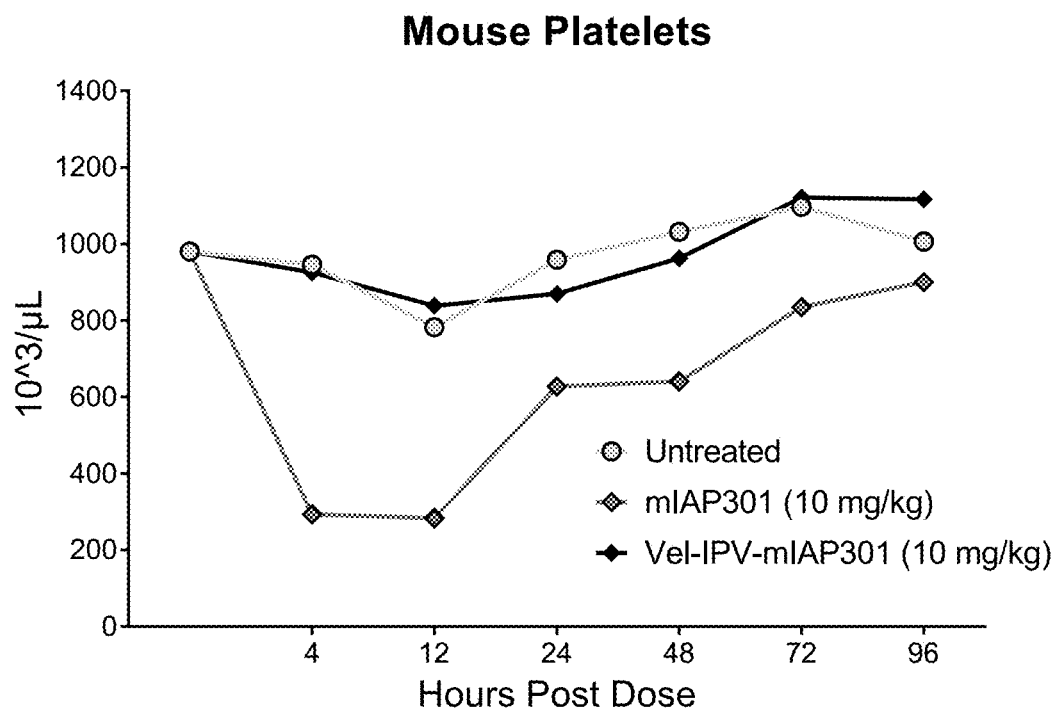

The anti-mouse CD47 antibody mIAP301 drives depletion of platelets in BALB/c mice when administered at a single IV dose of 10 mg/kg. In contrast, this depletion was not observed when mice were administered masked Vel-IPV-mIAP301 and Vel-M2-mIAP301 antibodies at a dose of 10 mg/kg IV (FIG. 22A).

Figure 22B:
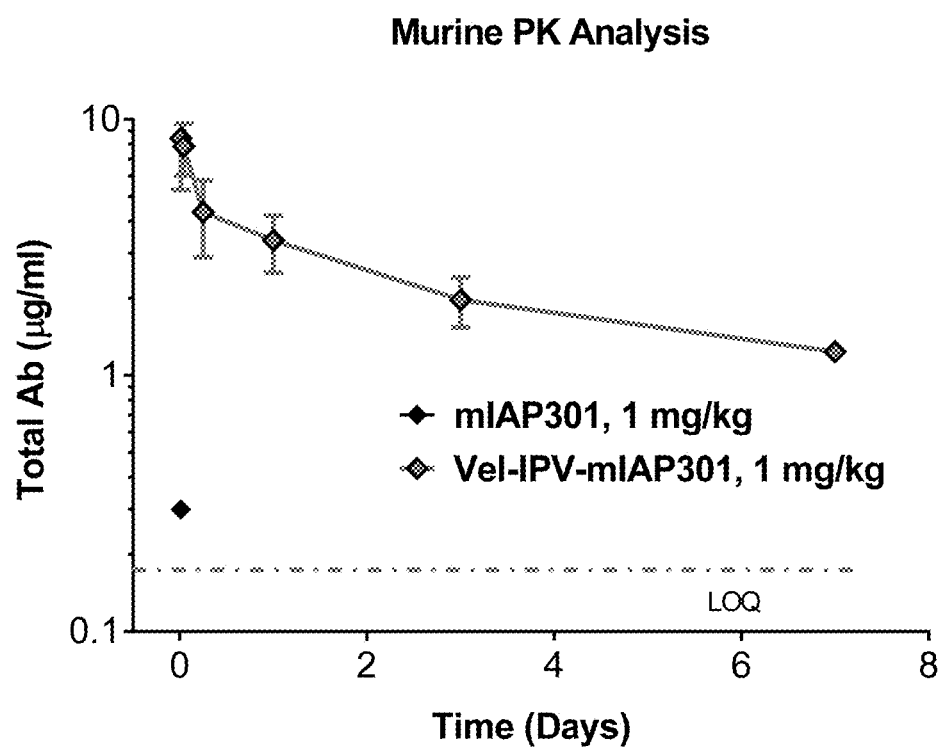

The masked Vel-IPV-mIAP301 antibody had greatly improved pharmacokinetics in plasma of BALB/c mice compared to unmasked mIAP301, demonstrating that the masked antibody is able to avoid target-mediated drug disposition encountered by typical anti-CD47 antibodies. Vel-IPV-mIAP301 and mIAP301 antibodies were labeled with $^3$H-proprionate via lysine conjugation and were administered to BALB/c mice at an IV dose of 1 mg/kg. Antibody concentration was determined by scintillation counting of plasma drawn at different timepoints FIG. 22B). The concentration of mIAP301 in plasma was below detectable amounts within 15 min, whereas Vel-IPV-mIAP301 concentrations could be measured up to 7 days post-dose.

Figure 37A:
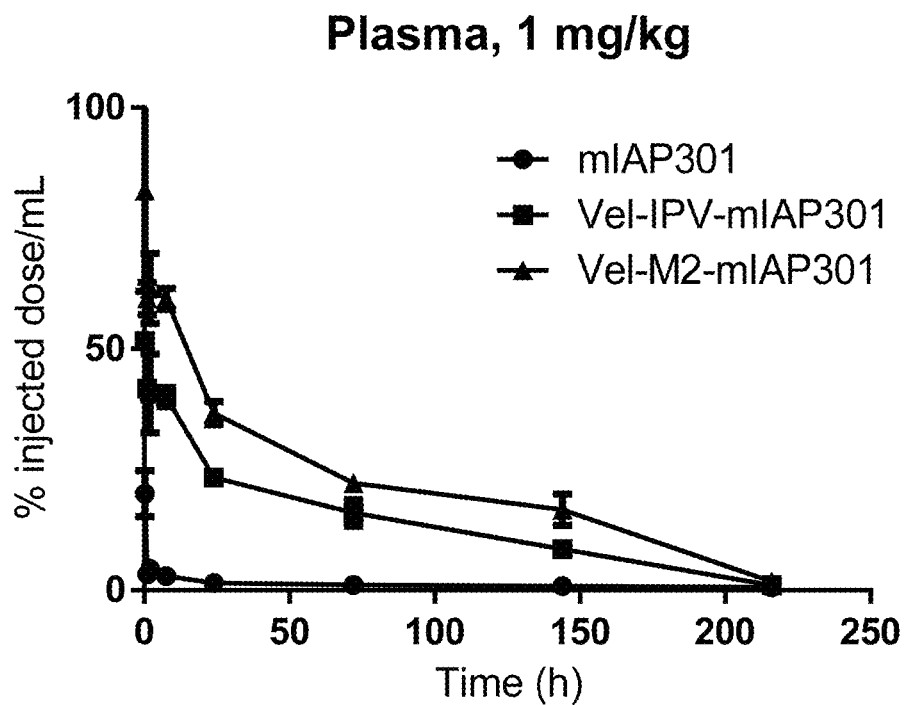
Figure 37B:
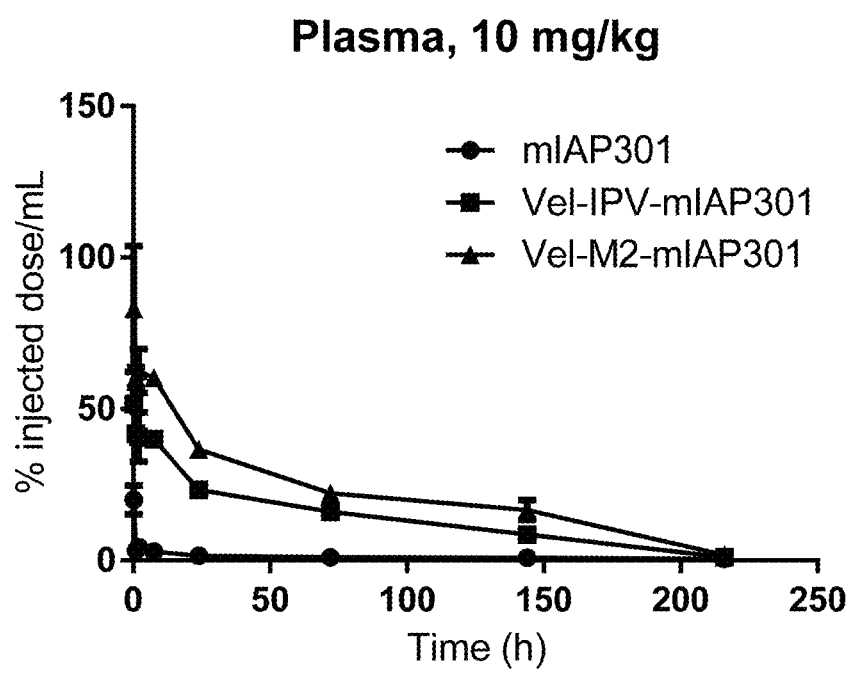
Figure 37C:
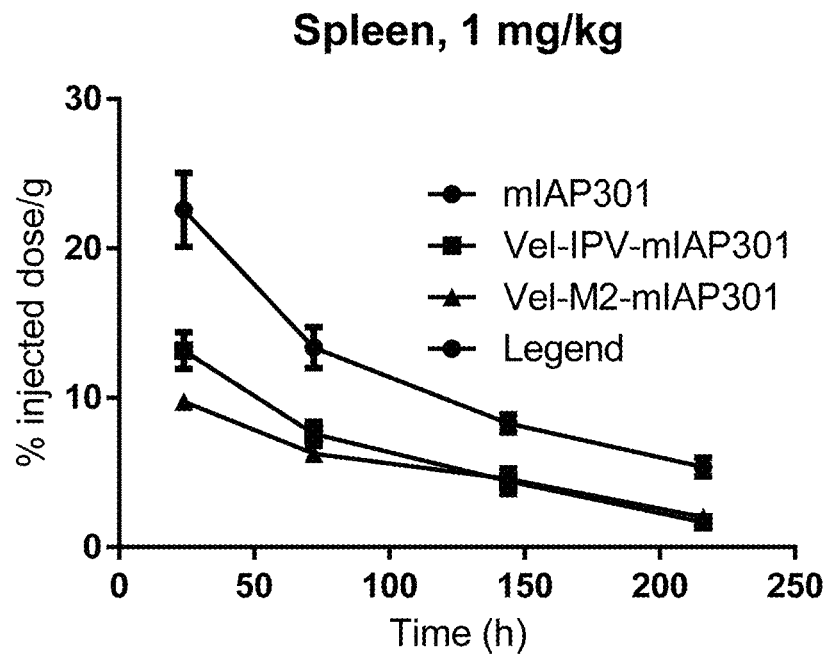
Figure 37D:
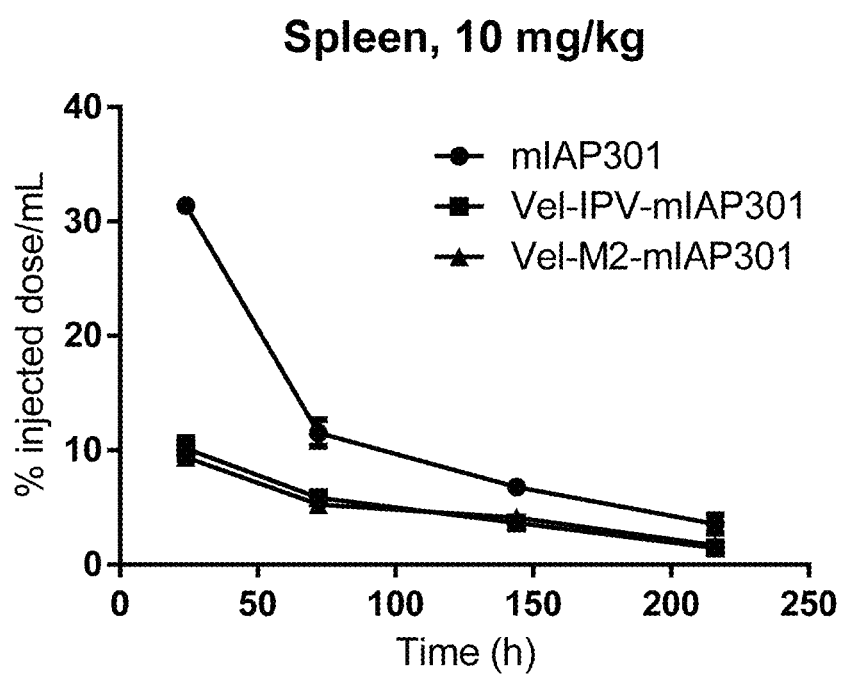

The biodistribution of masked Vel-IPV-mIAP301, and Vel-M2-mIAP301 and unmasked mIAP301 was tested in A20-bearing BALB/c mice using $^3$H-labeled antibodies at doses of 1 and 10 mg/kg. Antibodies were administered once tumors had reached 250 mm$^3$. At designated timepoints, mice were sacrificed and the concentration of antibody in plasma, blood, tumor, spleen, and liver was determined by scintillation counting. As shown in FIGS. 37A and 37B, the concentration of mIAP301 in plasma is negligible within one hour post-administration. Meanwhile, significantly less masked antibody is present in the spleen when compared to the unmasked mIAP301 antibody (FIGS. 37C and 37D). Similar results were seen in liver. (Data not shown). In contrast, by avoiding target-mediated disposition of CD47 in normal tissues, the masked Vel-IPV-mIAP301 and Vel-M2- mIAP301 antibodies demonstrate increased levels in the tumor compared to mIAP301 (FIGS. 37E and 37F).

Figure 23A:
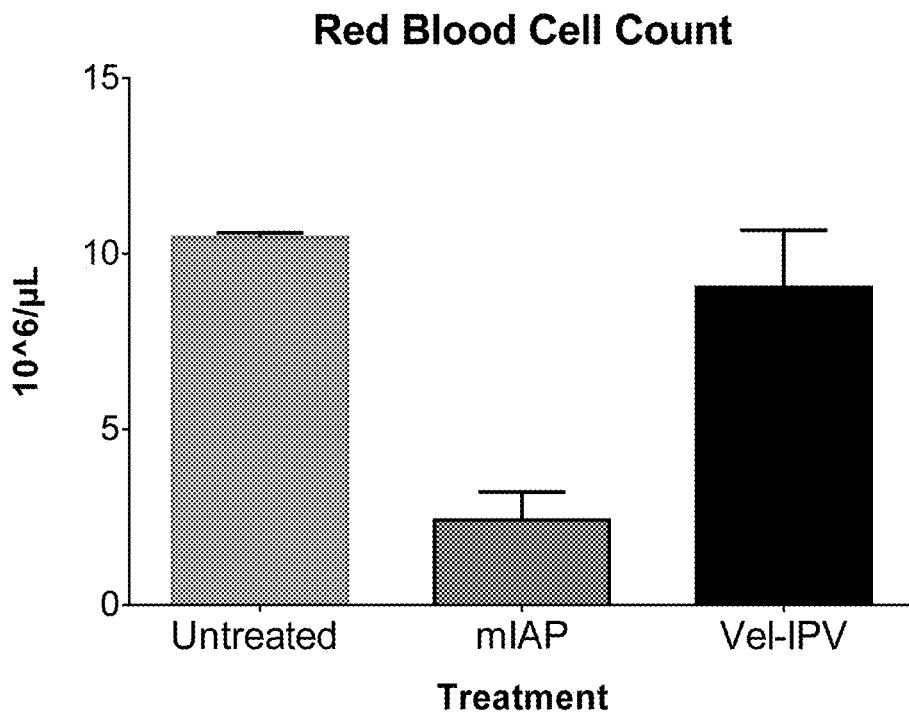
Figure 23B:
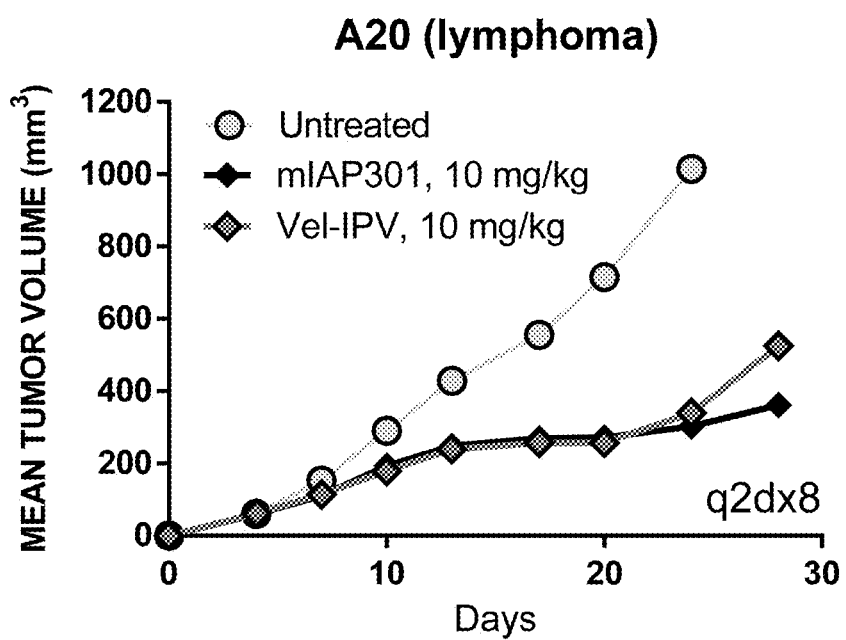
Figure 23C:
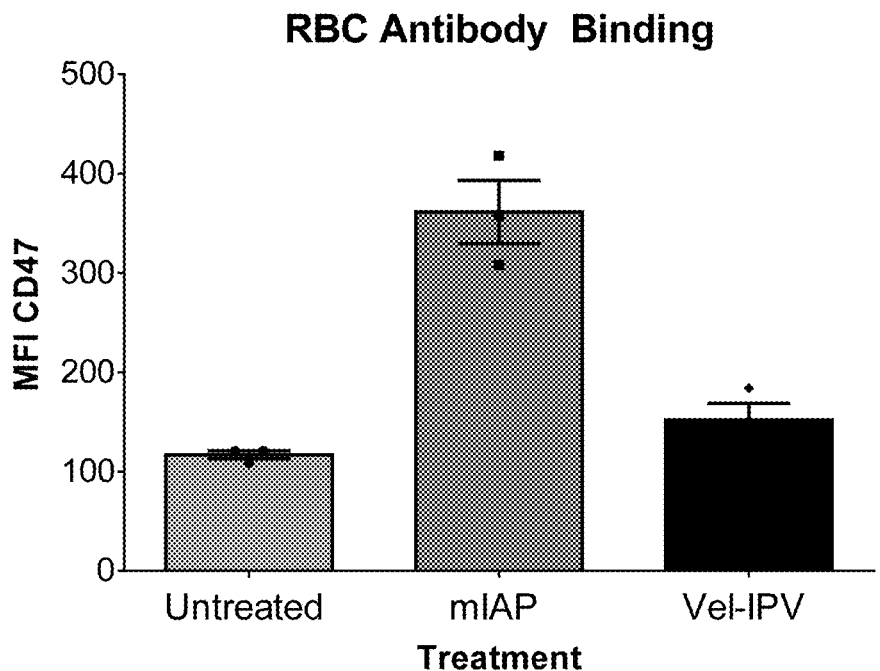
Figure 23D:
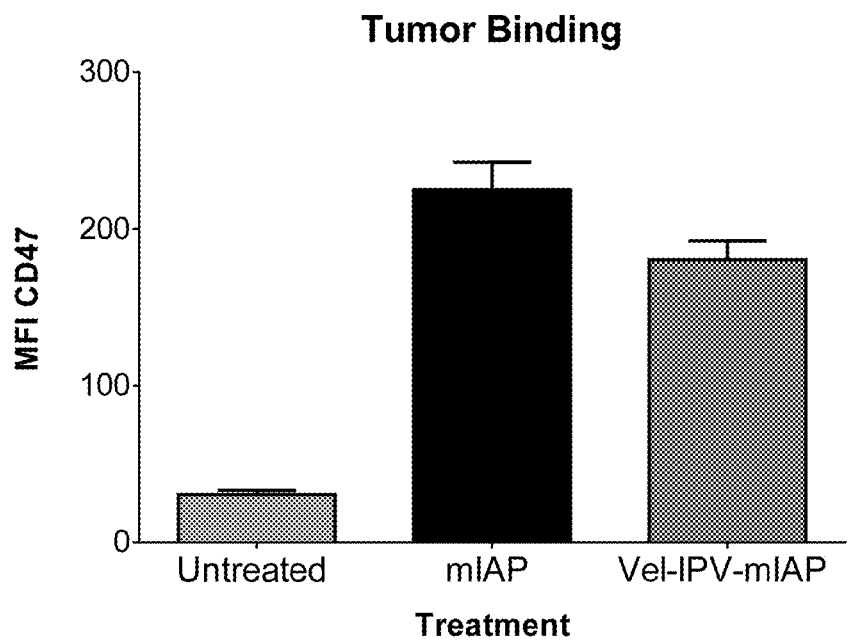

The anti-mouse CD47 antibody mIAP301 drove antitumor activity in the A20 lymphoma model but caused concomitant RBC depletion (FIG. 23A and FIG. 23B). The masked Vel-IPV-mIAP301 antibody conferred similar activity but abrogated effects on RBCs depletion. The Vel-IPV-mIAP301 antibody avoided the RBC antigen sink but maintained tumor binding as well (FIG. 23C and FIG. 23D) The A20 lymphoma model is described in further detail in Donnou et al. (Advances in Hematology, Article ID 701704, 2012) and Liu et al. (Nature Medicine, 21:1209-1215, 2015).

Figure 24:
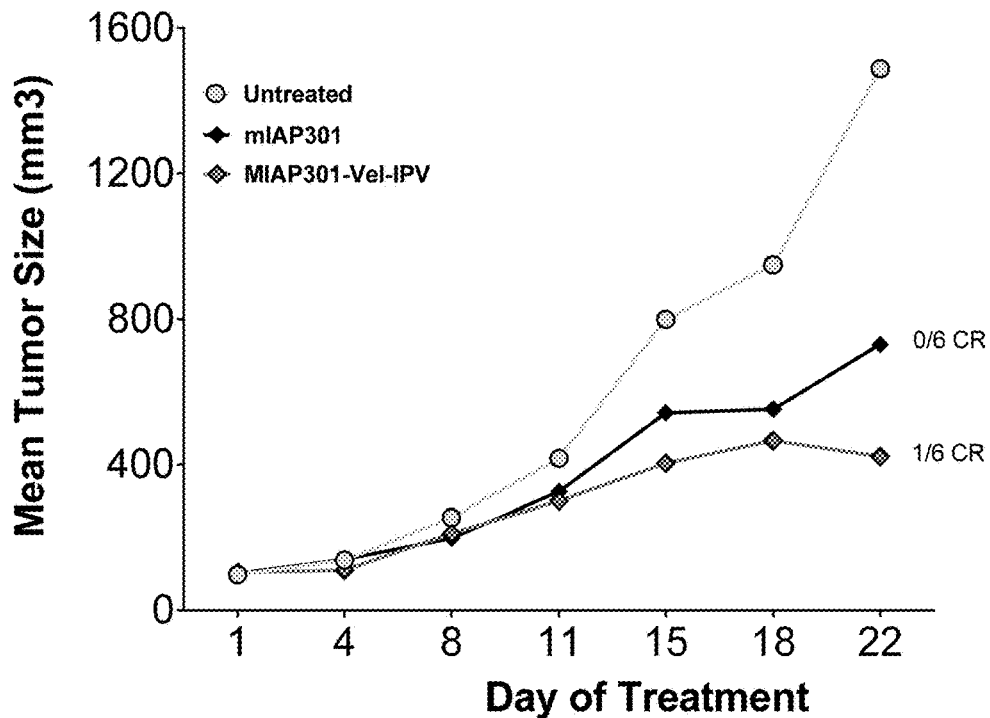

The anti-mouse CD47 antibody mIAP301 drove antitumor activity in the MC38 colon cancer model, which is known to be responsive to immune oncology agents. The activity of the masked mIAP301 antibody in this model showed superior efficacy as denoted by the animal exhibiting a complete response (FIG. 24). Re-challenge of this animal resulted in complete rejection of the tumor, demonstrating the induction of a long-lived memory T cell response (data not shown). The MC38 colon cancer model is described in further detail in Liu et al. (supra).

In addition to testing the combinatorial activity of the human anti-CD47 antibody with ADCs against Liv1a or CD30 we also assessed the combinatorial activity with other immune modulatory agents. To accomplish this, we moved into an immune complete mouse system and utilized the murine targeting anti-CD47 surrogate antibody mIAP. Using the A20 model we demonstrated that the masked anti-CD47 antibody synergizes with an anti-PD-1 surrogate antibody as well as an anti-SEA-CD40 antibody, SEA-1C10. These data provide evidence that engagement of both the innate and adaptive arms of the immune system along with a masked CD47 targeted agent is able to combine to drive robust anti-tumor responses.

Figure 25A:
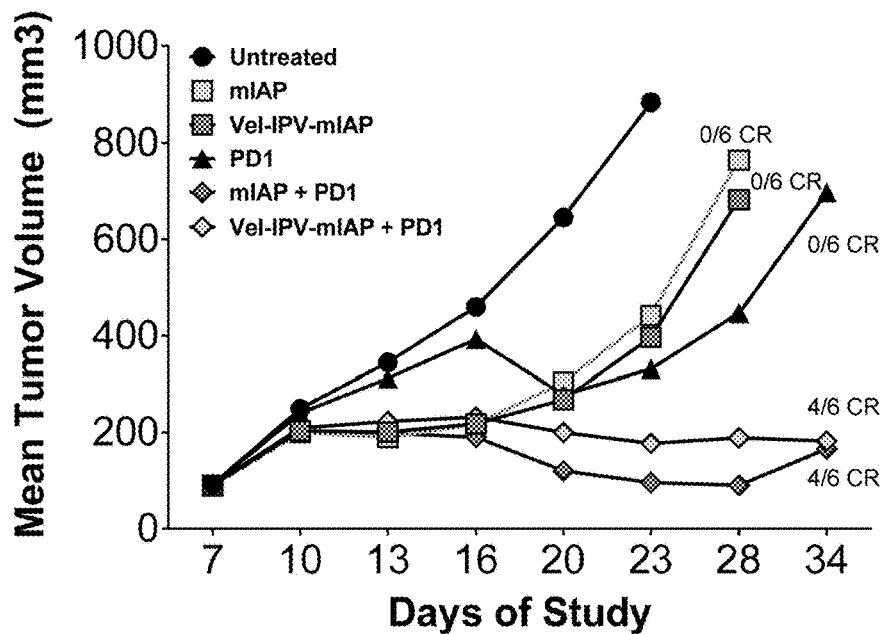
Figure 25B:
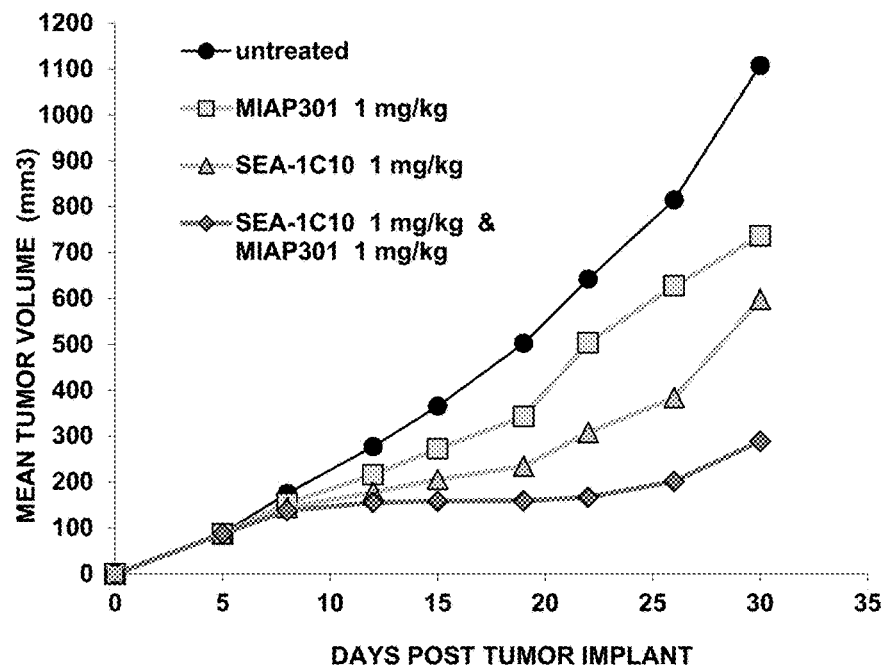

The parent and masked anti-murine CD47 antibody mIAP301 drove increased anti-tumor activity in combination with the anti-PD-1 surrogate antibody which resulted in 4/6 animals exhibiting CR responses (See, Dahan et al. Cancer Cell. 28:285-295. 2015, for reference to the PD-1 antibody, clone RMP1-14) (FIG. 25A). The parent anti-murine CD47 antibody mIAP301 drove increased anti-tumor activity in combination with the macrophage activating CD40 targeted SEA-enhanced surrogate antibody 1C10 (See, WO2016/069919 for reference to the 1C10 antibody; see, Lindberg et al. J. Biol. Chem. 269: 1567-1570. 1994, for reference to the mIAP301 antibody) (FIG. 25B).

The data showing anti-CD47 in combination with anti-PD-1 or anti-CD40 indicate that anti-CD47 therapy can enhance the activity of agents that enhance T cell activity as in the context of checkpoint inhibitor antibodies (anti-PD-1 antibodies) as well as those agents that enhance innate cell activity (anti-CD40 antibodies or other CD40 inhibitors). This supports the notion that an anti-CD47 antibody can be paired with multiple immune modulating agents in the clinic that support both the adaptive and innate arms of an anti-tumor response.

Example 5: Coiled Coil Domain Masked Antibodies

Figure 26:
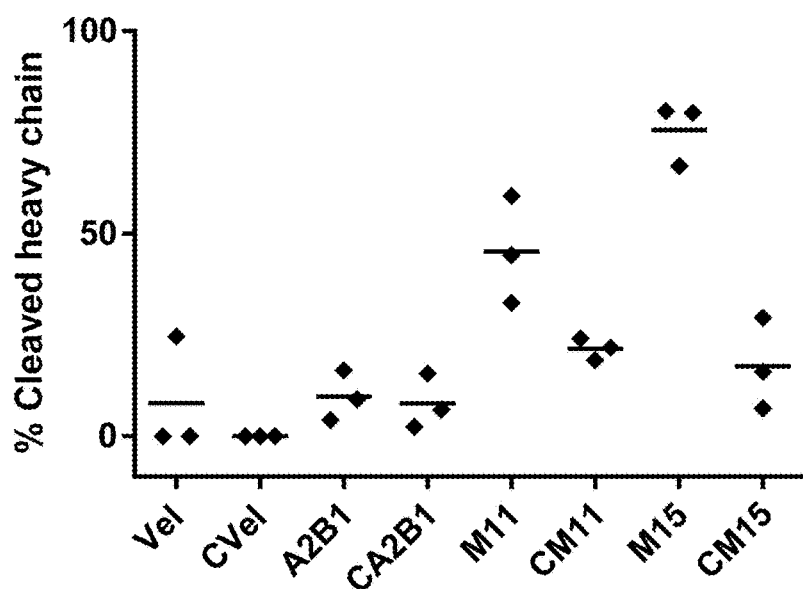
Figure 27A:
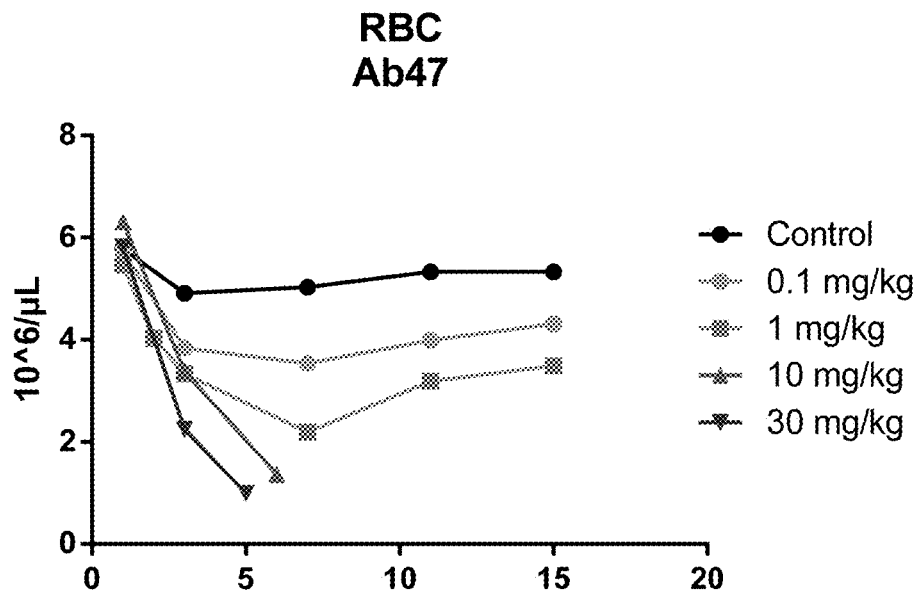
Figure 27B:
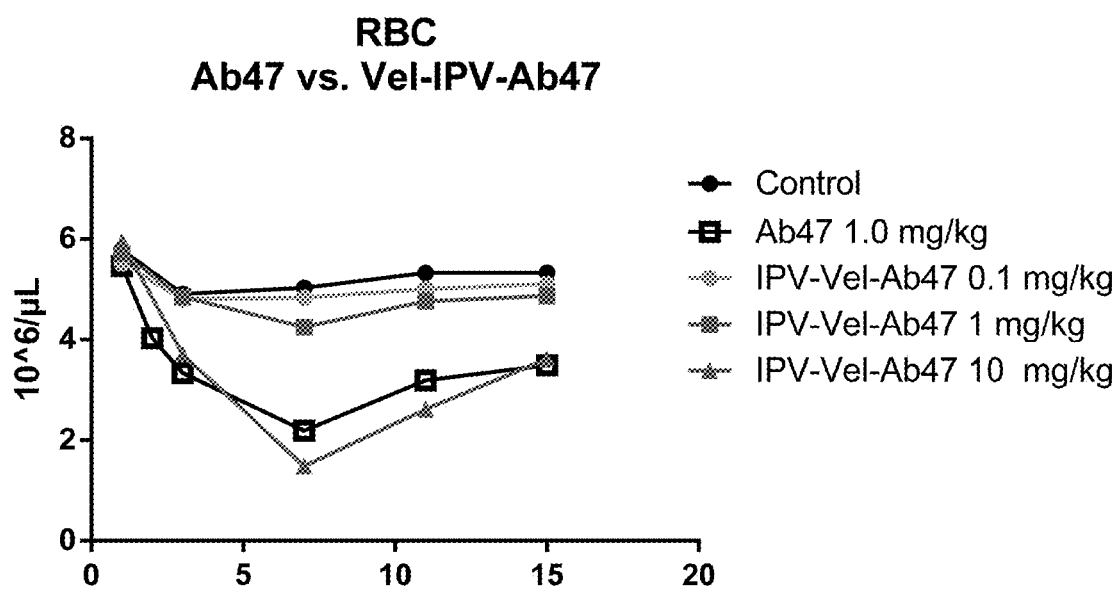
Figure 28:
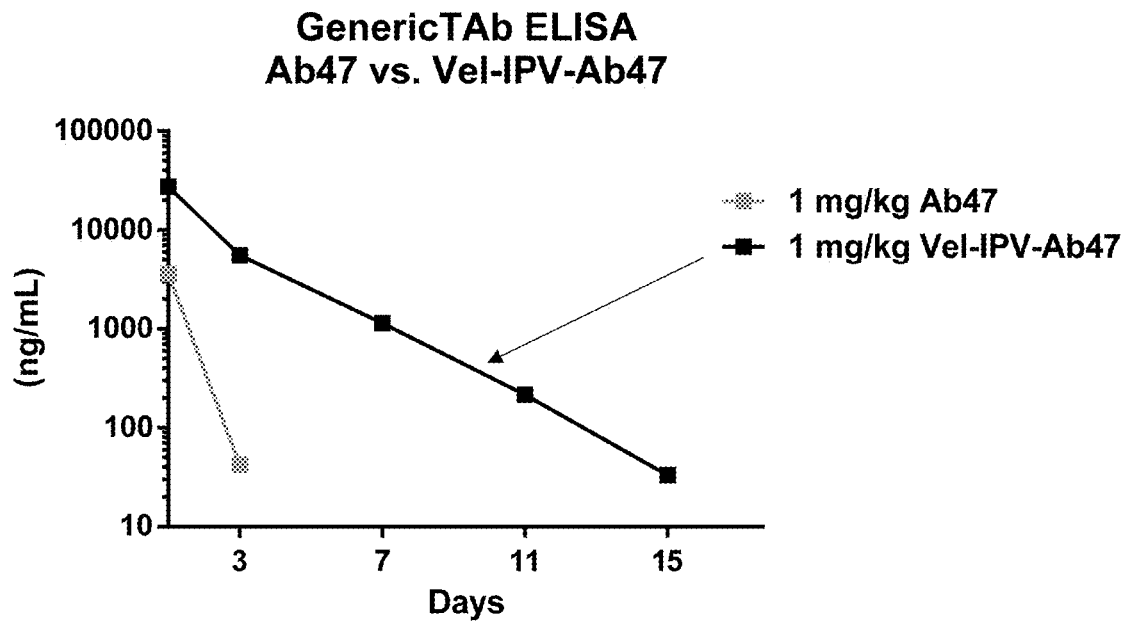
Figure 29:
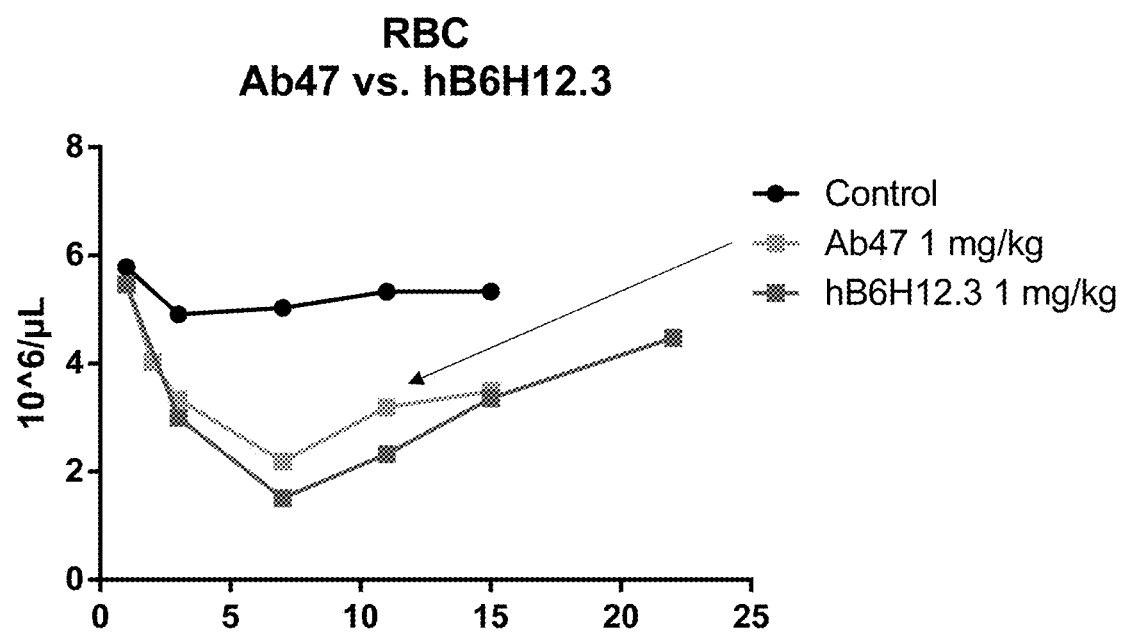
Figure 30:
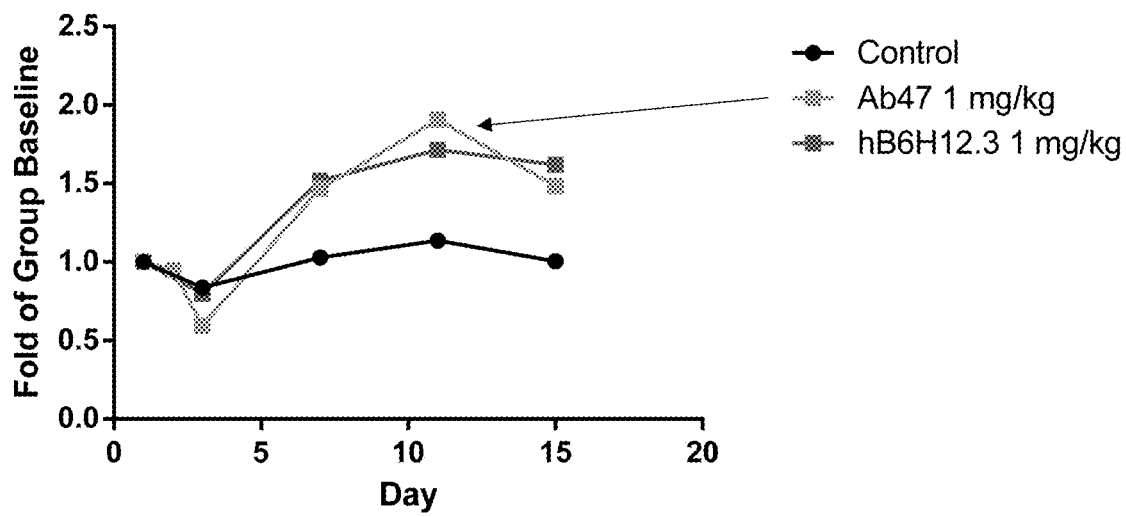
Figure 31:
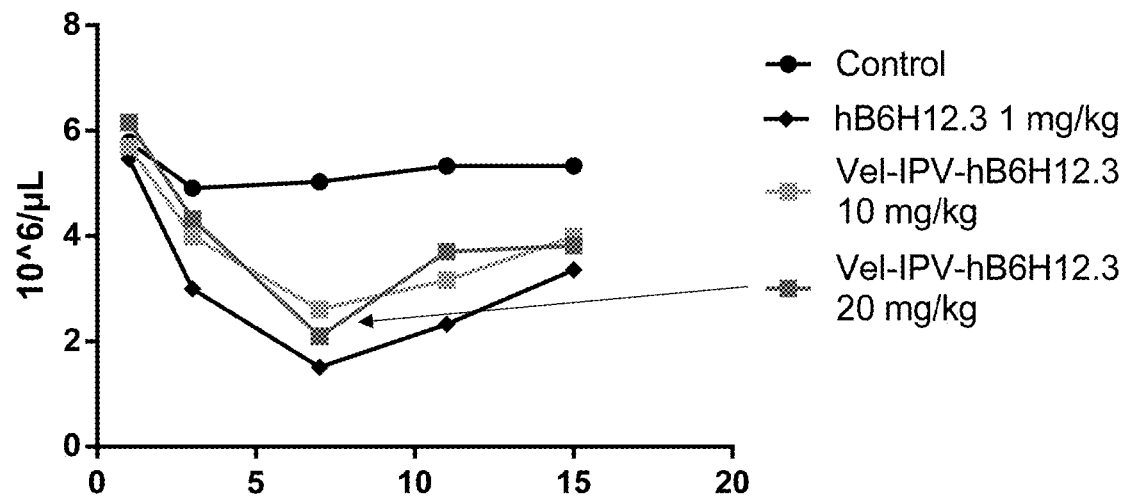

The stability of masked humanized B6H12 antibodies bearing different coiled coil domains was assessed using intravenous administration to BALB/c mice. Antibodies were dosed at 5 mg/kg. At the given time point (3 days), plasma was collected from dosed mice. Human antibody was purified from plasma using IgSelect resin. Captured antibody was reduced and separated by SDS-PAGE, then probed by Western blot using an HRP-conjugated anti-human Fc antibody. The percent cleaved antibody was assessed by densitometry of bands corresponding to masked and unmasked heavy chains, which differ in size by about 5 kDa (FIG. 26).

Table 23 shows the effects of masking with different coiled coil forming peptide pairs incorporated onto a humanized B6H12 antibody comprising a heavy chain (SEQ ID NO: 2) and a light chain (SEQ ID NO: 10) and tested on different cell lines. The antibody is also called Ab47 in the examples. The Kd (nM) is shown for each antibody, which was derived from saturation binding on each respective cell line. A high concentration of 2000 nM was used for each binding experiment. As shown in Table 23, a variety of coiled-coil domains were able to inhibit the binding of Ab47 to CD47 expressed on the cell surface, even when tested at concentrations of greater than 2 micromolar, whereas the unmasked Ab47 antibody displayed an $IC_{50}$ of 3.3-21 nM.

Figure 38A:
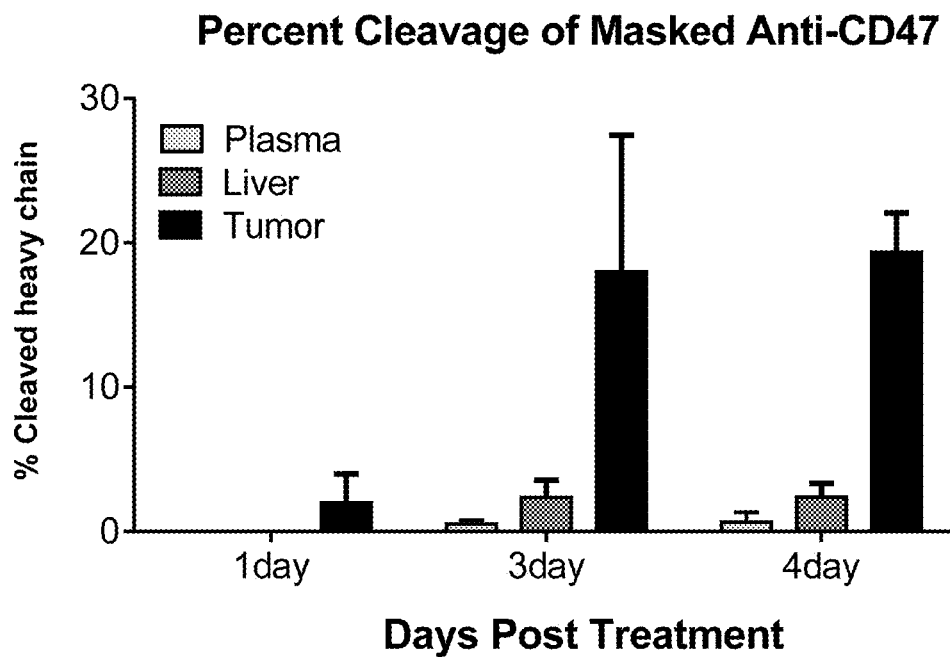
FIG. 38A-FIG. 38B depict the percent cleaved antibody in plasma, liver, and tumor (FIG. 38A). HT1080 tumors harvested from mice treated with Ab47 or Vel-IPV-Ab47 for 4 or 7 days were subjected to flow cytometry to determine the extent of antibody that was able to bind to and saturate the tumor expressed CD47 (FIG. 38B).
Figure 38B:
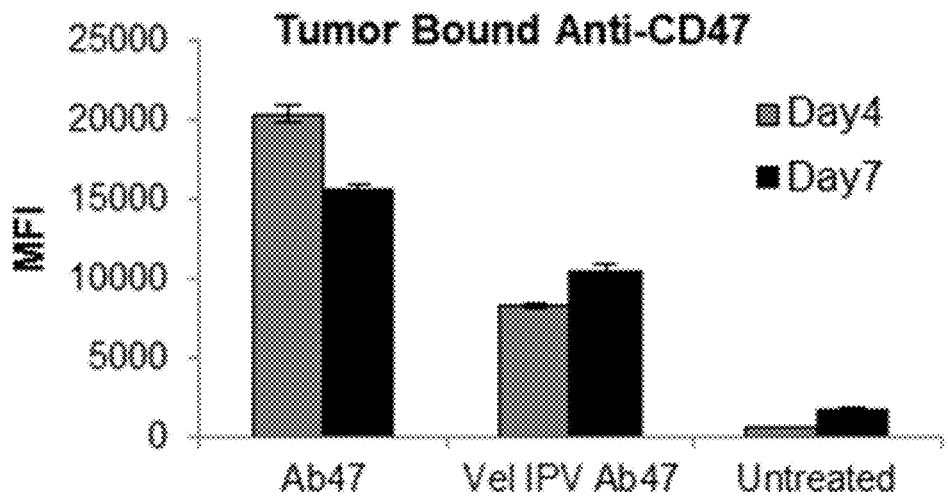
Figure 39A:
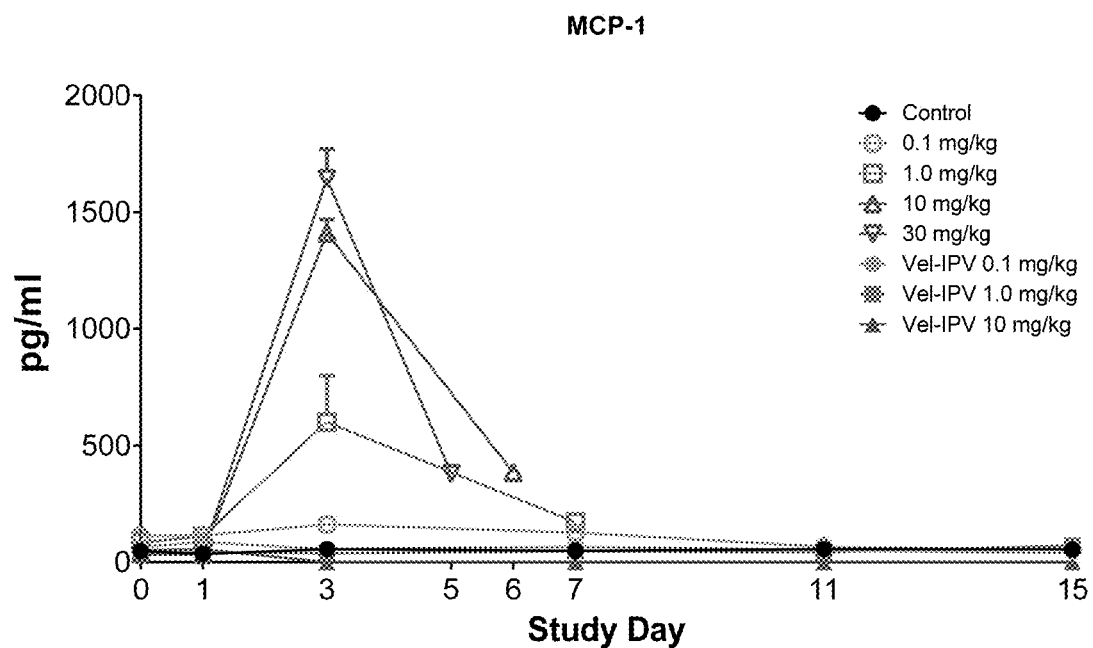
Figure 39B:
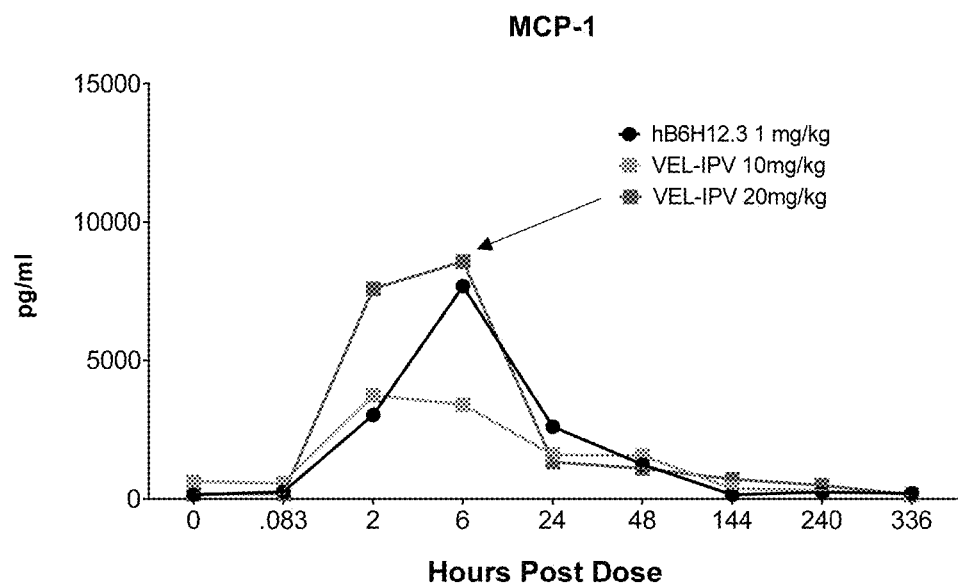
Figure 40A:
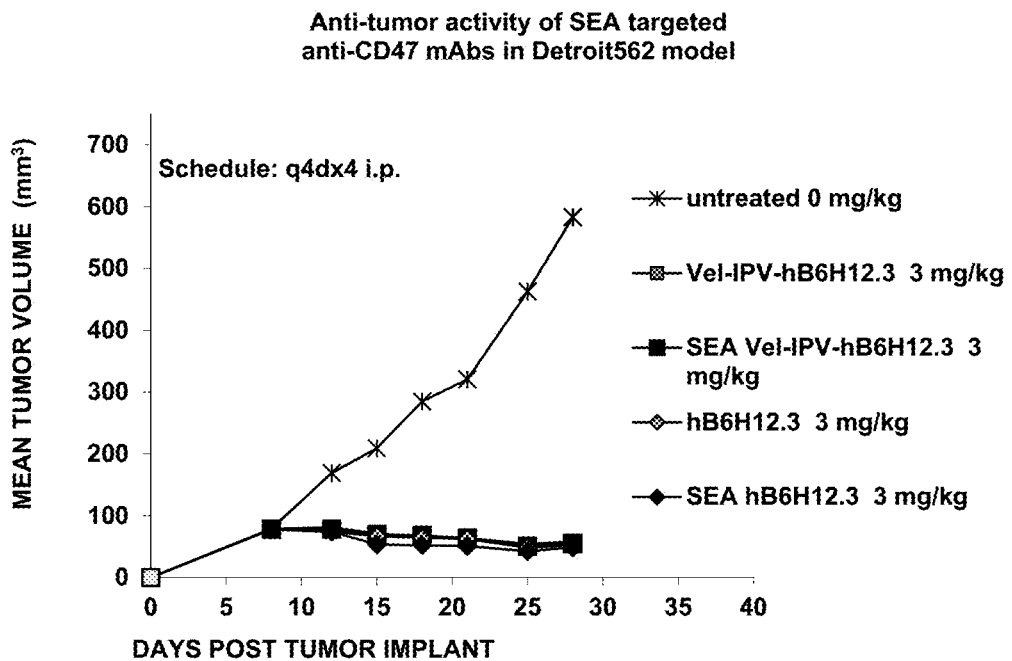
FIG. 40A-FIG. 40B depicts the relative antitumor activity by measuring mean tumor volume in xenograft models of Vel-IPV-hB6H12.3 and SEA-Vel-IPV-hB6H12.3 as well as the fucosylated and non-fucosylated SEA hB6H12.3 in a high (Detroit562) (FIG. 40A) and low (HT1080) (FIG. 40B) macrophage model.
Figure 40B:
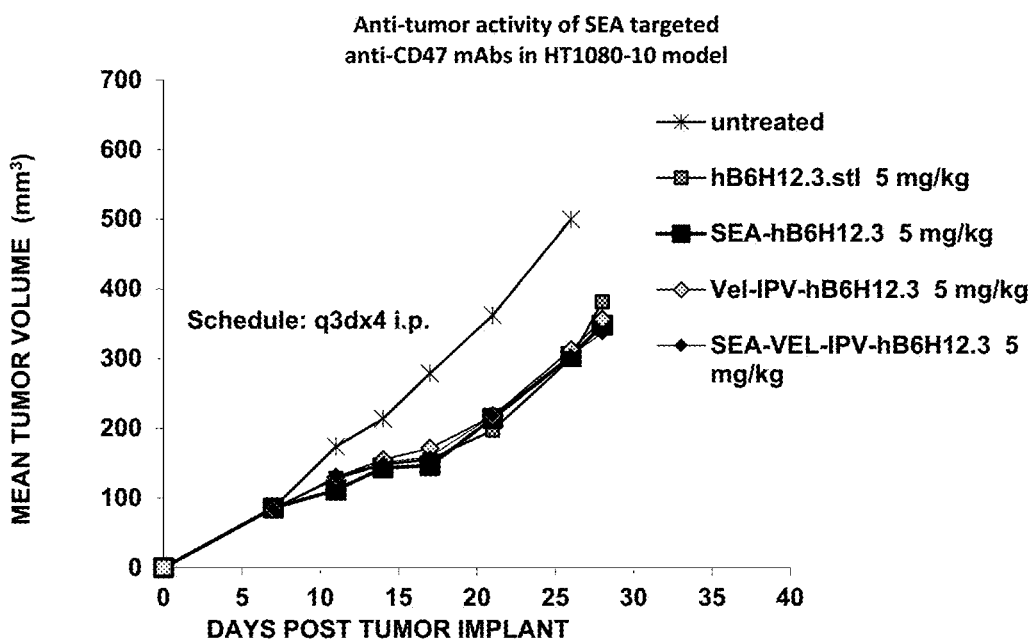

The stability and activation of masked humanized B6H12 antibodies bearing the Vel-IPV coiled coil and cleavage sequence were assessed in nude mice bearing a human HT1080 fibrosarcoma xenograft. Antibodies were dosed at 5 mg/kg IP. At given time points (1, 3, 4 days), mice were sacrificed and tissues and plasma collected. Tissues were homogenized and human antibody was purified from biological samples using IgSelect resin. Captured antibody was reduced and separated by SDS-PAGE, then probed by Western blot using an HRP-conjugated anti-human Fc antibody. The percent cleaved antibody was assessed by densitometry of bands corresponding to masked and unmasked heavy chains, which differ in size by about 5 kDa (FIGS. 38A and 38B). Very little unmasked antibody (<5%) was detected in plasma or liver at any timepoints tested. Meanwhile, upwards of 20-30% cleavage was detected in tumors, with the maximal amount of cleavage occurring at 3-4 days post-dose. Additionally, HT1080 tumors harvested from mice treated with Ab47 or Vel-IPV-Ab47 for 4 or 7 days were subjected to flow cytometry to determine the extent of antibody that was able to bind to and saturate the tumor expressed CD47 (FIG. 38B).

TABLE 23

Affinity (nM), derived by saturation binding flow cytometry, of a humanized B6H12 antibody (Ab47) bearing different antibody masking domains.

| Coiled coil | HT1080 | SW780 | HCT116 | Raji |
|---|---|---|---|---|
| Ab47 | 21 | 9.6 | 7.8 | 3.3 |
| A2B1 | >2000 | >2000 | 1775 | |
| CA2B1 | >2000 | >2000 | >2000 | |
| Vel | >2000 | >2000 | >2000 | |
| CVel | >2000 | >2000 | >2000 | >2000 |
| M11 | >2000 | >2000 | >2000 | |
| CM11 | >2000 | >2000 | >2000 | |
| M15 | >2000 | >2000 | >2000 | |
| CM15 | >2000 | >2000 | >2000 | |
| Fos-Jun | >2000 | >2000 | >2000 | |
| CFos-Jun | >2000 | >2000 | >2000 | |
| A4B4 | 1181 | 1684 | 1116 | 466 |
| Hinge | >2000 | 476 | 118 | 104 |

Activity and Pharmacokinetics of Humanized Anti-CD47 Antibodies and Demonstration of Improved Tolerability Through Masking in Cynomolgus Macaques To test the ability of masking to improve pharmacokinetics and tolerability of anti-CD47 IgG1 antibody variants, a series of IV single dose studies were conducted in cynomolgus macaques. The anti-CD47 IgG1 antibodies tested were cross-reactive with human and cyno CD47 that is highly conserved across these species in expression and sequence. Evaluation of protease activity by in situ gel zymography of a panel of cynomolgus macaque and human tissues indicated protease activity levels were also highly conserved across these species. Further, cynomolgus macaques have highly similar FcγR interactions with IgG1 antibodies and are considered toxicologically predictive of effector-function related effects of human IgG1 antibodies, making them a suitable model for evaluating the effects of IgG1 anti-CD47 antibodies (Warncke et al. J. Immunol. 188:4405-4411. 2012). Taken together, the cynomolgus macaque represents a relevant species for evaluating differing activities of anti-CD47 antibodies alone and further how this activity is altered with masking and modified effector function.

Alternatively Humanized B6H12, Ab47

To determine the tolerability and PK of B6H12 on an alternatively humanized IgG1 construct and further demonstrate proof of concept of the ability of the Vel-IPV mask and cleavage sequence to alter tolerability and pharmacokinetics, naïve cynomolgus macaques were dosed intravenously with 0.1, 1, 10, and 30 mg/kg of the alternatively humanized IgG1 B6H12 anti-CD47 antibody, Ab47. The humanized IgG1-based Ab47 demonstrated increased activity, demonstrated as red cell mass loss by hematology analysis, as compared to published data of the mB6H12 antibody on a humanized IgG4 platform (Liu, 2015). Whereas IgG4 B6H12, which lacks effector function to enable high ADCC, ADCP, and CDC activity in addition to blocking interactions with CD47, demonstrated tolerability of doses up to 30 mg/kg in cynomolgus macaques (Liu, 2015), Ab47 was not tolerated at doses greater than 1 mg/kg (FIG. 27A).

Ab47 vs. Vel-IPV-Ab47

To demonstrate the ability of the Vel-IPV mask to mitigate the activity of Ab47, cynomolgus macaques were administered doses of 0.1, 1, and 10 mg/kg. Notably, doses approximately 10 times higher were tolerated better than non-masked Ab47, as demonstrated by similar levels of red cell mass loss in blood samples collected for hematology analysis in animals treated with 1.0 mg/kg of Ab47 and 10 mg/kg of Vel-IPV-Ab47 (FIG. 27B). Animals treated with Ab47 demonstrated consistent clinical signs associated with hemolysis and a lack of tolerability (red urogenital discharge, hemolyzed samples, emesis, and hypoactivity) while there was a complete lack of adverse clinical signs observed in animals treated with masked antibody. This increase in tolerability with masked Ab47 was also demonstrated in the ability of masking to diminish increases in circulating plasma cytokines such as monocyte chemoattractant protein-1, MCP-1. The highest does tested of Vel-IPV-Ab47 (10 mg/kg) demonstrated levels similar to control and the lowest dose of Ab47 tested, 0.1 mg/kg (FIG. 39A). Additionally, masking improved the PK of the molecule dramatically. Where the 1 mg/kg dose of Ab47 was below the limit of detection for the Generic TAb (total antibody) assay on Study Day 3, 1 mg/kg Vel-IPV-Ab47 was detectable through the entire course of the study, Study Day 15 (FIG. 28). The Generic TAb ELISA uses 96-well microtiter plates coated with anti-human light chain kappa mAb that binds to human light chain kappa of Ab47 and Vel-IPV-Ab47. It does not cross-react with Cynomolgus monkey light chain kappa. Study samples were diluted into the dynamic range of the assay for Ab47 (10 (LLOQ) to 1280 ng/mL (ULOQ)) or Vel-IPV-Ab47 (20 (LLOQ) to 2560 ng/mL (ULOQ)) with naive pooled Cynomolgus monkey $K_2$EDTA plasma. The diluted samples, along with QCs and calibrators, were subjected to a Minimum Required Dilution (MRD) of 1:20 with assay buffer prior to addition to the blocked and washed plates. After incubation for 1 hour at RT, the plates were washed and bound analyte (Ab47 or Vel-IPV-Ab47) was detected with biotinylated anti-human light chain kappa mAb (identical clone as the capture reagent) followed by the addition of polymer horseradish peroxidase conjugated to streptavidin (poly-HRP-SA). Subsequent to incubation and washing, the HRP substrate 3,3',5,5'-tetramethyl-benzidine (TMB) was added to the plates and the color developed for 10 minutes. The reaction was stopped with 1N HCl and the plates were read on a Spectromax M5 plate reader at 450 nm-630 nm. The net absorbance values were imported into Watson LIMS v. 7.4.2 and a 5-PL nonlinear regression was performed for conversion of absorbance to ng/mL total antibody present in the samples.

Ab47 vs. hB6H12.3

Humanized B6H12.3, which features differential Kd, increased $B_{max}$, and decreased hemagglutination, was administered in a single IV bolus at a dose of 1 mg/kg to cynomolgus macaques to test for differential activity in vivo. While both hB6H12.3 and Ab47 at 1 mg/kg result in similar levels of erythrocyte depletion (FIG. 29), Ab47 also demonstrated depletion to approximately 40% of pre-dose platelet levels at 1 mg/kg whereas hB6H12.3 had only a 20% depletion, similar to control levels likely due to sampling bias (FIG. 30). An increase of platelets beginning on Study Day 7 occurred following treatment with both antibodies, likely due to a generally stimulated bone marrow.

hB6H12.3 vs. Vel-IPV-hB6H12

To demonstrate the ability of the Vel-IPV mask to mitigate the activity of hB6H12.3, cynomolgus macaques were administered doses of 10 and 20 mg/kg of antibody. 20 mg/kg, the highest dose tested, hematology testing demonstrated similar decreases in red cell mass loss as observed with 1 mg/kg of hB6H12.3 however with increased tolerability than non-masked hB6H12.3 at a 20-fold lower dose (FIG. 31). Similarly, masking of hB6H12.3 also demonstrated reductions in circulating cytokines including MCP-1, requiring 20-fold the dose of masked hB6H12.3 to yield responses similar to those achieved with unmasked hB6H12.3 (FIG. 39B). Animals administered Vel-IPV-hB6H12.3 experienced no clinical symptoms related to treatment, whereas clinical symptoms related to hemolysis were observed with non-masked hB6H12.3 at 1 mg/kg. Pharmacokinetic analysis using a Generic TAb ELISA demonstrated an improved pharmacokinetic profile as compared to non-masked hB6H12.3 (FIG. 39C).

Vel-IPV-hB6H12.3 vs. SEA-Vel-IPV-hB6H12.3

To further enhance the activity of the IgG1 masked anti-CD47 antibody, Vel-IPV-hB6H12.3, the antibody was produced utilizing Seattle Genetics' proprietary technology to produce sugar engineered antibodies, SEA, non-fucosylated antibodies with enhanced effector function (U.S. Pat. No. 8,163,551). The relative antitumor activity in xenograft models of Vel-IPV-hB6H12.3 and SEA-Vel-IPV-hB6H12.3 as well as the fucosylated and non-fucosylated SEA hB6H12.3 was assessed in a high (Detroit562) and low (HT1080) macrophage model. Removal of the core fucosylation and resultant SEA-hB6H12.3 and SEA-Vel-IPV-hB6H12.3 provided no evidence of benefit for antitumor activity in either model (FIGS. 40A and 40B). As these models are run in immune incomplete mice they may not take full advantage of the enhanced effector function imparted with an SEA backbone, the murine surrogate antibody mIAP301 was also non-fucosylated and anti-tumor activity with the fucosylated and non-fucosylated vel-IPV-mIAP301 were tested in the high activity A20 syngeneic lymphoma model as well as the lower activity CT26 syngeneic model. Removal of the core fucose to produce the SEA antibody did not appear to confer additional anti-tumor benefit.

Figure 32:
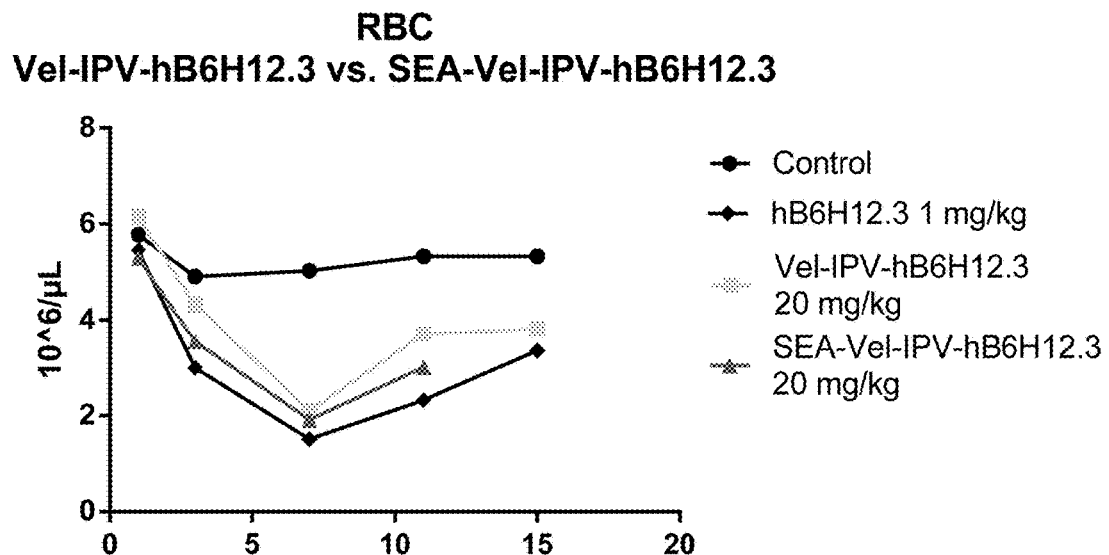
Figure 33:
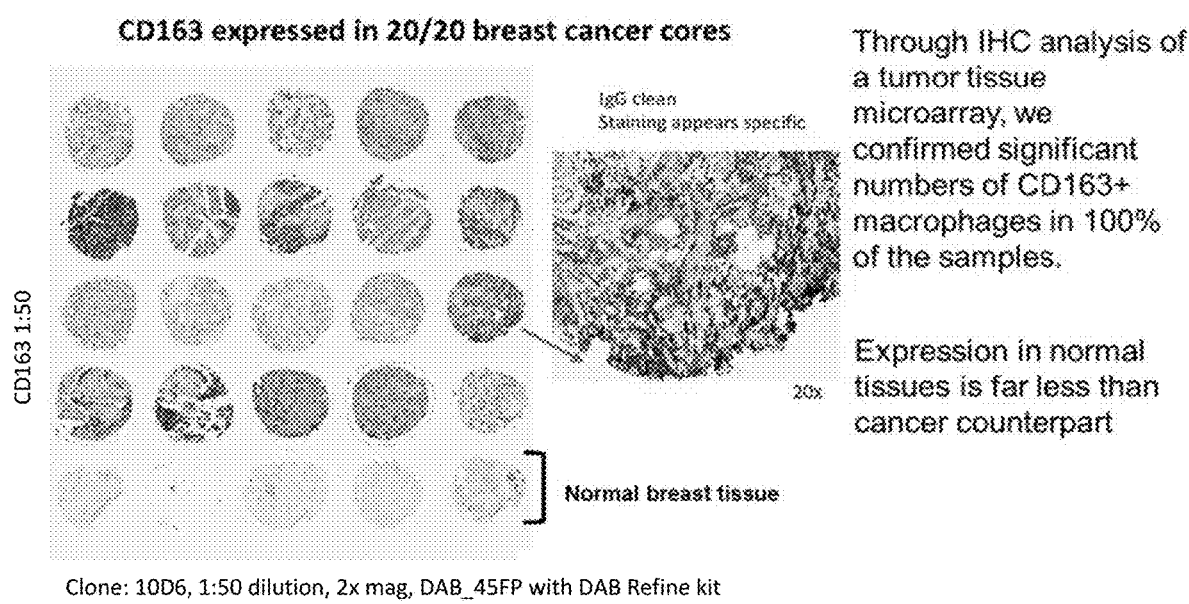
Figure 41A:
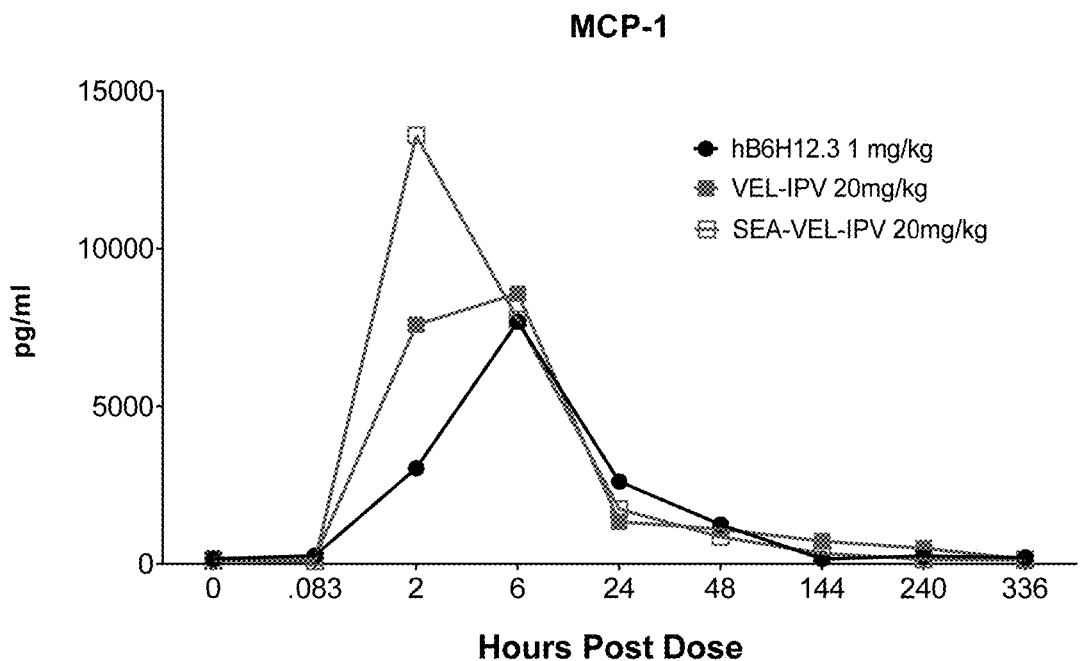
FIG. 41A-FIG. 41B depicts measurement of circulating MCP-1 cytokine levels with the Vel-IPV-hB6H12.3 and SEA-Vel-IPV-hB6H12.3 antibody (FIG. 41A). Pharmacokinetic analysis using a Generic TAb ELISA was performed between SEA and no-SEA Vel-IPV-hB6H12.3 antibodies (FIG. 41B).
Figure 41B:
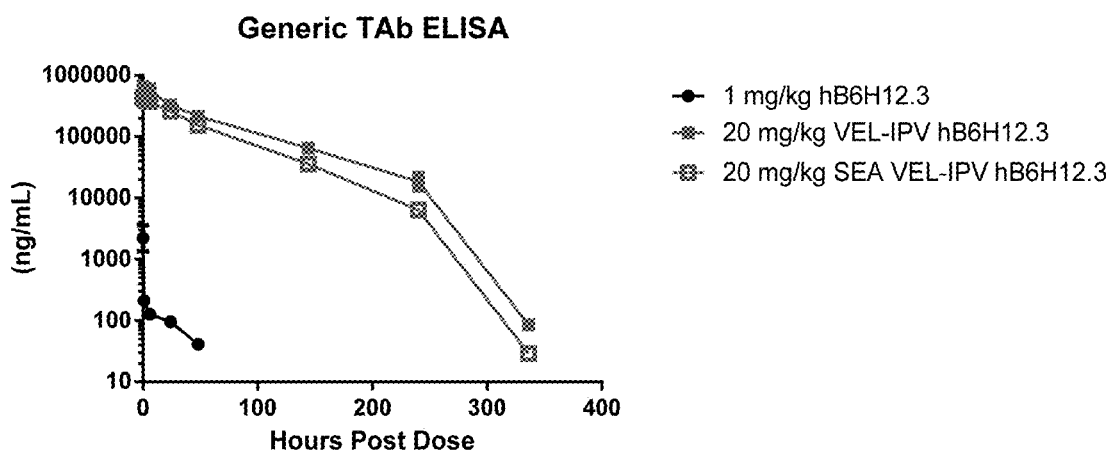
Figure 42:
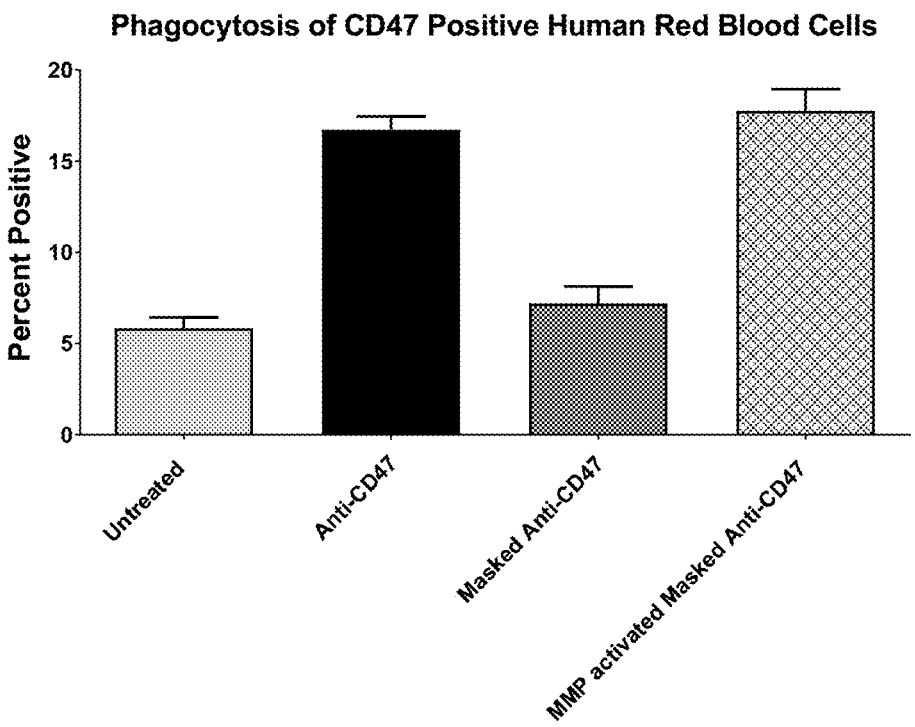
FIG. 42 depicts measurement of phagocytosis of CD47 positive human red blood cells following incubation with hB6H12.3 ("Anti-CD47"), Vel-IPV-hB6H12.3 ("Masked Anti-CD47"), MMP cleaved Vel-IPV-hB6H12.3 ("MMP activated Masked Anti-CD47"), or no antibody ("Untreated").
Figure 43:
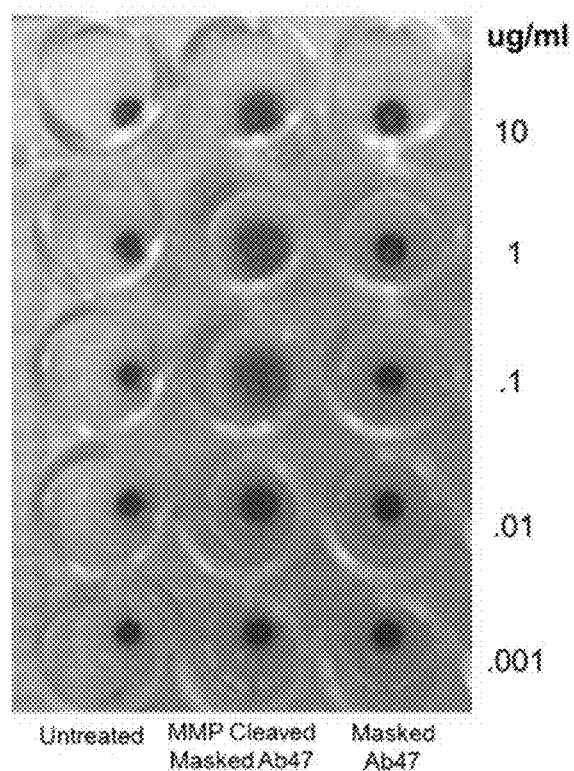
FIG. 43 depicts human red blood cells in a round bottom plate following incubation with Vel-IPV-Ab47 ("Masked Ab47"), MMP cleaved Vel-IPV-Ab47 ("MMP cleaved Masked Ab47"), or no antibody ("Untreated").
Figure 44:
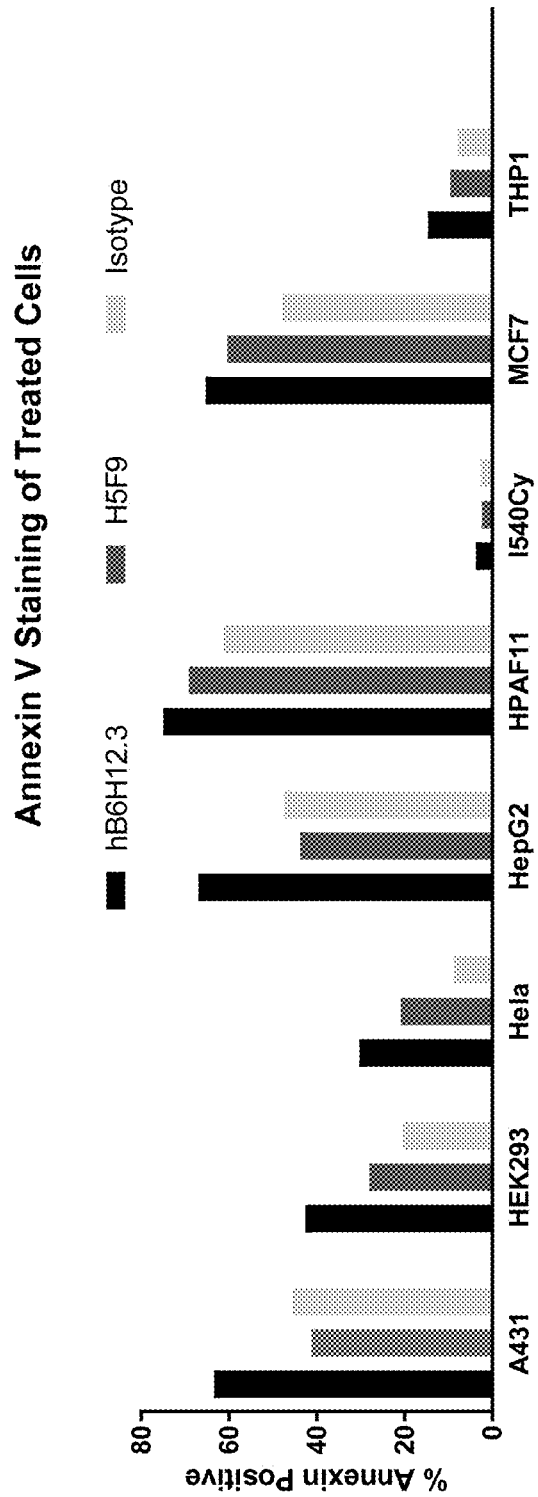
FIG. 44 depicts measurement of Annexin V positive cells following incubation with hB6H12.3, 5F9, or an IgG1 isotype control.
Figure 45A:
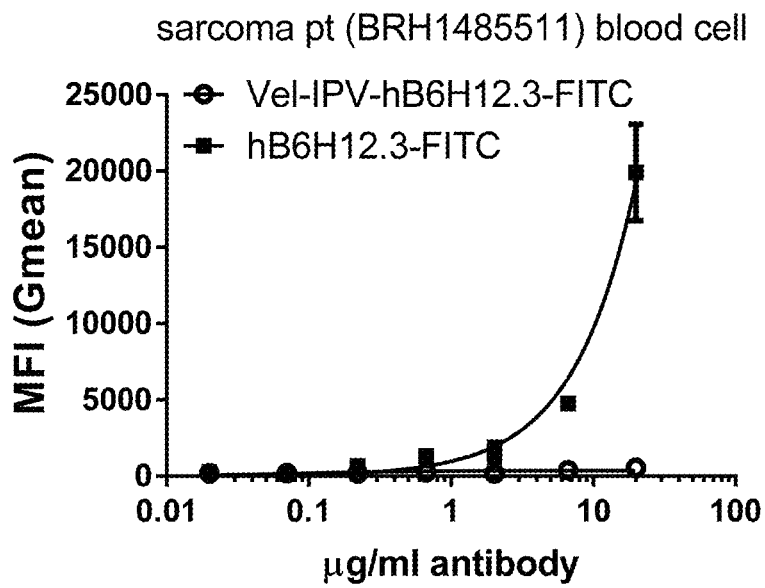
Figure 45B:
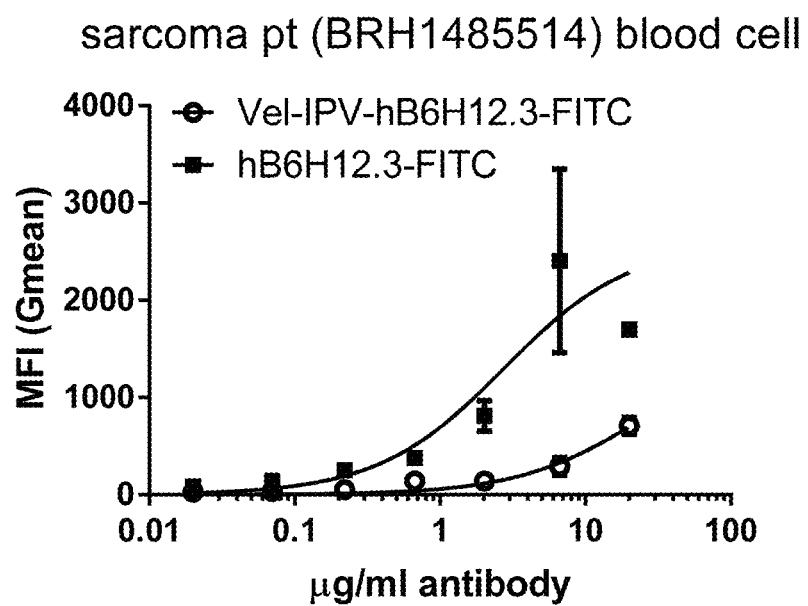

While SEA technology with other antibodies has resulted in increased activity, when the antibody is masked, both the SEA and non-SEA versions are well tolerated with similar red cell mass loss in hematology analysis to an identical maximum dose level tested, 20 mg/kg (FIG. 32). No adverse clinical signs were observed during treatment with either antibody, however circulating MCP-1 cytokine levels were increased for the SEA antibody (FIG. 41A). Pharmacokinetic analysis using a Generic TAb ELISA demonstrated generally similar pharmacokinetic profiles between SEA and no-SEA Vel-IPV-hB6H12.3 antibodies, with both improved as compared to non-masked hB6H12.3 (FIG. 41B).

Example 6: Treatment of Tumors in Subjects with Select Biomarkers

The disclosure further envisions treatment of subjects with tumors with the anti-CD47 antibodies of the invention based on select biomarkers within said subjects. Selection of subjects for treatment with the anti-CD47 antibodies of the invention will be based on 1) the higher levels and activity of MMPs within the tumor tissue relative to the surrounding non-tumor tissue; 2) the higher expression levels of CD47 on the tumor tissue relative to the surrounding non-tumor tissue; and 3) the higher level of macrophage infiltration in the tumor tissue relative to the surrounding non-tumor tissue.

Methods of determining the levels and activity of select biomarkers include immunohistochemistry and enzymology analysis. For example, the levels of macrophage infiltration may be determined by immunohistochemistry using an anti-CD163 antibody as a marker.

To demonstrate the ability to detect tumor infiltrating macrophages in a tumor vs. non-tumor tissue sample, breast cancer core samples and normal breast tissue samples were used. Immunohistochemistry was performed using an anti-CD163 antibody. Results demonstrate that tumor infiltrating macrophages can be readily detected in tumor samples over non-tumor samples (FIG. 33).

Example 7: Phagocytosis and Hemagglutination of CD47-Positive Cells by Vel-IPV-hB6H12.3

Phagocytosis of CD47-positive RBCs was monitored in order to evaluate the impact of masking on antibody functionality. Human red blood cells were labeled with fluorescent red PKH dye and opsonized for 30 minutes with 1 μg/mL of unmasked hB6H12.3, masked Vel-IPV-hB6H12.3, or MMP-activated Vel-IPV-hB6H12.3. Red blood cells were washed, then incubated with monocyte macrophages at a 10:1 ratio for two hours. The samples were then washed three times with ACK hypotonic lysis buffer. The extent of phagocytosis was evaluated by monitoring the uptake of fluorescently-labeled human RBCs by human macrophages via flow cytometry.

As shown in FIG. 42, masked Vel-IPV-hB6H12.3 did not exhibit an increase in phagocytosis above background levels of untreated RBCs, whereas both hB6H12.3 and MMP-activated Vel-IPV-hB6H12.3 showed similar levels of RBC phagocytosis.

Promotion of hemagglutination of human RBCs by masked Ab47 antibodies was tested as described in Example 2. Human RBCs were exposed to increasing concentrations of masked Vel-IPV-Ab47 or MMP-cleaved Vel-IPV-Ab47 for thirty minutes at 37° C. Hemagglutination was monitored by optical assessment of the diameter of the apparent spot within each well.

As shown in FIG. 43, hemagglutination was inhibited when Ab47 was masked, and hemagglutination was restored when the mask was removed by MMPs.

Example 8: hB6H12.3 Induces Apoptosis Directly

Cell surface CD47 ligation can induce apoptosis. It has been reported that anti-CD47 mAb clone B6H12 can induce apoptosis only when immobilized to a surface; however, hB6H12.3 demonstrated apoptosis activity without being bound to a surface. Eight different cell lines (A431, HEK293, Hela, HepG2, HPAF11, I540Cy, MCF7, and THP1) were each plated at 50,000 cells per well for 24 hours. The cells were treated with concentrations of from 5 to 0.05 μg/mL of hB6H12.3, 5F9 or an IgG1 isotype control for 18 hours. Cells were then collected, washed twice, stained for apoptosis marker Annexin V, and apoptosis was quantified using flow cytometry.

As shown in FIG. 44, in all eight cell types, cells treated with hB6H12.3 exhibited greater levels of apoptosis, as determined by relative levels of Annexin staining, than cells of the same type treated with 5F9 or IgG1 isotype control.

Example 9: hB6H12.3 Stability in Whole Blood and Plasma

Freshly harvested whole blood samples (4% sodium citrate) from 17 patients with various types of cancers (10 sarcoma, 3 NSCLC, 3 colon cancer, and 1 melanoma) were obtained from BioIVT. hB6H12.3 and masked Vel-IPV-hB6H12.3 antibodies were directly labeled with fluorescein isothiocyanate (FITC). Samples of the fresh whole blood were incubated with increasing concentrations (maximum concentration, 20 μg/ml) of FITC labeled hB6H12.3 or FITC labeled masked Vel-IPV-hB6H12.3 for 20 hours at 37° C. Binding of the antibodies to the blood cells was characterized by flow cytometry.

A portion of each of the sarcoma whole blood samples was used to extract plasma, and 20 μg/mL of recombinant CD47 was added to the plasma samples. Samples of plasma containing recombinant CD47 were then incubated with 20 μg/mL of hB6H12.3 or masked Vel-IPV-hB6H12.3 for four days at 37° C. The extent of cleavage of the Vel-IPV mask was assessed using a CD47 binding ELISA, as described in Example 2. Vel-IPV-hB6H12.3 did not bind to recombinant CD47 at the concentration spiked into plasma (20 μg/mL); therefore, any antibody-CD47 binding detected in plasma incubated with Vel-IPV-hB6H12.3 is due to binding of cleaved Vel-IPV-hB6H12.3 to CD47.

Of the 17 blood samples tested, masked Vel-IPV-hB6H12.3 showed greater than 10% binding to only one outlier sample (sarcoma, see FIG. 45B) at the top concentration. No binding by masked Vel-IPV-hB6H12.3 was detected in any of the other 16 samples (representative data shown in FIG. 45A). As shown in FIG. 45C, no more than 2% of masked Vel-IPV-hB6H12.3 was cleaved in any of the ten plasma samples from patients with sarcoma.

Example 10: Cytokine Production in Response to hB6H12.3

Samples of the fresh whole blood from cancer patients (10 sarcoma, 3 NSCLC, 3 colon cancer, and 1 melanoma) were incubated with increasing concentrations (maximum concentration, 20 μg/ml) of FITC labeled hB6H12.3 or FITC labeled Vel-IPV-hB6H12.3, or with 0.1 μg/mL LPS for 20 hours at 37° C. Cytokine levels were assessed using a 38-plex cytokine and chemokine magnetic bead panel.

Figure 46A:
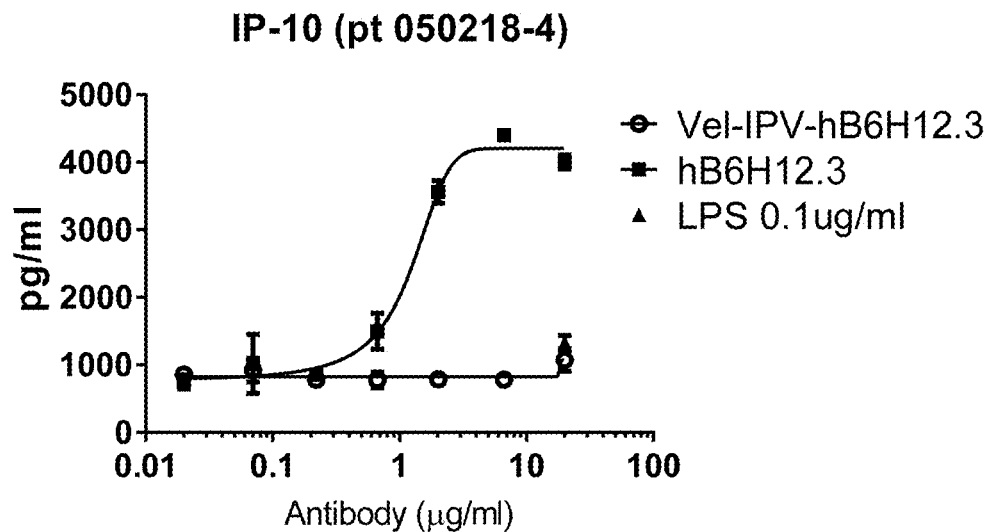
FIG. 46A-FIG. 46B depict representative cytokine production induced by incubation of cancer patient whole blood samples incubated with hB6H12.3 or Vel-IPV-hB6H12.3 for 20 hours at 37 C.
Figure 46B:
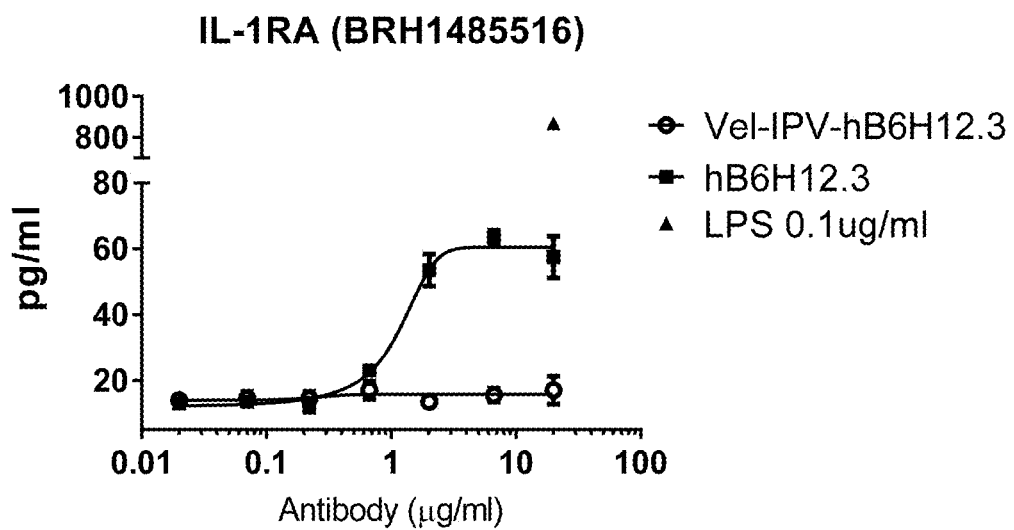

In a majority of patient samples tested, modest cytokine production was induced by hB6H12.3, but minimal cytokine production was induced by Vel-IPV-hB6H12.3. Cytokines IP-10, IL1-Ra, MIP-1α, and MIP-1α were most commonly induced by hB6H12.3. The levels of IL1-Ra (FIG. 46B), MIP-1α, and MIP-1β were below 200 pg/mL at the maximum concentration of hB6H12.3 tested, whereas IP-1β levels reached 4000-5000 ng/mL (FIG. 46A). Cytokine levels produced by Vel-IPV-hB6H12.3 were lower than those produced by hB6H12.3 in all cases, and were typically 100-1000 fold lower.

Example 11: hB6H12.3 Induces Apoptosis In Vivo

Nude mice bearing human HT1080 fibrosarcoma xenografts were administered a 5 mg/kg IP dose of hB6H12.3, Vel-IPV-hB6H12.3, or a hIgG1 isotype control when tumors reached 200 mm³. At given time points (24 and 96 hrs), mice were sacrificed and tumors collected. Tumors were homogenized and human HT1080 xenograft fibrosarcoma tumor cells were re-suspended at 1 million cells/ml in 1× Annexin V staining buffer (10× staining buffer containing 50 mM HEPES, 700 mM NaCl, 12.5 mM CaCl2 pH7.4 diluted 1:10 in water). Cells were transferred to a round bottom 96 well plate (100 μl/well) and 5 μl of FITC Annexin V staining reagent and 1 μl of 100 μg/ml ultra violet Live/Dead staining buffer were added to each well. Cells were stained for 30 minutes at room temperature. Samples were spun at 1550 g for 5 minutes, supernatant were removed, and cells were washed 3× with 1× ice cold Annexin V staining buffer. Cells were re-suspended in 100 μl of 1× Annexin V staining buffer. Apoptosis was assessed by flow cytometry on an LSRII cytometer as percent of cells positive for Annexin V binding to surface phosphatidyl serine. Cells that stained positive with the Live/Dead stain were excluded from the analysis.

Figure 47:
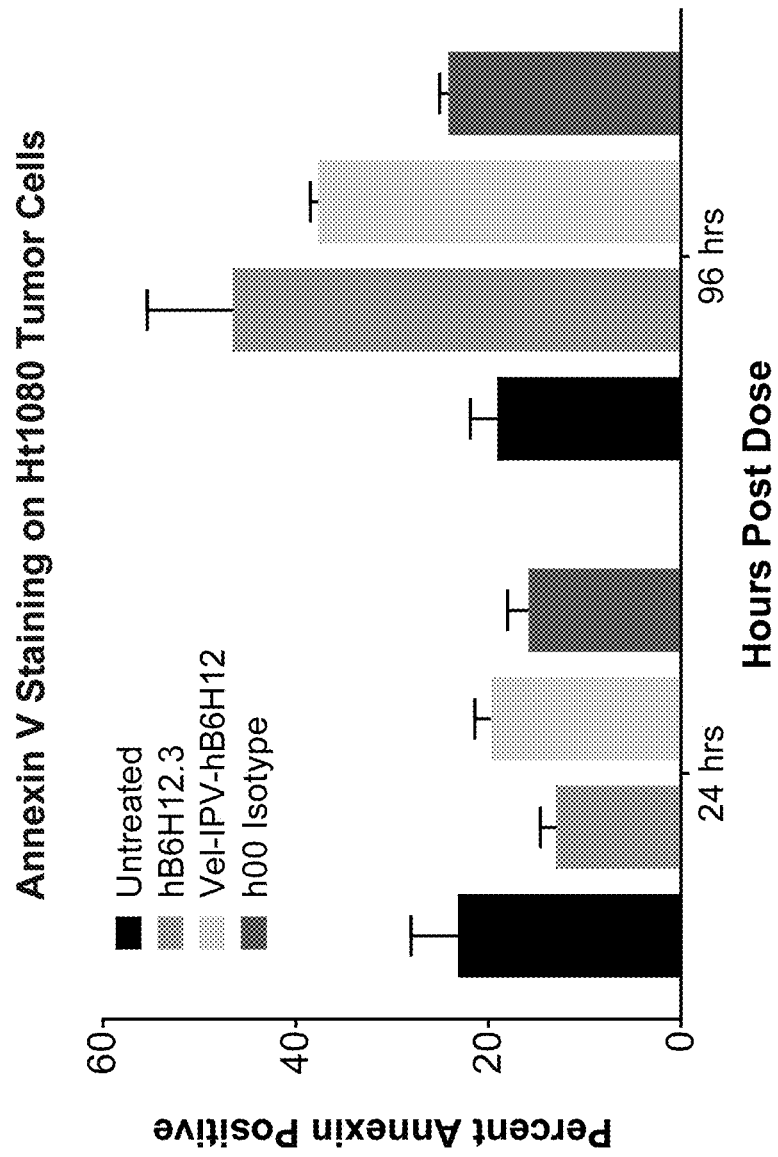
FIG. 47 shows annexin V staining on HT1080 tumor cells from HT1080 xenograft model mice administered hB6H12.3, Vel-IPV-hB6H12.3, or hIgG1 isotype control ("h00 isotype").

As shown in FIG. 47, tumors treated with both hB6H12.3 and Vel-IPV-hB6H12.3 exhibited increased Annexin V+ apoptotic cells 96 hours post treatment when compared to untreated and isotype control-treated tumor samples.

Certain Non-Limiting Embodiments

Embodiment 1. A humanized antibody or antigen-binding fragment thereof that specifically binds human CD47, the antibody or antigen-binding fragment comprising a light chain variable region and a heavy chain variable region, the heavy chain variable comprising:
 CDRs set forth as SEQ ID NOs: 16 (GYGMS), 17 (TITSGGTYTYYPDSVKG), and 18 (SLAGNAMDY); and
 a human IGHV3-23/HJ4 framework set forth in SEQ ID NO: 88, wherein framework positions H44, H49, H82, H89, H91, and H94 are donor residues, according to Kabat numbering.

Embodiment 2. A humanized antibody or antigen-binding fragment thereof that specifically binds human CD47, the antibody or antigen-binding fragment comprising a light chain variable region and a heavy chain variable region, the heavy chain variable comprising:
 CDRs set forth as SEQ ID NOs: 16 (GYGMS), 17 (TITSGGTYTYYPDSVKG), and 18 (SLAGNAMDY); and
 a human IGHV3-48/HJ4 framework set forth in SEQ ID NO: 89, wherein framework position H49 is a donor residue, according to Kabat numbering.

Embodiment 3. A humanized antibody or antigen-binding fragment thereof that specifically binds human CD47, the antibody or antigen-binding fragment comprising a light chain variable region and a heavy chain variable region, the heavy chain variable comprising:
 CDRs set forth as SEQ ID NOs: 16 (GYGMS), 17 (TITSGGTYTYYPDSVKG), and 18 (SLAGNAMDY); and
 a human IGHV3-66/HJ4 framework set forth in SEQ ID NO: 90, wherein framework position H29, H49, and H82 is a donor residue, according to Kabat numbering.

Embodiment 4. A humanized antibody or antigen-binding fragment thereof that specifically binds human CD47, the antibody or antigen-binding fragment comprising a light chain variable region and a heavy chain variable region, the heavy chain variable comprising:
 CDRs set forth as SEQ ID NOs: 16 (GYGMS), 17 (TITSGGTYTYYPDSVKG), and 18 (SLAGNAMDY); and
 a human IGHV3-74/HJ4 framework set forth in SEQ ID NO: 91, wherein framework position H49 is a donor residue, according to Kabat numbering.

Embodiment 5. The humanized antibody or antigen-binding fragment thereof of any one of embodiments 1-4, wherein the light chain variable region comprises:
 CDRs set forth as SEQ ID NOs: 31 (RASQTISDYLH), 32 (FASQSIS), and 33 (QNGHGFPRT); and
 a human IGKV6-21/KJ2 framework set forth in SEQ ID NO: 92, wherein framework positions L4, L21, L69, and L85 are donor residues, according to Kabat numbering.

Embodiment 6. The humanized antibody or antigen-binding fragment of any one of embodiments 1-4, wherein the light chain variable region comprises:
 CDRs set forth as SEQ ID NOs: 31 (RASQTISDYLH), 32 (FASQSIS), and 33 (QNGHGFPRT); and
 a human IGKV1-27/KJ2 framework set forth in SEQ ID NO: 93, wherein framework positions L21, L49, and L69 are donor residues, according to Kabat numbering.

Embodiment 7. The antibody or antigen-binding fragment of any one of embodiments 1-4, wherein H29 is occupied by F, H44 is occupied by R or G, H49 is occupied by A, H82 is occupied by M or I, H89 is occupied by I or V, H91 is occupied by F or Y, and H94 is occupied by R, according to Kabat numbering.

Embodiment 8. The antibody or antigen-binding fragment of embodiment 5, wherein L4 is occupied by M, L21 is occupied by L, L49 is occupied by K, L69 is occupied by T or S, L85 is occupied by V or T, according to Kabat numbering.

Embodiment 9. The antibody or antigen-binding fragment of any one of embodiments 1-4, comprising a heavy chain variable region (HCVR) having at least 90% sequence identity to any one of SEQ ID NOs: 2, 3, 4, 5, 6, 7 and 8, and a light chain variable region (LCVR) having at least 90% sequence identity to any one of SEQ ID NOs: 10, 11, 12, 13, 14 and 15.

Embodiment 10. The antibody or antigen-binding fragment of embodiment 5, further comprising a G91A mutation in LCDR3, according to Kabat numbering.

Embodiment 11. The antibody or antigen-binding fragment of any one of embodiments 1-4, wherein the antibody or antigen-binding fragment is of an IgG1 isotype.

Embodiment 12. The antibody or antigen-binding fragment of any one of embodiments 1-4, wherein the antibody or antigen-binding fragment has enhanced antibody dependent cellular cytotoxicity (ADCC) compared to its parental antibody.

Embodiment 13. The antibody or antigen-binding fragment of any one of embodiments 1-4, wherein the antibody or antigen-binding fragment has enhanced antibody dependent cellular phagocytosis (ADCP) compared to its parental antibody.

Embodiment 14. The antibody or antigen-binding fragment of any one of embodiments 1-4, having reduced core fucosylation compared to its parental antibody.

Embodiment 15. The antibody or antigen-binding fragment of any one of embodiments 1-4, wherein the antibody or antigen-binding fragment blocks an interaction between CD47 and SIRPα.

Embodiment 16. The antibody or antigen-binding fragment of any one of embodiments 1-4, wherein the antibody or antigen-binding fragment has reduced hemagglutination of red blood cells compared to its parental antibody.

Embodiment 17. A nucleic acid sequence encoding the antibody or antigen-binding fragment of any one of embodiments 1-4.

Embodiment 18. The antigen-binding fragment of embodiment 1, comprising a Fab, a Fab', a F(ab')$_2$, a Fv fragment, a diabody, a single-chain antibody, an scFv fragment or an scFv-Fc.

Embodiment 19. A method for treating a CD47-expressing cancer in a subject, comprising administering to the subject a therapeutically effective amount of an anti-CD47 antibody or antigen-binding fragment thereof comprising a masking agent, wherein the masking agent comprises one or more coiled coil peptides that reduce binding affinity of the antibody or antigen-binding fragment to human CD47 compared to the antibody or antigen-binding fragment thereof without the masking agent.

Embodiment 20. The method of embodiment 19, wherein a protease-cleavable linker attaches the masking agent the antibody or antigen-binding fragment thereof.

Embodiment 21. The method of embodiment 20, wherein the protease-cleavable linker has an amino acid sequence comprising IPVSLRSG (SEQ ID NO: 73) or GPLGVR (SEQ ID NO: 57).

Embodiment 22. The method of embodiment 20, wherein the protease-cleavable linker comprises a matrix metalloprotease (MMP) cleavage site.

Embodiment 23. The method of embodiment 22, wherein the MMP cleavage site is selected from the group consisting of an MMP2 cleavage site, an MMP7 cleavage site, an MMP9 cleavage site and an MMP13 cleavage site.

Embodiment 24. The method of embodiment 22, wherein the masking agent is released from the anti-CD47 antibody or antigen-binding fragment thereof subsequent to cleavage of an MMP cleavage site in a tumor microenvironment by an MMP.

Embodiment 25. The method of embodiment 24, wherein the cleaved anti-CD47 antibody has a stub amino acid remnant of the MMP cleavage site.

Embodiment 26. The method of embodiment 25, wherein the stub amino acid remnant comprises the sequence of LRSG, SG, or VR at the N terminus of the antibody.

Embodiment 27. The method of embodiment 19, wherein one or more coiled coil peptides comprise one or more sequences selected from the group consisting of SEQ ID NOs: 44, 45, 46, 47, 48, 49, 50, 51, 52, 53, 54, 55 and 56.

Embodiment 28. The method of embodiment 19, wherein antibody or antigen-binding fragment binding to CD47 is reduced at least about 100-fold compared to the antibody or antigen-binding fragment thereof without the masking agent.

Embodiment 29. The method of embodiment 19, wherein antibody or antigen-binding fragment binding to CD47 is reduced between about 200-fold and about 1500-fold compared to the antibody or antigen-binding fragment thereof without the masking agent.

Embodiment 30. The method of embodiment 19, wherein the CD47-expressing cancer is a hematological cancer that causes a solid cancer.

Embodiment 31. The method of embodiment 30, wherein the hematological cancer is selected from the group consisting of non-Hodgkin lymphoma, B-lymphoblastic lymphoma; B-cell chronic lymphocytic leukemia/small lymphocytic lymphoma, Richter's syndrome, follicular lymphoma, multiple myeloma, myelofibrosis, polycythemia vera, cutaneous T-cell lymphoma, monoclonal gammopathy of unknown significance (MGUS), myelodysplastic syndrome (MDS), immunoblastic large cell lymphoma, precursor B-lymphoblastic lymphoma, acute myeloid leukemia (AML), and anaplastic large cell lymphoma.

Embodiment 32. The method of embodiment 19, wherein the CD47-expressing cancer is a solid tumor.

Embodiment 33. The method of embodiment 32, wherein the solid tumor is selected from the group consisting of lung cancer, pancreatic cancer, breast cancer, liver cancer, ovarian cancer, testicular cancer, kidney cancer, bladder cancer, spinal cancer, brain cancer, cervical cancer, endometrial cancer, colon/rectum cancer, anal cancer, endometrial cancer, esophageal cancer, gallbladder cancer, gastrointestinal cancer, skin cancer, prostate cancer, pituitary cancer, stomach cancer, uterine cancer, vaginal cancer and thyroid cancer.

Embodiment 34. The method of embodiment 32, wherein the solid tumor is selected from the group consisting of lung cancer, soft tissue sarcoma, colorectal cancer, head and neck cancer, and breast cancer.

Embodiment 35. The method of embodiment 19, wherein the subject is a human suffering from a solid cancer.

Embodiment 36. The method of embodiment 19, wherein the anti-CD47 antibody is administered in combination with an inhibitor of an immune checkpoint molecule chosen from one or more of programmed cell death protein 1 (PD-1), programmed death-ligand 1 (PD-L1), PD-L2, cytotoxic T lymphocyte-associated protein 4 (CTLA-4), T cell immunoglobulin and mucin domain containing 3 (TIM-3), lymphocyte activation gene 3 (LAG-3), carcinoembryonic antigen related cell adhesion molecule 1 (CEACAM-1), CEACAM-5, V-domain Ig suppressor of T cell activation (VISTA), B and T lymphocyte attenuator (BTLA), T cell immunoreceptor with Ig and ITIM domains (TIGIT), leukocyte-associated immunoglobulin-like receptor 1 (LAIR1), CD160, 2B4 or TGFR.

Embodiment 37. An antibody or antigen-binding fragment thereof that specifically binds to the human CD47 protein comprising a masking agent, wherein the masking agent comprises one or more coiled coil peptides comprising the sequence of SEQ ID NO: 95 (QGASTTVAQLEEKVKTLRAENYELKSEVQRLE-EQVAQLGS) and/or SEQ ID NO: 94 (QGASTSVDELQAEVDQLEDENYALKTK-VAQLRKKVEKLGS), and wherein the one or more coiled coil peptides reduce binding affinity of the antibody or antigen-binding fragment to human CD47 protein compared to the antibody or antigen-binding fragment thereof without the masking agent.

Embodiment 38. The antibody or antigen-binding fragment of embodiment 37, comprising a heavy chain variable region (HCVR) having at least 90% sequence identity to any one of SEQ ID NOs: 2, 3, 4, 5, 6, 7 and 8, and a light chain variable region (LCVR) having at least 90% sequence identity to any one of SEQ ID NOs: 10, 11, 12, 13, 14 and 15.

Embodiment 39. The antibody or antigen-binding fragment of embodiment 37, wherein the masking agent is attached to the antibody or antigen-binding fragment thereof via a protease-cleavable linker.

Embodiment 40. The antibody or antigen-binding fragment of embodiment 39, wherein the protease-cleavable linker has an amino acid sequence comprising IPVSLRSG (SEQ ID NO: 73) or GPLGVR (SEQ ID NO: 57).

Embodiment 41. The antibody or antigen-binding fragment of embodiment 39, wherein the protease-cleavable linker comprises a matrix metalloprotease (MMP) cleavage site.

Embodiment 42. The antibody or antigen-binding fragment of embodiment 41, wherein the MMP cleavage site is selected from the group consisting of an MMP2 cleavage site, an MMP7 cleavage site, an MMP9 cleavage site and an MMP13 cleavage site.

Embodiment 43. The antibody of embodiment 37, wherein the masking agent is removed from the anti-CD47 antibody after cleavage of an MMP cleavage site by an MMP.

Embodiment 44. The antibody of embodiment 43, wherein the anti-CD47 antibody has a stub amino acid remnant of the MMP cleavage site after cleavage of an MMP cleavage site by an MMP.

Embodiment 45. The antibody of embodiment 44, wherein the stub amino acid remnant comprises the sequence of LRSG, SG, or VR at the N terminus of the antibody.

Embodiment 46. The antibody or antigen-binding fragment of embodiment 37, wherein binding is reduced at least about 100-fold compared to the antibody or antigen-binding fragment thereof without the masking agent.

Embodiment 47. The antibody or antigen-binding fragment of embodiment 37, wherein the binding is reduced between about 200-fold and about 1500-fold compared to the antibody or antigen-binding fragment thereof without the masking agent.

Embodiment 48. 48 The antibody or antigen-binding fragment of embodiment 37, comprising a heavy chain sequence of SEQ ID NO: 42 and a light chain sequence of SEQ ID NO: 43.

Embodiment 49. The antibody or antigen-binding fragment of any of embodiments 37-48, comprising a variant Fc region which confers enhanced effector function selected from ADCC and/or CDC activity.

Embodiment 50. The antibody or antigen-binding fragment of embodiment 49, which is afucosylated.

Embodiment 51. A humanized antibody or antigen-binding fragment thereof that specifically binds human CD47, wherein the antibody is an IgG1 isotype.

Embodiment 52. The antibody of embodiment 51, comprising enhanced ADCC, enhanced ADCP, and/or enhanced CDC activity.

Embodiment 53. A method for treating a CD47-expressing cancer in a subject, comprising the steps of:
 a) identifying the subject as having elevated levels of MMP in the cancer relative to surrounding non-cancer tissue; and
 b) administering to the subject a therapeutically effective amount of an anti-CD47 antibody or antigen-binding fragment thereof comprising a masking agent, wherein the masking agent comprises coiled coil peptides that reduce binding affinity of the antibody or antigen-binding fragment to human CD47 compared to the antibody or antigen-binding fragment thereof without the masking agent, if the subject has elevated levels of MMP in the cancer relative to surrounding non-cancer tissue.

Embodiment 54. The method of embodiment 53, wherein the MMP is selected from the group consisting of: MMP2, MMP7, MMP9, and MMP13.

Embodiment 55. The method of embodiment 53, wherein step a) comprises:
 i) isolating cancer tissue and non-cancer tissue from the subject;
 ii) detecting MMPs in the isolated cancer tissue and the non-cancer tissue; and
 iii) comparing the amount of staining in the cancer tissue relative to the non-cancer tissue.

Embodiment 56. A method for treating a CD47-expressing cancer in a subject, comprising the steps of:
 a) identifying the subject as having elevated levels of CD47 in the cancer relative to surrounding non-cancer tissue; and
 b) administering to the subject a therapeutically effective amount of an anti-CD47 antibody or antigen-binding fragment thereof comprising a masking agent, wherein the masking agent comprises coiled coil peptides that reduce binding affinity of the antibody or antigen-binding fragment to human CD47 compared to the antibody or antigen-binding fragment thereof without the masking agent, if the subject has elevated levels of CD47 in the cancer relative to surrounding non-cancer tissue.

Embodiment 57. The method of embodiment 56, wherein step a) comprises:
 i) isolating cancer tissue and surrounding non-cancer tissue from the subject;
 ii) detecting CD47 in the isolated cancer tissue and surrounding non-cancer tissue; and
 iii) comparing the amount of CD47 staining in the cancer tissue relative to CD47 staining the non-cancer tissue.

Embodiment 58. A method for treating a CD47-expressing cancer in a subject, comprising the steps of:
 a) identifying the subject as having elevated levels of macrophage infiltration in cancer tissue relative to non-cancer tissue; and
 b) administering to the subject a therapeutically effective amount of an anti-CD47 antibody or antigen-binding fragment thereof comprising a masking agent, wherein the masking agent comprises one or more coiled coil peptides that reduce binding affinity of the antibody or antigen-binding fragment to human CD47 compared to the antibody or antigen-binding fragment thereof without the masking agent, if the subject has elevated levels of macrophage infiltration in the cancer relative to the non-cancer tissue.

Embodiment 59. The method of embodiment 58, wherein step a) comprises:
 i) isolating cancer tissue and surrounding non-cancer tissue from the subject;

ii) detecting macrophages in the isolated cancer tissue and in non-cancer tissue; and iii) comparing the amount of staining in the cancer tissue relative to the non-cancer tissue.

Embodiment 60. The method of embodiment 58, wherein the macrophage staining is performed with an anti-CD163 antibody.

Embodiment 61. A humanized antibody or antigen-binding fragment thereof that specifically binds human CD47, comprising a heavy chain variable region (HCVR) having at least 90% sequence identity to any one of SEQ ID NOs: 2, 3, 4, 5, 6, 7 and 8, and a light chain variable region (LCVR) having at least 90% sequence identity to any one of SEQ ID NOs: 10, 11, 12, 13, 14 and 15, wherein the antibody further comprises the sequence LRSG, SG, or VR at the N terminus of the HCVR and/or the LCVR.

Embodiment 62. A method of treating cancer by administering a combination of the masked CD47 antibody of embodiment 37 with an agonistic CD40 antibody.

Embodiment 63. The method of embodiment 62, wherein the agonistic CD40 antibody has low fucosylation levels, e.g., SEA-CD40 antibody.

Embodiment 64. A method of treating cancer by administering a combination of the masked CD47 antibody of embodiment 37 with an antibody drug conjugate (ADC), wherein the antibody of the ADC specifically binds to a protein that is expressed on the extracellular surface of a cancer cell and the antibody is conjugated to a drug-linker comprising a cytotoxic agent.

Embodiment 65. The method of embodiment 64, wherein the cytotoxic agent is an auristatin.

Embodiment 66. The method of embodiment 64, wherein the antibody of the ADC is conjugated to a drug linker selected from the group consisting of vcMMAE and mcMMAF.

SEQUENCE LISTING

```
<160> NUMBER OF SEQ ID NOS: 95

<210> SEQ ID NO 1
<211> LENGTH: 118
<212> TYPE: PRT
<213> ORGANISM: unknown
<220> FEATURE:
<223> OTHER INFORMATION: Murine

<400> SEQUENCE: 1

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Gly Tyr
            20                  25                  30

Gly Met Ser Trp Val Arg Gln Thr Pro Asp Lys Arg Leu Glu Trp Val
        35                  40                  45

Ala Thr Ile Thr Ser Gly Gly Thr Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Ile Asp Ser Leu Lys Ser Glu Asp Thr Ala Ile Tyr Phe Cys
                85                  90                  95

Ala Arg Ser Leu Ala Gly Asn Ala Met Asp Tyr Trp Gly Gln Gly Thr
            100                 105                 110

Ser Val Thr Val Ser Ser
        115

<210> SEQ ID NO 2
<211> LENGTH: 118
<212> TYPE: PRT
<213> ORGANISM: Artificial Sequence
<220> FEATURE:
<223> OTHER INFORMATION: Humanized heavy chain variable region

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Gly Met Ser Trp Val Arg Gln Ala Pro Gly Lys Gly Leu Glu Trp Val
        35                  40                  45
```

Ala Thr Ile Thr Ser Gly Gly Thr Tyr Thr Tyr Tyr Pro Asp Ser Val
            50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Ser Leu Ala Gly Asn Ala Met Asp Tyr Trp Gly Gln Gly Thr
            100                 105                 110

Leu Val Thr Val Ser Ser
            115

<210> SEQ ID NO 3
<211> LENGTH: 118
<212> TYPE: PRT
<213> ORGANISM: Artificial Sequence
<220> FEATURE:
<223> OTHER INFORMATION: Humanized heavy chain variable region

<400> SEQUENCE: 3

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Gly Tyr
                20                  25                  30

Gly Met Ser Trp Val Arg Gln Ala Pro Gly Lys Arg Leu Glu Trp Val
            35                  40                  45

Ala Thr Ile Thr Ser Gly Gly Thr Tyr Thr Tyr Tyr Pro Asp Ser Val
            50                  55                  60

Lys Gly Arg Phe Thr Ile Ser Arg Asp Asn Lys Asn Thr Leu Tyr
 65                  70                  75                  80

Leu Gln Met Asn Ser Leu Arg Ala Glu Asp Thr Ala Ile Tyr Phe Cys
                85                  90                  95

Ala Arg Ser Leu Ala Gly Asn Ala Met Asp Tyr Trp Gly Gln Gly Thr
            100                 105                 110

Leu Val Thr Val Ser Ser
            115

<210> SEQ ID NO 4
<211> LENGTH: 118
<212> TYPE: PRT
<213> ORGANISM: Artificial Sequence
<220> FEATURE:
<223> OTHER INFORMATION: Humanized heavy chain variable region

<400> SEQUENCE: 4

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ala Thr Ile Thr Ser Gly Gly Thr Tyr Thr Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Phe Cys
                85                  90                  95

Ala Arg Ser Leu Ala Gly Asn Ala Met Asp Tyr Trp Gly Gln Gly Thr
            100                 105                 110

Leu Val Thr Val Ser Ser
        115

<210> SEQ ID NO 5
<211> LENGTH: 118
<212> TYPE: PRT
<213> ORGANISM: Artificial Sequence
<220> FEATURE:
<223> OTHER INFORMATION: Humanized heavy chain variable region

<400> SEQUENCE: 5

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Thr Ile Thr Ser Gly Gly Thr Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Ile Asn Ser Leu Arg Ala Glu Asp Thr Ala Val Tyr Phe Cys
                85                  90                  95

Ala Arg Ser Leu Ala Gly Asn Ala Met Asp Tyr Trp Gly Gln Gly Thr
            100                 105                 110

Leu Val Thr Val Ser Ser
        115

<210> SEQ ID NO 6
<211> LENGTH: 118
<212> TYPE: PRT
<213> ORGANISM: Artificial Sequence
<220> FEATURE:
<223> OTHER INFORMATION: Humanized heavy chain variable region

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Asn Trp Val Arg Gln Ala Pro Gly Lys Gly Leu Glu Trp Val
        35                  40                  45

Ala Thr Ile Thr Ser Gly Gly Thr Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Gly Asn Ala Met Asp Tyr Trp Gly Gln Gly Thr
            100                 105                 110

Leu Val Thr Val Ser Ser
        115

<210> SEQ ID NO 7
<211> LENGTH: 118
<212> TYPE: PRT
<213> ORGANISM: Artificial Sequence
<220> FEATURE:
<223> OTHER INFORMATION: Humanized heavy chain variable region

```
<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Gly Met Ser Trp Val Arg Gln Ala Pro Gly Lys Gly Leu Glu Trp Val
        35                  40                  45

Ala Thr Ile Thr Ser Gly Gly Thr Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Ile Asn Ser Leu Arg Ala Glu Asp Thr Ala Val Tyr Tyr Cys
                85                  90                  95

Ala Arg Ser Leu Ala Gly Asn Ala Met Asp Tyr Trp Gly Gln Gly Thr
            100                 105                 110

Leu Val Thr Val Ser Ser
            115

<210> SEQ ID NO 8
<211> LENGTH: 118
<212> TYPE: PRT
<213> ORGANISM: Artificial Sequence
<220> FEATURE:
<223> OTHER INFORMATION: Humanized heavy chain variable region

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Val Trp Val
        35                  40                  45

Ala Thr Ile Thr Ser Gly Gly Thr Tyr Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Gly Asn Ala Met Asp Tyr Trp Gly Gln Gly Thr
            100                 105                 110

Leu Val Thr Val Ser Ser
            115

<210> SEQ ID NO 9
<211> LENGTH: 108
<212> TYPE: PRT
<213> ORGANISM: unknown
<220> FEATURE:
<223> OTHER INFORMATION: Murine

<400> SEQUENCE: 9

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Thr Ile Ser Asp Tyr
            20                  25                  30

Leu His Trp Tyr Gln Gln Lys Ser His Glu Ser Pro Arg Leu Leu Ile
        35                  40                  45
```

Lys Phe Ala Ser Gln Ser Ile Ser Gly Ile Pro Ser Arg Phe Ser Gly
       50                     55                    60

Ser Gly Ser Gly Ser Asp Phe Thr Leu Ser Ile Asn Ser Val Glu Pro
65                     70                     75                  80

Glu Asp Val Gly Val Tyr Tyr Cys Gln Asn Gly His Gly Phe Pro Arg
               85                     90                     95

Thr Phe Gly Gly Gly Thr Lys Leu Glu Ile Lys Arg
          100                 105

<210> SEQ ID NO 10
<211> LENGTH: 108
<212> TYPE: PRT
<213> ORGANISM: Artificial Sequence
<220> FEATURE:
<223> OTHER INFORMATION: Humanized light chain variable region

<400> SEQUENCE: 10

Glu Ile Val Leu Thr Gln Ser Pro Ala Thr Leu Ser Leu Ser Pro Gly
1                5                    10                 15

Glu Arg Ala Thr Leu Ser Cys Arg Ala Ser Gln Thr Ile Ser Asp Tyr
               20                     25                     30

Leu His Trp Tyr Gln Gln Lys Pro Gly Gln Ala Pro Arg Leu Leu Ile
               35                     40                     45

Lys Phe Ala Ser Gln Ser Ile Ser Gly Ile Pro Ala Arg Phe Ser Gly
       50                     55                    60

Ser Gly Ser Gly Thr Asp Phe Thr Leu Thr Ile Ser Ser Leu Glu Pro
65                     70                     75                  80

Glu Asp Phe Ala Val Tyr Tyr Cys Gln Asn Gly His Gly Phe Pro Arg
               85                     90                     95

Thr Phe Gly Gln Gly Thr Lys Val Glu Ile Lys Arg
          100                 105

<210> SEQ ID NO 11
<211> LENGTH: 108
<212> TYPE: PRT
<213> ORGANISM: Artificial Sequence
<220> FEATURE:
<223> OTHER INFORMATION: Humanized light chain variable region

<400> SEQUENCE: 11

Glu Ile Val Met Thr Gln Ser Pro Asp Phe Gln Ser Val Thr Pro Lys
1                5                    10                 15

Glu Lys Val Thr Leu Thr Cys Arg Ala Ser Gln Thr Ile Ser Asp Tyr
               20                     25                     30

Leu His Trp Tyr Gln Gln Lys Pro Asp Gln Ser Pro Lys Leu Leu Ile
               35                     40                     45

Lys Phe Ala Ser Gln Ser Ile Ser Gly Val Pro Ser Arg Phe Ser Gly
       50                     55                    60

Ser Gly Ser Gly Thr Asp Phe Thr Leu Thr Ile Asn Ser Leu Glu Ala
65                     70                     75                  80

Glu Asp Ala Ala Val Tyr Tyr Cys Gln Asn Gly His Gly Phe Pro Arg
               85                     90                     95

Thr Phe Gly Gln Gly Thr Lys Leu Glu Ile Lys Arg
          100                 105

<210> SEQ ID NO 12
<211> LENGTH: 108
<212> TYPE: PRT

-continued

<213> ORGANISM: Artificial Sequence
<220> FEATURE:
<223> OTHER INFORMATION: Humanized light chain variable region

<400> SEQUENCE: 12

```
Glu Ile Val Met Thr Gln Ser Pro Asp Phe Gln Ser Val Thr Pro Lys
1               5                   10                  15

Glu Lys Val Thr Leu Thr Cys Arg Ala Ser Gln Thr Ile Ser Asp Tyr
            20                  25                  30

Leu His Trp Tyr Gln Gln Lys Pro Asp Gln Ser Pro Lys Leu Leu Ile
        35                  40                  45

Lys Phe Ala Ser Gln Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Asn Gly His Gly Phe Pro Arg
                85                  90                  95

Thr Phe Gly Gln Gly Thr Lys Leu Glu Ile Lys Arg
            100                 105
```

<210> SEQ ID NO 13
<211> LENGTH: 108
<212> TYPE: PRT
<213> ORGANISM: Artificial Sequence
<220> FEATURE:
<223> OTHER INFORMATION: Humanized light chain variable region

<400> SEQUENCE: 13

```
Glu Ile Val Met Thr Gln Ser Pro Asp Phe Gln Ser Val Thr Pro Lys
1               5                   10                  15

Glu Lys Val Thr Leu Thr Cys Arg Ala Ser Gln Thr Ile Ser Asp Tyr
            20                  25                  30

Leu His Trp Tyr Gln Gln Lys Pro Asp Gln Ser Pro Lys Leu Leu Ile
        35                  40                  45

Lys Phe Ala Ser Gln Ser Ile Ser Gly Val Pro Ser Arg Phe Ser Gly
    50                  55                  60

Ser Gly Ser Gly Ser Asp Phe Thr Leu Thr Ile Asn Ser Leu Glu Ala
65                  70                  75                  80

Glu Asp Ala Ala Thr Tyr Tyr Cys Gln Asn Gly His Gly Phe Pro Arg
                85                  90                  95

Thr Phe Gly Gln Gly Thr Lys Leu Glu Ile Lys Arg
            100                 105
```

<210> SEQ ID NO 14
<211> LENGTH: 108
<212> TYPE: PRT
<213> ORGANISM: Artificial Sequence
<220> FEATURE:
<223> OTHER INFORMATION: Humanized light chain variable region

<400> SEQUENCE: 14

```
Asp Ile Gln Met Thr Gln Ser Pro Ser Ser Leu Ser Ala Ser Val Gly
1               5                   10                  15

Asp Arg Val Thr Leu Thr Cys Arg Ala Ser Gln Thr Ile Ser Asn Tyr
            20                  25                  30

Leu Ala Trp Tyr Gln Gln Lys Pro Gly Lys Val Pro Lys Leu Leu Ile
        35                  40                  45

Lys Phe Ala Ser Thr Leu Gln Ser Gly Val Pro Ser Arg Phe Ser Gly
    50                  55                  60
```

```
Ser Gly Ser Gly Ser Asp Phe Thr Leu Thr Ile Ser Ser Leu Gln Pro
65                  70                  75                  80

Glu Asp Val Ala Thr Tyr Tyr Cys Gln Asn Gly His Gly Phe Pro Arg
                85                  90                  95

Thr Phe Gly Gln Gly Thr Lys Leu Glu Ile Lys Arg
            100                 105
```

<210> SEQ ID NO 15
<211> LENGTH: 108
<212> TYPE: PRT
<213> ORGANISM: Artificial Sequence
<220> FEATURE:
<223> OTHER INFORMATION: Humanized light chain variable region

<400> SEQUENCE: 15

```
Glu Ile Val Met Thr Gln Ser Pro Asp Phe Gln Ser Val Thr Pro Lys
1               5                   10                  15

Glu Lys Val Thr Leu Thr Cys Arg Ala Ser Gln Thr Ile Ser Asp Tyr
                20                  25                  30

Leu His Trp Tyr Gln Gln Lys Pro Asp Gln Ser Pro Lys Leu Leu Ile
            35                  40                  45

Lys Phe Ala Ser Gln Ser Ile Ser Gly Val Pro Ser Arg Phe Ser Gly
        50                  55                  60

Ser Gly Ser Gly Ser Asp Phe Thr Leu Thr Ile Asn Ser Leu Glu Ala
65                  70                  75                  80

Glu Asp Ala Ala Thr Tyr Tyr Cys Gln Asn Ala His Gly Phe Pro Arg
                85                  90                  95

Thr Phe Gly Gln Gly Thr Lys Leu Glu Ile Lys Arg
            100                 105
```

<210> SEQ ID NO 16
<211> LENGTH: 5
<212> TYPE: PRT
<213> ORGANISM: Artificial Sequence
<220> FEATURE:
<223> OTHER INFORMATION: Heavy chain CDR sequence

<400> SEQUENCE: 16

```
Gly Tyr Gly Met Ser
1               5
```

<210> SEQ ID NO 17
<211> LENGTH: 17
<212> TYPE: PRT
<213> ORGANISM: Artificial Sequence
<220> FEATURE:
<223> OTHER INFORMATION: Heavy chain CDR sequence

<400> SEQUENCE: 17

```
Thr Ile Thr Ser Gly Gly Thr Tyr Thr Tyr Tyr Pro Asp Ser Val Lys
1               5                   10                  15

Gly
```

<210> SEQ ID NO 18
<211> LENGTH: 9
<212> TYPE: PRT
<213> ORGANISM: Artificial Sequence
<220> FEATURE:
<223> OTHER INFORMATION: Heavy chain CDR sequence

<400> SEQUENCE: 18

```
Ser Leu Ala Gly Asn Ala Met Asp Tyr
1               5

<210> SEQ ID NO 19
<211> LENGTH: 5
<212> TYPE: PRT
<213> ORGANISM: Artificial Sequence
<220> FEATURE:
<223> OTHER INFORMATION: Heavy chain CDR sequence

<400> SEQUENCE: 19

Ser Tyr Ala Met Ser
1               5

<210> SEQ ID NO 20
<211> LENGTH: 17
<212> TYPE: PRT
<213> ORGANISM: Artificial Sequence
<220> FEATURE:
<223> OTHER INFORMATION: Heavy chain CDR sequence

<400> SEQUENCE: 20

Thr Ile Thr Ser Gly Gly Thr Tyr Thr Tyr Tyr Ala Asp Ser Val Lys
1               5                   10                  15

Gly

<210> SEQ ID NO 21
<211> LENGTH: 5
<212> TYPE: PRT
<213> ORGANISM: Artificial Sequence
<220> FEATURE:
<223> OTHER INFORMATION: Heavy chain CDR sequence

<400> SEQUENCE: 21

Ser Tyr Gly Met Asn
1               5

<210> SEQ ID NO 22
<211> LENGTH: 17
<212> TYPE: PRT
<213> ORGANISM: Artificial Sequence
<220> FEATURE:
<223> OTHER INFORMATION: Heavy chain CDR sequence

<400> SEQUENCE: 22

Thr Ile Thr Ser Gly Gly Thr Tyr Ile Tyr Tyr Ala Asp Ser Val Lys
1               5                   10                  15

Gly

<210> SEQ ID NO 23
<211> LENGTH: 5
<212> TYPE: PRT
<213> ORGANISM: Artificial Sequence
<220> FEATURE:
<223> OTHER INFORMATION: Heavy chain CDR sequence

<400> SEQUENCE: 23

Ser Tyr Gly Met His
1               5

<210> SEQ ID NO 24
<211> LENGTH: 17
<212> TYPE: PRT
<213> ORGANISM: Artificial Sequence
<220> FEATURE:
<223> OTHER INFORMATION: Heavy chain CDR sequence
```

```
<400> SEQUENCE: 24

Thr Ile Thr Ser Gly Gly Thr Tyr Thr Ser Tyr Ala Asp Ser Val Lys
1               5                   10                  15
Gly

<210> SEQ ID NO 25
<211> LENGTH: 8
<212> TYPE: PRT
<213> ORGANISM: Artificial Sequence
<220> FEATURE:
<223> OTHER INFORMATION: Heavy chain CDR sequence

<400> SEQUENCE: 25

Gly Phe Thr Phe Ser Gly Tyr Gly
1               5

<210> SEQ ID NO 26
<211> LENGTH: 8
<212> TYPE: PRT
<213> ORGANISM: Artificial Sequence
<220> FEATURE:
<223> OTHER INFORMATION: Heavy chain CDR sequence

<400> SEQUENCE: 26

Ile Thr Ser Gly Gly Thr Tyr Thr
1               5

<210> SEQ ID NO 27
<211> LENGTH: 11
<212> TYPE: PRT
<213> ORGANISM: Artificial Sequence
<220> FEATURE:
<223> OTHER INFORMATION: Heavy chain CDR sequence

<400> SEQUENCE: 27

Ala Arg Ser Leu Ala Gly Asn Ala Met Asp Tyr
1               5                   10

<210> SEQ ID NO 28
<211> LENGTH: 8
<212> TYPE: PRT
<213> ORGANISM: Artificial Sequence
<220> FEATURE:
<223> OTHER INFORMATION: Heavy chain CDR sequence

<400> SEQUENCE: 28

Gly Phe Thr Phe Ser Ser Tyr Ala
1               5

<210> SEQ ID NO 29
<211> LENGTH: 8
<212> TYPE: PRT
<213> ORGANISM: Artificial Sequence
<220> FEATURE:
<223> OTHER INFORMATION: Heavy chain CDR sequence

<400> SEQUENCE: 29

Gly Phe Thr Phe Ser Ser Tyr Gly
1               5

<210> SEQ ID NO 30
<211> LENGTH: 8
<212> TYPE: PRT
<213> ORGANISM: Artificial Sequence
<220> FEATURE:
```

```
<223> OTHER INFORMATION: Heavy chain CDR sequence

<400> SEQUENCE: 30

Ile Thr Ser Gly Gly Thr Tyr Ile
1               5

<210> SEQ ID NO 31
<211> LENGTH: 11
<212> TYPE: PRT
<213> ORGANISM: Artificial Sequence
<220> FEATURE:
<223> OTHER INFORMATION: Light chain CDR sequence

<400> SEQUENCE: 31

Arg Ala Ser Gln Thr Ile Ser Asp Tyr Leu His
1               5                   10

<210> SEQ ID NO 32
<211> LENGTH: 7
<212> TYPE: PRT
<213> ORGANISM: Artificial Sequence
<220> FEATURE:
<223> OTHER INFORMATION: Light chain CDR sequence

<400> SEQUENCE: 32

Phe Ala Ser Gln Ser Ile Ser
1               5

<210> SEQ ID NO 33
<211> LENGTH: 9
<212> TYPE: PRT
<213> ORGANISM: Artificial Sequence
<220> FEATURE:
<223> OTHER INFORMATION: Light chain CDR sequence

<400> SEQUENCE: 33

Gln Asn Gly His Gly Phe Pro Arg Thr
1               5

<210> SEQ ID NO 34
<211> LENGTH: 11
<212> TYPE: PRT
<213> ORGANISM: Artificial Sequence
<220> FEATURE:
<223> OTHER INFORMATION: Light chain CDR sequence

<400> SEQUENCE: 34

Arg Ala Ser Gln Thr Ile Ser Asn Tyr Leu Ala
1               5                   10

<210> SEQ ID NO 35
<211> LENGTH: 7
<212> TYPE: PRT
<213> ORGANISM: Artificial Sequence
<220> FEATURE:
<223> OTHER INFORMATION: Light chain CDR sequence

<400> SEQUENCE: 35

Phe Ala Ser Thr Leu Gln Ser
1               5

<210> SEQ ID NO 36
<211> LENGTH: 9
<212> TYPE: PRT
<213> ORGANISM: Artificial Sequence
<220> FEATURE:
<223> OTHER INFORMATION: Light chain CDR sequence
```

```
<400> SEQUENCE: 36

Gln Asn Ala His Gly Phe Pro Arg Thr
1               5

<210> SEQ ID NO 37
<211> LENGTH: 6
<212> TYPE: PRT
<213> ORGANISM: Artificial Sequence
<220> FEATURE:
<223> OTHER INFORMATION: Light chain CDR sequence

<400> SEQUENCE: 37

Gln Thr Ile Ser Asp Tyr
1               5

<210> SEQ ID NO 38
<211> LENGTH: 3
<212> TYPE: PRT
<213> ORGANISM: Artificial Sequence
<220> FEATURE:
<223> OTHER INFORMATION: Light chain CDR sequence

<400> SEQUENCE: 38

Phe Ala Ser
1

<210> SEQ ID NO 39
<211> LENGTH: 9
<212> TYPE: PRT
<213> ORGANISM: Artificial Sequence
<220> FEATURE:
<223> OTHER INFORMATION: Light chain CDR sequence

<400> SEQUENCE: 39

Gln Asn Gly His Gly Phe Pro Arg Thr
1               5

<210> SEQ ID NO 40
<211> LENGTH: 6
<212> TYPE: PRT
<213> ORGANISM: Artificial Sequence
<220> FEATURE:
<223> OTHER INFORMATION: Light chain CDR sequence

<400> SEQUENCE: 40

Gln Thr Ile Ser Asn Tyr
1               5

<210> SEQ ID NO 41
<211> LENGTH: 9
<212> TYPE: PRT
<213> ORGANISM: Artificial Sequence
<220> FEATURE:
<223> OTHER INFORMATION: Light chain CDR sequence

<400> SEQUENCE: 41

Gln Asn Ala His Gly Phe Pro Arg Thr
1               5

<210> SEQ ID NO 42
<211> LENGTH: 488
<212> TYPE: PRT
<213> ORGANISM: Artificial Sequence
<220> FEATURE:
<223> OTHER INFORMATION: Masked heavy chain
```

-continued

```
<400> SEQUENCE: 42

Gln Gly Ala Ser Thr Ser Val Asp Glu Leu Gln Ala Glu Val Asp Gln
1               5                   10                  15

Leu Glu Asp Glu Asn Tyr Ala Leu Lys Thr Lys Val Ala Gln Leu Arg
            20                  25                  30

Lys Lys Val Glu Lys Leu Gly Ser Ile Pro Val Ser Leu Arg Ser Gly
        35                  40                  45

Glu Val Gln Leu Leu Glu Ser Gly Gly Gly Leu Val Gln Pro Gly Gly
    50                  55                  60

Ser Leu Arg Leu Ser Cys Ala Ala Ser Gly Phe Thr Phe Ser Gly Tyr
65                  70                  75                  80

Gly Met Ser Trp Val Arg Gln Ala Pro Gly Lys Arg Leu Glu Trp Val
                85                  90                  95

Ala Thr Ile Thr Ser Gly Gly Thr Tyr Thr Tyr Tyr Pro Asp Ser Val
            100                 105                 110

Lys Gly Arg Phe Thr Ile Ser Arg Asp Asn Ser Lys Asn Thr Leu Tyr
        115                 120                 125

Leu Gln Met Asn Ser Leu Arg Ala Glu Asp Thr Ala Ile Tyr Phe Cys
    130                 135                 140

Ala Arg Ser Leu Ala Gly Asn Ala Met Asp Tyr Trp Gly Gln Gly Thr
145                 150                 155                 160

Leu Val Thr Val Ser Ser Ala Ser Thr Lys Gly Pro Ser Val Phe Pro
                165                 170                 175

Leu Ala Pro Ser Ser Lys Ser Thr Ser Gly Gly Thr Ala Ala Leu Gly
            180                 185                 190

Cys Leu Val Lys Asp Tyr Phe Pro Glu Pro Val Thr Val Ser Trp Asn
        195                 200                 205

Ser Gly Ala Leu Thr Ser Gly Val His Thr Phe Pro Ala Val Leu Gln
    210                 215                 220

Ser Ser Gly Leu Tyr Ser Leu Ser Ser Val Val Thr Val Pro Ser Ser
225                 230                 235                 240

Ser Leu Gly Thr Gln Thr Tyr Ile Cys Asn Val Asn His Lys Pro Ser
                245                 250                 255

Asn Thr Lys Val Asp Lys Lys Val Glu Pro Lys Ser Cys Asp Lys Thr
            260                 265                 270

His Thr Cys Pro Pro Cys Pro Ala Pro Glu Leu Leu Gly Gly Pro Ser
        275                 280                 285

Val Phe Leu Phe Pro Pro Lys Pro Lys Asp Thr Leu Met Ile Ser Arg
    290                 295                 300

Thr Pro Glu Val Thr Cys Val Val Val Asp Val Ser His Glu Asp Pro
305                 310                 315                 320

Glu Val Lys Phe Asn Trp Tyr Val Asp Gly Val Glu Val His Asn Ala
                325                 330                 335

Lys Thr Lys Pro Arg Glu Glu Gln Tyr Asn Ser Thr Tyr Arg Val Val
            340                 345                 350

Ser Val Leu Thr Val Leu His Gln Asp Trp Leu Asn Gly Lys Glu Tyr
        355                 360                 365

Lys Cys Lys Val Ser Asn Lys Ala Leu Pro Ala Pro Ile Glu Lys Thr
    370                 375                 380

Ile Ser Lys Ala Lys Gly Gln Pro Arg Glu Pro Gln Val Tyr Thr Leu
385                 390                 395                 400

Pro Pro Ser Arg Asp Glu Leu Thr Lys Asn Gln Val Ser Leu Thr Cys
                405                 410                 415
```

Leu Val Lys Gly Phe Tyr Pro Ser Asp Ile Ala Val Glu Trp Glu Ser
                420                 425                 430

Asn Gly Gln Pro Glu Asn Asn Tyr Lys Thr Thr Pro Pro Val Leu Asp
            435                 440                 445

Ser Asp Gly Ser Phe Phe Leu Tyr Ser Lys Leu Thr Val Asp Lys Ser
    450                 455                 460

Arg Trp Gln Gln Gly Asn Val Phe Ser Cys Ser Val Met His Glu Ala
465                 470                 475                 480

Leu His Asn His Tyr Thr Gln Lys
                485

<210> SEQ ID NO 43
<211> LENGTH: 262
<212> TYPE: PRT
<213> ORGANISM: Artificial Sequence
<220> FEATURE:
<223> OTHER INFORMATION: Masked light chain

<400> SEQUENCE: 43

Gln Gly Ala Ser Thr Thr Val Ala Gln Leu Glu Glu Lys Val Lys Thr
1               5                   10                  15

Leu Arg Ala Glu Asn Tyr Glu Leu Lys Ser Glu Val Gln Arg Leu Glu
            20                  25                  30

Glu Gln Val Ala Gln Leu Gly Ser Ile Pro Val Ser Leu Arg Ser Gly
        35                  40                  45

Glu Ile Val Met Thr Gln Ser Pro Asp Phe Gln Ser Val Thr Pro Lys
    50                  55                  60

Glu Lys Val Thr Leu Thr Cys Arg Ala Ser Gln Thr Ile Ser Asp Tyr
65                  70                  75                  80

Leu His Trp Tyr Gln Gln Lys Pro Asp Gln Ser Pro Lys Leu Leu Ile
                85                  90                  95

Lys Phe Ala Ser Gln Ser Ile Ser Gly Val Pro Ser Arg Phe Ser Gly
            100                 105                 110

Ser Gly Ser Gly Ser Asp Phe Thr Leu Thr Ile Asn Ser Leu Glu Ala
        115                 120                 125

Glu Asp Ala Ala Thr Tyr Tyr Cys Gln Asn Gly His Gly Phe Pro Arg
    130                 135                 140

Thr Phe Gly Gln Gly Thr Lys Leu Glu Ile Lys Arg Thr Val Ala Ala
145                 150                 155                 160

Pro Ser Val Phe Ile Phe Pro Pro Ser Asp Glu Gln Leu Lys Ser Gly
                165                 170                 175

Thr Ala Ser Val Val Cys Leu Leu Asn Asn Phe Tyr Pro Arg Glu Ala
            180                 185                 190

Lys Val Gln Trp Lys Val Asp Asn Ala Leu Gln Ser Gly Asn Ser Gln
        195                 200                 205

Glu Ser Val Thr Glu Gln Asp Ser Lys Asp Ser Thr Tyr Ser Leu Ser
    210                 215                 220

Ser Thr Leu Thr Leu Ser Lys Ala Asp Tyr Glu Lys His Lys Val Tyr
225                 230                 235                 240

Ala Cys Glu Val Thr His Gln Gly Leu Ser Ser Pro Val Thr Lys Ser
                245                 250                 255

Phe Asn Arg Gly Glu Cys
            260

<210> SEQ ID NO 44

```
<211> LENGTH: 54
<212> TYPE: PRT
<213> ORGANISM: Artificial Sequence
<220> FEATURE:
<223> OTHER INFORMATION: Masking domain sequence

<400> SEQUENCE: 44

Gly Ala Ser Thr Ser Val Asp Glu Leu Gln Ala Glu Val Asp Gln Leu
1               5                   10                  15

Gln Asp Glu Asn Tyr Ala Leu Lys Thr Lys Val Ala Gln Leu Arg Lys
                20                  25                  30

Lys Val Glu Lys Leu Ser Glu Gly Gly Gly Gly Pro Leu Gly Val
        35                  40                  45

Arg Gly Gly Gly Gly Ser
    50

<210> SEQ ID NO 45
<211> LENGTH: 54
<212> TYPE: PRT
<213> ORGANISM: Artificial Sequence
<220> FEATURE:
<223> OTHER INFORMATION: Masking domain sequence

<400> SEQUENCE: 45

Gly Ala Ser Thr Thr Val Ala Gln Leu Arg Glu Arg Val Lys Thr Leu
1               5                   10                  15

Arg Ala Gln Asn Tyr Glu Leu Glu Ser Glu Val Gln Arg Leu Arg Glu
                20                  25                  30

Gln Val Ala Gln Leu Ala Ser Gly Gly Gly Gly Pro Leu Gly Val
        35                  40                  45

Arg Gly Gly Gly Gly Ser
    50

<210> SEQ ID NO 46
<211> LENGTH: 55
<212> TYPE: PRT
<213> ORGANISM: Artificial Sequence
<220> FEATURE:
<223> OTHER INFORMATION: Masking domain sequence

<400> SEQUENCE: 46

Leu Glu Ile Glu Ala Ala Phe Leu Glu Arg Glu Asn Thr Ala Leu Glu
1               5                   10                  15

Thr Arg Val Ala Glu Leu Arg Gln Arg Val Gln Arg Ala Arg Asn Arg
                20                  25                  30

Val Ser Gln Tyr Arg Thr Arg Tyr Gly Gly Gly Gly Pro Leu Gly
        35                  40                  45

Val Arg Gly Gly Gly Gly Ser
    50                  55

<210> SEQ ID NO 47
<211> LENGTH: 55
<212> TYPE: PRT
<213> ORGANISM: Artificial Sequence
<220> FEATURE:
<223> OTHER INFORMATION: Masking domain sequence

<400> SEQUENCE: 47

Leu Glu Ile Arg Ala Ala Phe Leu Arg Gln Arg Asn Thr Ala Leu Arg
1               5                   10                  15

Thr Glu Val Ala Glu Leu Glu Gln Glu Val Gln Arg Leu Glu Asn Glu
                20                  25                  30
```

Val Ser Gln Tyr Glu Thr Arg Tyr Gly Gly Gly Gly Gly Pro Leu Gly
        35                  40                  45

Val Arg Gly Gly Gly Gly Ser
    50                  55

<210> SEQ ID NO 48
<211> LENGTH: 56
<212> TYPE: PRT
<213> ORGANISM: Artificial Sequence
<220> FEATURE:
<223> OTHER INFORMATION: Masking domain sequence

<400> SEQUENCE: 48

Leu Glu Ile Arg Ala Ala Phe Leu Arg Arg Arg Asn Thr Ala Leu Arg
1               5                   10                  15

Thr Arg Val Ala Glu Leu Arg Gln Arg Val Gln Arg Leu Arg Asn Ile
            20                  25                  30

Val Ser Gln Tyr Glu Thr Arg Tyr Gly Gly Gly Gly Gly Pro Leu
        35                  40                  45

Gly Val Arg Gly Gly Gly Gly Ser
    50                  55

<210> SEQ ID NO 49
<211> LENGTH: 56
<212> TYPE: PRT
<213> ORGANISM: Artificial Sequence
<220> FEATURE:
<223> OTHER INFORMATION: Masking domain sequence

<400> SEQUENCE: 49

Leu Glu Ile Glu Ala Ala Phe Leu Glu Gln Glu Asn Thr Ala Leu Glu
1               5                   10                  15

Thr Glu Val Ala Glu Leu Glu Gln Glu Val Gln Arg Leu Glu Asn Ile
            20                  25                  30

Val Ser Gln Tyr Glu Thr Arg Tyr Gly Gly Gly Gly Gly Pro Leu
        35                  40                  45

Gly Val Arg Gly Gly Gly Gly Ser
    50                  55

<210> SEQ ID NO 50
<211> LENGTH: 47
<212> TYPE: PRT
<213> ORGANISM: Artificial Sequence
<220> FEATURE:
<223> OTHER INFORMATION: Masking domain sequence

<400> SEQUENCE: 50

Gly Ala Ser Thr Ser Val Asp Glu Leu Gln Ala Glu Val Asp Gln Leu
1               5                   10                  15

Glu Asp Glu Asn Tyr Ala Leu Lys Thr Lys Val Ala Gln Leu Arg Lys
            20                  25                  30

Lys Val Glu Lys Leu Gly Ser Ile Pro Val Ser Leu Arg Ser Gly
        35                  40                  45

<210> SEQ ID NO 51
<211> LENGTH: 47
<212> TYPE: PRT
<213> ORGANISM: Artificial Sequence
<220> FEATURE:
<223> OTHER INFORMATION: Masking domain sequence

<400> SEQUENCE: 51

Gly Ala Ser Thr Thr Val Ala Gln Leu Glu Glu Lys Val Lys Thr Leu
1               5                   10                  15

Arg Ala Glu Asn Tyr Glu Leu Lys Ser Glu Val Gln Arg Leu Glu Glu
                20                  25                  30

Gln Val Ala Gln Leu Gly Ser Ile Pro Val Ser Leu Arg Ser Gly
            35                  40                  45

<210> SEQ ID NO 52
<211> LENGTH: 57
<212> TYPE: PRT
<213> ORGANISM: Artificial Sequence
<220> FEATURE:
<223> OTHER INFORMATION: Masking domain sequence

<400> SEQUENCE: 52

Gly Ala Leu Thr Asp Thr Leu Gln Ala Glu Thr Asp Gln Leu Glu Asp
1               5                   10                  15

Lys Lys Ser Ala Leu Gln Thr Glu Ile Ala Asn Leu Leu Lys Glu Lys
                20                  25                  30

Glu Lys Leu Glu Phe Ile Leu Ala Ala His Gly Gly Gly Gly Gly Pro
            35                  40                  45

Leu Gly Val Arg Gly Gly Gly Gly Ser
        50                  55

<210> SEQ ID NO 53
<211> LENGTH: 57
<212> TYPE: PRT
<213> ORGANISM: Artificial Sequence
<220> FEATURE:
<223> OTHER INFORMATION: Masking domain sequence

<400> SEQUENCE: 53

Gly Ala Arg Ile Ala Arg Leu Glu Glu Lys Val Lys Thr Leu Lys Ala
1               5                   10                  15

Gln Asn Ser Glu Leu Ala Ser Thr Ala Asn Met Leu Arg Glu Gln Val
                20                  25                  30

Ala Gln Leu Lys Gln Lys Val Met Asn Tyr Gly Gly Gly Gly Gly Pro
            35                  40                  45

Leu Gly Val Arg Gly Gly Gly Gly Ser
        50                  55

<210> SEQ ID NO 54
<211> LENGTH: 44
<212> TYPE: PRT
<213> ORGANISM: Artificial Sequence
<220> FEATURE:
<223> OTHER INFORMATION: Masking domain sequence

<400> SEQUENCE: 54

Gly Lys Ile Ala Ala Leu Lys Gln Lys Ile Ala Ala Leu Lys Tyr Lys
1               5                   10                  15

Asn Ala Ala Leu Lys Lys Lys Ile Ala Ala Leu Lys Gln Gly Gly Gly
                20                  25                  30

Gly Gly Pro Leu Gly Val Arg Gly Gly Gly Gly Ser
            35                  40

<210> SEQ ID NO 55
<211> LENGTH: 44
<212> TYPE: PRT
<213> ORGANISM: Artificial Sequence
<220> FEATURE:

<223> OTHER INFORMATION: Masking domain sequence

<400> SEQUENCE: 55

Gly Glu Ile Ala Ala Leu Glu Gln Glu Ile Ala Ala Leu Glu Lys Glu
1               5                   10                  15

Asn Ala Ala Leu Glu Trp Glu Ile Ala Ala Leu Glu Gln Gly Gly Gly
            20                  25                  30

Gly Gly Pro Leu Gly Val Arg Gly Gly Gly Ser
        35                  40

<210> SEQ ID NO 56

<400> SEQUENCE: 56

000

<210> SEQ ID NO 57
<211> LENGTH: 6
<212> TYPE: PRT
<213> ORGANISM: Artificial Sequence
<220> FEATURE:
<223> OTHER INFORMATION: Protease cleavage sequence

<400> SEQUENCE: 57

Gly Pro Leu Gly Val Arg
1               5

<210> SEQ ID NO 58
<211> LENGTH: 8
<212> TYPE: PRT
<213> ORGANISM: Artificial Sequence
<220> FEATURE:
<223> OTHER INFORMATION: Protease cleavage sequence

<400> SEQUENCE: 58

Ile Pro Val Ser Leu Arg Ser Gly
1               5

<210> SEQ ID NO 59
<211> LENGTH: 5
<212> TYPE: PRT
<213> ORGANISM: Artificial Sequence
<220> FEATURE:
<223> OTHER INFORMATION: exemplary linker

<400> SEQUENCE: 59

Gly Ser Gly Gly Ser
1               5

<210> SEQ ID NO 60
<211> LENGTH: 4
<212> TYPE: PRT
<213> ORGANISM: Artificial Sequence
<220> FEATURE:
<223> OTHER INFORMATION: exemplary linker

<400> SEQUENCE: 60

Gly Gly Gly Ser
1

<210> SEQ ID NO 61
<211> LENGTH: 12
<212> TYPE: PRT
<213> ORGANISM: Artificial Sequence
<220> FEATURE:
<223> OTHER INFORMATION: exemplary linker

```
<400> SEQUENCE: 61

Ser Gly Gly Gly Gly Gly Gly Gly Gly Ser
1               5                   10

<210> SEQ ID NO 62
<211> LENGTH: 4
<212> TYPE: PRT
<213> ORGANISM: Artificial Sequence
<220> FEATURE:
<223> OTHER INFORMATION: exemplary linker

<400> SEQUENCE: 62

Gly Gly Ala Ala
1

<210> SEQ ID NO 63
<211> LENGTH: 5
<212> TYPE: PRT
<213> ORGANISM: Artificial Sequence
<220> FEATURE:
<223> OTHER INFORMATION: exemplary linker

<400> SEQUENCE: 63

Gly Gly Gly Gly Ser
1               5

<210> SEQ ID NO 64
<211> LENGTH: 5
<212> TYPE: PRT
<213> ORGANISM: Artificial Sequence
<220> FEATURE:
<223> OTHER INFORMATION: exemplary linker

<400> SEQUENCE: 64

Leu Ala Ala Ala Ala
1               5

<210> SEQ ID NO 65
<211> LENGTH: 4
<212> TYPE: PRT
<213> ORGANISM: Artificial Sequence
<220> FEATURE:
<223> OTHER INFORMATION: exemplary linker

<400> SEQUENCE: 65

Gly Gly Ser Gly
1

<210> SEQ ID NO 66
<211> LENGTH: 5
<212> TYPE: PRT
<213> ORGANISM: Artificial Sequence
<220> FEATURE:
<223> OTHER INFORMATION: exemplary linker

<400> SEQUENCE: 66

Gly Gly Ser Gly Gly
1               5

<210> SEQ ID NO 67
<211> LENGTH: 5
<212> TYPE: PRT
<213> ORGANISM: Artificial Sequence
<220> FEATURE:
<223> OTHER INFORMATION: exemplary linker
```

```
<400> SEQUENCE: 67

Gly Ser Gly Ser Gly
1               5

<210> SEQ ID NO 68
<211> LENGTH: 5
<212> TYPE: PRT
<213> ORGANISM: Artificial Sequence
<220> FEATURE:
<223> OTHER INFORMATION: exemplary linker

<400> SEQUENCE: 68

Gly Ser Gly Gly Gly
1               5

<210> SEQ ID NO 69
<211> LENGTH: 5
<212> TYPE: PRT
<213> ORGANISM: Artificial Sequence
<220> FEATURE:
<223> OTHER INFORMATION: exemplary linker

<400> SEQUENCE: 69

Gly Gly Gly Ser Gly
1               5

<210> SEQ ID NO 70
<211> LENGTH: 5
<212> TYPE: PRT
<213> ORGANISM: Artificial Sequence
<220> FEATURE:
<223> OTHER INFORMATION: exemplary linker

<400> SEQUENCE: 70

Gly Ser Ser Ser Gly
1               5

<210> SEQ ID NO 71
<211> LENGTH: 6
<212> TYPE: PRT
<213> ORGANISM: Artificial Sequence
<220> FEATURE:
<223> OTHER INFORMATION: exemplary protease site
<220> FEATURE:
<221> NAME/KEY: misc_feature
<222> LOCATION: (4)..(6)
<223> OTHER INFORMATION: Xaa can be any naturally occurring amino acid

<400> SEQUENCE: 71

Pro Leu Gly Xaa Xaa Xaa
1               5

<210> SEQ ID NO 72
<211> LENGTH: 5
<212> TYPE: PRT
<213> ORGANISM: Artificial Sequence
<220> FEATURE:
<223> OTHER INFORMATION: exemplary protease site

<400> SEQUENCE: 72

Pro Leu Gly Val Arg
1               5

<210> SEQ ID NO 73
<211> LENGTH: 8
<212> TYPE: PRT
<213> ORGANISM: Artificial Sequence
```

```
<220> FEATURE:
<223> OTHER INFORMATION: exemplary protease site

<400> SEQUENCE: 73

Ile Pro Val Ser Leu Arg Ser Gly
1               5

<210> SEQ ID NO 74
<211> LENGTH: 8
<212> TYPE: PRT
<213> ORGANISM: Artificial Sequence
<220> FEATURE:
<223> OTHER INFORMATION: exemplary protease site

<400> SEQUENCE: 74

Leu Ser Gly Arg Ser Asp Asn Tyr
1               5

<210> SEQ ID NO 75
<211> LENGTH: 57
<212> TYPE: PRT
<213> ORGANISM: Artificial Sequence
<220> FEATURE:
<223> OTHER INFORMATION: Masking domain sequence

<400> SEQUENCE: 75

Glu Ala Cys Gly Ala Ser Thr Ser Val Asp Glu Leu Gln Ala Glu Val
1               5                   10                  15

Asp Gln Leu Gln Asp Glu Asn Tyr Ala Leu Lys Thr Lys Val Ala Gln
            20                  25                  30

Leu Arg Lys Lys Val Glu Lys Leu Ser Glu Gly Gly Gly Gly Gly Pro
        35                  40                  45

Leu Gly Val Arg Gly Gly Gly Gly Ser
    50                  55

<210> SEQ ID NO 76
<211> LENGTH: 57
<212> TYPE: PRT
<213> ORGANISM: Artificial Sequence
<220> FEATURE:
<223> OTHER INFORMATION: Masking domain sequence

<400> SEQUENCE: 76

Glu Ala Cys Gly Ala Ser Thr Thr Val Ala Gln Leu Arg Glu Arg Val
1               5                   10                  15

Lys Thr Leu Arg Ala Gln Asn Tyr Glu Leu Glu Ser Glu Val Gln Arg
            20                  25                  30

Leu Arg Glu Gln Val Ala Gln Leu Ala Ser Gly Gly Gly Gly Gly Pro
        35                  40                  45

Leu Gly Val Arg Gly Gly Gly Gly Ser
    50                  55

<210> SEQ ID NO 77
<211> LENGTH: 58
<212> TYPE: PRT
<213> ORGANISM: Artificial Sequence
<220> FEATURE:
<223> OTHER INFORMATION: Masking domain sequence

<400> SEQUENCE: 77

Glu Ala Cys Leu Glu Ile Glu Ala Ala Phe Leu Glu Arg Glu Asn Thr
1               5                   10                  15

Ala Leu Glu Thr Arg Val Ala Glu Leu Arg Gln Arg Val Gln Arg Ala
```

```
                    20                  25                  30

Arg Asn Arg Val Ser Gln Tyr Arg Thr Arg Tyr Gly Gly Gly Gly
            35                  40                  45

Pro Leu Gly Val Arg Gly Gly Gly Gly Ser
        50                  55

<210> SEQ ID NO 78
<211> LENGTH: 58
<212> TYPE: PRT
<213> ORGANISM: Artificial Sequence
<220> FEATURE:
<223> OTHER INFORMATION: Masking domain sequence

<400> SEQUENCE: 78

Glu Ala Cys Leu Glu Ile Arg Ala Ala Phe Leu Arg Gln Arg Asn Thr
1               5                   10                  15

Ala Leu Arg Thr Glu Val Ala Glu Leu Glu Gln Glu Val Gln Arg Leu
                20                  25                  30

Glu Asn Glu Val Ser Gln Tyr Glu Thr Arg Tyr Gly Gly Gly Gly
            35                  40                  45

Pro Leu Gly Val Arg Gly Gly Gly Gly Ser
        50                  55

<210> SEQ ID NO 79
<211> LENGTH: 59
<212> TYPE: PRT
<213> ORGANISM: Artificial Sequence
<220> FEATURE:
<223> OTHER INFORMATION: Masking domain sequence

<400> SEQUENCE: 79

Glu Ala Cys Leu Glu Ile Arg Ala Ala Phe Leu Arg Arg Arg Asn Thr
1               5                   10                  15

Ala Leu Arg Thr Arg Val Ala Glu Leu Arg Gln Arg Val Gln Arg Leu
                20                  25                  30

Arg Asn Ile Val Ser Gln Tyr Glu Thr Arg Tyr Gly Gly Gly Gly
            35                  40                  45

Gly Pro Leu Gly Val Arg Gly Gly Gly Gly Ser
        50                  55

<210> SEQ ID NO 80
<211> LENGTH: 59
<212> TYPE: PRT
<213> ORGANISM: Artificial Sequence
<220> FEATURE:
<223> OTHER INFORMATION: Masking domain sequence

<400> SEQUENCE: 80

Glu Ala Cys Leu Glu Ile Glu Ala Ala Phe Leu Glu Gln Glu Asn Thr
1               5                   10                  15

Ala Leu Glu Thr Glu Val Ala Glu Leu Glu Gln Glu Val Gln Arg Leu
                20                  25                  30

Glu Asn Ile Val Ser Gln Tyr Glu Thr Arg Tyr Gly Gly Gly Gly
            35                  40                  45

Gly Pro Leu Gly Val Arg Gly Gly Gly Gly Ser
        50                  55

<210> SEQ ID NO 81
<211> LENGTH: 50
<212> TYPE: PRT
<213> ORGANISM: Artificial Sequence
```

<220> FEATURE:
<223> OTHER INFORMATION: Masking domain sequence

<400> SEQUENCE: 81

Glu Ala Cys Gly Ala Ser Thr Ser Val Asp Glu Leu Gln Ala Glu Val
1               5                   10                  15

Asp Gln Leu Glu Asp Glu Asn Tyr Ala Leu Lys Thr Lys Val Ala Gln
            20                  25                  30

Leu Arg Lys Lys Val Glu Lys Leu Gly Ser Ile Pro Val Ser Leu Arg
        35                  40                  45

Ser Gly
    50

<210> SEQ ID NO 82
<211> LENGTH: 50
<212> TYPE: PRT
<213> ORGANISM: Artificial Sequence
<220> FEATURE:
<223> OTHER INFORMATION: Masking domain sequence

<400> SEQUENCE: 82

Glu Ala Cys Gly Ala Ser Thr Thr Val Ala Gln Leu Glu Gln Lys Val
1               5                   10                  15

Lys Thr Leu Arg Ala Glu Asn Tyr Glu Leu Lys Ser Glu Val Gln Arg
            20                  25                  30

Leu Glu Glu Gln Val Ala Gln Leu Gly Ser Ile Pro Val Ser Leu Arg
        35                  40                  45

Ser Gly
    50

<210> SEQ ID NO 83
<211> LENGTH: 60
<212> TYPE: PRT
<213> ORGANISM: Artificial Sequence
<220> FEATURE:
<223> OTHER INFORMATION: Masking domain sequence

<400> SEQUENCE: 83

Glu Ala Cys Gly Ala Leu Thr Asp Thr Leu Gln Ala Glu Thr Asp Gln
1               5                   10                  15

Leu Glu Asp Lys Lys Ser Ala Leu Gln Thr Glu Ile Ala Asn Leu Leu
            20                  25                  30

Lys Glu Lys Glu Lys Leu Glu Phe Ile Leu Ala Ala His Gly Gly Gly
        35                  40                  45

Gly Gly Pro Leu Gly Val Arg Gly Gly Gly Ser
    50                  55                  60

<210> SEQ ID NO 84
<211> LENGTH: 60
<212> TYPE: PRT
<213> ORGANISM: Artificial Sequence
<220> FEATURE:
<223> OTHER INFORMATION: Masking domain sequence

<400> SEQUENCE: 84

Glu Ala Cys Gly Ala Arg Ile Ala Arg Leu Glu Lys Val Lys Thr
1               5                   10                  15

Leu Lys Ala Gln Asn Ser Glu Leu Ala Ser Thr Ala Asn Met Leu Arg
            20                  25                  30

Glu Gln Val Ala Gln Leu Lys Gln Lys Val Met Asn Tyr Gly Gly Gly
        35                  40                  45

```
Gly Gly Pro Leu Gly Val Arg Gly Gly Gly Ser
        50                  55                  60

<210> SEQ ID NO 85
<211> LENGTH: 47
<212> TYPE: PRT
<213> ORGANISM: Artificial Sequence
<220> FEATURE:
<223> OTHER INFORMATION: Masking domain sequence

<400> SEQUENCE: 85

Glu Ala Cys Gly Lys Ile Ala Ala Leu Lys Gln Lys Ile Ala Ala Leu
1               5                   10                  15

Lys Tyr Lys Asn Ala Ala Leu Lys Lys Lys Ile Ala Ala Leu Lys Gln
            20                  25                  30

Gly Gly Gly Gly Gly Pro Leu Gly Val Arg Gly Gly Gly Ser
            35                  40                  45

<210> SEQ ID NO 86
<211> LENGTH: 47
<212> TYPE: PRT
<213> ORGANISM: Artificial Sequence
<220> FEATURE:
<223> OTHER INFORMATION: Masking domain sequence

<400> SEQUENCE: 86

Glu Ala Cys Gly Glu Ile Ala Ala Leu Glu Gln Glu Ile Ala Ala Leu
1               5                   10                  15

Glu Lys Glu Asn Ala Ala Leu Glu Trp Glu Ile Ala Ala Leu Glu Gln
            20                  25                  30

Gly Gly Gly Gly Gly Pro Leu Gly Val Arg Gly Gly Gly Ser
            35                  40                  45

<210> SEQ ID NO 87

<400> SEQUENCE: 87

000

<210> SEQ ID NO 89
<211> LENGTH: 113
<212> TYPE: PRT
<213> ORGANISM: Homo sapiens

<400> SEQUENCE: 89

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Phe Asp Tyr Trp Gly Gln Gly Thr Leu Val Thr Val Ser
            100                 105                 110

Ser

<210> SEQ ID NO 90
<211> LENGTH: 112
<212> TYPE: PRT
<213> ORGANISM: Homo sapiens

<400> SEQUENCE: 90

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Tyr Phe Asp Tyr Trp Gly Gln Gly Thr Leu Val Thr Val Ser Ser
            100                 105                 110

<210> SEQ ID NO 91
<211> LENGTH: 113
<212> TYPE: PRT
<213> ORGANISM: Homo sapiens

<400> SEQUENCE: 91

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Ser Thr Ser Tyr Ala Asp Ser Val

```
                50                  55                  60
Lys Gly Arg Phe Thr Ile Ser Arg Asp Asn Ala Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Tyr Phe Asp Tyr Trp Gly Gln Gly Thr Leu Val Thr Val Ser
                100                 105                 110

Ser

<210> SEQ ID NO 92
<211> LENGTH: 107
<212> TYPE: PRT
<213> ORGANISM: Homo sapiens

<400> SEQUENCE: 92

Glu Ile Val Leu Thr Gln Ser Pro Asp Phe Gln Ser Val Thr Pro Lys
  1               5                  10                  15

Glu Lys Val Thr Ile Thr Cys Arg Ala Ser Gln Ser Ile Gly Ser Ser
                 20                  25                  30

Leu His Trp Tyr Gln Gln Lys Pro Asp Gln Ser Pro Lys Leu Leu Ile
                 35                  40                  45

Lys Tyr Ala Ser Gln Ser Ile Ser Gly Val Pro Ser Arg Phe Ser Gly
 50                  55                  60

Ser Gly Ser Gly Thr Asp Phe Thr Leu Thr Ile Asn Ser Leu Glu Ala
 65                  70                  75                  80

Glu Asp Ala Ala Thr Tyr Tyr Cys His Gln Ser Ser Ser Leu Pro Thr
                 85                  90                  95

Phe Gly Gln Gly Thr Lys Leu Glu Ile Lys Arg
                100                 105

<210> SEQ ID NO 93
<211> LENGTH: 107
<212> TYPE: PRT
<213> ORGANISM: Homo sapiens

<400> SEQUENCE: 93

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Ser Asn Tyr
                 20                  25                  30

Leu Ala Trp Tyr Gln Gln Lys Pro Gly Lys Val Pro Lys Leu Leu Ile
                 35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Lys Tyr Asn Ser Ala Pro Thr
                 85                  90                  95

Phe Gly Gln Gly Thr Lys Leu Glu Ile Lys Arg
                100                 105

<210> SEQ ID NO 94
<211> LENGTH: 40
<212> TYPE: PRT
<213> ORGANISM: Artificial Sequence
<220> FEATURE:
<223> OTHER INFORMATION: Masking domain sequence
```

```
<400> SEQUENCE: 94

Gln Gly Ala Ser Thr Ser Val Asp Glu Leu Gln Ala Glu Val Asp Gln
1               5                   10                  15

Leu Glu Asp Glu Asn Tyr Ala Leu Lys Thr Lys Val Ala Gln Leu Arg
            20                  25                  30

Lys Lys Val Glu Lys Leu Gly Ser
        35                  40

<210> SEQ ID NO 95
<211> LENGTH: 40
<212> TYPE: PRT
<213> ORGANISM: Artificial Sequence
<220> FEATURE:
<223> OTHER INFORMATION: Masking domain sequence

<400> SEQUENCE: 95

Gln Gly Ala Ser Thr Thr Val Ala Gln Leu Glu Glu Lys Val Lys Thr
1               5                   10                  15

Leu Arg Ala Glu Asn Tyr Glu Leu Lys Ser Glu Val Gln Arg Leu Glu
            20                  25                  30

Glu Gln Val Ala Gln Leu Gly Ser
        35                  40
```

What is claimed:

1. A method for treating a CD47-expressing cancer in a subject, comprising administering to the subject a therapeutically effective amount of an anti-CD47 antibody or antigen-binding fragment thereof, wherein the antibody or antigen-binding fragment comprises a light chain variable region and a heavy chain variable region, wherein the antibody or antigen-binding fragment thereof comprises HCDR1, HCDR2, HCDR3, LCDR1, LCDR2, and LCDR3 selected from SEQ ID NOs: 16, 17, 18, 31, 32, and 33; SEQ ID NOs: 16, 17, 18, 34, 35, and 33; SEQ ID NOs: 16, 20, 18, 31, 32, and 33; SEQ ID NOs: 16, 20, 18, 34, 35, and 33; SEQ ID NOs: 16, 17, 18, 31, 32, and 36; and SEQ ID NOs: 16, 20, 18, 31, 32, and 36, wherein the heavy chain variable region comprises an amino acid sequence with at least 97% identity to an amino acid sequence selected from SEQ ID NOs: 3 and 7, and wherein the light chain variable region comprises an amino acid sequence with at least 85% identity to an amino acid sequence selected from SEQ ID NOs: 11, 12, 13, 14, and 15.

2. The method of claim 1, wherein the method comprises:
identifying the subject as having a CD47-expressing cancer.

3. The method of claim 2, wherein the identifying comprises:
i) isolating cancer tissue; and
ii) detecting CD47 in the isolated cancer tissue.

4. The method of claim 1, wherein the method comprises:
identifying the subject as having elevated levels of macrophage infiltration in cancer tissue relative to non-cancer tissue.

5. The method of claim 4, wherein the identifying comprises:
i) isolating cancer tissue and surrounding non-cancer tissue from the subject;
ii) detecting macrophages in the isolated cancer tissue and in non-cancer tissue; and
iii) comparing the amount of staining in the cancer tissue relative to the non-cancer tissue.

6. The method of claim 5, wherein the macrophage staining is performed with an anti-CD163 antibody.

7. The method of claim 1, wherein the CD47-expressing cancer is a hematological cancer or a solid cancer.

8. The method of claim 1, wherein the CD47-expressing cancer is selected from non-Hodgkin lymphoma, B-lymphoblastic lymphoma; B-cell chronic lymphocytic leukemia/small lymphocytic lymphoma, Richter's syndrome, follicular lymphoma, multiple myeloma, myelofibrosis, polycythemia vera, cutaneous T-cell lymphoma, monoclonal gammopathy of unknown significance (MGUS), myelodysplastic syndrome (MDS), immunoblastic large cell lymphoma, precursor B-lymphoblastic lymphoma, acute myeloid leukemia (AML), and anaplastic large cell lymphoma.

9. The method of claim 1, wherein the CD47-expressing cancer is selected from lung cancer, pancreatic cancer, breast cancer, liver cancer, ovarian cancer, testicular cancer, kidney cancer, bladder cancer, spinal cancer, brain cancer, cervical cancer, endometrial cancer, colorectal cancer, anal cancer, endometrial cancer, esophageal cancer, gallbladder cancer, gastrointestinal cancer, gastric cancer, carcinoma, head and neck cancer, skin cancer, melanoma, prostate cancer, pituitary cancer, stomach cancer, uterine cancer, vaginal cancer and thyroid cancer.

10. The method of claim 1, wherein the CD47-expressing cancer is selected from lung cancer, sarcoma, colorectal cancer, head and neck cancer, ovarian cancer, pancreatic cancer, gastric cancer, melanoma, and breast cancer.

11. The method of claim 1, wherein the anti-CD47 antibody or antigen-binding fragment thereof is administered in combination with an inhibitor of an immune checkpoint molecule chosen from one or more of programmed cell death protein 1 (PD-1), programmed death-ligand 1 (PD-L1), PD-L2, cytotoxic T lymphocyte-associated protein 4 (CTLA-4), T cell immunoglobulin and mucin domain containing 3 (TIM-3), lymphocyte activation gene 3 (LAG-3), carcinoembryonic antigen related cell adhesion molecule 1 (CEACAM-1), CEACAM-5, V-domain Ig suppressor of T cell activation (VISTA), B and T lymphocyte attenuator (BTLA), T cell immunoreceptor with Ig and ITIM domains (TIGIT), leukocyte-associated immunoglobulin-like receptor 1 (LAIR1), CD160, 2B4, and TGFR.

12. The method of claim 1, wherein the anti-CD47 antibody or antigen-binding fragment thereof is administered in combination with an agonistic anti-CD40 antibody.

13. The method of claim 12, wherein the agonistic anti-CD40 antibody has low fucosylation levels or is afucosylated.

14. The method of claim 1, wherein the anti-CD47 antibody or antigen-binding fragment thereof is administered in combination with an antibody drug conjugate (ADC), wherein the antibody of the ADC specifically binds to a protein that is expressed on the extracellular surface of a cancer cell and the antibody is conjugated to a drug-linker comprising a cytotoxic agent.

15. The method of claim 14, wherein the cytotoxic agent is an auristatin.

16. The method of claim 15, wherein the antibody of the ADC is conjugated to a drug-linker selected from the group consisting of vcMMAE and mcMMAF.

17. A method of inducing apoptosis of a CD47-expressing cell comprising contacting the cell with an anti-CD47 antibody or antigen-binding fragment thereof, wherein the antibody or antigen-binding fragment comprises a light chain variable region and a heavy chain variable region, wherein the antibody or antigen-binding fragment thereof comprises HCDR1, HCDR2, HCDR3, LCDR1, LCDR2, and LCDR3 selected from SEQ ID NOs: 16, 17, 18, 31, 32, and 33; SEQ ID NOs: 16, 17, 18, 34, 35, and 33; SEQ ID NOs: 16, 20, 18, 31, 32, and 33; SEQ ID NOs: 16, 20, 18, 34, 35, and 33; SEQ ID NOs: 16, 17, 18, 31, 32, and 36; and SEQ ID NOs: 16, 20, 18, 31, 32, and 36, wherein the heavy chain variable region comprises an amino acid sequence with at least 97% identity to an amino acid sequence selected from SEQ ID NOs: 3 and 7, and wherein the light chain variable region comprises an amino acid sequence with at least 85% identity to an amino acid sequence selected from SEQ ID NOs: 11, 12, 13, 14, and 15.

18. The method of claim 17, wherein the cell is in vitro.

19. The method of claim 17, wherein the cell is in vivo.

20. The method of claim 1, wherein the heavy chain variable region and light chain variable region comprise SEQ ID NOs: 3 and 11; SEQ ID NOs: 3 and 12; SEQ ID NOs: 3 and 13; SEQ ID NOs: 3 and 14; SEQ ID NOs: 7 and 11; SEQ ID NOs: 7 and 12; SEQ ID NOs: 7 and 13; or SEQ ID NOs: 7 and 14.

21. The method of claim 17, wherein the heavy chain variable region and light chain variable region comprise SEQ ID NOs: 3 and 11; SEQ ID NOs: 3 and 12; SEQ ID NOS: 3 and 13; SEQ ID NOs: 3 and 14; SEQ ID NOs: 7 and 11; SEQ ID NOs: 7 and 12; SEQ ID NOs: 7 and 13; or SEQ ID NOs: 7 and 14.

22. The method of claim 1, wherein the heavy chain variable region comprises HCDR1 of SEQ ID NO: 16, HCDR2 of SEQ ID NO: 17, and HCDR3 of SEQ ID NO: 18; and wherein the light chain variable region comprises LCDR1 of SEQ ID NO: 31, LCDR2 of SEQ ID NO: 32, and LCDR3 of SEQ ID NO: 33; and wherein the heavy chain variable region comprises an amino acid sequence with at least 97% identity to SEQ ID NO: 3 and the light chain variable region comprises an amino acid sequence with at least 85% identity to SEQ ID NO: 13; and wherein the antibody has reduced hemagglutination of red blood cells compared to Ab47 comprising a heavy chain variable region comprising the amino acid sequence of SEQ ID NO: 2 and a light chain variable region comprising the amino acid sequence of SEQ ID NO: 10.

23. The method of claim 1, wherein the heavy chain variable region comprises the amino acid sequence of SEQ ID NO: 3 and the light chain variable region comprises the amino acid sequence of SEQ ID NO: 13.

24. The method of claim 23, wherein the CD47-expressing cancer is a hematological cancer or a solid cancer.

25. The method of claim 23, wherein the CD47-expressing cancer is selected from non-Hodgkin lymphoma, B-lymphoblastic lymphoma; B-cell chronic lymphocytic leukemia/small lymphocytic lymphoma, Richter's syndrome, follicular lymphoma, multiple myeloma, myelofibrosis, polycythemia vera, cutaneous T-cell lymphoma, monoclonal gammopathy of unknown significance (MGUS), myelodysplastic syndrome (MDS), immunoblastic large cell lymphoma, precursor B-lymphoblastic lymphoma, acute myeloid leukemia (AML), and anaplastic large cell lymphoma.

26. The method of claim 23, wherein the CD47-expressing cancer is selected from lung cancer, pancreatic cancer, breast cancer, liver cancer, ovarian cancer, testicular cancer, kidney cancer, bladder cancer, spinal cancer, brain cancer, cervical cancer, endometrial cancer, colorectal cancer, anal cancer, endometrial cancer, esophageal cancer, gallbladder cancer, gastrointestinal cancer, gastric cancer, carcinoma, head and neck cancer, skin cancer, melanoma, prostate cancer, pituitary cancer, stomach cancer, uterine cancer, vaginal cancer and thyroid cancer.

27. The method of claim 23, wherein the CD47-expressing cancer is selected from lung cancer, sarcoma, colorectal cancer, head and neck cancer, ovarian cancer, pancreatic cancer, gastric cancer, melanoma, and breast cancer.

28. The method of claim 23, wherein the anti-CD47 antibody or antigen-binding fragment thereof is administered in combination with an inhibitor of an immune checkpoint molecule chosen from one or more of programmed cell death protein 1 (PD-1), programmed death-ligand 1 (PD-L1), PD-L2, cytotoxic T lymphocyte-associated protein 4 (CTLA-4), T cell immunoglobulin and mucin domain containing 3 (TIM-3), lymphocyte activation gene 3 (LAG-3), carcinoembryonic antigen related cell adhesion molecule 1 (CEACAM-1), CEACAM-5, V-domain Ig suppressor of T cell activation (VISTA), B and T lymphocyte attenuator (BTLA), T cell immunoreceptor with Ig and ITIM domains (TIGIT), leukocyte-associated immunoglobulin-like receptor 1 (LAIR1), CD160, 2B4, and TGFR.

29. The method of claim 23, wherein the anti-CD47 antibody or antigen-binding fragment thereof is administered in combination with an agonistic anti-CD40 antibody.

30. The method of claim 29, wherein the agonistic anti-CD40 antibody has low fucosylation levels or is afucosylated.

31. The method of claim 23, wherein the anti-CD47 antibody or antigen-binding fragment thereof is administered in combination with an antibody drug conjugate (ADC), wherein the antibody of the ADC specifically binds to a protein that is expressed on the extracellular surface of a cancer cell and the antibody is conjugated to a drug-linker comprising a cytotoxic agent.

32. The method of claim 31, wherein the cytotoxic agent is an auristatin.

33. The method of claim 32, wherein the antibody of the ADC is conjugated to a drug-linker selected from the group consisting of vcMMAE and mcMMAF.

* * * * *